US011274144B2

(12) United States Patent
Goodman et al.

(10) Patent No.: US 11,274,144 B2
(45) Date of Patent: Mar. 15, 2022

(54) COMPOSITIONS AND METHODS FOR THE REMOVAL OF BIOFILMS

(71) Applicant: Research Institute at Nationwide Children's Hospital, Columbus, OH (US)

(72) Inventors: Steven D. Goodman, Hilliard, OH (US); Lauren O. Bakaletz, Hilliard, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 15/999,215

(22) Filed: Aug. 16, 2018

(65) Prior Publication Data

US 2020/0002409 A1 Jan. 2, 2020

Related U.S. Application Data

(60) Division of application No. 15/078,987, filed on Mar. 23, 2016, now abandoned, and a continuation-in-part of application No. 14/967,228, filed on Dec. 11, 2015, now abandoned, which is a continuation of application No. PCT/US2014/042201, filed on Jun. 12, 2014.

(60) Provisional application No. 62/199,952, filed on Jul. 31, 2015, provisional application No. 61/834,846, filed on Jun. 13, 2013.

(51) Int. Cl.
| | | |
|---|---|---|
| *A61K 39/40* | (2006.01) | |
| *A61K 45/06* | (2006.01) | |
| *C07K 16/12* | (2006.01) | |
| *A61K 39/02* | (2006.01) | |
| *C07K 16/40* | (2006.01) | |
| *G01N 33/68* | (2006.01) | |
| *G01N 33/569* | (2006.01) | |
| *A01N 37/46* | (2006.01) | |
| *A61K 39/395* | (2006.01) | |
| *A61K 39/00* | (2006.01) | |

(52) U.S. Cl.
CPC .......... *C07K 16/1242* (2013.01); *A01N 37/46* (2013.01); *A61K 39/0208* (2013.01); *A61K 39/39541* (2013.01); *A61K 39/40* (2013.01); *A61K 45/06* (2013.01); *C07K 16/12* (2013.01); *C07K 16/1232* (2013.01); *C07K 16/40* (2013.01); *G01N 33/56911* (2013.01); *G01N 33/6854* (2013.01); *G01N 33/6893* (2013.01); *A61K 2039/505* (2013.01); *C07K 2317/34* (2013.01); *C07K 2317/76* (2013.01); *G01N 2500/04* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 6,551,795 B1 | 4/2003 | Rubenfield et al. | |
| 6,663,863 B2 | 12/2003 | Horvath et al. | |
| 6,696,550 B2 | 2/2004 | Larosa et al. | |
| 6,846,651 B2 | 1/2005 | Fleischmann et al. | |
| 7,241,867 B2 * | 7/2007 | Bakaletz | A61P 31/00 530/350 |
| 7,413,868 B2 | 8/2008 | Kauvar et al. | |
| 7,638,282 B2 | 12/2009 | Bakaletz et al. | |
| 7,811,591 B2 | 10/2010 | Bakaletz et al. | |
| 7,816,086 B2 | 10/2010 | Bakaletz et al. | |
| 7,939,344 B2 | 5/2011 | Kauvar et al. | |
| 7,998,490 B2 | 8/2011 | Bakaletz et al. | |
| 8,236,494 B2 | 8/2012 | Bakaletz et al. | |
| 8,283,114 B2 | 10/2012 | Bakaletz et al. | |
| 8,628,917 B2 | 1/2014 | Bakaletz et al. | |
| 8,652,773 B2 | 2/2014 | Bakaletz et al. | |
| 8,758,764 B2 | 6/2014 | Masignani et al. | |
| 8,933,029 B2 | 1/2015 | Mcnicol et al. | |
| 8,999,291 B2 | 4/2015 | Goodman et al. | |
| 9,017,656 B2 | 4/2015 | Hancock et al. | |
| 9,034,642 B2 | 5/2015 | Bakaletz et al. | |
| 9,155,792 B2 | 10/2015 | Cottarel et al. | |
| 9,745,366 B2 | 8/2017 | Goodman et al. | |
| 10,233,234 B2 | 3/2019 | Kauvar et al. | |
| 10,570,193 B2 | 2/2020 | Kauvar et al. | |

(Continued)

FOREIGN PATENT DOCUMENTS

| | | |
|---|---|---|
| JP | 2005-519998 | 7/2005 |
| JP | 2006-506441 | 2/2006 |
| JP | 2006-506467 | 2/2006 |
| JP | 2008-520552 | 6/2008 |
| JP | 2013-529893 | 7/2013 |

(Continued)

OTHER PUBLICATIONS

U.S. Appl. No. 16/297,094, filed Mar. 8, 2019, Goodman et al.
U.S. Appl. No. 16/746,708, filed Jan. 17, 2020, Kauvar et al.
Adams et al., (2007) "Epitope-mapping the immune response of children with otitis media and adults with chronic obstructive pulmonary disease to the PilA protein of nontypeable Haemophilus influenzae type IV pilus," 107th General Meeting, American Society for Microbiology; 2007; Toronto, ON.

(Continued)

*Primary Examiner* — Oluwatosin A Ogunbiyi
(74) *Attorney, Agent, or Firm* — Foley & Lardner LLP

(57) ABSTRACT

This disclosure provides isolated or recombinant polypeptides that are useful to vaccinate individuals suffering from chronic/recurrent biofilm disease or as a therapeutic for those with an existing infection. The individual's immune system will then naturally generate antibodies which prevent or clear these bacteria from the host by interfering with the construction and or maintenance of a functional protective biofilm. Alternatively, antibodies to the polypeptides can be administered to treat or prevent infection. Bacteria that cannot form functional biofilms are more readily cleared by the remainder of the host's immune system and/or traditional antibiotics.

21 Claims, 32 Drawing Sheets

Specification includes a Sequence Listing.

(56) References Cited

U.S. PATENT DOCUMENTS

| | | |
|---|---|---|
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0049402 A1 | 3/2005 | Babcook et al. |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0099207 A1 | 5/2006 | Wu et al. |
| 2006/0121047 A1 | 6/2006 | Tracey |
| 2006/0228384 A1 | 10/2006 | Eldridge |
| 2006/0240045 A1 | 10/2006 | Berthet et al. |
| 2007/0154529 A1 | 7/2007 | Bullerdiek |
| 2007/0264256 A1 | 11/2007 | Bakaletz et al. |
| 2009/0029929 A1 | 1/2009 | Nakajima et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0310569 A1 | 12/2010 | Bakaletz et al. |
| 2011/0135646 A1 | 6/2011 | Bakaletz et al. |
| 2011/0236306 A1 | 9/2011 | Goodman et al. |
| 2011/0293624 A1* | 12/2011 | Bakaletz ............. A61P 37/04 424/139.1 |
| 2012/0128701 A1 | 5/2012 | Goodman et al. |
| 2012/0148615 A1* | 6/2012 | Masignani ............. A61P 31/04 424/190.1 |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0086542 A1 | 3/2015 | Goodman et al. |
| 2015/0086561 A1 | 3/2015 | Kauvar et al. |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0218231 A1 | 8/2015 | Bakaletz et al. |
| 2015/0299298 A1 | 10/2015 | Kauvar et al. |
| 2016/0095316 A1 | 4/2016 | Goodman et al. |
| 2016/0175440 A1 | 6/2016 | Goodman et al. |
| 2016/0194384 A1 | 7/2016 | Goodman et al. |
| 2016/0237145 A1 | 8/2016 | Kauvar et al. |
| 2016/0244489 A1 | 8/2016 | Masignani et al. |
| 2016/0289278 A1 | 10/2016 | Bakaletz et al. |
| 2017/0182205 A1 | 6/2017 | Zupancic et al. |
| 2018/0303900 A1 | 10/2018 | Bakaletz et al. |
| 2019/0000971 A1 | 1/2019 | Bakaletz et al. |
| 2019/0040127 A1 | 2/2019 | Wadehra et al. |
| 2019/0055304 A1 | 2/2019 | Kauvar et al. |
| 2019/0337996 A1 | 11/2019 | Bakaletz et al. |
| 2019/0338018 A1 | 11/2019 | Bakaletz et al. |
| 2020/0190170 A1 | 6/2020 | Kauvar et al. |

FOREIGN PATENT DOCUMENTS

| | | |
|---|---|---|
| WO | WO-00/47104 A2 | 8/2000 |
| WO | WO-02/085295 | 10/2002 |
| WO | WO-02/085295 A2 | 10/2002 |
| WO | WO-03/026691 A1 | 4/2003 |
| WO | WO-03/026691 A2 | 4/2003 |
| WO | WO-2004/014418 A2 | 2/2004 |
| WO | WO-2004/044001 A2 | 5/2004 |
| WO | WO-2004/072094 A2 | 8/2004 |
| WO | WO-2005/025604 A2 | 3/2005 |
| WO | WO-2006/017816 A2 | 2/2006 |
| WO | WO-2006/083301 A2 | 8/2006 |
| WO | WO-2006/114805 A2 | 11/2006 |
| WO | WO-2006/138527 A2 | 12/2006 |
| WO | WO-2007/001422 A2 | 1/2007 |
| WO | WO-2009/006699 A1 | 1/2009 |
| WO | WO-2012/034090 A1 | 3/2012 |
| WO | WO-2014/201305 A1 | 12/2014 |
| WO | WO-2015/038339 A1 | 3/2015 |
| WO | WO-2015/048484 A2 | 4/2015 |
| WO | WO-2016/154491 A1 | 9/2016 |
| WO | WO-2017/192594 A1 | 11/2017 |
| WO | WO-2018/042385 A2 | 3/2018 |

OTHER PUBLICATIONS

Adams et al., (2007) "Epitope-mapping the immune response of children with otitis media and adults with chronic obstructive pulmonary disease to the PilA protein of nontypeable Haemophilus influenzae type IV pilus," 9th International Symposium on Recent Advances in Otitis Media; St. Pete Beach, FL.

Andersson, U. et al. (2011) "HMGB1 Is a Therapeutic Target for Sterile Inflammation and Infection," Annu. Rev. Immunol. 29:139-162.

Bakaletz et al., (1997) "Relative immunogenicity and efficacy of two synthetic chimeric peptides of fimbrin as vaccinogens against nasopharyngeal colonization by nontypeable Haemophilus influenzae in the chincilla," Vaccine 15(9): 955-961.

Bakaletz, L.O. et al. (1999) "Protection against Development of Otitis Media Induced by Nontypeable Haemophilus influenzae by Both Active and Passive Immunization in a Chinchilla Model of Virus-Bacterium Superinfection," Infecion and Immunity 67(6): 2746-2762.

Bakaletz, L.O., Biofilms can be dispersed by focusing the immune system on a common family of bacterial nucleoid associated proteins, 6th ASM Conference on Biofilms, Miami, FL, Sep.29-Oct. 4, 2012 (presentation).

Bakaletz, L.O., New strategies to target bacterial biofilms, 28th Annual North American Cystic Fibrosis Conference (NACFC), Atlanta, GA, Oct. 9-11, 2014 (presentation).

Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation).

Barve, M.P. et al. (2003) "Cloning and characterization of the mating type (MAT) locus from Ascochyta rabiei (teleomorph: Didymella rabiei) and a MAT phylogeny of legume-associated Ascochyta spp.," Fungal Genetics and Biology 39(2):151-167.

Bass, J.I.F. et al. (2010) "Extracellular DNA: A Major Proinflammatory Component of Pseudomonas aeruginosa Biofilms," The Journal of Immunology 184:6386-6395.

Beech, I.B. et al. (2005) "Microbe-surface interactions in biofouling and biocorrosion processes," International Microbiology 8:157-168.

Bjarnsholt, T. (2013) "The role of bacterial biofilms in chronic infections," APMIS 121 (Suppl. 136):1-51.

Boles, B.R. et al. (2011) "Staphylococcal biofilm disassembly," Trends in Microbiology 19(9):449-455.

Brady, R.A. et al. (2006) "Identification of *Staphylococcus aureus* Proteins Recognized by the Antibody-Mediated Immune Response to a Biofilm Infection," Infection and Immunity 74(6):3415-3426.

Brandstetter, K.A. et al. (2013) "Antibodies Directed Against Integration Host Factor Mediate Biofilm Clearance From Nasopore," The Laryngoscope 123(11 ):2626-2632.

Brockson et al., "Evaluation of the kinetics and mechanism of action of anti-integration host factor-mediated disruption of bacterial biofilms," Molecular Microbiology, DOI: 10.1111/mmi.12735 (Aug. 19, 2014).

Brockson, M.E. et al. (2014) "Evaluation of the kinetics and mechanism of action of anti-integration host factor-mediated disruption of bacterial biofilms," Molecular Microbiology 93(6): 1246-1258.

Brockson, M.E. et al. (2014) "Evaluation of the kinetics and mechanism of action of anti-integration host factor-mediated disruption of bacterial biofilms," Molecular Microbiology 93(6):1246-1258: Supplementary Material, 6 pages.

Catlin, B.W. (1956) "Extracellular Deoxyribonucleic Acid of Bacteria and a Deoxyribonuclease Inhibitor," Science 124:441-442.

(56) References Cited

OTHER PUBLICATIONS

Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.
Chen, C. et al. (2004) "Substrate specificity of Helicobacter pylori histone-like HU protein is determined by insufficient stabilization of DNA flexure points," Biochem J. 383:343-351.
Chen, M. et al. (2013) "Novel Strategies for the Prevention and Treatment of Biofilm Related Infections," Int. J. Mol. Sci. 14:18488-18501.
Cho, J.H. et al. (2001) "The modulation of the biological activities of mitochondrial histone Abf2p by yeast PKA and its possible role in the regulation of mitochondrial DNA content during glucose repression," Biochimica et Biophysica Acta 1522(3):175-186.
Coenye, T. et al. (2010) "In vitro and in vivo model systems to study microbial biofilm formation," Journal of Microbiological Methods 83:89-105.
Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.
Collarini, E.J. et al. (2009) "Potent High-Affinity Antibodies for Treatment and Prophylaxis of Respiratory Syncytial Virus Derived from B Cells of Infected Patients," J Immunol 183:6338-6345.
Dalai, B. et al. (2009) "Histone-like protein H-NS regulates biofilm formation and virulence of Actinobacillus pheuropneumonia," Microbial Pathogenesis 46:128-134.
Darouiche, R.O. et al. (2004) "Treatment of Infections Associated with Surgical Implants," N Engl J Med 350:1422-1429.
De La Fuente-Nunez, C. et al., (2014) "Broad-Spectrum Antibiofilm Peptide That Targets a Cellular Stress Response," PLoS Pathog. 10(5):e1004152.
Devaraj, A. et al., "DNABII proteins play a central role in UPEC biofilm structure", Molecular Microbiology, 2017, 96(6):1119-1135.
Dominguez-Herrera, J. et al. (2011) "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy 56(2):613-617.
Donlan, R.M. et al. (2002) "Biofilms: Survival Mechanisms of Clinically Relevant Microorganisms," Clinical Microbiology Reviews 15(2):167-193.
Durocher, Y. et al. (2002) "High-level and high-throughput recombinant protein production by transient transfection of suspension-growing human 293-EBNA1 cells," Nucleic Acids Research 30(2):e9, 1-9.
Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.
Estelles, A. et al. (2016) "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy 60(4):2292-2301.
Estrela, A.B. et al. (2010) "Combining Biofilm-Controlling Compounds and Antibiotics as a Promising New Way to Control Biofilm Infections," Pharmaceuticals 3:1374-1393.
Falciola, L. et al. (1994) "Mutational analysis of the DNA binding domain A of chromosomal protein HMG1," Nucleic Acids Research 22(3):285-292.
Fan, Z. et al. (2002) "HMG2 Interacts with the Nucleosome Assembly Protein SET and is a Target of the Cytotoxic T-Lymphocyte Protease Granzyme A," Molecular and Cellular Biology 22(8):2810-2820.
Fedorov, O. et al. (2012) "Kinase Inhibitor Selectivity Profiling Using Differential Scanning Fluorimetry," Kinase Inhibitors: Methods and Protocols, Methods in Molecular Biology 795:109-118.
Final Office Action in U.S. Appl. No. 14/967,228, dated Nov. 22, 2017.
Final Office Action in U.S. Appl. No. 15/078,987, dated Dec. 28, 2016.
Garcia-Contreras, R. et al. (2008) "Protein Translation and Cell Death: The Role of Rare tRNAs in Biofilm Formation and in Activating Dormant Phage Killer Genes," PLoS ONE 3(6):e2394, 1-15.
Gerstel et al., "Complex Regulation of csgD Promoter Activity by Global Regulatory Proteins," Molecular Microbiology, vol. 49, No. 3, Aug. 2003, pp. 639-654.
Goldenberg et al., "Genetic and biochemical analysis of IHF/HU hybrid proteins", BioChimie (Paris, FR), vol. 76, No. 10-11, pp. 941-950 (Jan. 1, 1994).
Goodman S D et al., "Biofilms can be dispersed by focusing the immune system on a common family of bacterial nucleoid-associated proteins", Mucosal Immuno, Nature Publishing Group, vol. 4, No. 6, Nov. 1, 2011, pp. 625-637.
Goodman, S.D. et al. (1999) "In Vitro Selection of Integration Host Factor Binding Sites," Journal of Bacteriology 181(10):3246-3255.
Goodman, S.D. et al. (1999) "Replacement of Integration Host Factor Protein-induced DNA Bending by Flexible Regions of DNA," The Journal of Biological Chemistry 274(52):37004-37011.
Goodman, S.D., A new immunotherapeutic approach that disperses biofilms, Banff Conference on Infectious Diseases, Banff, Alberta, Canada, May 18, 2012 (presentation).
Goodman, S.D., Making and breaking biofilms, Ohio Branch American Society for Microbiology Annual Meeting, Columbus, OH, Apr. 11-12, 2014 (presentation).
Goodman, S.D., Nucleoprotein complexes in the extracellular matrix are critical for the structural integrity of bacterial biofilms, 112th General Meeting, American Society for Microbiology, San Francisco, CA, Jun. 18, 2012 (presentation).
Goodman, S.D., The DNABII family of proteins: Diagnostic markers and therapeutic targets of bacterial biofilms, International Congress on Bacteriology and Infectious Disease, Baltimore, MD, Nov. 21, 2013.
Goshima et al., "Chimeric HU-IHF proteins that alter DNA-binding ability," GENE, vol. 118, No. 1, pp. 97-102 (Sep. 1, 1992).
Govan, J.R. et al. (1996) "Microbial pathogenesis in cystic fibrosis: mucoid Pseudomonas aeruginosa and Burkholderia cepacia," Microbiol. Rev. 60(3):539-574.
Granston, A.E. et al. (1993) "Characterization of a Set of Integration Host Factor Mutants Deficient for DNA Binding," J. Mol. Biol. 234:45-59.
Greenspan, N.S. et al. (1999) "Defining epitopes: It's not as easy as it seems," Nature Biotechnology 17:936-937.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster).
Gustave et al., Biofilms recovered from the sputum of CF patients contain the bacterial protein integration host factor (IHF), Abst. 25th Annual North American Cystic Fibrosis Conference, Anaheim, CA, Nov. 3-5, 2011.
Hall-Stoodley, L. et al. (2004) "Bacterial Biofilms: From the Natural Environment to Infectious Diseases," Nature Reviews, Microbiology 2:95-108.
Hall-Stoodley, L. et al. (2006) "Direct Detection of Bacterial Biofilms on the Middle-Ear Mucosa of Children With Chronic Otitis Media," JAMA 296(2):202-211.
Hall-Stoodley, L. et al. (2008) "Characterization of biofilm matrix, degradation by DNase treatment and evidence of capsule downregulation in *Streptococcus pneumoniae* clinical isolates," BMC Microbiology 8:173, 16 pages.
Hall-Stoodley, L. et al. (2009) "Evolving concepts in biofilm infections", Cellular Microbiology 11(7):1034-1043.
Haluzi, H. et al. (1991) "Genes Coding for Integration Host Factor Are Conserve in Gram-Negative Bacteria," Journal of Bacteriology 173(19):6297-6299.

(56) References Cited

OTHER PUBLICATIONS

Harley, V.R. et al. (2003) "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews 24(4):466-487.
Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta, I. et al. (2008) "A possible role of histone-like DNA-binding protein of *Streptococcus* intermedius in the pathogenesis of bile duct damage in primary biliary cirrhosis," Clinical Immunology 127(2):245-251.
Haruta, I. et al. (2010) "Long-term bacterial exposure can trigger nonsuppurative destructive cholangitis associated with multifocal epithelial inflammation," Laboratory Investigation 90:577-588.
Hoyle, B. et al. (1991) "Bacterial Resistance to Antibiotics: The Role of Biofilms," Prog. Drug Res. 37:91-105.
Idicula, W.K. et al. (2016) "Identification of Biofilms in Post-tympanostomy Tube Otorrhea," The Laryngoscope 126(8):1946-1951.
International Search Report and Written Opinion for PCT Patent Application No. PCT/US2014/042201, dated Nov. 28, 2014.
Janeway, C.A. et al. (2001) "Manipulating the immune response to fight infection," Immunobiology: The Immune System in Health and Disease, 5th ed.; retrieved online from https://www.ncbi.nlm.nih.gov/books/NBK27131/.
Jiao, Y. et al. (2011) "Identification of Biofilm Matrix-Associated Proteins from an Acid Mine Drainage Microbial Community," Appl & Environ Microbiol. 77:5230-5237.
Jodar, L. et al. (2002) "Development of vaccines against meningococcal disease," Lancet 359:1499-1508.
John, A-K. et al. (2011) "Reversible Daptomycin Tolerance of Adherent Staphylococci in an Implant Infection Model," Antimicrobial Agents and Chemotherapy 55(7):3510-3516.
Johnson, R. et al. (2008) "Chapter 8: Bending and Compaction of DNA by Proteins," Protein-Nucleic Acid Interactions: Structural Biology:176-220.
Joo, H-S. et al. (2012) "Molecular Basis of In Vivo Formation by Bacterial Pathogens," Chemistry & Biology 19:1503-1513.
Jurcisek, J. et al. (2005) "Role of Sialic Acid and Complex Carbohydrate Biosynthesis in Biofilm Formation by Nontypeable Haemophilus influenzae in the Chinchilla Middle Ear," Infection and Immunity 73:3210-3218.
Jurcisek, J.A. et al. (2007) "Biofilms Formed by Nontypeable Haemophilus influenzae In Vivo Contain both Double-Stranded DNA and Type IV Pilin Protein," Journal of Bacteriology 189(10):3868-3875.
Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kamashev, D. et al. (2000) "The histone-like protein HU binds specifically to DNA recombination and repair intermediates," The EMBO Journal 19(23):6527-6535.
Kennedy, B-J. et al. (2000) "Passive Transfer of Antiserum Specific for Immunogens Derived from a Nontypeable Haemophilus influenzae Adhesin and Lipoprotein D Prevents Otitis Media after Heterologous Challenge," Infection and Immunity 68(5):2756-2765.
Khrapunov, S. et al. (2006) "Binding then bending: A mechanism for wrapping DNA," PNAS 103(51):19217-19218.
Kim, D-H. et al. (2014) "Beta-Arm flexibility of HU from *Staphylococcus aureus* dictates the DNA-binding and recognition mechanism," Acta Cryst. D70:3273-3289.
Kim, N. et al. (2002) "Proteins Released by Helicobacter pylori In Vitro," Journal of Bacteriology 184(22):6155-6162.
Kirketerp-Moller, K. et al. (2008) "Distribution, Organization, and Ecology of Bacteria in Chronic Wounds," Journal of Clinical Microbiology 46(8):2717-2722.
Kornblit, B. et al. (2007) "The genetic variation of the human HMG1 gene," Tissue Antigens 70:151-156.
Kristian, S.A. et al. (2003) "Alanylation of Teichoic Acids Protects *Staphylococcus aureus* against Toll-like Receptor 2-Dependent Host Defense in a Mouse Tissue Cage Infection Model," The Journal of Infectoius Diseases 188:414-423.
Kyd, J.M. et al. (2003) "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity 71(8):4691-4699.
Labbé, E. et al. (2000) "Association of Smads with lymphoid enhancer binding factor 1/T cell-specific factor mediates cooperative signaling by the transforming growth factor-β and Wnt pathways," Proc. Natl. Acad. Sci. USA 97(15):8358-8363.
Laura A. Novotny et al., "Monoclonal antibodies against DNA-binding tips of DNABII proteins disrupt biofilms in vitro and induce bacterial clearance in vivo", EBIOMEDICINE, vol. 10, Aug. 1, 2016, pp. 33-44.
Lebeaux, D. et al. (2013) "From in vitro to in vivo Models of Bacterial Biofilm-Related Infections," Pathogens 2:288-356.
Li, L. et al. (2000) "Retroviral cDNA Integration: Stimulation by HMG I Family Proteins," Journal of Virology 74(23):10965-10974.
Liu, D. et al. (2008) "Histone-like DNA binding protein of *Streptococcus* intermedius induces the expression of pro-inflammatory cytokines in human monocytes via activation of ERK1/2 and JNK pathways," Cellular Microbiology 10(1):262-276.
Liu, D. et al. (2008) "The essentiality and involvement of *Streptococcus* intermedius histone-like DNA-binding protein in bacterial viability and normal growth," Molecular Microbiology 68(5):1268-1282.
Lunsford, R.D. et al. (1996) "DNA-Binding Activities in *Streptococcus gordonii*: Indentification of a Receptor-Nickase and a Histone-like Protein," Current Microbiology 32:95-100.
Lutz, H.U. et al. (1990) "Covalent binding of detergent-solubilized membrane glycoproteins to 'Chemobond' plates for ELISA," Journal of Immunological Methods 129:211-220.
M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014,pp. 1-22.
Malhotra et al., Defining the functional epitopes of Integration Host Factor (IHF) to develop a novel biofilm-focused immunotherapeutic against nontypeable Haemophilus influenzae-induced chronic and recurrent otitis media, 18th International Symposium on Recent Advances in Otitis Media, National Harbor, MD, Jun. 7-11, 2015 (poster).
Malhotra et al., Defining the functional epitopes of Integration Host Factor (IHF) to develop a novel biofilm-focused immunotherapeutic against nontypeable Haemophilus influenzae-induced chronic and recurrent otitis media, Abst. 18th International Symposium on Recent Advances in Otitis Media, National Harbor, MD, Jun. 7-11, 2015.
Malhotra et al., Fine mapping the functional epitopes within integration host factor, a novel therapeutic target for nontypeable Haemophilus influenza-induced diseases of the respiratory tract, Abst. 12th Annual AMA Research Symposium, Dallas, TX, Nov. 7, 2014.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster).
Malhotra et al., Identification of immunoprotective domains within the bacterial DNA-binding protein, integration host factor, Abst. 20th Annual Midwest Microbial Pathogenesis Meeting. The Ohio State University, Columbus, OH, Aug. 23-25, 2013.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013.

(56) References Cited

OTHER PUBLICATIONS

Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Mann, E.E. et al. (2009) "Modulation of eDNA Release and Degradation Affects *Staphylococcus aureus* Biofilm Maturation," PLoS ONE 4(6):e5822, 1-12.
Martinez-Antonio A et al. (2008), "Functional organization of *Escherichia coli* transcriptional regulatory network", J. Mol. Biol. vol. 381, p. 238-247.
Meluleni et al., (1995) "Mucoid Pseudomonas aeruginosa Growing in a Biofilm In Vitro are Killed by Opsonic Antibodies to the Mucoid Exopolysaccharide Capsule but Not by Antibodies Produced During Chronic Lung Infection in Cystic Fibrosis Patients," J. Immunology, 155:2029-2038.
Mouw, K.W. et al. (2007) "Shaping the Borrelia burgdorferi genome: crystal structure and binding properties of the DNA-bending protein Hbb," Molecular Microbiology 63(5):1319-1330.
Mukherjee, J. et al. (2011) "Quantitative protein expression and cell surface characteristics of *Escherichia coli* MG1655 biofilms," Proteomics 11:339-351.
Murphy, T.F. et al. (2002) "Biofilm formation by nontypeable Haemophilus influenzae: strain variablitiy, outer membrane antigen expression and role of pili," BMC Microbiology 2:7, 1-8.
Murphy, T.F. et al. (2009) "Microbial Interactions in the Respiratory Tract," The Pediatric Infectious Disease Journal 28:S121-S126.
Nakamura, Y. et al. (2001) "HMG Box A in HMG3 Protein Functions as a Mediator of DNA Structural Alteration Together with Box B," J. Biochem. 1129:643-651.
Nash, H.A. et al. (1987) "Overproduction of *Escherichia coli* integration Host Factor, a Protein with Nonidentical Subunits," Journal of Bacteriology 169(9):4124-4127.
NCBI GenBank AAC74782.1 (Jul. 28, 2009).
NCBI Genebank: P0A6Y1 (Sep. 13, 2005).
NCBI Sequence NP_415432.1 (Jul. 30, 2009).
Non-Final Office Action in U.S. Appl. No. 14/967,228, dated May 19, 2017.
Non-Final Office Action in U.S. Appl. No. 15/078,987, dated Jul. 14, 2016.
Non-Final Office Action in U.S. Appl. No. 15/078,987, dated Jun. 14, 2017.
Non-Final Office Action in U.S. Appl. No. 15/078,987, dated Mar. 16, 2018.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).
Novotny et al., Development of a novel biofilm-focused immunotherapeutic against NTHI-induced otitis media 18th International Symposium on Recent Advances in Otitis Media, National Harbor, MD, Jun. 7-11, 2015 (presentation).
Novotny, L.A. et al. (2000) "Epitope mapping of the Outer Membrane Protein P5-Homologous Fimbrin Adhesin of Nontypeable Haemophilus influenzae," Infection and Immunity 68(4):2119-2128.
Novotny, L.A. et al. (2002) "Detection and characterization of pediatric serum antibody to the OMP P5-homologous adhesin of nontypeable Haemophilus influenzae during acute otitis media," Vaccine 20(29-30):3590-3597.
Novotny, L.A. et al. (2003) "The Fourth Surface-Exposed Region of the Outer Membrane Protein P5-Homologous Adhesin of the Nontypable Haemophilus influenzae is an Immunodominant But Nonprotective Decoying Epitope," The Journal of Immunology 171 (4):1978-1983.
Novotny, L.A. et al. (2006) "Passive immunization with human anti-protein D antibodies induced by polysaccharide protein D conjugates protects chinchillas against otitis media after intranasal challenge with Haemophilus influenzae," Vaccine 24(22):4804-4811.
Novotny, L.A. et al. (2010) "Epitope mapping immunodominant regions of the PilA protein of nontypeable Haemophilus influenzae (NTHI) to facilitate the design of two novel chimeric vaccine candidates," Vaccine 28(1):279-289.
Novotny, L.A. et al. (2013) "Structural Stability of Burkholderia cenocepacia Biofilms is Reliant on eDNA Structure and Presence of a Bacterial Nucleic Acid Binding Protein," PLOS ONE 8(6):e67629, 15 pages.
Novotny, L.A. et al. (2016) "Monoclonal antibodies against DNA-binding tips of DNABII proteins disrupt biofilms in vitro and induce bacterial clearance in vivo," EBioMedicine 10:33-44.
Nowakowska, J. et al. (2014) "Foreign Body Infection Models to Study Host-Pathogen Response and Antimicrobial Tolerance of Bacterial Biofilm," Antibiotics 3:378-397.
Oberto, J. et al. (1994) "Histones, HMG, HU, IHF: Même combat," Biochimie 76:901-908.
Ordway, D.J. et al. (2010) "Evaluation of Standard Chemotherapy in the Guinea Pig Model of Tuberculosis," Antimicrobial Agents and Chemotherapy 54:1820-1833.
Otto, M. (2009) "*Staphylococcus* epidermidis—the 'accidental' pathogen," Nature Reviews Microbiology 7:555-567.
PDB ID: 1IHF: Rice, P.A et al. (1996), 1 page; retrieved online from http://www.rcsb.org/pdb/explore.do?structureId=IHF.
Pedulla, M.L. et al. (1996) "A novel host factor for integration of mycobacteriophage L5," Proc. Natl. Acad. Sci. USA 93:15411-15416.
Percival, S.L. et al. (2015) "Biofilms and Wounds: An Overview of the Evidence," Advances in Wound Care 4(7):373-381.
Petersen, F.C. et al. (2004) "Biofilm Mode of Growth of *Streptococcus* intermedius Favoreed by a Competence-Stimulating Signaling Peptide," Journal of Bateriology 186(18):6327-6331.
Pethe, K. et al. (2001) "*Mycobacterium smegmatis* laminin-binding glycoprotein shares epitopes with *Mycobacterium tuberculosis* heparin-binding haemagglutinin," Molecular Microbiology 39(1):89-99.
Prymula, R. et al. (2006) "Pneumococcal capsular polysaccharides conjugated to protein D for prevention of acute otitis media caused by both *Streptococcus pneumoniae* and non-typable Haemophilus influenzae: a randomized double-blind efficacy study," Lancet 367(9512):740-748.
Reffuveille et al., "A Broad-Spectrum Antibiofilm Peptide Enhances Antibiotic Action against Bacterial Biofilms", Antimicrobial Agents and Chemotherapy, pp. 5363-5371, Jun. 30, 2014.
Restriction Requirement in U.S. Appl. No. 14/967,228, dated Dec. 23, 2016.
Rice et al., "Crystal Structure of an IHF-DNA Complex: A Protein-Induced DNA U-Turn," CELL, vol. 87, No. 7, pp. 1295-1306 (Dec. 27, 1996).
Rice, P.A. et al. (1996) "Crystal Structure of an IHF-DNA Complex: A Protein-Induced DNA U-Turn," CELL 87(7):1295-1306.
Rudikoff, S. et al. (1982) "Single amino acid substitution altering antigen-binding specificity," Proc. Natl. Acad. Sci. USA 79(6):1979-1983.
Sapi, E. et al. (2012) "Characterization of Biofilm Formation by Borrelia burgdorferi In Vitro," PLOS One 7(10):e44277, 1-11.
Schwartz, K. et al. (2012) "Functional Amyloids Composed of Phenol Soluble Modulins Stabilize *Staphylococcus aureus* Biofilms," PLOS Pathogens 8:e1002744, 1-11.
Segall, A.M. et al. (1994) "Architectural elements in nucleoprotein complexes: interchangeability of specific and non-specific DNA binding proteins," The EMBO Journal 13(19):4536-4548.
Shahrooei, M. et al. (2009) "Inhibition of *Staphylococcus epidermidis* Biofilm Formation by Rabbit Polyclonal Antibodies against the SesC Protein," Infection and Immunity 77(9):3670-3678.
Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.
Singh, P.K. et al. (2000) "Quorum-sensing signals indicate that cystic fibrosis lungs are infected with bacterial biofilms," Nature 407(12):762-764.
Skolnick, J. et al. (2000) "From genes to protein structure and function: novel applications of computational approaches in the genomic era," Trends in Biotechnology 18:34-39.

(56) References Cited

OTHER PUBLICATIONS

Smith, J.J. et al. (1996) "Cystic Fibrosis Airway Epithelia Fail to Kill Bacteria Because of Abnormal Airway Surface Fluid," Cell 85:229-236.
Stinson, M.W. et al. (1998) "Streptococcal Histone-Like Protein: Primary Structure of hlpA and Protein Binding to Lipoteichoic Acid and Epithelial Cells," Infection and Immunity 66(1):259-265.
Stoltz, D.A. et al. (2010) "Cystic Fibrosis Pigs Develop Lung Disease and Exhibit Defective Bacterial Eradication at Birth," www.ScienceTranslationMedicine.org 2(29)29ra31:1-8.
Stros, M. et al. (2007) "The HMG-box: a versatile protein domain occurring in a wide variety of DNA-binding proteins," Cell. Mol. Life Sci. 64(19-20):2590-2606.
Sun, D. et al. (2005) "Inhibition of Biofilm Formation by Monoclonal Antibodies against *Staphylococcus epidermindis* RP62A Accumulation-Associated Protein," Clinical & Diagnostic Laboratory Immunology 12(1):93-100.
Swinger et al., (2004) "IHF and HU: flexible architects of bent DNA," Current Opinion in Structural Biology 14(1): 28-35.
Swinger, Kerren K. et al., "IHF and HU: flexible architects of bent DNA," Current Opinion in Structural Biology 2004, 14: 28-35.
Takeda, T. (2012) "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech:177-186.
Taudte, S. et al. (2000) "Alanine mutagenesis of high-mobility-group-protein-1 box B (HMG1-B)," Biochem. J. 347:807-814.
Teter, B. et al. (2000) "DNA Bending and Twisting Properties of Integration Host Factor Determined by DNA Cyclization," Plasmid 43:73-84.
Tetz, G.V. et al. (2009) "Effect of DNase and Antibiotics on Biofilm Characteristics," Antimicrobial Agents and Chemotherapy 53(3):1204-1209.
Thomas, J.O. (2001) "HMG1 and 2: architectural DNA-binding proteins," Biochemical Society Transactions 29(Pt 4):395-401.
Thurnheer et al., Colonisation of gingival epithelia by subgingival biofilms in vitro: role of "red complex" bacteria. Arch Oral Biol. (2014), 59(9):977-86; Abstract; p. 2, 1st para; p. 10, 1st para.
Tsaras, G. et al. (2012) "Incidence, Secular Trends, and Outcomes of Prosthetic Joint Infection: A Population-Based Study, Olmsted County, Minnesota, 1969-2007," Infect Control Hosp Epidemiol 33(12):1207-1212.
Van Schaik, E.J. et al. (2005) "DNA Binding: a Novel Function of Pseudomonas aeruginosa Type IV Pili," Journal of Bacteriology 187(4):1455-1464.
Whitchurch, C.B. et al. (2002) "Extracellular DNA Required for Bacterial Biofilm Formation," Science 295(5559):1487.
Whitchurch, C.B. et al. (2002) "Extracellular DNA Required for Bacterial Biofilm Formation," Science 295(5559):1487: Supplementary Material, 2 pages.
Winters, B.D. et al. (1993) "Isolation and Characterization of a *Streptococcus pyogenes* Protein that Binds to Basal Laminae of Human Cardiac Muscle," Infection and Immunity 61(8):3259-3264.
Winther, B. et al. (2009) "Location of Bacterial Biofilm in the Mucus Overlying the Adenoid by Light Microscopy," Head & Neck Surgery 135(12):1239-1245.
Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.
Woischnig et al., "High Affinity Native Human Monoclonal Antibody with Broad Cross-Species Biofilm Disrupting Activity", (Sep. 20, 2015) [Retrieved from the Internet Dec. 25, 2016: ].
Yoshida, M. (1996) SEIKAGAKU Biochemistry 68(12):1829-1834.
Zimmerli, W. et al. (1982) "Pathogenesis of Foreign Body Infection: Description and Characteristics of an Animal Model," The Journal of Infectious Diseases 146(4):487-497.
Zimmerli, W. et al. (1984) "Pathogenesis of Foreign Body Infection," J. Clin. Invest. 73:1191-1200.
Zulianello et al., "The HimA and HimD subunits of integration host factor can specifically bind to DNA as homodimers," The EMBO Journal, pp. 1534-1540 (Apr. 1, 1994).
Lappann M, et al. A dual role of extracellular DNA during biofilm formation of Neisseria meningitidis. Molecular microbiology. 2010;75(6):1355-71. doi: 10.1111/j.1365-2958.2010.07054.x. PubMed PMID: 20180907.
Priyadarshini R, et al, The nucleoid-associated protein HUß affects global gene expression in Porphyromonas gingivalis. Microbiology. 2013; 159(Pt 2):219-29.First Published: Feb. 1, 2013.
Rouviere-Yaniv J, et al. Characterization of a novel, low-molecular-weight DNA—binding protein from *Escherichia coli*. Proceedings of the National Academy of Sciences of the United States of America. 1975;72(9):3428-32. Epub Sep. 1, 1975. PubMed PMID: 1103148; PMCID: 433007.
Zimmerli et al., Pathogenesis of Foreign Body Infection: Description and Characteristics of an Animal Model, The Journal of Infectious Diseases, vol. 146, No. 4, Oct. 1982, pp. 487-497.
U.S. Appl. No. 17/150,731, filed Jan. 15, 2021, The Research Institute at Nationwide Children's Hospital.
Brockson Me, et al., Evaluation of the kinetics and mechanism of action of anti-integration host factor-mediated disruption of bacterial biofilms. Molecular microbiology. 2014;93(6): 1246-58. Epub Jul. 30, 2014, doi: 10.1 1 1 1/mmi. 12735, PubMed PMID: 25069521 ; PMCID: 4160410.
Devaraj A, et al. DNABII proteins play a central role in UPEC biofilm structure. Molecular microbiology. 2015. doi: 10.1111/mmi. 12994. PubMed PMID: 25757804.
Gustave Je et al. Targeting bacterial integration host factor to disrupt biofilms associated with cystic fibrosis. Journal of cystic fibrosis : official journal of the European Cystic Fibrosis Society.2013;12(4):384-9. Epub Nov. 22, 2012. doi: 10.1016/j.jcf.2012.10.011. PubMed PMID: 23168017; PMCID: 3582735.
Haurum. "Recombinant polyclonal antibodies: the next generation of antibody therapeutics?" Drug Discovery Today. Jul. 2006;11(13-14):655-60.
Jurcisek Ja, and Bakaletz Lo. Biofilms formed by nontypeable Haemophilus influenzae in vivo contain both double-stranded DNA and type IV pilin protein. Journal of bacteriology.2007;189(10):3868-75. Epub Feb. 27, 2007. doi: 10.1128/JB.01935-06. PubMed PMID: 17322318; PMCID: 1913342.
Kamashev D, and Rouviere-Yaniv J. The histone-like protein HU binds specifically to DNA recombination and repair intermediates. The EMBO journal.2000;19(23):6527-35.
Novotny La, et al. Structural stability of Burkholderia cenocepacia biofilms is reliant on eDNA structure and presence of a bacterial nucleic acid binding protein. PloS one.2013;8(6):e67629. Epub Jun. 27, 2013. doi: 10.1371/journal.pone.0067629. PubMed PMID: 23799151; PMCID: 3682984.

\* cited by examiner

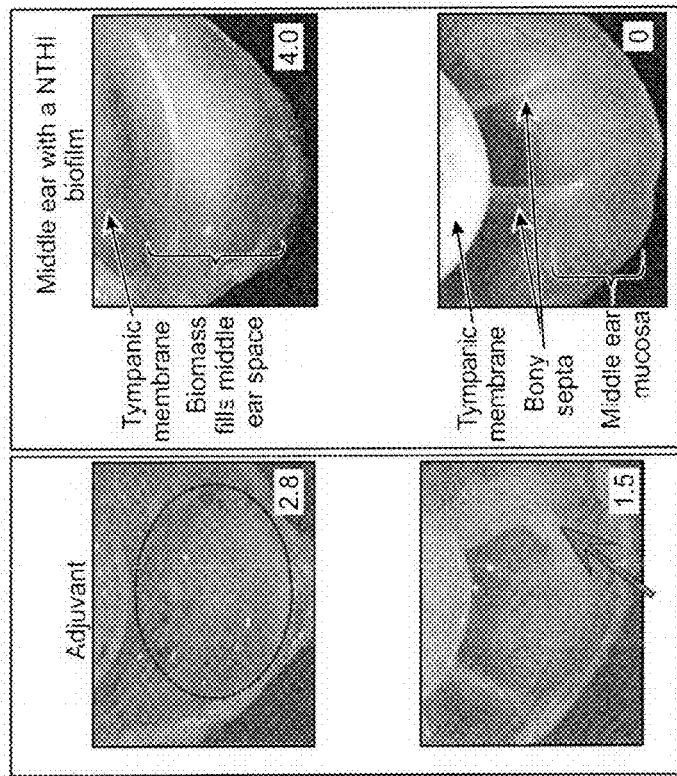
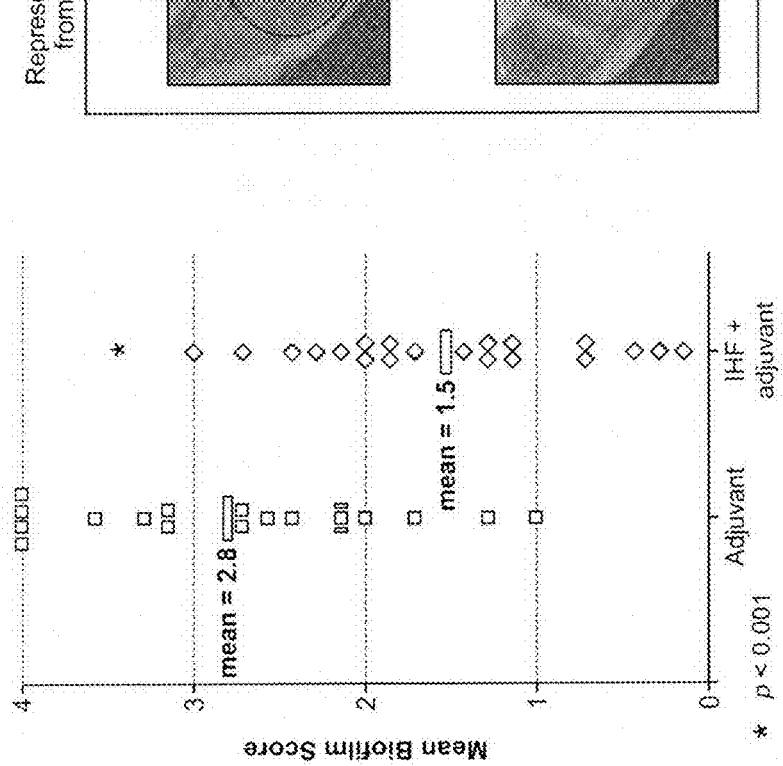
FIG. 9B
FIG. 9A

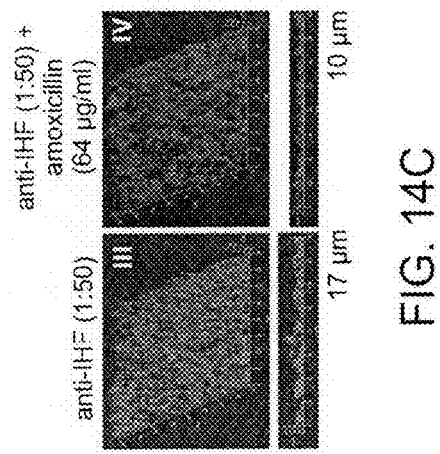
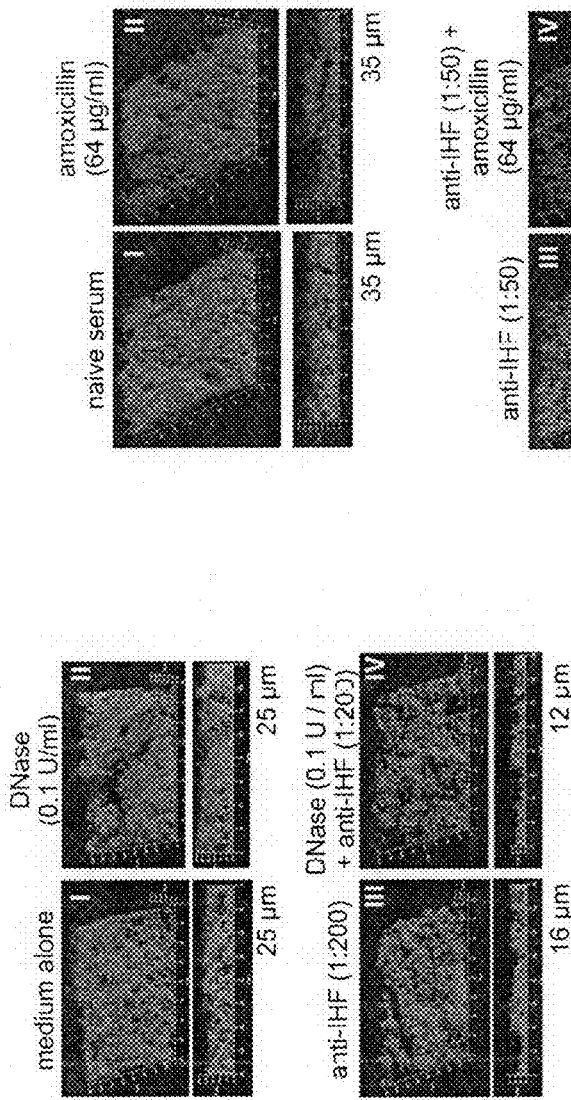
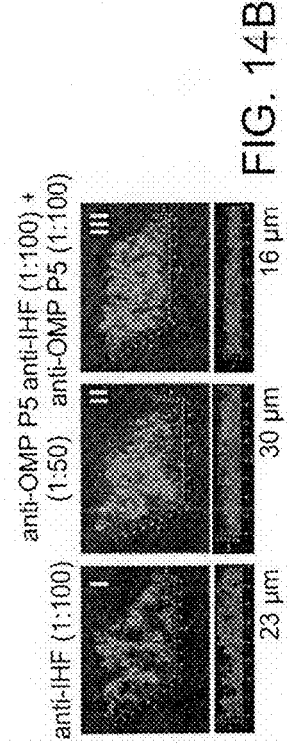
FIG. 14C
FIG. 14A
FIG. 14B

FIG. 18

SEQUENCE LISTING

```
<160> NUMBER OF SEQ ID NOS: 458

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (2)..(2)
<223> OTHER INFORMATION: Lys, Gln, Glu, Ala, Val, or Tyr
<220> FEATURE:
<221> NAME/KEY: MOD_RES
<222> LOCATION: (3)..(3)
<223> OTHER INFORMATION: Lys, Leu, Ile, Val, or Phe
<220> FEATURE:
<221> NAME/KEY: MOD_RES
<222> LOCATION: (4)..(4)
<223> OTHER INFORMATION: Ser, Ile, Arg, or Val
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (8)..(8)
<223> OTHER INFORMATION: Asn, Ser, Thr, or Lys

<400> SEQUENCE: 1

Xaa Xaa Xaa Xaa Xaa Phe Gly Xaa Phe
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Lys Lys Ser Gly Phe Gly Asn Phe
1               5

<210> SEQ ID NO 3
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Lys, or absent
<220> FEATURE:
<221> NAME/KEY: MOD_RES
<222> LOCATION: (2)..(2)
<223> OTHER INFORMATION: Arg, Ile, Lys, or absent
<220> FEATURE:
<221> NAME/KEY: MOD_RES
<222> LOCATION: (3)..(3)
<223> OTHER INFORMATION: Asn or Val
<220> FEATURE:
<221> NAME/KEY: MOD_RES
<222> LOCATION: (4)..(4)
<223> OTHER INFORMATION: Pro or Ile
<220> FEATURE:
<221> NAME/KEY: MOD_RES
<222> LOCATION: (5)..(5)
<223> OTHER INFORMATION: Lys, Gln, Ser, or Gly
<220> FEATURE:
<221> NAME/KEY: MOD_RES
<222> LOCATION: (6)..(6)
<223> OTHER INFORMATION: Thr, Lys, or Ser
<220> FEATURE:
<221> NAME/KEY: MOD_RES
<222> LOCATION: (7)..(7)
<223> OTHER INFORMATION: Gly, Lys, Gln, or Asp

<400> SEQUENCE: 3

Xaa Xaa Xaa Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys or Gln

<400> SEQUENCE: 4

Asn Pro Xaa Thr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Gln

<400> SEQUENCE: 5

Gly Arg Asn Pro Xaa Thr Gly
1               5

<210> SEQ ID NO 6
<211> LENGTH: 96
<212> TYPE: PRT
<213> ORGANISM: Haemophilus influenzae
```

```
<400> SEQUENCE: 6

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
                20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
        50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 7
<211> LENGTH: 136
<212> TYPE: PRT
<213> ORGANISM: Haemophilus influenzae

<400> SEQUENCE: 7

Met Arg Phe Val Thr Ile Phe Ile Asn His Ala Phe Asn Ser Ser Gln
1               5                   10                  15

Val Arg Leu Ser Phe Ala Gln Phe Leu Arg Gln Ile Arg Lys Asp Thr
                20                  25                  30

Phe Lys Glu Ser Asn Phe Leu Phe Asn Arg Arg Tyr Lys Phe Met Asn
            35                  40                  45

Lys Thr Asp Leu Ile Asp Ala Ile Ala Asn Ala Glu Leu Asn Lys
        50                  55                  60

Lys Gln Ala Lys Ala Ala Leu Glu Ala Thr Leu Asp Ala Ile Thr Ala
65                  70                  75                  80

Ser Leu Lys Glu Gly Glu Pro Val Gln Leu Ile Gly Phe Gly Thr Phe
                85                  90                  95

Lys Val Asn Glu Arg Ala Ala Arg Thr Gly Arg Asn Pro Gln Thr Gly
            100                 105                 110

Ala Glu Ile Gln Ile Ala Ala Ser Lys Val Pro Ala Phe Val Ser Gly
        115                 120                 125

Lys Ala Leu Lys Asp Ala Ile Lys
    130                 135

<210> SEQ ID NO 8
<211> LENGTH: 96
<212> TYPE: PRT
<213> ORGANISM: Haemophilus influenzae

<400> SEQUENCE: 8

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
                20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
        50                  55                  60
```

```
Asn Pro Lys Thr Gly Asp Val Val Pro Val Ser Ala Arg Arg Val Val
 65                  70                  75                  80

Thr Phe Lys Pro Gly Gln Lys Leu Arg Ala Arg Val Glu Lys Thr Lys
                 85                  90                  95

<210> SEQ ID NO 9
<211> LENGTH: 96
<212> TYPE: PRT
<213> ORGANISM: Haemophilus influenzae

<400> SEQUENCE: 9

Met Ala Thr Ile Thr Lys Leu Asp Ile Ile Glu Tyr Leu Ser Asp Lys
  1               5                  10                  15

Tyr His Leu Ser Lys Gln Asp Thr Lys Asn Val Val Glu Asn Phe Leu
                 20                  25                  30

Glu Glu Ile Arg Leu Ser Leu Glu Ser Gly Gln Asp Val Lys Leu Ser
             35                  40                  45

Gly Phe Gly Asn Phe Glu Leu Arg Asp Lys Ser Ser Arg Pro Gly Arg
 50                  55                  60

Asn Pro Lys Thr Gly Asp Val Val Pro Val Ser Ala Arg Arg Val Val
 65                  70                  75                  80

Thr Phe Lys Pro Gly Gln Lys Leu Arg Ala Arg Val Glu Lys Thr Lys
                 85                  90                  95

<210> SEQ ID NO 10
<211> LENGTH: 99
<212> TYPE: PRT
<213> ORGANISM: Escherichia coli

<400> SEQUENCE: 10

Met Ala Leu Thr Lys Ala Glu Met Ser Glu Tyr Leu Phe Asp Lys Leu
  1               5                  10                  15

Gly Leu Ser Lys Arg Asp Ala Lys Glu Leu Val Glu Leu Phe Phe Glu
                 20                  25                  30

Glu Ile Arg Arg Ala Leu Glu Asn Gly Glu Gln Val Lys Leu Ser Gly
             35                  40                  45

Phe Gly Asn Phe Asp Leu Arg Asp Lys Asn Gln Arg Pro Gly Arg Asn
 50                  55                  60

Pro Lys Thr Gly Glu Asp Ile Pro Ile Thr Ala Arg Arg Val Val Thr
 65                  70                  75                  80

Phe Arg Pro Gly Gln Lys Leu Lys Ser Arg Val Glu Asn Ala Ser Pro
                 85                  90                  95

Lys Asp Glu

<210> SEQ ID NO 11
<211> LENGTH: 100
<212> TYPE: PRT
<213> ORGANISM: Pseudomonas aeruginosa

<400> SEQUENCE: 11

Met Gly Ala Leu Thr Lys Ala Glu Ile Ala Glu Arg Leu Tyr Glu Glu
  1               5                  10                  15

Leu Gly Leu Asn Lys Arg Glu Ala Lys Glu Leu Val Glu Leu Phe Phe
                 20                  25                  30

Glu Glu Ile Arg Gln Ala Leu Glu His Asn Glu Gln Val Lys Leu Ser
             35                  40                  45

Gly Phe Gly Asn Phe Asp Leu Arg Asp Lys Arg Gln Arg Pro Gly Arg
 50                  55                  60
```

-continued

```
Asn Pro Lys Thr Gly Glu Glu Ile Pro Ile Thr Ala Arg Arg Val Val
 65                  70                  75                  80

Thr Phe Arg Pro Gly Gln Lys Leu Lys Ala Arg Val Glu Ala Tyr Ala
                 85                  90                  95

Gly Thr Lys Ser
            100

<210> SEQ ID NO 12
<211> LENGTH: 6
<212> TYPE: PRT
<213> ORGANISM: Escherichia coli

<400> SEQUENCE: 12

Thr Phe Arg Pro Gly Gln
1               5

<210> SEQ ID NO 13
<211> LENGTH: 14
<212> TYPE: PRT
<213> ORGANISM: Escherichia coli

<400> SEQUENCE: 13

Lys Leu Lys Ser Arg Val Glu Asn Ala Ser Pro Lys Asp Glu
1               5                   10

<210> SEQ ID NO 14
<211> LENGTH: 6
<212> TYPE: PRT
<213> ORGANISM: Escherichia coli

<400> SEQUENCE: 14

His Phe Lys Pro Gly Lys
1               5

<210> SEQ ID NO 15
<211> LENGTH: 10
<212> TYPE: PRT
<213> ORGANISM: Escherichia coli

<400> SEQUENCE: 15

Glu Leu Arg Asp Arg Ala Asn Ile Tyr Gly
1               5                   10

<210> SEQ ID NO 16
<211> LENGTH: 6
<212> TYPE: PRT
<213> ORGANISM: Haemophilus influenzae

<400> SEQUENCE: 16

Thr Phe Lys Pro Gly Gln
1               5

<210> SEQ ID NO 17
<211> LENGTH: 10
<212> TYPE: PRT
<213> ORGANISM: Haemophilus influenzae

<400> SEQUENCE: 17

Lys Leu Arg Ala Arg Val Glu Lys Thr Lys
1               5                   10
```

```
<210> SEQ ID NO 18
<211> LENGTH: 6
<212> TYPE: PRT
<213> ORGANISM: Haemophilus influenzae

<400> SEQUENCE: 18

Thr Phe Lys Pro Gly Gln
1               5

<210> SEQ ID NO 19
<211> LENGTH: 10
<212> TYPE: PRT
<213> ORGANISM: Haemophilus influenzae

<400> SEQUENCE: 19

Lys Leu Arg Ala Arg Val Glu Asn Thr Lys
1               5                   10

<210> SEQ ID NO 20
<211> LENGTH: 6
<212> TYPE: PRT
<213> ORGANISM: Haemophilus influenzae

<400> SEQUENCE: 20

Thr Phe Lys Pro Gly Gln
1               5

<210> SEQ ID NO 21
<211> LENGTH: 10
<212> TYPE: PRT
<213> ORGANISM: Haemophilus influenzae

<400> SEQUENCE: 21

Lys Leu Arg Ala Arg Val Glu Lys Thr Lys
1               5                   10

<210> SEQ ID NO 22
<211> LENGTH: 6
<212> TYPE: PRT
<213> ORGANISM: Haemophilus influenzae

<400> SEQUENCE: 22

Thr Phe Lys Pro Gly Gln
1               5

<210> SEQ ID NO 23
<211> LENGTH: 10
<212> TYPE: PRT
<213> ORGANISM: Haemophilus influenzae

<400> SEQUENCE: 23

Lys Leu Arg Ala Arg Val Glu Lys Thr Lys
1               5                   10

<210> SEQ ID NO 24
<211> LENGTH: 6
<212> TYPE: PRT
<213> ORGANISM: Escherichia coli

<400> SEQUENCE: 24

Thr Phe Arg Pro Gly Gln
1               5
```

```
<210> SEQ ID NO 25
<211> LENGTH: 14
<212> TYPE: PRT
<213> ORGANISM: Escherichia coli

<400> SEQUENCE: 25

Lys Leu Lys Ser Arg Val Glu Asn Ala Ser Pro Lys Asp Glu
1               5                   10

<210> SEQ ID NO 26
<211> LENGTH: 6
<212> TYPE: PRT
<213> ORGANISM: Pseudomonas aeruginosa

<400> SEQUENCE: 26

Thr Phe Arg Pro Gly Gln
1               5

<210> SEQ ID NO 27
<211> LENGTH: 14
<212> TYPE: PRT
<213> ORGANISM: Pseudomonas aeruginosa

<400> SEQUENCE: 27

Lys Leu Lys Ala Arg Val Glu Ala Tyr Ala Gly Thr Lys Ser
1               5                   10

<210> SEQ ID NO 28
<211> LENGTH: 90
<212> TYPE: PRT
<213> ORGANISM: Escherichia coli

<400> SEQUENCE: 28

Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
                20                  25                  30

Thr Glu Ser Leu Lys Glu Gly Asp Ala Val Gln Leu Val Gly Phe Gly
            35                  40                  45

Thr Phe Lys Val Asn His Arg Ala Glu Arg Thr Gly Arg Asn Pro Gln
        50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90

<210> SEQ ID NO 29
<211> LENGTH: 90
<212> TYPE: PRT
<213> ORGANISM: Escherichia coli

<400> SEQUENCE: 29

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
            35                  40                  45

Thr Phe Ala Val Lys Glu Arg Ala Ala Arg Thr Gly Arg Asn Pro Gln
        50                  55                  60
```

```
Thr Gly Lys Glu Ile Thr Ile Ala Ala Ala Lys Val Pro Ser Phe Arg
 65                  70                  75                  80

Ala Gly Lys Ala Leu Lys Asp Ala Val Asn
                85                  90

<210> SEQ ID NO 30
<211> LENGTH: 6
<212> TYPE: PRT
<213> ORGANISM: Escherichia coli

<400> SEQUENCE: 30

Ala Phe Val Ser Gly Lys
1               5

<210> SEQ ID NO 31
<211> LENGTH: 7
<212> TYPE: PRT
<213> ORGANISM: Escherichia coli

<400> SEQUENCE: 31

Ala Leu Lys Asp Ala Val Lys
1               5

<210> SEQ ID NO 32
<211> LENGTH: 6
<212> TYPE: PRT
<213> ORGANISM: Escherichia coli

<400> SEQUENCE: 32

Ser Phe Arg Ala Gly Lys
1               5

<210> SEQ ID NO 33
<211> LENGTH: 7
<212> TYPE: PRT
<213> ORGANISM: Escherichia coli

<400> SEQUENCE: 33

Ala Leu Lys Asp Ala Val Asn
1               5

<210> SEQ ID NO 34
<211> LENGTH: 20
<212> TYPE: PRT
<213> ORGANISM: Escherichia coli

<400> SEQUENCE: 34

Thr Phe Arg Pro Gly Gln Lys Leu Lys Ser Arg Val Glu Asn Ala Ser
1               5                  10                  15

Pro Lys Asp Glu
            20

<210> SEQ ID NO 35
<211> LENGTH: 20
<212> TYPE: PRT
<213> ORGANISM: Escherichia coli

<400> SEQUENCE: 35

Lys Tyr Val Pro His Phe Lys Pro Gly Lys Glu Leu Arg Asp Arg Ala
1               5                  10                  15

Asn Ile Tyr Gly
            20
```

-continued

```
<210> SEQ ID NO 36
<211> LENGTH: 13
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (7)..(10)
<223> OTHER INFORMATION: a, c, t, g, unknown or other

<400> SEQUENCE: 36
watcaannnn ttr                                                           13

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Pro Ser Leu Lys Leu
1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Pro Ser Leu
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Ser Leu Lys
1

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Pro Ser Leu Lys
1               5

<210> SEQ ID NO 41
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 41

Ser Leu Lys Leu
1

<210> SEQ ID NO 42
<211> LENGTH: 99
<212> TYPE: PRT
<213> ORGANISM: Escherichia coli

<400> SEQUENCE: 42

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
        35                  40                  45

Phe Gly Asn Phe Asp Leu Arg Asp Lys Asn Gln Arg Pro Gly Arg Asn
    50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Asp Glu

<210> SEQ ID NO 43
<211> LENGTH: 99
<212> TYPE: PRT
<213> ORGANISM: Salmonella enterica

<400> SEQUENCE: 43

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
        35                  40                  45

Phe Gly Asn Phe Asp Leu Arg Asp Lys Asn Gln Arg Pro Gly Arg Asn
    50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Glu Glu

<210> SEQ ID NO 44
<211> LENGTH: 98
<212> TYPE: PRT
<213> ORGANISM: Vibrio cholerae

<400> SEQUENCE: 44

Met Ala Leu Thr Lys Ala Glu Leu Ala Glu Ala Leu Phe Glu Gln Leu
1               5                   10                  15

Gly Met Ser Lys Arg Asp Ala Lys Asp Thr Val Glu Val Phe Phe Glu
            20                  25                  30
```

```
Glu Ile Arg Lys Ala Leu Glu Ser Gly Glu Gln Val Lys Leu Ser Gly
            35                  40                  45

Phe Gly Asn Phe Asp Leu Arg Asp Lys Asn Glu Arg Pro Gly Arg Asn
 50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ala Arg Val Glu Asn Ile Lys Val
                85                  90                  95

Glu Lys

<210> SEQ ID NO 45
<211> LENGTH: 100
<212> TYPE: PRT
<213> ORGANISM: Pseudomonas aeruginosa

<400> SEQUENCE: 45

Met Gly Ala Leu Thr Lys Ala Glu Ile Ala Glu Arg Leu Tyr Glu Glu
1               5                   10                  15

Leu Gly Leu Asn Lys Arg Glu Ala Lys Glu Leu Val Glu Leu Phe Phe
                20                  25                  30

Glu Glu Ile Arg Gln Ala Leu Glu His Asn Glu Gln Val Lys Leu Ser
            35                  40                  45

Gly Phe Gly Asn Phe Asp Leu Arg Asp Lys Arg Gln Arg Pro Gly Arg
 50                  55                  60

Asn Pro Lys Thr Gly Glu Glu Ile Pro Ile Thr Ala Arg Arg Val Val
65                  70                  75                  80

Thr Phe Arg Pro Gly Gln Lys Leu Lys Ala Arg Val Glu Ala Tyr Ala
                85                  90                  95

Gly Thr Lys Ser
            100

<210> SEQ ID NO 46
<211> LENGTH: 96
<212> TYPE: PRT
<213> ORGANISM: Haemophilus influenzae

<400> SEQUENCE: 46

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
                20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
 50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 47
<211> LENGTH: 98
<212> TYPE: PRT
<213> ORGANISM: Aggregatibacter actinomycetemcomitans
```

```
<400> SEQUENCE: 47

Met Thr Leu Thr Lys Val Glu Leu Ala Glu Asn Leu Ile Glu Lys Phe
1               5                  10                  15

His Leu Ser Lys Arg Glu Ala Lys Asp Leu Val Glu Ser Phe Phe Glu
            20                  25                  30

Glu Ile Arg Val Ala Leu Glu Thr Gly Asn Asp Val Lys Leu Ser Gly
        35                  40                  45

Phe Gly Asn Phe Glu Leu Arg Asp Lys Ala Ser Arg Pro Gly Arg Asn
50                  55                  60

Pro Lys Thr Gly Glu Ser Val Pro Val Ser Ala Arg Arg Val Val
65                  70                  75                  80

Phe Lys Pro Gly Gln Lys Leu Arg Asn Arg Val Glu Lys Val Lys Pro
                85                  90                  95

Lys Ala

<210> SEQ ID NO 48
<211> LENGTH: 98
<212> TYPE: PRT
<213> ORGANISM: Moraxella catarrhalis

<400> SEQUENCE: 48

Met Gly Ala Leu Thr Lys Ala Asp Met Val Asp Glu Leu Thr Ile Arg
1               5                  10                  15

Leu Arg Leu Thr Arg Gln Gln Ala Arg Lys Leu Val Asp Gly Phe Phe
            20                  25                  30

Glu Glu Ile Ser Gln Ser Leu Ala Gln Gly His Glu Val Lys Leu Ser
        35                  40                  45

Gly Phe Gly Asn Phe Glu Leu Lys Asp Lys Lys Pro Arg Pro Gly Arg
50                  55                  60

Asn Pro Lys Thr Gly Glu Ser Val Pro Ile Gln Ala Arg Arg Val Val
65                  70                  75                  80

Thr Phe Lys Ala Gly Gln Lys Leu Arg Gly Trp Ile Asp Ser Gln Asn
                85                  90                  95

Glu Gly

<210> SEQ ID NO 49
<211> LENGTH: 100
<212> TYPE: PRT
<213> ORGANISM: Neisseria gonorrhoeae

<400> SEQUENCE: 49

Met Thr Leu Thr Lys Ala Glu Leu Ala Asp Ile Leu Asp Lys Val
1               5                  10                  15

Ser Asn Val Thr Lys Asn Asp Ala Lys Glu Ile Val Glu Leu Phe Phe
            20                  25                  30

Glu Glu Ile Arg Ser Thr Leu Ala Ser Gly Glu Glu Ile Lys Ile Ser
        35                  40                  45

Gly Phe Gly Asn Phe Gln Leu Arg Asp Lys Pro Gln Arg Pro Gly Arg
50                  55                  60

Asn Pro Lys Thr Gly Glu Glu Val Pro Ile Thr Ala Arg Arg Val Val
65                  70                  75                  80

Thr Phe His Ala Ser Gln Lys Leu Lys Gly Met Val Glu His Tyr Tyr
                85                  90                  95

Asp Lys Gln Arg
            100
```

-continued

```
<210> SEQ ID NO 50
<211> LENGTH: 100
<212> TYPE: PRT
<213> ORGANISM: Neisseria meningitidis

<400> SEQUENCE: 50

Met Thr Leu Thr Lys Ala Glu Leu Ala Asp Ile Leu Val Asp Lys Val
1               5                   10                  15

Ser Asn Val Thr Lys Asn Asp Ala Lys Glu Ile Val Glu Leu Phe Phe
            20                  25                  30

Glu Glu Ile Arg Ser Thr Leu Ala Ser Gly Glu Glu Ile Lys Ile Ser
        35                  40                  45

Gly Phe Gly Asn Phe Gln Leu Arg Asp Lys Pro Gln Arg Pro Gly Arg
    50                  55                  60

Asn Pro Lys Thr Gly Glu Glu Val Pro Ile Thr Ala Arg Arg Val Val
65                  70                  75                  80

Thr Phe His Ala Ser Gln Lys Leu Lys Ser Met Val Glu His Tyr Tyr
                85                  90                  95

Asp Lys Gln Arg
            100

<210> SEQ ID NO 51
<211> LENGTH: 101
<212> TYPE: PRT
<213> ORGANISM: Burkholderia cenocepacia

<400> SEQUENCE: 51

Ala Ser Thr Glu Thr Pro Thr Leu Thr Lys Ala Glu Leu Ala Glu Leu
1               5                   10                  15

Leu Phe Asp Ser Val Gly Leu Asn Lys Arg Glu Ala Lys Asp Met Val
            20                  25                  30

Glu Ala Phe Phe Glu Val Ile Arg Asp Ala Leu Glu Asn Gly Glu Ser
        35                  40                  45

Val Lys Leu Ser Gly Phe Gly Asn Phe Gln Leu Arg Asp Lys Pro Gln
    50                  55                  60

Arg Pro Gly Arg Asn Pro Lys Thr Gly Glu Ala Ile Pro Ile Ala Ala
65                  70                  75                  80

Arg Arg Val Val Thr Phe His Ala Ser Gln Lys Leu Lys Ala Leu Val
                85                  90                  95

Glu Asn Gly Ala Glu
            100

<210> SEQ ID NO 52
<211> LENGTH: 107
<212> TYPE: PRT
<213> ORGANISM: Burkholderia pseudomallei

<400> SEQUENCE: 52

Thr Ser Ala Gly Asp Thr Pro Thr Leu Thr Lys Ala Glu Leu Ala Glu
1               5                   10                  15

Leu Leu Phe Asp Ser Val Gly Leu Asn Lys Arg Glu Ala Lys Asp Met
            20                  25                  30

Val Glu Ala Phe Phe Glu Val Ile Arg Asp Ala Leu Glu Asn Gly Glu
        35                  40                  45

Ser Val Lys Leu Ser Gly Phe Gly Asn Phe Gln Leu Arg Asp Lys Pro
    50                  55                  60

Gln Arg Pro Gly Arg Asn Pro Asn Thr Gly Glu Ala Ile Pro Ile Ala
65                  70                  75                  80
```

-continued

Ala Arg Arg Val Val Thr Phe His Ala Ser Gln Lys Leu Lys Ala Leu
                85                  90                  95

Val Glu Asn Gly Ala Glu Pro Asp Leu Ala Arg
            100                 105

<210> SEQ ID NO 53
<211> LENGTH: 113
<212> TYPE: PRT
<213> ORGANISM: Bordetella pertussis

<400> SEQUENCE: 53

Met Gly Thr Thr Met Leu Ala Glu Pro Arg Thr Leu Thr Lys Ala Glu
1               5                   10                  15

Leu Ala Glu Leu Leu Phe Glu Arg Val Gly Leu Asn Lys Arg Glu Ala
                20                  25                  30

Lys Asp Ile Val Asp Thr Phe Phe Glu Glu Ile Arg Asp Ala Leu Ala
            35                  40                  45

Arg Gly Asp Ser Val Lys Leu Ser Gly Phe Gly Asn Phe Gln Val Arg
        50                  55                  60

Asp Lys Pro Pro Arg Pro Gly Arg Asn Pro Lys Thr Gly Glu Thr Ile
65                  70                  75                  80

Pro Ile Ala Ala Arg Arg Val Val Thr Phe His Ala Ser Gln Lys Leu
                85                  90                  95

Lys Ser Val Val Glu Gln Pro Asn Ser Pro Pro Asp Pro Ala Ser Ala
            100                 105                 110

Glu

<210> SEQ ID NO 54
<211> LENGTH: 97
<212> TYPE: PRT
<213> ORGANISM: Prevotella melaninogenica

<400> SEQUENCE: 54

Met Asn Asn Lys Glu Phe Ile Ala Ala Leu Ala Ala Arg Thr Gly Tyr
1               5                   10                  15

Thr Gln Asp Glu Ser Gln Lys Met Val Lys Thr Val Val Asp Met Met
                20                  25                  30

Gly Lys Ser Phe Glu Thr Gly Asp Pro Val Pro Val Ile Gly Phe Gly
            35                  40                  45

Thr Phe Glu Val Lys Lys Arg Leu Glu Arg Val Met Val Asn Pro Ser
        50                  55                  60

Thr Gly Leu Arg Met Leu Val Pro Pro Lys Leu Val Leu Asn Phe Lys
65                  70                  75                  80

Pro Ala Ala Thr Ile Lys Gly His Val Arg Lys Gly Gly Gln Asp Asn
                85                  90                  95

Gly

<210> SEQ ID NO 55
<211> LENGTH: 95
<212> TYPE: PRT
<213> ORGANISM: Prevotella intermedia

<400> SEQUENCE: 55

Met Asn Asn Lys Glu Phe Ile Thr Ala Leu Ala Asn Arg Val Gly Arg
1               5                   10                  15

Ser Gln Asp Glu Thr Gln Lys Leu Val Lys Thr Ala Leu Gln Ala Met
                20                  25                  30

```
Gly Asp Asn Phe Glu Ser Gly Pro Val Leu Val Ser Gly Phe Gly
            35                  40                  45

Ser Phe Glu Val Lys Lys Arg Leu Glu Arg Ile Met Thr Asn Pro Ala
 50                  55                  60

Thr Gly Leu Arg Met Leu Val Pro Pro Lys Leu Val Leu Asn Phe Arg
 65                  70                  75                  80

Ala Thr Ala Ser Val Lys Glu Lys Leu Lys Gly Gly Ala Glu
                85                  90                  95

<210> SEQ ID NO 56
<211> LENGTH: 105
<212> TYPE: PRT
<213> ORGANISM: Treponema palladium

<400> SEQUENCE: 56

Met Lys Arg Val Arg Arg Thr Arg Ser Phe Val Val Asp Ala Leu Cys
 1               5                  10                  15

Asp Glu Val Asp Leu Ser Arg Arg His Val Ala Arg Val Val Asp Ser
                20                  25                  30

Phe Val Ser Val Val Thr Ala Ala Leu Glu Arg Gly Glu Thr Val Glu
            35                  40                  45

Leu Arg Asp Phe Gly Val Phe Glu Ser Arg Val Arg Lys Ala Ser Val
 50                  55                  60

Gly Lys Ser Ile Asn Thr Gly Glu Val Val Ser Ile Pro Ser His Cys
 65                  70                  75                  80

Val Val Val Phe Arg Pro Ser Lys Arg Leu Lys Ser Ala Val Arg Gly
                85                  90                  95

Tyr Arg Ser Gly Glu Val Gly Ala Asp
            100                 105

<210> SEQ ID NO 57
<211> LENGTH: 101
<212> TYPE: PRT
<213> ORGANISM: Prevotella melaninogenica

<400> SEQUENCE: 57

Met Ala Lys Ser Ala Ile Gln Leu Ile Thr Ser Ala Leu Ala Lys Gln
 1               5                  10                  15

His Asn Leu Ser Ala Asp Asp Ala Ala Phe Val Asp Ala Phe Phe
                20                  25                  30

Asp Ile Ile Ser Ser Glu Leu Lys Asn Gly Asn Gln Val Lys Ile Lys
            35                  40                  45

Gly Leu Gly Thr Phe Lys Val Gln Ala Val Lys Pro Arg Glu Ser Val
 50                  55                  60

Asn Val Asn Thr Gly Glu Arg Val Leu Ile Glu Gly His Asp Lys Ile
 65                  70                  75                  80

Ser Phe Thr Pro Asp Thr Val Met Lys Glu Leu Val Asn Lys Pro Phe
                85                  90                  95

Ser Gln Phe Glu Thr
            100

<210> SEQ ID NO 58
<211> LENGTH: 101
<212> TYPE: PRT
<213> ORGANISM: Prevotella intermedia
```

```
<400> SEQUENCE: 58

Met Ala Lys Thr Ala Leu Gln Leu Ile Ala Asp Ala Val Ala Lys Lys
1               5                   10                  15

His Lys Ile Thr Val Lys Glu Ala Glu Lys Phe Val Ser Ala Ile Phe
            20                  25                  30

Asp Val Val Asn Glu Gly Leu Lys Thr Asp Lys Leu Val Lys Val Lys
            35                  40                  45

Gly Leu Gly Thr Phe Lys Val Gln Ala Val Lys Pro Arg Glu Ser Val
50                  55                  60

Asn Val Asn Thr Gly Glu Arg Val Leu Ile Glu Gly His Glu Lys Val
65                  70                  75                  80

Ser Phe Thr Pro Asp Ala Thr Met Lys Glu Leu Val Asn Lys Pro Phe
                85                  90                  95

Ala Gln Phe Glu Thr
            100

<210> SEQ ID NO 59
<211> LENGTH: 90
<212> TYPE: PRT
<213> ORGANISM: Staphylococcus aureus

<400> SEQUENCE: 59

Met Asn Lys Thr Asp Leu Ile Asn Ala Val Ala Glu Gln Ala Asp Leu
1               5                   10                  15

Thr Lys Lys Glu Ala Gly Ser Ala Val Asp Ala Val Phe Glu Ser Ile
            20                  25                  30

Gln Asn Ser Leu Ala Lys Gly Glu Lys Val Gln Leu Ile Gly Phe Gly
            35                  40                  45

Asn Phe Glu Val Arg Glu Arg Ala Ala Arg Lys Gly Arg Asn Pro Gln
            50                  55                  60

Thr Gly Lys Glu Ile Asp Ile Pro Ala Ser Lys Val Pro Ala Phe Lys
65                  70                  75                  80

Ala Gly Lys Ala Leu Lys Asp Ala Val Lys
                85                  90

<210> SEQ ID NO 60
<211> LENGTH: 90
<212> TYPE: PRT
<213> ORGANISM: Escherichia coli

<400> SEQUENCE: 60

Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
            20                  25                  30

Thr Glu Ser Leu Lys Glu Gly Asp Ala Val Gln Leu Val Gly Phe Gly
            35                  40                  45

Thr Phe Lys Val Asn His Arg Ala Glu Arg Thr Gly Arg Asn Pro Gln
            50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90
```

```
<210> SEQ ID NO 61
<211> LENGTH: 90
<212> TYPE: PRT
<213> ORGANISM: Staphylococcus epidermidis

<400> SEQUENCE: 61

Met Asn Lys Thr Asp Leu Ile Asn Ala Val Ala Glu Gln Ala Asp Leu
1               5                   10                  15

Thr Lys Lys Glu Ala Gly Ser Ala Val Asp Ala Val Phe Glu Ser Ile
            20                  25                  30

Gln Asn Ser Leu Ala Lys Gly Glu Lys Val Gln Leu Ile Gly Phe Gly
        35                  40                  45

Asn Phe Glu Val Arg Glu Arg Ala Ala Arg Lys Gly Arg Asn Pro Gln
    50                  55                  60

Thr Gly Lys Glu Ile Asp Ile Pro Ala Ser Lys Val Pro Ala Phe Lys
65                  70                  75                  80

Ala Gly Lys Ala Leu Lys Asp Ala Val Lys
                85                  90

<210> SEQ ID NO 62
<211> LENGTH: 91
<212> TYPE: PRT
<213> ORGANISM: Streptococcus sobrinus

<400> SEQUENCE: 62

Met Ala Asn Lys Gln Asp Leu Ile Ala Lys Val Ala Glu Ala Thr Glu
1               5                   10                  15

Leu Thr Lys Lys Asp Ser Ala Ala Val Asp Thr Val Phe Ser Ser
            20                  25                  30

Ile Glu Gly Phe Leu Ser Lys Gly Glu Lys Val Gln Leu Ile Gly Phe
        35                  40                  45

Gly Asn Phe Glu Val Arg Glu Arg Ala Ala Arg Lys Gly Arg Asn Pro
    50                  55                  60

Gln Thr Gly Ala Glu Ile Lys Ile Ala Ala Ser Lys Val Pro Ala Phe
65                  70                  75                  80

Lys Ala Gly Lys Ala Leu Lys Asp Ala Val Lys
                85                  90

<210> SEQ ID NO 63
<211> LENGTH: 91
<212> TYPE: PRT
<213> ORGANISM: Streptococcus pyogeneses

<400> SEQUENCE: 63

Met Ala Asn Lys Gln Asp Leu Ile Ala Lys Val Ala Glu Ala Thr Glu
1               5                   10                  15

Leu Thr Lys Lys Asp Ser Ala Ala Val Asp Ala Val Phe Ser Thr
            20                  25                  30

Ile Glu Ala Phe Leu Ala Glu Gly Glu Lys Val Gln Leu Ile Gly Phe
        35                  40                  45

Gly Asn Phe Glu Val Arg Glu Arg Ala Ala Arg Lys Gly Arg Asn Pro
    50                  55                  60

Gln Thr Gly Ala Glu Ile Glu Ile Ala Ala Ser Lys Val Pro Ala Phe
65                  70                  75                  80

Lys Ala Gly Lys Ala Leu Lys Asp Ala Val Lys
                85                  90
```

```
<210> SEQ ID NO 64
<211> LENGTH: 91
<212> TYPE: PRT
<213> ORGANISM: Streptococcus gallolyticus

<400> SEQUENCE: 64

Met Ala Asn Lys Gln Asp Leu Ile Ala Lys Val Ala Glu Ala Thr Glu
1               5                   10                  15

Leu Thr Lys Lys Asp Ser Ala Ala Val Asp Ala Val Phe Ser Ala
            20                  25                  30

Ile Glu Ser Phe Leu Ser Glu Gly Glu Lys Val Gln Leu Ile Gly Phe
        35                  40                  45

Gly Asn Phe Glu Val Arg Glu Arg Ala Ala Arg Lys Gly Arg Asn Pro
    50                  55                  60

Gln Thr Gly Glu Glu Ile Glu Ile Ala Ala Ser Lys Val Pro Ala Phe
65                  70                  75                  80

Lys Ala Gly Lys Ala Leu Lys Asp Ala Val Lys
                85                  90

<210> SEQ ID NO 65
<211> LENGTH: 91
<212> TYPE: PRT
<213> ORGANISM: Streptococcus agalactiae

<400> SEQUENCE: 65

Met Ala Asn Lys Gln Asp Leu Ile Ala Lys Val Ala Glu Ala Thr Glu
1               5                   10                  15

Leu Thr Lys Lys Asp Ser Ala Ala Val Asp Ala Val Phe Ala Ala
            20                  25                  30

Val Ala Asp Tyr Leu Ala Glu Gly Glu Lys Val Gln Leu Ile Gly Phe
        35                  40                  45

Gly Asn Phe Glu Val Arg Glu Arg Ala Ala Arg Lys Gly Arg Asn Pro
    50                  55                  60

Gln Thr Gly Ala Glu Ile Glu Ile Ala Ala Ser Lys Val Pro Ala Phe
65                  70                  75                  80

Lys Ala Gly Lys Ala Leu Lys Asp Ala Val Lys
                85                  90

<210> SEQ ID NO 66
<211> LENGTH: 91
<212> TYPE: PRT
<213> ORGANISM: Streptococcus pneumoniae

<400> SEQUENCE: 66

Met Ala Asn Lys Gln Asp Leu Ile Ala Lys Val Ala Glu Ala Thr Glu
1               5                   10                  15

Leu Thr Lys Lys Asp Ser Ala Ala Val Glu Ala Val Phe Ala Ala
            20                  25                  30

Val Ala Asp Tyr Leu Ala Ala Gly Glu Lys Val Gln Leu Ile Gly Phe
        35                  40                  45

Gly Asn Phe Glu Val Arg Glu Arg Ala Glu Arg Lys Gly Arg Asn Pro
    50                  55                  60

Gln Thr Gly Lys Glu Met Thr Ile Ala Ala Ser Lys Val Pro Ala Phe
65                  70                  75                  80

Lys Ala Gly Lys Ala Leu Lys Asp Ala Val Lys
                85                  90
```

<210> SEQ ID NO 67
<211> LENGTH: 91
<212> TYPE: PRT
<213> ORGANISM: Streptococcus gordonii

<400> SEQUENCE: 67

Met Ala Asn Lys Gln Asp Leu Ile Ala Lys Val Ala Ala Thr Glu
1               5                   10                  15

Leu Thr Lys Lys Asp Ser Ala Ala Val Asp Ala Val Phe Ala Ala
                20                  25                  30

Val Thr Glu Tyr Leu Ser Lys Gly Glu Lys Val Gln Leu Ile Gly Phe
            35                  40                  45

Gly Asn Phe Glu Val Arg Glu Arg Ala Ala Arg Lys Gly Arg Asn Pro
        50                  55                  60

Gln Thr Gly Lys Glu Ile Lys Ile Ala Ala Ser Lys Val Pro Ala Phe
65                  70                  75                  80

Lys Ala Gly Lys Ala Leu Lys Asp Ala Val Lys
                85                  90

<210> SEQ ID NO 68
<211> LENGTH: 91
<212> TYPE: PRT
<213> ORGANISM: Streptococcus mutans

<400> SEQUENCE: 68

Met Ala Asn Lys Gln Asp Leu Ile Ala Lys Val Ala Glu Ala Thr Glu
1               5                   10                  15

Leu Thr Lys Lys Asp Ser Ala Ala Val Asp Ala Val Phe Ser Ala
                20                  25                  30

Val Ser Ser Tyr Leu Ala Lys Gly Glu Lys Val Gln Leu Ile Gly Phe
            35                  40                  45

Gly Asn Phe Glu Val Arg Glu Arg Ala Ala Arg Lys Gly Arg Asn Pro
        50                  55                  60

Gln Thr Gly Glu Glu Ile Lys Ile Lys Ala Ser Lys Val Pro Ala Phe
65                  70                  75                  80

Lys Ala Gly Lys Ala Leu Lys Asp Ala Val Lys
                85                  90

<210> SEQ ID NO 69
<211> LENGTH: 91
<212> TYPE: PRT
<213> ORGANISM: Enterococcus faecalis

<400> SEQUENCE: 69

Met Ala Asn Lys Ala Glu Leu Ile Glu Asn Val Ala Ser Ser Thr Gly
1               5                   10                  15

Leu Thr Lys Lys Asp Ala Thr Ala Ala Val Asp Ala Val Phe Ser Thr
                20                  25                  30

Ile Gln Glu Thr Leu Ala Lys Gly Glu Lys Val Gln Leu Ile Gly Phe
            35                  40                  45

Gly Asn Phe Glu Val Arg Glu Arg Ala Ala Arg Lys Gly Arg Asn Pro
        50                  55                  60

Gln Thr Gly Gln Glu Ile Gln Ile Ala Ala Ser Lys Val Pro Ala Phe
65                  70                  75                  80

Lys Pro Gly Lys Ala Leu Lys Asp Ala Val Lys
                85                  90

```
<210> SEQ ID NO 70
<211> LENGTH: 90
<212> TYPE: PRT
<213> ORGANISM: Haemophilus influenzae

<400> SEQUENCE: 70

Met Asn Lys Thr Asp Leu Ile Asp Ala Ile Ala Asn Ala Ala Glu Leu
1               5                   10                  15

Asn Lys Lys Gln Ala Lys Ala Ala Leu Glu Ala Thr Leu Asp Ala Ile
            20                  25                  30

Thr Ala Ser Leu Lys Glu Gly Glu Pro Val Gln Leu Ile Gly Phe Gly
        35                  40                  45

Thr Phe Lys Val Asn Glu Arg Ala Ala Arg Thr Gly Arg Asn Pro Gln
    50                  55                  60

Thr Gly Ala Glu Ile Gln Ile Ala Ala Ser Lys Val Pro Ala Phe Val
65                  70                  75                  80

Ser Gly Lys Ala Leu Lys Asp Ala Ile Lys
                85                  90

<210> SEQ ID NO 71
<211> LENGTH: 90
<212> TYPE: PRT
<213> ORGANISM: Vibrio cholerae

<400> SEQUENCE: 71

Met Asn Lys Thr Gln Leu Ile Asp Phe Ile Ala Glu Lys Ala Asp Leu
1               5                   10                  15

Thr Lys Val Gln Ala Lys Ala Ala Leu Glu Ala Thr Leu Gly Ala Val
            20                  25                  30

Glu Gly Ala Leu Lys Asp Gly Asp Gln Val Gln Leu Ile Gly Phe Gly
        35                  40                  45

Thr Phe Lys Val Asn His Arg Ser Ala Arg Thr Gly Arg Asn Pro Gln
    50                  55                  60

Thr Gly Glu Glu Ile Lys Ile Ala Ala Ala Asn Val Pro Ala Phe Val
65                  70                  75                  80

Ala Gly Lys Ala Leu Lys Asp Ala Ile Lys
                85                  90

<210> SEQ ID NO 72
<211> LENGTH: 90
<212> TYPE: PRT
<213> ORGANISM: Pseudomonas aeruginosa

<400> SEQUENCE: 72

Met Asn Lys Ser Glu Leu Ile Asp Ala Ile Ala Ala Ser Ala Asp Ile
1               5                   10                  15

Pro Lys Ala Val Ala Gly Arg Ala Leu Asp Ala Val Ile Glu Ser Val
            20                  25                  30

Thr Gly Ala Leu Lys Ala Gly Asp Ser Val Val Leu Val Gly Phe Gly
        35                  40                  45

Thr Phe Ala Val Lys Glu Arg Ala Ala Arg Thr Gly Arg Asn Pro Gln
    50                  55                  60

Thr Gly Lys Pro Ile Lys Ile Ala Ala Ala Lys Ile Pro Gly Phe Lys
65                  70                  75                  80

Ala Gly Lys Ala Leu Lys Asp Ala Val Asn
                85                  90
```

<210> SEQ ID NO 73
<211> LENGTH: 90
<212> TYPE: PRT
<213> ORGANISM: Aggregatibacter actinomycetemcomitans

<400> SEQUENCE: 73

Met Asn Lys Thr Asp Leu Ile Asp Ala Ile Ser Ser Ala Glu Leu
1               5                   10                  15

Asn Lys Lys Gln Ala Lys Ala Leu Glu Ala Thr Leu Asp Ala Ile
            20                  25                  30

Thr Gly Ser Leu Lys Lys Gly Glu Ala Val Gln Leu Ile Gly Phe Gly
        35                  40                  45

Thr Phe Lys Val Asn Ala Arg Lys Ala Arg Thr Gly Arg Asn Pro Gln
    50                  55                  60

Thr Gly Ala Glu Ile Lys Ile Ala Ala Ser Lys Val Pro Ala Phe Val
65                  70                  75                  80

Ser Gly Lys Ala Leu Lys Asp Ala Val Lys
                85                  90

<210> SEQ ID NO 74
<211> LENGTH: 90
<212> TYPE: PRT
<213> ORGANISM: Vibrio cholerae

<400> SEQUENCE: 74

Met Asn Lys Thr Gln Leu Val Glu Gln Ile Ala Ala Asn Ala Asp Ile
1               5                   10                  15

Ser Lys Ala Ser Ala Gly Arg Ala Leu Asp Ala Phe Ile Glu Ala Val
            20                  25                  30

Ser Gly Thr Leu Gln Ser Gly Asp Gln Val Ala Leu Val Gly Phe Gly
        35                  40                  45

Thr Phe Ser Val Arg Thr Arg Ala Ala Arg Thr Gly Arg Asn Pro Lys
    50                  55                  60

Thr Gly Glu Glu Ile Lys Ile Ala Glu Ala Lys Val Pro Ser Phe Lys
65                  70                  75                  80

Ala Gly Lys Ala Leu Lys Asp Ala Cys Asn
                85                  90

<210> SEQ ID NO 75
<211> LENGTH: 90
<212> TYPE: PRT
<213> ORGANISM: Escherichia coli

<400> SEQUENCE: 75

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
            20                  25                  30

Thr Glu Ser Leu Lys Glu Gly Asp Asp Val Ala Leu Val Gly Phe Gly
        35                  40                  45

Thr Phe Ala Val Lys Glu Arg Ala Ala Arg Thr Gly Arg Asn Pro Gln
    50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90

```
<210> SEQ ID NO 76
<211> LENGTH: 90
<212> TYPE: PRT
<213> ORGANISM: Moraxella catarrhalis

<400> SEQUENCE: 76

Met Asn Lys Ser Glu Leu Val Asp Ser Ile Ala Gln Ser Ala Gly Leu
1               5                   10                  15

Thr Lys Glu Gln Ala Ala Lys Ala Val Asn Ala Phe Thr Glu Ser Val
            20                  25                  30

Gln Gly Ala Leu Gln Arg Gly Asp Asp Val Val Leu Val Gly Phe Gly
        35                  40                  45

Thr Phe Ser Val Lys Glu Arg Ala Ala Arg Met Gly Arg Asn Pro Lys
    50                  55                  60

Thr Gly Glu Ala Ile Gln Ile Ala Ala Ser Lys Val Pro Ser Phe Lys
65                  70                  75                  80

Ala Gly Lys Val Leu Lys Glu Ser Val Asn
                85                  90

<210> SEQ ID NO 77
<211> LENGTH: 90
<212> TYPE: PRT
<213> ORGANISM: Bordetella pertussis

<400> SEQUENCE: 77

Met Asn Lys Thr Glu Leu Ile Asp His Ile Ala Ser Lys Ala Asp Ile
1               5                   10                  15

Ser Lys Ala Ala Ala Gly Arg Ser Leu Asp Ala Leu Ile Gly Ala Val
            20                  25                  30

Lys Thr Thr Leu Lys Lys Gly Gly Thr Val Thr Leu Val Gly Phe Gly
        35                  40                  45

Thr Phe Ala Val Ser Ala Arg Ala Ala Arg Thr Gly Arg Asn Pro Arg
    50                  55                  60

Thr Gly Glu Thr Ile Lys Ile Lys Lys Ala Lys Val Pro Lys Phe Arg
65                  70                  75                  80

Pro Gly Lys Ala Leu Lys Asp Ala Val Asn
                85                  90

<210> SEQ ID NO 78
<211> LENGTH: 99
<212> TYPE: PRT
<213> ORGANISM: Moraxella catarrhalis

<400> SEQUENCE: 78

Met Gln Ala Val Ile Asn Lys Ser Asn Leu Ile Ala Asn Leu Ala Ser
1               5                   10                  15

Val Cys Glu Glu Leu Glu Glu Asp Val Val Asp Glu Ala Val Arg Leu
            20                  25                  30

Met Ile Ala Met Met Val Asn Glu Leu Val Tyr Asp Gly Arg Ile Glu
        35                  40                  45

Val Arg Gly Phe Gly Ser Phe Cys Leu His His Arg Ser Ala Arg Ile
    50                  55                  60

Ala Arg Asn Pro Arg Thr Gly Glu Ser Val Ser Val Lys Ala Lys Ala
65                  70                  75                  80

Thr Pro Tyr Phe Lys Pro Gly Lys Ala Leu Arg Glu Ser Val Asn Leu
                85                  90                  95

Val Asn Asp
```

```
<210> SEQ ID NO 79
<211> LENGTH: 91
<212> TYPE: PRT
<213> ORGANISM: Prevotella melaninogenica

<400> SEQUENCE: 79

Met Asn Lys Thr Glu Leu Ile Glu Lys Ile Ala Ala Asn Ala Glu Val
1               5                   10                  15

Ser Lys Ala Ala Ala Lys Lys Ala Leu Asp Ala Thr Thr Glu Ala Ile
                20                  25                  30

Lys Glu Ala Leu Ala Ala Gly Asp Lys Val Gln Leu Val Gly Phe Gly
            35                  40                  45

Thr Phe Ala Thr Thr Glu Arg Pro Ala His Glu Gly Ile Asn Pro Arg
        50                  55                  60

Ser Lys Glu Lys Ile Lys Ile Ala Ala Lys Lys Val Ala Lys Phe Lys
65                  70                  75                  80

Ala Gly Ala Glu Leu Ala Asp Ala Val Asn Lys
                85                  90

<210> SEQ ID NO 80
<211> LENGTH: 91
<212> TYPE: PRT
<213> ORGANISM: Prevotella intermedia

<400> SEQUENCE: 80

Met Asn Lys Thr Glu Leu Ile Glu Lys Ile Ala Ala Gly Ala Gly Leu
1               5                   10                  15

Ser Lys Ala Asp Ser Lys Lys Ala Leu Asp Ala Met Thr Ala Ala Ile
                20                  25                  30

Lys Glu Ala Leu Val Ala Gly Asp Lys Val Gln Leu Val Gly Phe Gly
            35                  40                  45

Thr Tyr Ser Val Thr Glu Arg Pro Ala His Glu Gly Ile Asn Pro Ala
        50                  55                  60

Thr Lys Gln Lys Ile Gln Ile Ala Ala Lys Lys Val Ala Lys Phe Lys
65                  70                  75                  80

Pro Gly Ala Glu Leu Ala Asp Ala Val Asn Ala
                85                  90

<210> SEQ ID NO 81
<211> LENGTH: 106
<212> TYPE: PRT
<213> ORGANISM: Treponema denticola

<400> SEQUENCE: 81

Met Lys Gln Lys Arg Ser Lys Ile Asp Ile Asp Ser Val Tyr Arg
1               5                   10                  15

Asn Asn Pro Gln Tyr Gln Leu Lys Gln Ile Asn Ala Ile Ala Asn Leu
                20                  25                  30

Phe Leu Asp Glu Leu Ser Val Leu Leu Gln Gln Gly Ile Pro Val Glu
            35                  40                  45

Ile Arg Gly Leu Gly Ser Phe Asp Phe Ala Val Leu His Gly Arg Lys
        50                  55                  60

Asn Ala Arg Asn Pro Lys Thr Gly Glu Ala Val Leu Thr Ala Asp Arg
65                  70                  75                  80

Cys Lys Val Arg Phe Lys Pro Gly Lys Glu Leu Lys Glu Ala Leu His
                85                  90                  95

Lys Ile Asp Thr Gln Glu Leu Ile Glu Ser
                100                 105
```

-continued

```
<210> SEQ ID NO 82
<211> LENGTH: 88
<212> TYPE: PRT
<213> ORGANISM: Porphyromonas gingivalis

<400> SEQUENCE: 82

Met Asn Lys Thr Asp Phe Ile Ala Ala Val Ala Glu Lys Ala Asn Leu
1               5                   10                  15

Thr Lys Ala Asp Ala Gln Arg Ala Val Asn Ala Phe Ala Glu Val Val
            20                  25                  30

Thr Glu Gln Met Asn Ala Gly Glu Lys Ile Ala Leu Ile Gly Phe Gly
        35                  40                  45

Thr Phe Ser Val Ser Glu Arg Ala Ala Arg Lys Gly Ile Asn Pro Lys
    50                  55                  60

Thr Lys Lys Ser Ile Ser Ile Pro Ala Arg Lys Val Val Arg Phe Lys
65                  70                  75                  80

Pro Gly Ser Thr Leu Glu Leu Lys
                85

<210> SEQ ID NO 83
<211> LENGTH: 94
<212> TYPE: PRT
<213> ORGANISM: Helicobacter pylori

<400> SEQUENCE: 83

Met Asn Lys Ala Glu Phe Ile Asp Leu Val Lys Glu Ala Gly Lys Tyr
1               5                   10                  15

Asn Ser Lys Arg Glu Ala Glu Glu Ala Ile Ser Ala Phe Thr Leu Ala
            20                  25                  30

Val Glu Thr Ala Leu Ser Lys Gly Glu Ser Val Glu Leu Ile Gly Phe
        35                  40                  45

Gly Lys Phe Glu Thr Ala Glu Gln Lys Gly Lys Glu Gly Lys Val Pro
    50                  55                  60

Gly Ser Asp Lys Thr Tyr Lys Thr Glu Asp Lys Arg Val Pro Lys Phe
65                  70                  75                  80

Lys Phe Gly Lys Thr Leu Lys Gln Lys Val Glu Glu Gly Lys
                85                  90

<210> SEQ ID NO 84
<211> LENGTH: 92
<212> TYPE: PRT
<213> ORGANISM: Prevotella melaninogenica

<400> SEQUENCE: 84

Met Thr Lys Ala Asp Ile Ile Asn Glu Ile Ala Thr Ser Thr Gly Ile
1               5                   10                  15

Ala Lys Lys Asp Val Ser Ala Val Val Glu Ser Phe Met Glu Thr Ile
            20                  25                  30

Lys Asp Ser Leu Leu Glu Lys Lys Glu Asn Val Tyr Leu Arg Gly Phe
        35                  40                  45

Gly Ser Phe Ile Val Lys His Arg Ala Glu Lys Thr Ala Arg Asn Ile
    50                  55                  60

Ser Lys Asn Thr Thr Ile Thr Ile Pro Ala His Asp Phe Pro Ser Phe
65                  70                  75                  80

Lys Pro Ala Lys Thr Phe Ile Glu Asp Met Lys Lys
                85                  90
```

```
<210> SEQ ID NO 85
<211> LENGTH: 92
<212> TYPE: PRT
<213> ORGANISM: Prevotella intermedia

<400> SEQUENCE: 85

Met Thr Lys Ala Asp Ile Ile Asn Glu Ile Ala Ser Ser Thr Gly Ile
1               5                   10                  15

Ser Lys Lys Asp Val Ser Ala Val Glu Ser Phe Met Asp Ala Ile
            20                  25                  30

Lys Asp Ser Leu Leu Glu Asn Lys Glu Asn Val Tyr Leu Arg Gly Phe
        35                  40                  45

Gly Ser Phe Ile Val Lys His Arg Ala Glu Lys Thr Ala Arg Asn Ile
    50                  55                  60

Ser Lys Asn Thr Thr Ile Thr Ile Pro Ala His Asp Phe Pro Ser Phe
65                  70                  75                  80

Lys Pro Ala Lys Thr Phe Ile Glu Asp Met Lys Lys
                85                  90

<210> SEQ ID NO 86
<211> LENGTH: 92
<212> TYPE: PRT
<213> ORGANISM: Porphyromonas gingivalis

<400> SEQUENCE: 86

Met Thr Lys Ala Asp Val Val Asn Ala Ile Ala Lys Ser Thr Gly Ile
1               5                   10                  15

Asp Lys Glu Thr Thr Leu Lys Val Val Glu Ser Phe Met Asp Thr Ile
            20                  25                  30

Lys Asp Ser Leu Ser Glu Gly Asp Asn Val Tyr Leu Arg Gly Phe Gly
        35                  40                  45

Ser Phe Ile Val Lys Glu Arg Ala Glu Lys Thr Ala Arg Asn Ile Ser
    50                  55                  60

Lys Gln Thr Thr Ile Ile Ile Pro Lys Arg Asn Ile Pro Ala Phe Lys
65                  70                  75                  80

Pro Ser Lys Ile Phe Met Ser Gln Met Lys Gln Asp
                85                  90

<210> SEQ ID NO 87
<211> LENGTH: 100
<212> TYPE: PRT
<213> ORGANISM: Mycobacterium tuberculosis

<400> SEQUENCE: 87

Met Asn Lys Ala Glu Leu Ile Asp Val Leu Thr Gln Lys Leu Gly Ser
1               5                   10                  15

Asp Arg Arg Gln Ala Thr Ala Ala Val Glu Asn Val Val Asp Thr Ile
            20                  25                  30

Val Arg Ala Val His Lys Gly Asp Ser Val Thr Ile Thr Gly Phe Gly
        35                  40                  45

Val Phe Glu Gln Arg Arg Arg Ala Ala Arg Val Ala Arg Asn Pro Arg
    50                  55                  60

Thr Gly Glu Thr Val Lys Val Lys Pro Thr Ser Val Pro Ala Phe Arg
65                  70                  75                  80

Phe Gly Ala Gln Phe Lys Ala Val Val Ser Gly Ala Gln Arg Leu Pro
                85                  90                  95

Ala Glu Gly Pro
            100
```

-continued

```
<210> SEQ ID NO 88
<211> LENGTH: 100
<212> TYPE: PRT
<213> ORGANISM: Mycobacterium smegmatis

<400> SEQUENCE: 88

Met Asn Lys Ala Glu Leu Ile Asp Val Leu Thr Thr Lys Met Gly Thr
1               5                   10                  15

Asp Arg Arg Gln Ala Thr Ala Ala Val Glu Asn Val Val Asp Thr Ile
                20                  25                  30

Val Arg Ala Val His Lys Gly Asp Ser Val Thr Ile Thr Gly Phe Gly
            35                  40                  45

Val Phe Glu Gln Arg Arg Arg Ala Ala Arg Val Ala Arg Asn Pro Arg
        50                  55                  60

Thr Gly Glu Thr Val Lys Val Lys Pro Thr Ser Val Pro Ala Phe Arg
65                  70                  75                  80

Phe Gly Ala Gln Phe Lys Ala Val Ile Ser Gly Ala Gln Lys Leu Pro
                85                  90                  95

Ala Asp Gly Pro
            100

<210> SEQ ID NO 89
<211> LENGTH: 94
<212> TYPE: PRT
<213> ORGANISM: Escherichia coli

<400> SEQUENCE: 89

Met Thr Lys Ser Glu Leu Ile Glu Arg Leu Ala Thr Gln Gln Ser His
1               5                   10                  15

Ile Pro Ala Lys Thr Val Glu Asp Ala Val Lys Glu Met Leu Glu His
                20                  25                  30

Met Ala Ser Thr Leu Ala Gln Gly Glu Arg Ile Glu Ile Arg Gly Phe
            35                  40                  45

Gly Ser Phe Ser Leu His Tyr Arg Ala Pro Arg Thr Gly Arg Asn Pro
        50                  55                  60

Lys Thr Gly Asp Lys Val Glu Leu Glu Gly Lys Tyr Val Pro His Phe
65                  70                  75                  80

Lys Pro Gly Lys Glu Leu Arg Asp Arg Ala Asn Ile Tyr Gly
                85                  90

<210> SEQ ID NO 90
<211> LENGTH: 94
<212> TYPE: PRT
<213> ORGANISM: Salmonella enterica

<400> SEQUENCE: 90

Met Thr Lys Ser Glu Leu Ile Glu Arg Leu Ala Thr Gln Gln Ser His
1               5                   10                  15

Ile Pro Ala Lys Ala Val Glu Asp Ala Val Lys Glu Met Leu Glu His
                20                  25                  30

Met Ala Ser Thr Leu Ala Gln Gly Glu Arg Ile Glu Ile Arg Gly Phe
            35                  40                  45

Gly Ser Phe Ser Leu His Tyr Arg Ala Pro Arg Thr Gly Arg Asn Pro
        50                  55                  60

Lys Thr Gly Asp Lys Val Glu Leu Glu Gly Lys Tyr Val Pro His Phe
65                  70                  75                  80

Lys Pro Gly Lys Glu Leu Arg Asp Arg Ala Asn Ile Tyr Gly
                85                  90
```

```
<210> SEQ ID NO 91
<211> LENGTH: 92
<212> TYPE: PRT
<213> ORGANISM: Vibrio cholerae

<400> SEQUENCE: 91

Met Thr Lys Ser Glu Leu Ile Glu Arg Leu Cys Ala Glu Gln Thr His
1               5                   10                  15

Leu Ser Ala Lys Glu Ile Glu Asp Ala Val Lys Asn Ile Leu Glu His
            20                  25                  30

Met Ala Ser Thr Leu Glu Ala Gly Glu Arg Ile Glu Ile Arg Gly Phe
        35                  40                  45

Gly Ser Phe Ser Leu His Tyr Arg Glu Pro Arg Val Gly Arg Asn Pro
    50                  55                  60

Lys Thr Gly Asp Lys Val Glu Leu Glu Gly Lys Tyr Val Pro His Phe
65                  70                  75                  80

Lys Pro Gly Lys Glu Leu Arg Glu Arg Val Asn Leu
                85                  90

<210> SEQ ID NO 92
<211> LENGTH: 94
<212> TYPE: PRT
<213> ORGANISM: Pseudomonas aeruginosa

<400> SEQUENCE: 92

Met Thr Lys Ser Glu Leu Ile Glu Arg Ile Val Thr His Gln Gly Gln
1               5                   10                  15

Leu Ser Ala Lys Asp Val Glu Leu Ala Ile Lys Thr Met Leu Glu Gln
            20                  25                  30

Met Ser Gln Ala Leu Ala Thr Gly Asp Arg Ile Glu Ile Arg Gly Phe
        35                  40                  45

Gly Ser Phe Ser Leu His Tyr Arg Ala Pro Arg Val Gly Arg Asn Pro
    50                  55                  60

Lys Thr Gly Glu Ser Val Arg Leu Asp Gly Lys Phe Val Pro His Phe
65                  70                  75                  80

Lys Pro Gly Lys Glu Leu Arg Asp Arg Val Asn Glu Pro Glu
                85                  90

<210> SEQ ID NO 93
<211> LENGTH: 94
<212> TYPE: PRT
<213> ORGANISM: Haemophilus influenzae

<400> SEQUENCE: 93

Met Thr Lys Ser Glu Leu Met Glu Lys Leu Ser Ala Lys Gln Pro Thr
1               5                   10                  15

Leu Pro Ala Lys Glu Ile Glu Asn Met Val Lys Gly Ile Leu Glu Phe
            20                  25                  30

Ile Ser Gln Ser Leu Glu Asn Gly Asp Arg Val Glu Val Arg Gly Phe
        35                  40                  45

Gly Ser Phe Ser Leu His His Arg Gln Pro Arg Leu Gly Arg Asn Pro
    50                  55                  60

Lys Thr Gly Asp Ser Val Asn Leu Ser Ala Lys Ser Val Pro Tyr Phe
65                  70                  75                  80

Lys Ala Gly Lys Glu Leu Lys Ala Arg Val Asp Val Gln Ala
                85                  90
```

```
<210> SEQ ID NO 94
<211> LENGTH: 95
<212> TYPE: PRT
<213> ORGANISM: Aggregatibacter actinomycetemcomitans

<400> SEQUENCE: 94

Met Thr Lys Ser Glu Leu Ile Glu Leu Leu Val Gln Lys Asn Ser Asn
1               5                   10                  15

Ile Pro Val Lys His Val Glu Ala Val Lys Ala Ile Leu Glu Gln
            20                  25                  30

Met Ser Tyr Val Leu Glu His Gly Glu Arg Ile Glu Val Arg Gly Phe
            35                  40                  45

Gly Ser Phe Ser Leu His Cys Arg Gln Pro Arg Ile Gly Arg Asn Pro
        50                  55                  60

Lys Thr Gly Glu Gln Val Lys Leu Asp Ala Lys Cys Val Pro Tyr Phe
65                  70                  75                  80

Lys Ala Gly Lys Glu Leu Arg Glu Arg Val Asp Val Tyr Ala Ala
                85                  90                  95

<210> SEQ ID NO 95
<211> LENGTH: 98
<212> TYPE: PRT
<213> ORGANISM: Neisseria gonorrhoeae

<400> SEQUENCE: 95

Met Val Arg Leu Ala Glu Val Phe Ala Ala Lys Asn Gly Thr His Leu
1               5                   10                  15

Leu Ala Lys Asp Val Glu Tyr Ser Val Lys Val Leu Val Asp Thr Met
            20                  25                  30

Thr Arg Ser Leu Ala Arg Gly Gln Arg Ile Glu Ile Arg Gly Phe Gly
            35                  40                  45

Ser Phe Asp Leu Asn His Arg Pro Ala Arg Ile Gly Arg Asn Pro Lys
        50                  55                  60

Thr Gly Glu Arg Val Glu Val Pro Glu Lys His Val Pro His Phe Lys
65                  70                  75                  80

Pro Gly Lys Glu Leu Arg Glu Arg Val Asp Leu Ala Leu Lys Glu Asn
                85                  90                  95

Ala Asn

<210> SEQ ID NO 96
<211> LENGTH: 104
<212> TYPE: PRT
<213> ORGANISM: Neisseria meningitidis

<400> SEQUENCE: 96

Met Thr Lys Ser Glu Leu Met Val Arg Leu Ala Glu Val Phe Ala Ala
1               5                   10                  15

Lys Asn Gly Thr His Leu Leu Ala Lys Asp Val Glu Tyr Ser Val Lys
            20                  25                  30

Val Leu Val Asp Thr Met Thr Arg Ser Leu Ala Arg Gly Gln Arg Ile
            35                  40                  45

Glu Ile Arg Gly Phe Gly Ser Phe Asp Leu Asn His Arg Pro Ala Arg
        50                  55                  60

Ile Gly Arg Asn Pro Lys Thr Gly Glu Arg Val Glu Val Pro Glu Lys
65                  70                  75                  80
```

His Val Pro His Phe Lys Pro Gly Lys Glu Leu Arg Glu Arg Val Asp
                85                  90                  95

Leu Ala Leu Lys Glu Asn Ala Asn
            100

<210> SEQ ID NO 97
<211> LENGTH: 107
<212> TYPE: PRT
<213> ORGANISM: Burkholderia cenocepacia

<400> SEQUENCE: 97

Met Thr Lys Ser Glu Leu Val Ala Gln Leu Ala Ser Arg Phe Pro Gln
1               5                   10                  15

Leu Val Leu Lys Asp Ala Asp Phe Ala Val Lys Thr Met Leu Asp Ala
            20                  25                  30

Met Ser Asp Ala Leu Ala Lys Gly His Arg Ile Glu Ile Arg Gly Phe
        35                  40                  45

Gly Ser Phe Gly Leu Asn Arg Arg Pro Ala Arg Val Gly Arg Asn Pro
    50                  55                  60

Lys Ser Gly Glu Lys Val Gln Val Pro Glu Lys Phe Val Pro His Phe
65                  70                  75                  80

Lys Pro Gly Lys Glu Leu Arg Glu Arg Val Asp Gly Arg Ala Gly Glu
                85                  90                  95

Pro Leu Lys Ala Asp Asp Pro Asp Asp Arg
            100                 105

<210> SEQ ID NO 98
<211> LENGTH: 107
<212> TYPE: PRT
<213> ORGANISM: Burkholderia pseudomallei

<400> SEQUENCE: 98

Met Thr Lys Ser Glu Leu Val Ala Gln Leu Ala Ser Arg Phe Pro Gln
1               5                   10                  15

Leu Val Leu Lys Asp Ala Asp Phe Ala Val Lys Thr Met Leu Asp Ala
            20                  25                  30

Met Ser Asp Ala Leu Ser Lys Gly His Arg Ile Glu Ile Arg Gly Phe
        35                  40                  45

Gly Ser Phe Gly Leu Asn Arg Arg Pro Ala Arg Val Gly Arg Asn Pro
    50                  55                  60

Lys Ser Gly Glu Lys Val Gln Val Pro Glu Lys His Val Pro His Phe
65                  70                  75                  80

Lys Pro Gly Lys Glu Leu Arg Glu Arg Val Asp Gly Arg Ala Gly Glu
                85                  90                  95

Pro Leu Lys Asn Asp Glu Pro Glu Asp Ala Gln
            100                 105

<210> SEQ ID NO 99
<211> LENGTH: 101
<212> TYPE: PRT
<213> ORGANISM: Bordetella pertussis

<400> SEQUENCE: 99

Met Thr Lys Ser Glu Leu Ile Ala Ala Leu Ala Ala Arg Tyr Pro Gln
1               5                   10                  15

Leu Ala Ala Arg Asp Thr Asp Tyr Ala Val Lys Thr Met Leu Asp Ala
            20                  25                  30

```
Met Thr Gln Ala Leu Ala Ser Gly Gln Arg Ile Glu Ile Arg Gly Phe
            35                  40                  45

Gly Ser Phe Ser Leu Ser Gln Arg Ser Pro Arg Ile Gly Arg Asn Pro
 50                  55                  60

Lys Ser Gly Glu Gln Val Leu Val Pro Gly Lys Gln Val Pro His Phe
 65                  70                  75                  80

Lys Pro Gly Lys Glu Leu Arg Glu Trp Val Asp Leu Val Gly Asn Asp
                 85                  90                  95

Gln Gly Asp Asp Ser
            100
```

<210> SEQ ID NO 100
<211> LENGTH: 108
<212> TYPE: PRT
<213> ORGANISM: Borrelia burgdorferi

<400> SEQUENCE: 100

```
Met Ser Phe Ser Arg Arg Pro Lys Val Thr Lys Ser Asp Ile Val Asp
 1               5                  10                  15

Gln Ile Ser Leu Asn Ile Lys Asn Asn Asn Leu Lys Leu Glu Lys Lys
             20                  25                  30

Tyr Ile Arg Leu Val Ile Asp Ala Phe Phe Glu Glu Leu Lys Ser Asn
         35                  40                  45

Leu Cys Ser Asn Asn Val Ile Glu Phe Arg Ser Phe Gly Thr Phe Glu
     50                  55                  60

Val Arg Lys Arg Lys Gly Arg Leu Asn Ala Arg Asn Pro Gln Thr Gly
 65                  70                  75                  80

Glu Tyr Val Lys Val Leu Asp His His Val Ala Tyr Phe Arg Pro Gly
                 85                  90                  95

Lys Asp Leu Lys Glu Arg Val Trp Gly Ile Lys Gly
            100                 105
```

<210> SEQ ID NO 101
<211> LENGTH: 16
<212> TYPE: PRT
<213> ORGANISM: Streptococcus sp.

<400> SEQUENCE: 101

```
Glu Val Arg Glu Arg Ala Ala Arg Lys Gly Arg Asn Pro Gln Thr Gly
 1               5                  10                  15
```

<210> SEQ ID NO 102
<211> LENGTH: 16
<212> TYPE: PRT
<213> ORGANISM: Escherichia coli

<400> SEQUENCE: 102

```
Asp Leu Arg Asp Lys Asn Gln Arg Pro Gly Arg Asn Pro Lys Thr Gly
 1               5                  10                  15
```

<210> SEQ ID NO 103
<211> LENGTH: 16
<212> TYPE: PRT
<213> ORGANISM: Salmonella enterica

<400> SEQUENCE: 103

```
Asp Leu Arg Asp Lys Asn Gln Arg Pro Gly Arg Asn Pro Lys Thr Gly
 1               5                  10                  15
```

```
<210> SEQ ID NO 104
<211> LENGTH: 16
<212> TYPE: PRT
<213> ORGANISM: Vibrio cholerae

<400> SEQUENCE: 104

Asp Leu Arg Asp Lys Asn Glu Arg Pro Gly Arg Asn Pro Lys Thr Gly
1               5                   10                  15

<210> SEQ ID NO 105
<211> LENGTH: 16
<212> TYPE: PRT
<213> ORGANISM: Pseudomonas aeruginosa

<400> SEQUENCE: 105

Asp Leu Arg Asp Lys Arg Gln Arg Pro Gly Arg Asn Pro Lys Thr Gly
1               5                   10                  15

<210> SEQ ID NO 106
<211> LENGTH: 16
<212> TYPE: PRT
<213> ORGANISM: Haemophilus influenzae

<400> SEQUENCE: 106

Glu Leu Arg Asp Lys Ser Ser Arg Pro Gly Arg Asn Pro Lys Thr Gly
1               5                   10                  15

<210> SEQ ID NO 107
<211> LENGTH: 16
<212> TYPE: PRT
<213> ORGANISM: Aggregatibacter actinomycetemcomitans

<400> SEQUENCE: 107

Glu Leu Arg Asp Lys Ala Ser Arg Pro Gly Arg Asn Pro Lys Thr Gly
1               5                   10                  15

<210> SEQ ID NO 108
<211> LENGTH: 16
<212> TYPE: PRT
<213> ORGANISM: Moraxella catarrhalis

<400> SEQUENCE: 108

Glu Leu Lys Asp Lys Lys Pro Arg Pro Gly Arg Asn Pro Lys Thr Gly
1               5                   10                  15

<210> SEQ ID NO 109
<211> LENGTH: 16
<212> TYPE: PRT
<213> ORGANISM: Neisseria gonorrhoeae

<400> SEQUENCE: 109

Gln Leu Arg Asp Lys Pro Gln Arg Pro Gly Arg Asn Pro Lys Thr Gly
1               5                   10                  15

<210> SEQ ID NO 110
<211> LENGTH: 16
<212> TYPE: PRT
<213> ORGANISM: Neisseria meningitidis

<400> SEQUENCE: 110

Gln Leu Arg Asp Lys Pro Gln Arg Pro Gly Arg Asn Pro Lys Thr Gly
1               5                   10                  15
```

```
<210> SEQ ID NO 111
<211> LENGTH: 16
<212> TYPE: PRT
<213> ORGANISM: Burkholderia cenocepacia

<400> SEQUENCE: 111

Gln Leu Arg Asp Lys Pro Gln Arg Pro Gly Arg Asn Pro Lys Thr Gly
1               5                   10                  15

<210> SEQ ID NO 112
<211> LENGTH: 16
<212> TYPE: PRT
<213> ORGANISM: Burkholderia pseudomallei

<400> SEQUENCE: 112

Gln Leu Arg Asp Lys Pro Gln Arg Pro Gly Arg Asn Pro Asn Thr Gly
1               5                   10                  15

<210> SEQ ID NO 113
<211> LENGTH: 16
<212> TYPE: PRT
<213> ORGANISM: Bordetella pertussis

<400> SEQUENCE: 113

Gln Val Arg Asp Lys Pro Pro Arg Pro Gly Arg Asn Pro Lys Thr Gly
1               5                   10                  15

<210> SEQ ID NO 114
<211> LENGTH: 16
<212> TYPE: PRT
<213> ORGANISM: Prevotella melaninogenica

<400> SEQUENCE: 114

Glu Val Lys Lys Arg Leu Glu Arg Val Met Val Asn Pro Ser Thr Gly
1               5                   10                  15

<210> SEQ ID NO 115
<211> LENGTH: 16
<212> TYPE: PRT
<213> ORGANISM: Prevotella intermedia

<400> SEQUENCE: 115

Glu Val Lys Lys Arg Leu Glu Arg Ile Met Thr Asn Pro Ala Thr Gly
1               5                   10                  15

<210> SEQ ID NO 116
<211> LENGTH: 16
<212> TYPE: PRT
<213> ORGANISM: Treponema palladium

<400> SEQUENCE: 116

Glu Ser Arg Val Arg Lys Ala Ser Val Gly Lys Ser Ile Asn Thr Gly
1               5                   10                  15

<210> SEQ ID NO 117
<211> LENGTH: 16
<212> TYPE: PRT
<213> ORGANISM: Prevotella melaninogenica

<400> SEQUENCE: 117

Lys Val Gln Ala Val Lys Pro Arg Glu Ser Val Asn Val Asn Thr Gly
1               5                   10                  15
```

```
<210> SEQ ID NO 118
<211> LENGTH: 16
<212> TYPE: PRT
<213> ORGANISM: Prevotella intermedia

<400> SEQUENCE: 118

Lys Val Gln Ala Val Lys Pro Arg Glu Ser Val Asn Val Asn Thr Gly
 1               5                  10                  15

<210> SEQ ID NO 119
<211> LENGTH: 16
<212> TYPE: PRT
<213> ORGANISM: Staphylococcus aureus

<400> SEQUENCE: 119

Glu Val Arg Glu Arg Ala Ala Arg Lys Gly Arg Asn Pro Gln Thr Gly
 1               5                  10                  15

<210> SEQ ID NO 120
<211> LENGTH: 16
<212> TYPE: PRT
<213> ORGANISM: Escherichia coli

<400> SEQUENCE: 120

Lys Val Asn His Arg Ala Glu Arg Thr Gly Arg Asn Pro Gln Thr Gly
 1               5                  10                  15

<210> SEQ ID NO 121
<211> LENGTH: 16
<212> TYPE: PRT
<213> ORGANISM: Staphylococcus epidermidis

<400> SEQUENCE: 121

Glu Val Arg Glu Arg Ala Ala Arg Lys Gly Arg Asn Pro Gln Thr Gly
 1               5                  10                  15

<210> SEQ ID NO 122
<211> LENGTH: 16
<212> TYPE: PRT
<213> ORGANISM: Streptococcus sobrinus

<400> SEQUENCE: 122

Glu Val Arg Glu Arg Ala Ala Arg Lys Gly Arg Asn Pro Gln Thr Gly
 1               5                  10                  15

<210> SEQ ID NO 123
<211> LENGTH: 16
<212> TYPE: PRT
<213> ORGANISM: Streptococcus pyogeneses

<400> SEQUENCE: 123

Glu Val Arg Glu Arg Ala Ala Arg Lys Gly Arg Asn Pro Gln Thr Gly
 1               5                  10                  15

<210> SEQ ID NO 124
<211> LENGTH: 16
<212> TYPE: PRT
<213> ORGANISM: Streptococcus gallolyticus

<400> SEQUENCE: 124

Glu Val Arg Glu Arg Ala Ala Arg Lys Gly Arg Asn Pro Gln Thr Gly
 1               5                  10                  15
```

```
<210> SEQ ID NO 125
<211> LENGTH: 16
<212> TYPE: PRT
<213> ORGANISM: Streptococcus agalactiae

<400> SEQUENCE: 125

Glu Val Arg Glu Arg Ala Ala Arg Lys Gly Arg Asn Pro Gln Thr Gly
1               5                   10                  15

<210> SEQ ID NO 126
<211> LENGTH: 16
<212> TYPE: PRT
<213> ORGANISM: Streptococcus pneumoniae

<400> SEQUENCE: 126

Glu Val Arg Glu Arg Ala Glu Arg Lys Gly Arg Asn Pro Gln Thr Gly
1               5                   10                  15

<210> SEQ ID NO 127
<211> LENGTH: 16
<212> TYPE: PRT
<213> ORGANISM: Streptococcus gordonii

<400> SEQUENCE: 127

Glu Val Arg Glu Arg Ala Ala Arg Lys Gly Arg Asn Pro Gln Thr Gly
1               5                   10                  15

<210> SEQ ID NO 128
<211> LENGTH: 16
<212> TYPE: PRT
<213> ORGANISM: Streptococcus mutans

<400> SEQUENCE: 128

Glu Val Arg Glu Arg Ala Ala Arg Lys Gly Arg Asn Pro Gln Thr Gly
1               5                   10                  15

<210> SEQ ID NO 129
<211> LENGTH: 16
<212> TYPE: PRT
<213> ORGANISM: Enterococcus faecalis

<400> SEQUENCE: 129

Glu Val Arg Glu Arg Ala Ala Arg Lys Gly Arg Asn Pro Gln Thr Gly
1               5                   10                  15

<210> SEQ ID NO 130
<211> LENGTH: 16
<212> TYPE: PRT
<213> ORGANISM: Haemophilus influenzae

<400> SEQUENCE: 130

Lys Val Asn Glu Arg Ala Ala Arg Thr Gly Arg Asn Pro Gln Thr Gly
1               5                   10                  15

<210> SEQ ID NO 131
<211> LENGTH: 16
<212> TYPE: PRT
<213> ORGANISM: Vibrio cholerae

<400> SEQUENCE: 131

Lys Val Asn His Arg Ser Ala Arg Thr Gly Arg Asn Pro Gln Thr Gly
1               5                   10                  15
```

<210> SEQ ID NO 132
<211> LENGTH: 16
<212> TYPE: PRT
<213> ORGANISM: Bordetella pertussis

<400> SEQUENCE: 132

Ala Val Ser Ala Arg Ala Ala Arg Thr Gly Arg Asn Pro Arg Thr Gly
1               5                   10                  15

<210> SEQ ID NO 133
<211> LENGTH: 16
<212> TYPE: PRT
<213> ORGANISM: Pseudomonas aeruginosa

<400> SEQUENCE: 133

Ala Val Lys Glu Arg Ala Ala Arg Thr Gly Arg Asn Pro Gln Thr Gly
1               5                   10                  15

<210> SEQ ID NO 134
<211> LENGTH: 16
<212> TYPE: PRT
<213> ORGANISM: Aggregatibacter actinomycetemcomitans

<400> SEQUENCE: 134

Ser Val Arg Thr Arg Ala Ala Arg Thr Gly Arg Asn Pro Lys Thr Gly
1               5                   10                  15

<210> SEQ ID NO 135
<211> LENGTH: 16
<212> TYPE: PRT
<213> ORGANISM: Prevotella melaninogenica

<400> SEQUENCE: 135

Ala Thr Thr Glu Arg Pro Ala His Glu Gly Ile Asn Pro Arg Ser Lys
1               5                   10                  15

<210> SEQ ID NO 136
<211> LENGTH: 16
<212> TYPE: PRT
<213> ORGANISM: Prevotella intermedia

<400> SEQUENCE: 136

Ser Val Thr Glu Arg Pro Ala His Glu Gly Ile Asn Pro Ala Thr Lys
1               5                   10                  15

<210> SEQ ID NO 137
<211> LENGTH: 16
<212> TYPE: PRT
<213> ORGANISM: Treponema denticola

<400> SEQUENCE: 137

Phe Ala Val Leu His Gly Arg Lys Asn Ala Arg Asn Pro Lys Thr Gly
1               5                   10                  15

<210> SEQ ID NO 138
<211> LENGTH: 16
<212> TYPE: PRT
<213> ORGANISM: Porphyromonas gingivalis

<400> SEQUENCE: 138

Ser Val Ser Glu Arg Ala Ala Arg Lys Gly Ile Asn Pro Lys Thr Lys
1               5                   10                  15

-continued

```
<210> SEQ ID NO 139
<211> LENGTH: 16
<212> TYPE: PRT
<213> ORGANISM: Helicobacter pylori

<400> SEQUENCE: 139

Glu Thr Ala Glu Gln Lys Gly Lys Glu Gly Lys Val Pro Gly Ser Asp
1               5                   10                  15

<210> SEQ ID NO 140
<211> LENGTH: 17
<212> TYPE: PRT
<213> ORGANISM: Prevotella melaninogenica

<400> SEQUENCE: 140

Phe Ile Val Lys His Arg Ala Glu Lys Thr Ala Arg Asn Ile Ser Lys
1               5                   10                  15

Asn

<210> SEQ ID NO 141
<211> LENGTH: 17
<212> TYPE: PRT
<213> ORGANISM: Prevotella intermedia

<400> SEQUENCE: 141

Phe Ile Val Lys His Arg Ala Glu Lys Thr Ala Arg Asn Ile Ser Lys
1               5                   10                  15

Asn

<210> SEQ ID NO 142
<211> LENGTH: 16
<212> TYPE: PRT
<213> ORGANISM: Porphyromonas gingivalis

<400> SEQUENCE: 142

Ile Val Lys Glu Arg Ala Glu Lys Thr Ala Arg Asn Ile Ser Lys Gln
1               5                   10                  15

<210> SEQ ID NO 143
<211> LENGTH: 16
<212> TYPE: PRT
<213> ORGANISM: Mycobacterium tuberculosis

<400> SEQUENCE: 143

Glu Gln Arg Arg Arg Ala Ala Arg Val Ala Arg Asn Pro Arg Thr Gly
1               5                   10                  15

<210> SEQ ID NO 144
<211> LENGTH: 16
<212> TYPE: PRT
<213> ORGANISM: Mycobacterium smegmatis

<400> SEQUENCE: 144

Glu Gln Arg Arg Arg Ala Ala Arg Val Ala Arg Asn Pro Arg Thr Gly
1               5                   10                  15

<210> SEQ ID NO 145
<211> LENGTH: 16
<212> TYPE: PRT
<213> ORGANISM: Escherichia coli

<400> SEQUENCE: 145

Ser Leu His Tyr Arg Ala Pro Arg Thr Gly Arg Asn Pro Lys Thr Gly
1               5                   10                  15
```

<210> SEQ ID NO 146
<211> LENGTH: 16
<212> TYPE: PRT
<213> ORGANISM: Salmonella enterica

<400> SEQUENCE: 146

Ser Leu His Tyr Arg Ala Pro Arg Thr Gly Arg Asn Pro Lys Thr Gly
1               5                   10                  15

<210> SEQ ID NO 147
<211> LENGTH: 16
<212> TYPE: PRT
<213> ORGANISM: Vibrio cholerae

<400> SEQUENCE: 147

Ser Leu His Tyr Arg Glu Pro Arg Val Gly Arg Asn Pro Lys Thr Gly
1               5                   10                  15

<210> SEQ ID NO 148
<211> LENGTH: 16
<212> TYPE: PRT
<213> ORGANISM: Escherichia coli

<400> SEQUENCE: 148

Ala Val Lys Glu Arg Ala Ala Arg Thr Gly Arg Asn Pro Gln Thr Gly
1               5                   10                  15

<210> SEQ ID NO 149
<211> LENGTH: 16
<212> TYPE: PRT
<213> ORGANISM: Moraxella catarrhalis

<400> SEQUENCE: 149

Ser Val Lys Glu Arg Ala Ala Arg Met Gly Arg Asn Pro Lys Thr Gly
1               5                   10                  15

<210> SEQ ID NO 150
<211> LENGTH: 16
<212> TYPE: PRT
<213> ORGANISM: Pseudomonas aeruginosa

<400> SEQUENCE: 150

Ser Leu His Tyr Arg Ala Pro Arg Val Gly Arg Asn Pro Lys Thr Gly
1               5                   10                  15

<210> SEQ ID NO 151
<211> LENGTH: 16
<212> TYPE: PRT
<213> ORGANISM: Haemophilus influenzae

<400> SEQUENCE: 151

Ser Leu His His Arg Gln Pro Arg Leu Gly Arg Asn Pro Lys Thr Gly
1               5                   10                  15

<210> SEQ ID NO 152
<211> LENGTH: 16
<212> TYPE: PRT
<213> ORGANISM: Aggregatibacter actinomycetemcomitans

<400> SEQUENCE: 152

Ser Leu His Cys Arg Gln Pro Arg Ile Gly Arg Asn Pro Lys Thr Gly
1               5                   10                  15

-continued

```
<210> SEQ ID NO 153
<211> LENGTH: 16
<212> TYPE: PRT
<213> ORGANISM: Neisseria gonorrhoeae

<400> SEQUENCE: 153

Asp Leu Asn His Arg Pro Ala Arg Ile Gly Arg Asn Pro Lys Thr Gly
1               5                   10                  15

<210> SEQ ID NO 154
<211> LENGTH: 16
<212> TYPE: PRT
<213> ORGANISM: Neisseria meningitidis

<400> SEQUENCE: 154

Asp Leu Asn His Arg Pro Ala Arg Ile Gly Arg Asn Pro Lys Thr Gly
1               5                   10                  15

<210> SEQ ID NO 155
<211> LENGTH: 16
<212> TYPE: PRT
<213> ORGANISM: Burkholderia cenocepacia

<400> SEQUENCE: 155

Gly Leu Asn Arg Arg Pro Ala Arg Val Gly Arg Asn Pro Lys Ser Gly
1               5                   10                  15

<210> SEQ ID NO 156
<211> LENGTH: 16
<212> TYPE: PRT
<213> ORGANISM: Burkholderia pseudomallei

<400> SEQUENCE: 156

Gly Leu Asn Arg Arg Pro Ala Arg Val Gly Arg Asn Pro Lys Ser Gly
1               5                   10                  15

<210> SEQ ID NO 157
<211> LENGTH: 16
<212> TYPE: PRT
<213> ORGANISM: Bordetella pertussis

<400> SEQUENCE: 157

Ser Leu Ser Gln Arg Ser Pro Arg Ile Gly Arg Asn Pro Lys Ser Gly
1               5                   10                  15

<210> SEQ ID NO 158
<211> LENGTH: 16
<212> TYPE: PRT
<213> ORGANISM: Moraxella catarrhalis

<400> SEQUENCE: 158

Cys Leu His His Arg Ser Ala Arg Ile Ala Arg Asn Pro Arg Thr Gly
1               5                   10                  15

<210> SEQ ID NO 159
<211> LENGTH: 17
<212> TYPE: PRT
<213> ORGANISM: Borrelia burgdorferi

<400> SEQUENCE: 159

Glu Val Arg Lys Arg Lys Gly Arg Leu Asn Ala Arg Asn Pro Gln Thr
1               5                   10                  15

Gly
```

<210> SEQ ID NO 160
<211> LENGTH: 6
<212> TYPE: PRT
<213> ORGANISM: Streptococcus pyogeneses

<400> SEQUENCE: 160

Ala Phe Lys Ala Gly Lys
1               5

<210> SEQ ID NO 161
<211> LENGTH: 7
<212> TYPE: PRT
<213> ORGANISM: Streptococcus pyogeneses

<400> SEQUENCE: 161

Ala Leu Lys Asp Ala Val Lys
1               5

<210> SEQ ID NO 162
<211> LENGTH: 20
<212> TYPE: PRT
<213> ORGANISM: Streptococcus pyogeneses

<400> SEQUENCE: 162

Ile Ala Ala Ser Lys Val Pro Ala Phe Lys Ala Gly Lys Ala Leu Lys
1               5                   10                  15

Asp Ala Val Lys
            20

<210> SEQ ID NO 163
<211> LENGTH: 6
<212> TYPE: PRT
<213> ORGANISM: Streptococcus gallolyticus

<400> SEQUENCE: 163

Ala Phe Lys Ala Gly Lys
1               5

<210> SEQ ID NO 164
<211> LENGTH: 7
<212> TYPE: PRT
<213> ORGANISM: Streptococcus gallolyticus

<400> SEQUENCE: 164

Ala Leu Lys Asp Ala Val Lys
1               5

<210> SEQ ID NO 165
<211> LENGTH: 20
<212> TYPE: PRT
<213> ORGANISM: Streptococcus gallolyticus

<400> SEQUENCE: 165

Ile Ala Ala Ser Lys Val Pro Ala Phe Lys Ala Gly Lys Ala Leu Lys
1               5                   10                  15

Asp Ala Val Lys
            20

<210> SEQ ID NO 166
<211> LENGTH: 6
<212> TYPE: PRT
<213> ORGANISM: Streptococcus sobrinus

```
<400> SEQUENCE: 166

Ala Phe Lys Ala Gly Lys
1               5

<210> SEQ ID NO 167
<211> LENGTH: 7
<212> TYPE: PRT
<213> ORGANISM: Streptococcus sobrinus

<400> SEQUENCE: 167

Ala Leu Lys Asp Ala Val Lys
1               5

<210> SEQ ID NO 168
<211> LENGTH: 20
<212> TYPE: PRT
<213> ORGANISM: Streptococcus sobrinus

<400> SEQUENCE: 168

Ile Ala Ala Ser Lys Val Pro Ala Phe Lys Ala Gly Lys Ala Leu Lys
1               5                   10                  15

Asp Ala Val Lys
            20

<210> SEQ ID NO 169
<211> LENGTH: 6
<212> TYPE: PRT
<213> ORGANISM: Streptococcus agalactiae

<400> SEQUENCE: 169

Ala Phe Lys Ala Gly Lys
1               5

<210> SEQ ID NO 170
<211> LENGTH: 7
<212> TYPE: PRT
<213> ORGANISM: Streptococcus agalactiae

<400> SEQUENCE: 170

Ala Leu Lys Asp Ala Val Lys
1               5

<210> SEQ ID NO 171
<211> LENGTH: 20
<212> TYPE: PRT
<213> ORGANISM: Streptococcus agalactiae

<400> SEQUENCE: 171

Ile Ala Ala Ser Lys Val Pro Ala Phe Lys Ala Gly Lys Ala Leu Lys
1               5                   10                  15

Asp Ala Val Lys
            20

<210> SEQ ID NO 172
<211> LENGTH: 6
<212> TYPE: PRT
<213> ORGANISM: Streptococcus pneumoniae

<400> SEQUENCE: 172

Ala Phe Lys Ala Gly Lys
1               5
```

-continued

<210> SEQ ID NO 173
<211> LENGTH: 7
<212> TYPE: PRT
<213> ORGANISM: Streptococcus pneumoniae

<400> SEQUENCE: 173

Ala Leu Lys Asp Ala Val Lys
1               5

<210> SEQ ID NO 174
<211> LENGTH: 20
<212> TYPE: PRT
<213> ORGANISM: Streptococcus pneumoniae

<400> SEQUENCE: 174

Ile Ala Ala Ser Lys Val Pro Ala Phe Lys Ala Gly Lys Ala Leu Lys
1               5                   10                  15

Asp Ala Val Lys
            20

<210> SEQ ID NO 175
<211> LENGTH: 6
<212> TYPE: PRT
<213> ORGANISM: Streptococcus gordonii

<400> SEQUENCE: 175

Ala Phe Lys Ala Gly Lys
1               5

<210> SEQ ID NO 176
<211> LENGTH: 7
<212> TYPE: PRT
<213> ORGANISM: Streptococcus gordonii

<400> SEQUENCE: 176

Ala Leu Lys Asp Ala Val Lys
1               5

<210> SEQ ID NO 177
<211> LENGTH: 20
<212> TYPE: PRT
<213> ORGANISM: Streptococcus gordonii

<400> SEQUENCE: 177

Ile Ala Ala Ser Lys Val Pro Ala Phe Lys Ala Gly Lys Ala Leu Lys
1               5                   10                  15

Asp Ala Val Lys
            20

<210> SEQ ID NO 178
<211> LENGTH: 6
<212> TYPE: PRT
<213> ORGANISM: Streptococcus mutans

<400> SEQUENCE: 178

Ala Phe Lys Ala Gly Lys
1               5

<210> SEQ ID NO 179
<211> LENGTH: 7
<212> TYPE: PRT
<213> ORGANISM: Streptococcus mutans

```
<400> SEQUENCE: 179

Ala Leu Lys Asp Ala Val Lys
1               5

<210> SEQ ID NO 180
<211> LENGTH: 20
<212> TYPE: PRT
<213> ORGANISM: Streptococcus mutans

<400> SEQUENCE: 180

Ile Lys Ala Ser Lys Val Pro Ala Phe Lys Ala Gly Lys Ala Leu Lys
1               5                   10                  15

Asp Ala Val Lys
            20

<210> SEQ ID NO 181
<211> LENGTH: 6
<212> TYPE: PRT
<213> ORGANISM: Enterococcus faecalis

<400> SEQUENCE: 181

Ala Phe Lys Pro Gly Lys
1               5

<210> SEQ ID NO 182
<211> LENGTH: 7
<212> TYPE: PRT
<213> ORGANISM: Enterococcus faecalis

<400> SEQUENCE: 182

Ala Leu Lys Asp Ala Val Lys
1               5

<210> SEQ ID NO 183
<211> LENGTH: 20
<212> TYPE: PRT
<213> ORGANISM: Enterococcus faecalis

<400> SEQUENCE: 183

Ile Ala Ala Ser Lys Val Pro Ala Phe Lys Pro Gly Lys Ala Leu Lys
1               5                   10                  15

Asp Ala Val Lys
            20

<210> SEQ ID NO 184
<211> LENGTH: 6
<212> TYPE: PRT
<213> ORGANISM: Staphylococcus aureus

<400> SEQUENCE: 184

Ala Phe Lys Ala Gly Lys
1               5

<210> SEQ ID NO 185
<211> LENGTH: 7
<212> TYPE: PRT
<213> ORGANISM: Staphylococcus aureus

<400> SEQUENCE: 185

Ala Leu Lys Asp Ala Val Lys
1               5
```

```
<210> SEQ ID NO 186
<211> LENGTH: 20
<212> TYPE: PRT
<213> ORGANISM: Staphylococcus aureus

<400> SEQUENCE: 186

Ile Pro Ala Ser Lys Val Pro Ala Phe Lys Ala Gly Lys Ala Leu Lys
1               5                   10                  15

Asp Ala Val Lys
            20

<210> SEQ ID NO 187
<211> LENGTH: 6
<212> TYPE: PRT
<213> ORGANISM: Staphylococcus epidermidis

<400> SEQUENCE: 187

Ala Phe Lys Ala Gly Lys
1               5

<210> SEQ ID NO 188
<211> LENGTH: 7
<212> TYPE: PRT
<213> ORGANISM: Staphylococcus epidermidis

<400> SEQUENCE: 188

Ala Leu Lys Asp Ala Val Lys
1               5

<210> SEQ ID NO 189
<211> LENGTH: 20
<212> TYPE: PRT
<213> ORGANISM: Staphylococcus epidermidis

<400> SEQUENCE: 189

Ile Pro Ala Ser Lys Val Pro Ala Phe Lys Ala Gly Lys Ala Leu Lys
1               5                   10                  15

Asp Ala Val Lys
            20

<210> SEQ ID NO 190
<211> LENGTH: 6
<212> TYPE: PRT
<213> ORGANISM: Haemophilus influenzae

<400> SEQUENCE: 190

Ala Phe Val Ser Gly Lys
1               5

<210> SEQ ID NO 191
<211> LENGTH: 7
<212> TYPE: PRT
<213> ORGANISM: Haemophilus influenzae

<400> SEQUENCE: 191

Ala Leu Lys Asp Ala Ile Lys
1               5

<210> SEQ ID NO 192
<211> LENGTH: 20
<212> TYPE: PRT
<213> ORGANISM: Haemophilus influenzae
```

```
<400> SEQUENCE: 192

Ile Ala Ala Ser Lys Val Pro Ala Phe Val Ser Gly Lys Ala Leu Lys
1               5                   10                  15

Asp Ala Ile Lys
            20

<210> SEQ ID NO 193
<211> LENGTH: 6
<212> TYPE: PRT
<213> ORGANISM: Aggregatibacter actinomycetemcomitans

<400> SEQUENCE: 193

Ala Phe Val Ser Gly Lys
1               5

<210> SEQ ID NO 194
<211> LENGTH: 7
<212> TYPE: PRT
<213> ORGANISM: Aggregatibacter actinomycetemcomitans

<400> SEQUENCE: 194

Ala Leu Lys Asp Ala Val Lys
1               5

<210> SEQ ID NO 195
<211> LENGTH: 20
<212> TYPE: PRT
<213> ORGANISM: Aggregatibacter actinomycetemcomitans

<400> SEQUENCE: 195

Ile Ala Ala Ser Lys Val Pro Ala Phe Val Ser Gly Lys Ala Leu Lys
1               5                   10                  15

Asp Ala Val Lys
            20

<210> SEQ ID NO 196
<211> LENGTH: 6
<212> TYPE: PRT
<213> ORGANISM: Vibrio cholerae

<400> SEQUENCE: 196

Ala Phe Val Ala Gly Lys
1               5

<210> SEQ ID NO 197
<211> LENGTH: 7
<212> TYPE: PRT
<213> ORGANISM: Vibrio cholerae

<400> SEQUENCE: 197

Ala Leu Lys Asp Ala Ile Lys
1               5

<210> SEQ ID NO 198
<211> LENGTH: 20
<212> TYPE: PRT
<213> ORGANISM: Vibrio cholerae

<400> SEQUENCE: 198

Ile Ala Ala Ala Asn Val Pro Ala Phe Val Ala Gly Lys Ala Leu Lys
1               5                   10                  15

Asp Ala Ile Lys
            20
```

<210> SEQ ID NO 199
<211> LENGTH: 6
<212> TYPE: PRT
<213> ORGANISM: Escherichia coli

<400> SEQUENCE: 199

Ala Phe Val Ser Gly Lys
1               5

<210> SEQ ID NO 200
<211> LENGTH: 7
<212> TYPE: PRT
<213> ORGANISM: Escherichia coli

<400> SEQUENCE: 200

Ala Leu Lys Asp Ala Val Lys
1               5

<210> SEQ ID NO 201
<211> LENGTH: 20
<212> TYPE: PRT
<213> ORGANISM: Escherichia coli

<400> SEQUENCE: 201

Ile Ala Ala Ala Asn Val Pro Ala Phe Val Ser Gly Lys Ala Leu Lys
1               5                   10                  15

Asp Ala Val Lys
            20

<210> SEQ ID NO 202
<211> LENGTH: 6
<212> TYPE: PRT
<213> ORGANISM: Pseudomonas aeruginosa

<400> SEQUENCE: 202

Gly Phe Lys Ala Gly Lys
1               5

<210> SEQ ID NO 203
<211> LENGTH: 7
<212> TYPE: PRT
<213> ORGANISM: Pseudomonas aeruginosa

<400> SEQUENCE: 203

Ala Leu Lys Asp Ala Val Asn
1               5

<210> SEQ ID NO 204
<211> LENGTH: 20
<212> TYPE: PRT
<213> ORGANISM: Pseudomonas aeruginosa

<400> SEQUENCE: 204

Ile Ala Ala Ala Lys Ile Pro Gly Phe Lys Ala Gly Lys Ala Leu Lys
1               5                   10                  15

Asp Ala Val Asn
            20

<210> SEQ ID NO 205
<211> LENGTH: 6
<212> TYPE: PRT
<213> ORGANISM: Escherichia coli

```
<400> SEQUENCE: 205

Ser Phe Arg Ala Gly Lys
1               5

<210> SEQ ID NO 206
<211> LENGTH: 7
<212> TYPE: PRT
<213> ORGANISM: Escherichia coli

<400> SEQUENCE: 206

Ala Leu Lys Asp Ala Val Asn
1               5

<210> SEQ ID NO 207
<211> LENGTH: 20
<212> TYPE: PRT
<213> ORGANISM: Escherichia coli

<400> SEQUENCE: 207

Ile Ala Ala Ala Lys Val Pro Ser Phe Arg Ala Gly Lys Ala Leu Lys
1               5                   10                  15

Asp Ala Val Asn
            20

<210> SEQ ID NO 208
<211> LENGTH: 6
<212> TYPE: PRT
<213> ORGANISM: Vibrio cholerae

<400> SEQUENCE: 208

Ser Phe Lys Ala Gly Lys
1               5

<210> SEQ ID NO 209
<211> LENGTH: 7
<212> TYPE: PRT
<213> ORGANISM: Vibrio cholerae

<400> SEQUENCE: 209

Ala Leu Lys Asp Ala Cys Asn
1               5

<210> SEQ ID NO 210
<211> LENGTH: 20
<212> TYPE: PRT
<213> ORGANISM: Vibrio cholerae

<400> SEQUENCE: 210

Ile Ala Glu Ala Lys Val Pro Ser Phe Lys Ala Gly Lys Ala Leu Lys
1               5                   10                  15

Asp Ala Cys Asn
            20

<210> SEQ ID NO 211
<211> LENGTH: 6
<212> TYPE: PRT
<213> ORGANISM: Bordetella pertussis

<400> SEQUENCE: 211

Lys Phe Arg Pro Gly Lys
1               5
```

<210> SEQ ID NO 212
<211> LENGTH: 7
<212> TYPE: PRT
<213> ORGANISM: Bordetella pertussis

<400> SEQUENCE: 212

Ala Leu Lys Asp Ala Val Asn
1 5

<210> SEQ ID NO 213
<211> LENGTH: 20
<212> TYPE: PRT
<213> ORGANISM: Bordetella pertussis

<400> SEQUENCE: 213

Ile Lys Lys Ala Lys Val Pro Lys Phe Arg Pro Gly Lys Ala Leu Lys
1 5 10 15

Asp Ala Val Asn
20

<210> SEQ ID NO 214
<211> LENGTH: 6
<212> TYPE: PRT
<213> ORGANISM: Prevotella melaninogenica

<400> SEQUENCE: 214

Lys Phe Lys Ala Gly Ala
1 5

<210> SEQ ID NO 215
<211> LENGTH: 8
<212> TYPE: PRT
<213> ORGANISM: Prevotella melaninogenica

<400> SEQUENCE: 215

Glu Leu Ala Asp Ala Val Asn Lys
1 5

<210> SEQ ID NO 216
<211> LENGTH: 20
<212> TYPE: PRT
<213> ORGANISM: Prevotella melaninogenica

<400> SEQUENCE: 216

Ala Ala Lys Lys Val Ala Lys Phe Lys Ala Gly Ala Glu Leu Ala Asp
1 5 10 15

Ala Val Asn Lys
20

<210> SEQ ID NO 217
<211> LENGTH: 6
<212> TYPE: PRT
<213> ORGANISM: Prevotella intermedia

<400> SEQUENCE: 217

Lys Phe Lys Pro Gly Ala
1 5

<210> SEQ ID NO 218
<211> LENGTH: 8
<212> TYPE: PRT
<213> ORGANISM: Prevotella intermedia

```
<400> SEQUENCE: 218

Glu Leu Ala Asp Ala Val Asn Ala
1               5

<210> SEQ ID NO 219
<211> LENGTH: 20
<212> TYPE: PRT
<213> ORGANISM: Prevotella intermedia

<400> SEQUENCE: 219

Ala Ala Lys Lys Val Ala Lys Phe Lys Pro Gly Ala Glu Leu Ala Asp
1               5                   10                  15

Ala Val Asn Ala
            20

<210> SEQ ID NO 220
<211> LENGTH: 6
<212> TYPE: PRT
<213> ORGANISM: Moraxella catarrhalis

<400> SEQUENCE: 220

Ser Phe Lys Ala Gly Lys
1               5

<210> SEQ ID NO 221
<211> LENGTH: 7
<212> TYPE: PRT
<213> ORGANISM: Moraxella catarrhalis

<400> SEQUENCE: 221

Val Leu Lys Glu Ser Val Asn
1               5

<210> SEQ ID NO 222
<211> LENGTH: 20
<212> TYPE: PRT
<213> ORGANISM: Moraxella catarrhalis

<400> SEQUENCE: 222

Ile Ala Ala Ser Lys Val Pro Ser Phe Lys Ala Gly Lys Val Leu Lys
1               5                   10                  15

Glu Ser Val Asn
            20

<210> SEQ ID NO 223
<211> LENGTH: 6
<212> TYPE: PRT
<213> ORGANISM: Porphyromonas gingivalis

<400> SEQUENCE: 223

Arg Phe Lys Pro Gly Ser
1               5

<210> SEQ ID NO 224
<211> LENGTH: 5
<212> TYPE: PRT
<213> ORGANISM: Porphyromonas gingivalis

<400> SEQUENCE: 224

Thr Leu Glu Leu Lys
1               5
```

```
<210> SEQ ID NO 225
<211> LENGTH: 20
<212> TYPE: PRT
<213> ORGANISM: Porphyromonas gingivalis

<400> SEQUENCE: 225

Ile Ser Ile Pro Ala Arg Lys Val Val Arg Phe Lys Pro Gly Ser Thr
1               5                   10                  15

Leu Glu Leu Lys
            20

<210> SEQ ID NO 226
<211> LENGTH: 6
<212> TYPE: PRT
<213> ORGANISM: Helicobacter pylori

<400> SEQUENCE: 226

Lys Phe Lys Pro Gly Lys
1               5

<210> SEQ ID NO 227
<211> LENGTH: 10
<212> TYPE: PRT
<213> ORGANISM: Helicobacter pylori

<400> SEQUENCE: 227

Thr Leu Lys Gln Lys Val Glu Glu Gly Lys
1               5                   10

<210> SEQ ID NO 228
<211> LENGTH: 20
<212> TYPE: PRT
<213> ORGANISM: Helicobacter pylori

<400> SEQUENCE: 228

Lys Arg Val Pro Lys Phe Lys Pro Gly Lys Thr Leu Lys Gln Lys Val
1               5                   10                  15

Glu Glu Gly Lys
            20

<210> SEQ ID NO 229
<211> LENGTH: 6
<212> TYPE: PRT
<213> ORGANISM: Prevotella melaninogenica

<400> SEQUENCE: 229

Ser Phe Lys Pro Ala Lys
1               5

<210> SEQ ID NO 230
<211> LENGTH: 8
<212> TYPE: PRT
<213> ORGANISM: Prevotella melaninogenica

<400> SEQUENCE: 230

Thr Phe Ile Glu Asp Met Lys Lys
1               5

<210> SEQ ID NO 231
<211> LENGTH: 20
<212> TYPE: PRT
<213> ORGANISM: Prevotella melaninogenica
```

```
<400> SEQUENCE: 231

Pro Ala His Asp Phe Pro Ser Phe Lys Pro Ala Lys Thr Phe Ile Glu
1               5                   10                  15

Asp Met Lys Lys
            20

<210> SEQ ID NO 232
<211> LENGTH: 6
<212> TYPE: PRT
<213> ORGANISM: Prevotella intermedia

<400> SEQUENCE: 232

Ser Phe Lys Pro Ala Lys
1               5

<210> SEQ ID NO 233
<211> LENGTH: 8
<212> TYPE: PRT
<213> ORGANISM: Prevotella intermedia

<400> SEQUENCE: 233

Thr Phe Ile Glu Asp Met Lys Lys
1               5

<210> SEQ ID NO 234
<211> LENGTH: 20
<212> TYPE: PRT
<213> ORGANISM: Prevotella intermedia

<400> SEQUENCE: 234

Pro Ala His Asp Phe Pro Ser Phe Lys Pro Ala Lys Thr Phe Ile Glu
1               5                   10                  15

Asp Met Lys Lys
            20

<210> SEQ ID NO 235
<211> LENGTH: 6
<212> TYPE: PRT
<213> ORGANISM: Porphyromonas gingivalis

<400> SEQUENCE: 235

Ala Phe Lys Pro Ser Lys
1               5

<210> SEQ ID NO 236
<211> LENGTH: 9
<212> TYPE: PRT
<213> ORGANISM: Porphyromonas gingivalis

<400> SEQUENCE: 236

Ile Phe Met Ser Gln Met Lys Gln Asp
1               5

<210> SEQ ID NO 237
<211> LENGTH: 20
<212> TYPE: PRT
<213> ORGANISM: Porphyromonas gingivalis

<400> SEQUENCE: 237

Lys Arg Asn Ile Pro Ala Phe Lys Pro Ser Lys Ile Phe Met Ser Gln
1               5                   10                  15

Met Lys Gln Asp
            20
```

```
<210> SEQ ID NO 238
<211> LENGTH: 6
<212> TYPE: PRT
<213> ORGANISM: Mycobacterium tuberculosis

<400> SEQUENCE: 238

Ala Phe Arg Pro Gly Ala
1               5

<210> SEQ ID NO 239
<211> LENGTH: 22
<212> TYPE: PRT
<213> ORGANISM: Mycobacterium tuberculosis

<400> SEQUENCE: 239

Gln Phe Lys Ala Val Val Ser Gly Ala Gln Arg Leu Pro Ala Glu Gly
1               5                   10                  15

Pro Ala Val Lys Arg Gly
            20

<210> SEQ ID NO 240
<211> LENGTH: 20
<212> TYPE: PRT
<213> ORGANISM: Mycobacterium tuberculosis

<400> SEQUENCE: 240

Ala Lys Arg Pro Ala Thr Lys Ala Pro Ala Lys Lys Ala Thr Ala Arg
1               5                   10                  15

Arg Gly Arg Lys
            20

<210> SEQ ID NO 241
<211> LENGTH: 6
<212> TYPE: PRT
<213> ORGANISM: Mycobacterium smegmatis

<400> SEQUENCE: 241

Ala Phe Arg Pro Gly Ala
1               5

<210> SEQ ID NO 242
<211> LENGTH: 22
<212> TYPE: PRT
<213> ORGANISM: Mycobacterium smegmatis

<400> SEQUENCE: 242

Gln Phe Lys Ala Val Ile Ser Gly Ala Gln Lys Leu Pro Ala Asp Gly
1               5                   10                  15

Pro Ala Val Lys Arg Gly
            20

<210> SEQ ID NO 243
<211> LENGTH: 20
<212> TYPE: PRT
<213> ORGANISM: Mycobacterium smegmatis

<400> SEQUENCE: 243

Thr Lys Ala Pro Ala Lys Lys Ala Ala Ala Lys Lys Ala Pro Ala Lys
1               5                   10                  15

Lys Gly Arg Arg
            20
```

-continued

```
<210> SEQ ID NO 244
<211> LENGTH: 6
<212> TYPE: PRT
<213> ORGANISM: Prevotella melaninogenica

<400> SEQUENCE: 244

Asn Phe Lys Pro Ala Ala
1               5

<210> SEQ ID NO 245
<211> LENGTH: 14
<212> TYPE: PRT
<213> ORGANISM: Prevotella melaninogenica

<400> SEQUENCE: 245

Thr Ile Lys Gly His Val Arg Lys Gly Gly Gln Asp Asn Gly
1               5                   10

<210> SEQ ID NO 246
<211> LENGTH: 20
<212> TYPE: PRT
<213> ORGANISM: Prevotella melaninogenica

<400> SEQUENCE: 246

Asn Phe Lys Pro Ala Ala Thr Ile Lys Gly His Val Arg Lys Gly Gly
1               5                   10                  15

Gln Asp Asn Gly
            20

<210> SEQ ID NO 247
<211> LENGTH: 6
<212> TYPE: PRT
<213> ORGANISM: Prevotella intermedia

<400> SEQUENCE: 247

Asn Phe Arg Ala Thr Ala
1               5

<210> SEQ ID NO 248
<211> LENGTH: 12
<212> TYPE: PRT
<213> ORGANISM: Prevotella intermedia

<400> SEQUENCE: 248

Ser Val Lys Glu Lys Leu Lys Lys Gly Gly Ala Glu
1               5                   10

<210> SEQ ID NO 249
<211> LENGTH: 20
<212> TYPE: PRT
<213> ORGANISM: Prevotella intermedia

<400> SEQUENCE: 249

Val Leu Asn Phe Arg Ala Thr Ala Ser Val Lys Glu Lys Leu Lys Lys
1               5                   10                  15

Gly Gly Ala Glu
            20

<210> SEQ ID NO 250
<211> LENGTH: 6
<212> TYPE: PRT
<213> ORGANISM: Escherichia coli
```

```
<400> SEQUENCE: 250

Thr Phe Arg Pro Gly Gln
1               5

<210> SEQ ID NO 251
<211> LENGTH: 14
<212> TYPE: PRT
<213> ORGANISM: Escherichia coli

<400> SEQUENCE: 251

Lys Leu Lys Ser Arg Val Glu Asn Ala Ser Pro Lys Asp Glu
1               5                   10

<210> SEQ ID NO 252
<211> LENGTH: 20
<212> TYPE: PRT
<213> ORGANISM: Escherichia coli

<400> SEQUENCE: 252

Thr Phe Arg Pro Gly Gln Lys Leu Lys Ser Arg Val Glu Asn Ala Ser
1               5                   10                  15

Pro Lys Asp Glu
            20

<210> SEQ ID NO 253
<211> LENGTH: 6
<212> TYPE: PRT
<213> ORGANISM: Salmonella enterica

<400> SEQUENCE: 253

Thr Phe Arg Pro Gly Gln
1               5

<210> SEQ ID NO 254
<211> LENGTH: 14
<212> TYPE: PRT
<213> ORGANISM: Salmonella enterica

<400> SEQUENCE: 254

Lys Leu Lys Ser Arg Val Glu Asn Ala Ser Pro Lys Glu Glu
1               5                   10

<210> SEQ ID NO 255
<211> LENGTH: 20
<212> TYPE: PRT
<213> ORGANISM: Salmonella enterica

<400> SEQUENCE: 255

Thr Phe Arg Pro Gly Gln Lys Leu Lys Ser Arg Val Glu Asn Ala Ser
1               5                   10                  15

Pro Lys Glu Glu
            20

<210> SEQ ID NO 256
<211> LENGTH: 6
<212> TYPE: PRT
<213> ORGANISM: Vibrio cholerae

<400> SEQUENCE: 256

Thr Phe Arg Pro Gly Gln
1               5
```

<210> SEQ ID NO 257
<211> LENGTH: 13
<212> TYPE: PRT
<213> ORGANISM: Vibrio cholerae

<400> SEQUENCE: 257

Lys Leu Lys Ala Arg Val Glu Asn Ile Lys Val Glu Lys
1               5                   10

<210> SEQ ID NO 258
<211> LENGTH: 20
<212> TYPE: PRT
<213> ORGANISM: Vibrio cholerae

<400> SEQUENCE: 258

Val Thr Phe Arg Pro Gly Gln Lys Leu Lys Ala Arg Val Glu Asn Ile
1               5                   10                  15

Lys Val Glu Lys
            20

<210> SEQ ID NO 259
<211> LENGTH: 6
<212> TYPE: PRT
<213> ORGANISM: Pseudomonas aeruginosa

<400> SEQUENCE: 259

Thr Phe Arg Pro Gly Gln
1               5

<210> SEQ ID NO 260
<211> LENGTH: 14
<212> TYPE: PRT
<213> ORGANISM: Pseudomonas aeruginosa

<400> SEQUENCE: 260

Lys Leu Lys Ala Arg Val Glu Ala Tyr Ala Gly Thr Lys Ser
1               5                   10

<210> SEQ ID NO 261
<211> LENGTH: 20
<212> TYPE: PRT
<213> ORGANISM: Pseudomonas aeruginosa

<400> SEQUENCE: 261

Thr Phe Arg Pro Gly Gln Lys Leu Lys Ala Arg Val Glu Ala Tyr Ala
1               5                   10                  15

Gly Thr Lys Ser
            20

<210> SEQ ID NO 262
<211> LENGTH: 6
<212> TYPE: PRT
<213> ORGANISM: Burkholderia cenocepacia

<400> SEQUENCE: 262

Thr Phe His Ala Ser Gln
1               5

<210> SEQ ID NO 263
<211> LENGTH: 11
<212> TYPE: PRT
<213> ORGANISM: Burkholderia cenocepacia -continued

```
<400> SEQUENCE: 263

Lys Leu Lys Ala Leu Val Glu Asn Gly Ala Glu
1               5                   10

<210> SEQ ID NO 264
<211> LENGTH: 20
<212> TYPE: PRT
<213> ORGANISM: Burkholderia cenocepacia

<400> SEQUENCE: 264

Arg Val Val Thr Phe His Ala Ser Gln Lys Leu Lys Ala Leu Val Glu
1               5                   10                  15

Asn Gly Ala Glu
            20

<210> SEQ ID NO 265
<211> LENGTH: 6
<212> TYPE: PRT
<213> ORGANISM: Burkholderia pseudomallei

<400> SEQUENCE: 265

Thr Phe His Ala Ser Gln
1               5

<210> SEQ ID NO 266
<211> LENGTH: 16
<212> TYPE: PRT
<213> ORGANISM: Burkholderia pseudomallei

<400> SEQUENCE: 266

Lys Leu Lys Ala Leu Val Glu Asn Gly Ala Glu Pro Asp Leu Ala Arg
1               5                   10                  15

<210> SEQ ID NO 267
<211> LENGTH: 20
<212> TYPE: PRT
<213> ORGANISM: Burkholderia pseudomallei

<400> SEQUENCE: 267

His Ala Ser Gln Lys Leu Lys Ala Leu Val Glu Asn Gly Ala Glu Pro
1               5                   10                  15

Asp Leu Ala Arg
            20

<210> SEQ ID NO 268
<211> LENGTH: 6
<212> TYPE: PRT
<213> ORGANISM: Bordetella pertussis

<400> SEQUENCE: 268

Thr Phe His Ala Ser Gln
1               5

<210> SEQ ID NO 269
<211> LENGTH: 19
<212> TYPE: PRT
<213> ORGANISM: Bordetella pertussis

<400> SEQUENCE: 269

Lys Leu Lys Ser Val Val Glu Gln Pro Asn Ser Pro Pro Asp Pro Ala
1               5                   10                  15

Ser Ala Glu
```

<210> SEQ ID NO 270
<211> LENGTH: 20
<212> TYPE: PRT
<213> ORGANISM: Bordetella pertussis

<400> SEQUENCE: 270

Gln Lys Leu Lys Ser Val Val Glu Gln Pro Asn Ser Pro Pro Asp Pro
1               5                   10                  15

Ala Ser Ala Glu
            20

<210> SEQ ID NO 271
<211> LENGTH: 6
<212> TYPE: PRT
<213> ORGANISM: Neisseria gonorrhoeae

<400> SEQUENCE: 271

Thr Phe His Ala Ser Gln
1               5

<210> SEQ ID NO 272
<211> LENGTH: 14
<212> TYPE: PRT
<213> ORGANISM: Neisseria gonorrhoeae

<400> SEQUENCE: 272

Lys Leu Lys Gly Met Val Glu His Tyr Tyr Asp Lys Gln Arg
1               5                   10

<210> SEQ ID NO 273
<211> LENGTH: 20
<212> TYPE: PRT
<213> ORGANISM: Neisseria gonorrhoeae

<400> SEQUENCE: 273

Thr Phe His Ala Ser Gln Lys Leu Lys Gly Met Val Glu His Tyr Tyr
1               5                   10                  15

Asp Lys Gln Arg
            20

<210> SEQ ID NO 274
<211> LENGTH: 6
<212> TYPE: PRT
<213> ORGANISM: Neisseria meningitidis

<400> SEQUENCE: 274

Thr Phe His Ala Ser Gln
1               5

<210> SEQ ID NO 275
<211> LENGTH: 14
<212> TYPE: PRT
<213> ORGANISM: Neisseria meningitidis

<400> SEQUENCE: 275

Lys Leu Lys Ser Met Val Glu His Tyr Tyr Asp Lys Gln Arg
1               5                   10

<210> SEQ ID NO 276
<211> LENGTH: 20
<212> TYPE: PRT
<213> ORGANISM: Neisseria meningitidis

```
<400> SEQUENCE: 276

Thr Phe His Ala Ser Gln Lys Leu Lys Ser Met Val Glu His Tyr Tyr
1               5                   10                  15

Asp Lys Gln Arg
            20

<210> SEQ ID NO 277
<211> LENGTH: 6
<212> TYPE: PRT
<213> ORGANISM: Haemophilus influenzae

<400> SEQUENCE: 277

Thr Phe Lys Pro Gly Gln
1               5

<210> SEQ ID NO 278
<211> LENGTH: 10
<212> TYPE: PRT
<213> ORGANISM: Haemophilus influenzae

<400> SEQUENCE: 278

Lys Leu Arg Ala Arg Val Glu Lys Thr Lys
1               5                   10

<210> SEQ ID NO 279
<211> LENGTH: 20
<212> TYPE: PRT
<213> ORGANISM: Haemophilus influenzae

<400> SEQUENCE: 279

Arg Arg Val Val Thr Phe Lys Pro Gly Gln Lys Leu Arg Ala Arg Val
1               5                   10                  15

Glu Lys Thr Lys
            20

<210> SEQ ID NO 280
<211> LENGTH: 6
<212> TYPE: PRT
<213> ORGANISM: Aggregatibacter actinomycetemcomitans

<400> SEQUENCE: 280

Val Phe Lys Pro Gly Gln
1               5

<210> SEQ ID NO 281
<211> LENGTH: 13
<212> TYPE: PRT
<213> ORGANISM: Aggregatibacter actinomycetemcomitans

<400> SEQUENCE: 281

Lys Leu Arg Asn Arg Val Glu Lys Val Lys Pro Lys Ala
1               5                   10

<210> SEQ ID NO 282
<211> LENGTH: 20
<212> TYPE: PRT
<213> ORGANISM: Aggregatibacter actinomycetemcomitans

<400> SEQUENCE: 282

Val Val Phe Lys Pro Gly Gln Lys Leu Arg Asn Arg Val Glu Lys Val
1               5                   10                  15

Lys Pro Lys Ala
            20
```

-continued

```
<210> SEQ ID NO 283
<211> LENGTH: 6
<212> TYPE: PRT
<213> ORGANISM: Moraxella catarrhalis

<400> SEQUENCE: 283

Thr Phe Lys Ala Gly Gln
1               5

<210> SEQ ID NO 284
<211> LENGTH: 12
<212> TYPE: PRT
<213> ORGANISM: Moraxella catarrhalis

<400> SEQUENCE: 284

Lys Leu Arg Gly Trp Ile Asp Ser Gln Asn Glu Gly
1               5                   10

<210> SEQ ID NO 285
<211> LENGTH: 20
<212> TYPE: PRT
<213> ORGANISM: Moraxella catarrhalis

<400> SEQUENCE: 285

Val Val Thr Phe Lys Ala Gly Gln Lys Leu Arg Gly Trp Ile Asp Ser
1               5                   10                  15

Gln Asn Glu Gly
            20

<210> SEQ ID NO 286
<211> LENGTH: 6
<212> TYPE: PRT
<213> ORGANISM: Treponema palladium

<400> SEQUENCE: 286

Val Phe Arg Pro Ser Lys
1               5

<210> SEQ ID NO 287
<211> LENGTH: 17
<212> TYPE: PRT
<213> ORGANISM: Treponema palladium

<400> SEQUENCE: 287

Arg Leu Lys Ser Ala Val Arg Gly Tyr Arg Ser Gly Glu Val Gly Ala
1               5                   10                  15

Asp

<210> SEQ ID NO 288
<211> LENGTH: 20
<212> TYPE: PRT
<213> ORGANISM: Treponema palladium

<400> SEQUENCE: 288

Pro Ser Lys Arg Leu Lys Ser Ala Val Arg Gly Tyr Arg Ser Gly Glu
1               5                   10                  15

Val Gly Ala Asp
            20

<210> SEQ ID NO 289
<211> LENGTH: 6
<212> TYPE: PRT
<213> ORGANISM: Prevotella melaninogenica
```

```
<400> SEQUENCE: 289

Ser Phe Thr Pro Asp Thr
1               5

<210> SEQ ID NO 290
<211> LENGTH: 22
<212> TYPE: PRT
<213> ORGANISM: Prevotella melaninogenica

<400> SEQUENCE: 290

Val Met Lys Glu Leu Val Asn Lys Pro Phe Ser Gln Phe Glu Thr Val
1               5                  10                  15

Val Ile Asn Asp Gly Val
            20

<210> SEQ ID NO 291
<211> LENGTH: 20
<212> TYPE: PRT
<213> ORGANISM: Prevotella melaninogenica

<400> SEQUENCE: 291

Met Gln Ala Gly Asp Thr Met Lys Val Pro Lys Val Glu Leu Arg Pro
1               5                  10                  15

Glu Tyr Arg Lys
            20

<210> SEQ ID NO 292
<211> LENGTH: 6
<212> TYPE: PRT
<213> ORGANISM: Prevotella intermedia

<400> SEQUENCE: 292

Ser Phe Thr Pro Asp Ala
1               5

<210> SEQ ID NO 293
<211> LENGTH: 22
<212> TYPE: PRT
<213> ORGANISM: Prevotella intermedia

<400> SEQUENCE: 293

Thr Met Lys Glu Leu Val Asn Lys Pro Phe Ala Gln Phe Glu Thr Val
1               5                  10                  15

Val Leu Asn Asp Gly Val
            20

<210> SEQ ID NO 294
<211> LENGTH: 20
<212> TYPE: PRT
<213> ORGANISM: Prevotella intermedia

<400> SEQUENCE: 294

Ser Ala Gly Asp Thr Met Lys Val Pro Lys Val Glu Leu Arg Pro Gln
1               5                  10                  15

Tyr Arg Thr Lys
            20

<210> SEQ ID NO 295
<211> LENGTH: 6
<212> TYPE: PRT
<213> ORGANISM: Escherichia coli
```

```
<400> SEQUENCE: 295

His Phe Lys Pro Gly Lys
1               5

<210> SEQ ID NO 296
<211> LENGTH: 10
<212> TYPE: PRT
<213> ORGANISM: Escherichia coli

<400> SEQUENCE: 296

Glu Leu Arg Asp Arg Ala Asn Ile Tyr Gly
1               5                   10

<210> SEQ ID NO 297
<211> LENGTH: 20
<212> TYPE: PRT
<213> ORGANISM: Escherichia coli

<400> SEQUENCE: 297

Lys Tyr Val Pro His Phe Lys Pro Gly Lys Glu Leu Arg Asp Arg Ala
1               5                   10                  15

Asn Ile Tyr Gly
            20

<210> SEQ ID NO 298
<211> LENGTH: 6
<212> TYPE: PRT
<213> ORGANISM: Salmonella enterica

<400> SEQUENCE: 298

His Phe Lys Pro Gly Lys
1               5

<210> SEQ ID NO 299
<211> LENGTH: 10
<212> TYPE: PRT
<213> ORGANISM: Salmonella enterica

<400> SEQUENCE: 299

Glu Leu Arg Asp Arg Ala Asn Ile Tyr Gly
1               5                   10

<210> SEQ ID NO 300
<211> LENGTH: 20
<212> TYPE: PRT
<213> ORGANISM: Salmonella enterica

<400> SEQUENCE: 300

Lys Tyr Val Pro His Phe Lys Pro Gly Lys Glu Leu Arg Asp Arg Ala
1               5                   10                  15

Asn Ile Tyr Gly
            20

<210> SEQ ID NO 301
<211> LENGTH: 6
<212> TYPE: PRT
<213> ORGANISM: Vibrio cholerae

<400> SEQUENCE: 301

His Phe Lys Pro Gly Lys
1               5
```

-continued

<210> SEQ ID NO 302
<211> LENGTH: 8
<212> TYPE: PRT
<213> ORGANISM: Vibrio cholerae

<400> SEQUENCE: 302

Glu Leu Arg Glu Arg Val Asn Leu
1               5

<210> SEQ ID NO 303
<211> LENGTH: 20
<212> TYPE: PRT
<213> ORGANISM: Vibrio cholerae

<400> SEQUENCE: 303

Glu Gly Lys Tyr Val Pro His Phe Lys Pro Gly Lys Glu Leu Arg Glu
1               5                   10                  15

Arg Val Asn Leu
            20

<210> SEQ ID NO 304
<211> LENGTH: 6
<212> TYPE: PRT
<213> ORGANISM: Pseudomonas aeruginosa

<400> SEQUENCE: 304

His Phe Lys Pro Gly Lys
1               5

<210> SEQ ID NO 305
<211> LENGTH: 10
<212> TYPE: PRT
<213> ORGANISM: Pseudomonas aeruginosa

<400> SEQUENCE: 305

Glu Leu Arg Asp Arg Val Asn Glu Pro Glu
1               5                   10

<210> SEQ ID NO 306
<211> LENGTH: 20
<212> TYPE: PRT
<213> ORGANISM: Pseudomonas aeruginosa

<400> SEQUENCE: 306

Lys Phe Val Pro His Phe Lys Pro Gly Lys Glu Leu Arg Asp Arg Val
1               5                   10                  15

Asn Glu Pro Glu
            20

<210> SEQ ID NO 307
<211> LENGTH: 6
<212> TYPE: PRT
<213> ORGANISM: Haemophilus influenzae

<400> SEQUENCE: 307

Tyr Phe Lys Ala Gly Lys
1               5

<210> SEQ ID NO 308
<211> LENGTH: 10
<212> TYPE: PRT
<213> ORGANISM: Haemophilus influenzae

```
<400> SEQUENCE: 308

Glu Leu Lys Ala Arg Val Asp Val Gln Ala
1               5                   10

<210> SEQ ID NO 309
<211> LENGTH: 20
<212> TYPE: PRT
<213> ORGANISM: Haemophilus influenzae

<400> SEQUENCE: 309

Lys Ser Val Pro Tyr Phe Lys Ala Gly Lys Glu Leu Lys Ala Arg Val
1               5                   10                  15

Asp Val Gln Ala
            20

<210> SEQ ID NO 310
<211> LENGTH: 6
<212> TYPE: PRT
<213> ORGANISM: Aggregatibacter actinomycetemcomitans

<400> SEQUENCE: 310

Tyr Phe Lys Ala Gly Lys
1               5

<210> SEQ ID NO 311
<211> LENGTH: 11
<212> TYPE: PRT
<213> ORGANISM: Aggregatibacter actinomycetemcomitans

<400> SEQUENCE: 311

Glu Leu Arg Glu Arg Val Asp Val Tyr Ala Ala
1               5                   10

<210> SEQ ID NO 312
<211> LENGTH: 20
<212> TYPE: PRT
<213> ORGANISM: Aggregatibacter actinomycetemcomitans

<400> SEQUENCE: 312

Cys Val Pro Tyr Phe Lys Ala Gly Lys Glu Leu Arg Glu Arg Val Asp
1               5                   10                  15

Val Tyr Ala Ala
            20

<210> SEQ ID NO 313
<211> LENGTH: 6
<212> TYPE: PRT
<213> ORGANISM: Neisseria gonorrhoeae

<400> SEQUENCE: 313

His Phe Lys Pro Gly Lys
1               5

<210> SEQ ID NO 314
<211> LENGTH: 15
<212> TYPE: PRT
<213> ORGANISM: Neisseria gonorrhoeae

<400> SEQUENCE: 314

Glu Leu Arg Glu Arg Val Asp Leu Ala Leu Lys Glu Asn Ala Asn
1               5                   10                  15
```

-continued

```
<210> SEQ ID NO 315
<211> LENGTH: 20
<212> TYPE: PRT
<213> ORGANISM: Neisseria gonorrhoeae

<400> SEQUENCE: 315

Phe Lys Pro Gly Lys Glu Leu Arg Glu Arg Val Asp Leu Ala Leu Lys
1               5                   10                  15

Glu Asn Ala Asn
        20

<210> SEQ ID NO 316
<211> LENGTH: 6
<212> TYPE: PRT
<213> ORGANISM: Neisseria meningitidis

<400> SEQUENCE: 316

His Phe Lys Pro Gly Lys
1               5

<210> SEQ ID NO 317
<211> LENGTH: 15
<212> TYPE: PRT
<213> ORGANISM: Neisseria meningitidis

<400> SEQUENCE: 317

Glu Leu Arg Glu Arg Val Asp Leu Ala Leu Lys Glu Asn Ala Asn
1               5                   10                  15

<210> SEQ ID NO 318
<211> LENGTH: 20
<212> TYPE: PRT
<213> ORGANISM: Neisseria meningitidis

<400> SEQUENCE: 318

Phe Lys Pro Gly Lys Glu Leu Arg Glu Arg Val Asp Leu Ala Leu Lys
1               5                   10                  15

Glu Asn Ala Asn
        20

<210> SEQ ID NO 319
<211> LENGTH: 6
<212> TYPE: PRT
<213> ORGANISM: Burkholderia cenocepacia

<400> SEQUENCE: 319

His Phe Lys Pro Gly Lys
1               5

<210> SEQ ID NO 320
<211> LENGTH: 23
<212> TYPE: PRT
<213> ORGANISM: Burkholderia cenocepacia

<400> SEQUENCE: 320

Glu Leu Arg Glu Arg Val Asp Gly Arg Ala Gly Glu Pro Leu Lys Ala
1               5                   10                  15

Asp Asp Pro Asp Asp Arg
        20

<210> SEQ ID NO 321
<211> LENGTH: 20
<212> TYPE: PRT
<213> ORGANISM: Burkholderia cenocepacia
```

-continued

```
<400> SEQUENCE: 321

Glu Arg Val Asp Gly Arg Ala Gly Glu Pro Leu Lys Ala Asp Pro
1               5                   10                  15

Asp Asp Asp Arg
            20

<210> SEQ ID NO 322
<211> LENGTH: 6
<212> TYPE: PRT
<213> ORGANISM: Burkholderia pseudomallei

<400> SEQUENCE: 322

His Phe Lys Pro Gly Lys
1               5

<210> SEQ ID NO 323
<211> LENGTH: 23
<212> TYPE: PRT
<213> ORGANISM: Burkholderia pseudomallei

<400> SEQUENCE: 323

Glu Leu Arg Glu Arg Val Asp Gly Arg Ala Gly Glu Pro Leu Lys Asn
1               5                   10                  15

Asp Glu Pro Glu Asp Ala Gln
            20

<210> SEQ ID NO 324
<211> LENGTH: 20
<212> TYPE: PRT
<213> ORGANISM: Burkholderia pseudomallei

<400> SEQUENCE: 324

Glu Arg Val Asp Gly Arg Ala Gly Glu Pro Leu Lys Asn Asp Glu Pro
1               5                   10                  15

Glu Asp Ala Gln
            20

<210> SEQ ID NO 325
<211> LENGTH: 6
<212> TYPE: PRT
<213> ORGANISM: Bordetella pertussis

<400> SEQUENCE: 325

His Phe Lys Ala Gly Lys
1               5

<210> SEQ ID NO 326
<211> LENGTH: 22
<212> TYPE: PRT
<213> ORGANISM: Bordetella pertussis

<400> SEQUENCE: 326

Glu Leu Arg Glu Trp Val Asp Leu Val Gly Asn Asp Gln Gly Asp Asp
1               5                   10                  15

Ser Ser Asn Gly Ser Ser
            20

<210> SEQ ID NO 327
<211> LENGTH: 20
<212> TYPE: PRT
<213> ORGANISM: Bordetella pertussis
```

```
<400> SEQUENCE: 327

Asp Ser Ser Asn Gly Ser Ser Asp Pro Leu Gln Ser Val Met Asp Met
1               5                   10                  15

His Ala Met His
            20

<210> SEQ ID NO 328
<211> LENGTH: 6
<212> TYPE: PRT
<213> ORGANISM: Moraxella catarrhalis

<400> SEQUENCE: 328

Tyr Phe Lys Pro Gly Lys
1               5

<210> SEQ ID NO 329
<211> LENGTH: 11
<212> TYPE: PRT
<213> ORGANISM: Moraxella catarrhalis

<400> SEQUENCE: 329

Ala Leu Arg Glu Ser Val Asn Leu Val Asn Asp
1               5                   10

<210> SEQ ID NO 330
<211> LENGTH: 20
<212> TYPE: PRT
<213> ORGANISM: Moraxella catarrhalis

<400> SEQUENCE: 330

Ala Thr Pro Tyr Phe Lys Pro Gly Lys Ala Leu Arg Glu Ser Val Asn
1               5                   10                  15

Leu Val Asn Asp
            20

<210> SEQ ID NO 331
<211> LENGTH: 6
<212> TYPE: PRT
<213> ORGANISM: Borrelia burgdorferi

<400> SEQUENCE: 331

Tyr Phe Arg Pro Gly Lys
1               5

<210> SEQ ID NO 332
<211> LENGTH: 11
<212> TYPE: PRT
<213> ORGANISM: Borrelia burgdorferi

<400> SEQUENCE: 332

Asp Leu Lys Glu Arg Val Trp Gly Ile Lys Gly
1               5                   10

<210> SEQ ID NO 333
<211> LENGTH: 20
<212> TYPE: PRT
<213> ORGANISM: Borrelia burgdorferi

<400> SEQUENCE: 333

His Val Ala Tyr Phe Arg Pro Gly Lys Asp Leu Lys Glu Arg Val Trp
1               5                   10                  15

Gly Ile Lys Gly
            20
```

```
<210> SEQ ID NO 334
<211> LENGTH: 6
<212> TYPE: PRT
<213> ORGANISM: Treponema denticola

<400> SEQUENCE: 334

Arg Phe Lys Pro Gly Lys
1               5

<210> SEQ ID NO 335
<211> LENGTH: 17
<212> TYPE: PRT
<213> ORGANISM: Treponema denticola

<400> SEQUENCE: 335

Glu Leu Lys Glu Ala Leu His Lys Ile Asp Thr Gln Glu Leu Ile Glu
1               5                   10                  15

Ser

<210> SEQ ID NO 336
<211> LENGTH: 20
<212> TYPE: PRT
<213> ORGANISM: Treponema denticola

<400> SEQUENCE: 336

Pro Gly Lys Glu Leu Lys Glu Ala Leu His Lys Ile Asp Thr Gln Glu
1               5                   10                  15

Leu Ile Glu Ser
            20

<210> SEQ ID NO 337
<211> LENGTH: 12
<212> TYPE: PRT
<213> ORGANISM: Escherichia coli

<400> SEQUENCE: 337

Gly Arg Asn Pro Lys Thr Gly Glu Asp Ile Pro Ile
1               5                   10

<210> SEQ ID NO 338
<211> LENGTH: 12
<212> TYPE: PRT
<213> ORGANISM: Escherichia coli

<400> SEQUENCE: 338

Gly Arg Asn Pro Lys Thr Gly Asp Lys Val Glu Leu
1               5                   10

<210> SEQ ID NO 339
<211> LENGTH: 12
<212> TYPE: PRT
<213> ORGANISM: Escherichia coli

<400> SEQUENCE: 339

Gly Arg Asn Pro Gln Thr Gly Lys Glu Ile Lys Ile
1               5                   10

<210> SEQ ID NO 340
<211> LENGTH: 12
<212> TYPE: PRT
<213> ORGANISM: Escherichia coli
```

```
<400> SEQUENCE: 340

Gly Arg Asn Pro Gln Thr Gly Lys Glu Ile Thr Ile
1               5                   10

<210> SEQ ID NO 341
<211> LENGTH: 94
<212> TYPE: PRT
<213> ORGANISM: Haemophilus influenzae

<400> SEQUENCE: 341

Met Thr Lys Ser Glu Leu Met Glu Lys Leu Ser Ala Lys Gln Pro Thr
1               5                   10                  15

Leu Ser Ala Lys Glu Ile Glu Asn Met Val Lys Asp Ile Leu Glu Phe
            20                  25                  30

Ile Ser Gln Ser Leu Glu Asn Gly Asp Arg Val Glu Val Arg Gly Phe
        35                  40                  45

Gly Ser Phe Ser Leu His His Arg Gln Pro Arg Leu Gly Arg Asn Pro
    50                  55                  60

Lys Thr Gly Asp Ser Val Asn Leu Ser Ala Lys Ser Val Pro Tyr Phe
65                  70                  75                  80

Lys Ala Gly Lys Glu Leu Lys Ala Arg Val Asp Val Gln Ala
                85                  90

<210> SEQ ID NO 342
<211> LENGTH: 20
<212> TYPE: PRT
<213> ORGANISM: Haemophilus influenzae

<400> SEQUENCE: 342

Met Thr Lys Ser Glu Leu Met Glu Lys Leu Ser Ala Lys Gln Pro Thr
1               5                   10                  15

Leu Ser Ala Lys
            20

<210> SEQ ID NO 343
<211> LENGTH: 20
<212> TYPE: PRT
<213> ORGANISM: Haemophilus influenzae

<400> SEQUENCE: 343

Thr Leu Ser Ala Lys Glu Ile Glu Asn Met Val Lys Asp Ile Leu Glu
1               5                   10                  15

Phe Ile Ser Gln
            20

<210> SEQ ID NO 344
<211> LENGTH: 20
<212> TYPE: PRT
<213> ORGANISM: Haemophilus influenzae

<400> SEQUENCE: 344

Glu Phe Ile Ser Gln Ser Leu Glu Asn Gly Asp Arg Val Glu Val Arg
1               5                   10                  15

Gly Phe Gly Ser
            20

<210> SEQ ID NO 345
<211> LENGTH: 20
<212> TYPE: PRT
<213> ORGANISM: Haemophilus influenzae
```

```
<400> SEQUENCE: 345

Arg Gly Phe Gly Ser Phe Ser Leu His His Arg Gln Pro Arg Leu Gly
1               5                   10                  15

Arg Asn Pro Lys
            20

<210> SEQ ID NO 346
<211> LENGTH: 20
<212> TYPE: PRT
<213> ORGANISM: Haemophilus influenzae

<400> SEQUENCE: 346

Gly Arg Asn Pro Lys Thr Gly Asp Ser Val Asn Leu Ser Ala Lys Ser
1               5                   10                  15

Val Pro Tyr Phe
            20

<210> SEQ ID NO 347
<211> LENGTH: 19
<212> TYPE: PRT
<213> ORGANISM: Haemophilus influenzae

<400> SEQUENCE: 347

Ser Val Pro Tyr Phe Lys Ala Gly Lys Glu Leu Lys Ala Arg Val Asp
1               5                   10                  15

Val Gln Ala

<210> SEQ ID NO 348
<211> LENGTH: 20
<212> TYPE: PRT
<213> ORGANISM: Haemophilus influenzae

<400> SEQUENCE: 348

Met Ala Thr Ile Thr Lys Leu Asp Ile Ile Glu Tyr Leu Ser Asp Lys
1               5                   10                  15

Tyr His Leu Ser
            20

<210> SEQ ID NO 349
<211> LENGTH: 20
<212> TYPE: PRT
<213> ORGANISM: Haemophilus influenzae

<400> SEQUENCE: 349

Lys Tyr His Leu Ser Lys Gln Asp Thr Lys Asn Val Val Glu Asn Phe
1               5                   10                  15

Leu Glu Glu Ile
            20

<210> SEQ ID NO 350
<211> LENGTH: 20
<212> TYPE: PRT
<213> ORGANISM: Haemophilus influenzae

<400> SEQUENCE: 350

Phe Leu Glu Glu Ile Arg Leu Ser Leu Glu Ser Gly Gln Asp Val Lys
1               5                   10                  15

Leu Ser Gly Phe
            20
```

```
<210> SEQ ID NO 351
<211> LENGTH: 20
<212> TYPE: PRT
<213> ORGANISM: Haemophilus influenzae

<400> SEQUENCE: 351

Lys Leu Ser Gly Phe Gly Asn Phe Glu Leu Arg Asp Lys Ser Ser Arg
1               5                   10                  15

Pro Gly Arg Asn
            20

<210> SEQ ID NO 352
<211> LENGTH: 20
<212> TYPE: PRT
<213> ORGANISM: Haemophilus influenzae

<400> SEQUENCE: 352

Arg Pro Gly Arg Asn Pro Lys Thr Gly Asp Val Val Pro Val Ser Ala
1               5                   10                  15

Arg Arg Val Val
            20

<210> SEQ ID NO 353
<211> LENGTH: 21
<212> TYPE: PRT
<213> ORGANISM: Haemophilus influenzae

<400> SEQUENCE: 353

Ala Arg Arg Val Val Thr Phe Lys Pro Gly Gln Lys Leu Arg Ala Arg
1               5                   10                  15

Val Glu Lys Thr Lys
            20

<210> SEQ ID NO 354
<211> LENGTH: 16
<212> TYPE: PRT
<213> ORGANISM: Haemophilus influenzae

<400> SEQUENCE: 354

Ile Glu Tyr Leu Ser Asp Lys Tyr His Leu Ser Lys Gln Asp Thr Lys
1               5                   10                  15

<210> SEQ ID NO 355
<211> LENGTH: 22
<212> TYPE: PRT
<213> ORGANISM: Haemophilus influenzae

<400> SEQUENCE: 355

Asp Lys Ser Ser Arg Pro Gly Arg Asn Pro Lys Thr Gly Asp Val Val
1               5                   10                  15

Ala Ala Ser Ala Arg Arg
            20

<210> SEQ ID NO 356
<211> LENGTH: 21
<212> TYPE: PRT
<213> ORGANISM: Haemophilus influenzae

<400> SEQUENCE: 356

Asn Phe Glu Leu Arg Asp Lys Ser Ser Arg Pro Gly Arg Asn Pro Lys
1               5                   10                  15

Thr Gly Asp Val Val
            20
```

```
<210> SEQ ID NO 357
<211> LENGTH: 21
<212> TYPE: PRT
<213> ORGANISM: Haemophilus influenzae

<400> SEQUENCE: 357

Ser Leu His His Arg Gln Pro Arg Leu Gly Arg Asn Pro Lys Thr Gly
1               5                   10                  15

Asp Ser Val Asn Leu
            20

<210> SEQ ID NO 358
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358
gaggtgcagc tgcaggagtc tggacctggc ctggtgacgc cctcacagag cctgtccatg      60
acttgcactg tctctgggtt ttcattaacc agctatagtg tacactgggt tcgccagcct    120
ccaggaaaga gtctggagtg gctgggagta atatgggctg gtggaagcac aaattataat    180
tcggctctca tgtccagact gagcatcagc aaagacaact ccaagagcca agttttctta    240
aaaatggaca gtctgcaaac tgatgacaca gccatatact actgtgccag agaggactcc    300
tggggtcaag gaacctcagt caccgtctcc tca                                 333

<210> SEQ ID NO 359
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Glu Val Gln Leu Gln Glu Ser Gly Pro Gly Leu Val Thr Pro Ser Gln
1               5                   10                  15

Ser Leu Ser Met Thr Cys Thr Val Ser Gly Phe Ser Leu Thr Ser Tyr
            20                  25                  30

Ser Val His Trp Val Arg Gln Pro Pro Gly Lys Ser Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asp Ser Leu Gln Thr Asp Asp Thr Ala Ile Tyr Tyr Cys Ala
                85                  90                  95

Arg Glu Asp Ser Trp Gly Gln Gly Thr Ser Val Thr Val Ser Ser
            100                 105                 110

<210> SEQ ID NO 360
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 360
gacattgtga tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atcccacgtt cggagggggg     300
accaagttgg aaataaaa                                                    318

<210> SEQ ID NO 361
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Thr
                85                  90                  95

Phe Gly Gly Gly Thr Lys Leu Glu Ile Lys
            100                 105

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Phe Ser Leu Thr Ser Tyr Ser
1               5

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Phe Ser Leu Thr Ser Tyr Ser Val
1               5

<210> SEQ ID NO 364
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 364

Phe Ser Leu Thr Ser Tyr Ser Val His
1               5

<210> SEQ ID NO 365
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gly Phe Ser Leu Thr Ser Tyr Ser
1               5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ile Trp Ala Gly Gly Ser Thr
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Val Ile Trp Ala Gly Gly Ser Thr
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Val Ile Trp Ala Gly Gly Ser Thr
1               5

<210> SEQ ID NO 369
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Leu Gly Val Ile Trp Ala Gly Gly Ser Thr
1               5                   10
```

```
<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Trp Leu Gly Val Ile Trp Ala Gly Gly Ser Thr
1               5                   10

<210> SEQ ID NO 371
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ile Trp Ala Gly Gly Ser Thr Asn
1               5

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Val Ile Trp Ala Gly Gly Ser Thr Asn
1               5

<210> SEQ ID NO 373
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Val Ile Trp Ala Gly Gly Ser Thr Asn
1               5                   10

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Leu Gly Val Ile Trp Ala Gly Gly Ser Thr Asn
1               5                   10

<210> SEQ ID NO 375
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 375

Trp Leu Gly Val Ile Trp Ala Gly Gly Ser Thr Asn
1               5                   10

<210> SEQ ID NO 376
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ile Trp Ala Gly Gly Ser Thr Asn Tyr
1               5

<210> SEQ ID NO 377
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Val Ile Trp Ala Gly Gly Ser Thr Asn Tyr
1               5                   10

<210> SEQ ID NO 378
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gly Val Ile Trp Ala Gly Gly Ser Thr Asn Tyr
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Leu Gly Val Ile Trp Ala Gly Gly Ser Thr Asn Tyr
1               5                   10

<210> SEQ ID NO 380
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Trp Leu Gly Val Ile Trp Ala Gly Gly Ser Thr Asn Tyr
1               5                   10
```

```
<210> SEQ ID NO 381
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Arg Glu Asp Ser
1

<210> SEQ ID NO 382
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ala Arg Glu Asp Ser
1               5

<210> SEQ ID NO 383
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gln Asn Val Gly Thr Asn
1               5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gln Asn Val Gly Thr Asn Val
1               5

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gln Asn Val Gly Thr Asn Val Ala
1               5

<210> SEQ ID NO 386
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 386

Ser Ala Ser
1

<210> SEQ ID NO 387
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Tyr Ser Ala Ser
1

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ile Tyr Ser Ala Ser
1               5

<210> SEQ ID NO 389
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Leu Ile Tyr Ser Ala Ser
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Leu Ile Tyr Ser Ala Ser
1               5

<210> SEQ ID NO 391
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ser Ala Ser Tyr
1
```

```
<210> SEQ ID NO 392
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Tyr Ser Ala Ser Tyr
1               5

<210> SEQ ID NO 393
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ile Tyr Ser Ala Ser Tyr
1               5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Leu Ile Tyr Ser Ala Ser Tyr
1               5

<210> SEQ ID NO 395
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ala Leu Ile Tyr Ser Ala Ser Tyr
1               5

<210> SEQ ID NO 396
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ser Ala Ser Tyr Arg
1               5

<210> SEQ ID NO 397
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 397

Tyr Ser Ala Ser Tyr Arg
1               5

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Ile Tyr Ser Ala Ser Tyr Arg
1               5

<210> SEQ ID NO 399
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Leu Ile Tyr Ser Ala Ser Tyr Arg
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ala Leu Ile Tyr Ser Ala Ser Tyr Arg
1               5

<210> SEQ ID NO 401
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Ser Ala Ser Tyr Arg Tyr
1               5

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Tyr Ser Ala Ser Tyr Arg Tyr
1               5
```

```
<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ile Tyr Ser Ala Ser Tyr Arg Tyr
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Leu Ile Tyr Ser Ala Ser Tyr Arg Tyr
1               5

<210> SEQ ID NO 405
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Leu Ile Tyr Ser Ala Ser Tyr Arg Tyr
1               5                   10

<210> SEQ ID NO 406
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ser Ala Ser Tyr Arg Tyr Ser
1               5

<210> SEQ ID NO 407
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Tyr Ser Ala Ser Tyr Arg Tyr Ser
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 408

Ile Tyr Ser Ala Ser Tyr Arg Tyr Ser
1               5

<210> SEQ ID NO 409
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Leu Ile Tyr Ser Ala Ser Tyr Arg Tyr Ser
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ala Leu Ile Tyr Ser Ala Ser Tyr Arg Tyr Ser
1               5                   10

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gln Gln Tyr Asn Ser Tyr Pro
1               5

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gln Gln Tyr Asn Ser Tyr Pro Thr
1               5

<210> SEQ ID NO 413
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30
```

Ala Met Ser Trp Val Arg Gln Ala Pro Gly Lys Gly Leu Glu Trp Val
             35                  40                  45

Ser Ala Ile Ser Gly Asn Gly Asp Ser Tyr Tyr Ala Asp Ser Val
 50                  55                  60

Lys Gly Arg Phe Thr Thr Ser Arg Asp Lys Ser Lys Asn Thr Val Tyr
 65                  70                  75                  80

Leu Gln Met Asn Arg Leu Arg Ala Glu Asp Thr Ala Val Tyr Tyr Cys
                 85                  90                  95

Ala Lys Asp Met Arg Arg Tyr His Tyr Asp Ser Ser Gly Leu His Phe
                100                 105                 110

Trp Gly Gln Gly Thr Leu Val Thr Val Ser Ser
            115                 120

<210> SEQ ID NO 414
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Asp Ile Glu Leu Thr Gln Ala Pro Ser Val Ser Val Tyr Pro Gly Gln
 1               5                  10                  15

Thr Ala Arg Ile Thr Cys Ser Gly Asp Ala Leu Pro Lys Gln Tyr Ala
             20                  25                  30

Tyr Trp Tyr Gln Gln Lys Pro Gly Gln Ala Pro Val Val Val Ile Tyr
         35                  40                  45

Lys Asp Ser Glu Arg Pro Ser Gly Ile Ser Glu Arg Phe Ser Gly Ser
 50                  55                  60

Ser Ser Gly Thr Thr Val Thr Leu Thr Ile Ser Gly Val Gln Ala Gly
 65                  70                  75                  80

Asp Glu Ala Asp Tyr Tyr Cys Gln Ser Val Asp Thr Ser Val Ser Tyr
                 85                  90                  95

Tyr Val Val Phe Gly Gly Gly Thr Lys Leu Thr Val Leu
                100                 105

<210> SEQ ID NO 415
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser His Tyr
             20                  25                  30

Asn Met Asn Trp Val Arg Gln Ala Pro Gly Lys Gly Pro Glu Trp Val
         35                  40                  45

Ser Tyr Ile Ser Ser Gly Ser Asp Ile Ile Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Ala Leu Asp Arg Asp Gly Phe Asp Ile Trp Gly Gln Gly Thr
            100                 105                 110

Met Val Thr Val Ser Ser
            115

<210> SEQ ID NO 416
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Asp Ile Val Leu Thr Gln Ser Pro Ser Ser Leu Ser Ala Ser Val Gly
1               5                   10                  15

Asp Lys Val Thr Ile Thr Cys Arg Ala Ser Gln Ser Ile Ser Thr Phe
            20                  25                  30

Leu Asn Trp Tyr Gln His Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Val Glu Ile Lys
            100                 105

<210> SEQ ID NO 417
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Ala Asp Ser Tyr Tyr Ala Asp Ser Val
    50                  55                  60

Lys Gly Arg Phe Thr Thr Ser Arg Asp Lys Ser Lys Asn Thr Val Tyr
65                  70                  75                  80

Leu Gln Met Asn Arg Leu Arg Ala Glu Asp Thr Ala Val Tyr Tyr Cys
                85                  90                  95

Ala Lys Asp Met Arg Arg Tyr His Tyr Asp Ser Ser Gly Leu His Phe
            100                 105                 110

Trp Gly Gln Gly Thr Leu Val Thr Val Ser Ser
            115                 120

<210> SEQ ID NO 418
<211> LENGTH: 110
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 418

Asp Ile Met Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Thr Asn
            20                  25                  30

Tyr Val Ser Trp Phe Gln Gln Val Pro Gly Thr Ala Pro Lys Phe Leu
        35                  40                  45

Ile Tyr Asp Asn Tyr Lys Arg Pro Ser Glu Thr Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asn Tyr Tyr Cys Ala Thr Trp Asp Ser Ser Leu
                85                  90                  95

Ser Ala Trp Val Phe Gly Gly Gly Thr Lys Val Thr Val Leu
            100                 105                 110

<210> SEQ ID NO 419
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Gln Val Gln Leu Val Glu Ser Gly Pro Gly Leu Val Lys Pro Ser Glu
1               5                   10                  15

Thr Leu Ser Leu Thr Cys Arg Val Ser Gly Asp Ser Asn Arg Pro Ser
            20                  25                  30

Tyr Trp Ser Trp Ile Arg Gln Ala Pro Gly Lys Ala Met Glu Trp Ile
        35                  40                  45

Gly Tyr Val Tyr Asp Ser Gly Val Thr Ile Tyr Asn Pro Ser Leu Lys
    50                  55                  60

Gly Arg Val Thr Ile Ser Leu Asp Thr Ser Lys Thr Arg Phe Ser Leu
65                  70                  75                  80

Lys Leu Thr Ser Val Ile Ala Ala Asp Thr Ala Val Tyr Tyr Cys Ala
                85                  90                  95

Arg Glu Arg Phe Asp Arg Thr Ser Tyr Lys Ser Trp Trp Gly Gln Gly
            100                 105                 110

Thr Gln Val Thr Val Ser Ser
        115

<210> SEQ ID NO 420
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Asp Ile Val Leu Thr Gln Ala Pro Gly Thr Leu Ser Leu Ser Pro Gly
1               5                   10                  15

Asp Arg Ala Thr Leu Ser Cys Arg Ala Ser Gln Arg Leu Gly Gly Thr
            20                  25                  30
```

```
Ser Leu Ala Trp Tyr Gln His Arg Ser Gly Gln Ala Pro Arg Leu Ile
            35                  40                  45

Leu Tyr Gly Thr Ser Asn Arg Ala Thr Asp Thr Pro Asp Arg Phe Ser
 50                  55                  60

Gly Ser Gly Ser Gly Thr Asp Phe Val Leu Thr Ile Ser Ser Leu Glu
 65                  70                  75                  80

Pro Glu Asp Phe Ala Val Tyr Tyr Cys Gln Gln Tyr Gly Ser Pro Pro
                 85                  90                  95

Tyr Thr Phe Gly Gln Gly Thr Thr Leu Asp Ile Lys
                100                 105

<210> SEQ ID NO 421
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Gln Val Gln Leu Val Gln Ser Gly Gly Thr Leu Val Gln Pro Gly Gly
 1               5                  10                  15

Ser Leu Arg Leu Ser Cys Ala Ala Ser Gly Phe Thr Phe Ser Tyr Tyr
            20                  25                  30

Ser Met Ser Trp Val Arg Gln Ala Pro Gly Lys Gly Leu Glu Trp Val
        35                  40                  45

Ala Asn Ile Lys His Asp Gly Thr Glu Arg Asn Tyr Val Asp Ser Val
 50                  55                  60

Lys Gly Arg Phe Thr Ile Ser Arg Asp Asn Ser Glu Lys Ser Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Tyr Tyr Gly Ala Gly Thr Asn Tyr Pro Leu Lys Tyr Trp
                100                 105                 110

Gly Gln Gly Thr Arg Val Thr Val Ser Ser
            115                 120

<210> SEQ ID NO 422
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Asp Ile Leu Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80
```

```
Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg
            100                 105

<210> SEQ ID NO 423
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Gln Val Gln Leu Leu Glu Ser Gly Pro Gly Leu Val Arg Pro Ser Asp
1               5                   10                  15

Thr Leu Ser Leu Thr Cys Thr Phe Ser Ala Asp Leu Ser Thr Asn Ala
            20                  25                  30

Tyr Trp Thr Trp Ile Arg Gln Pro Pro Gly Lys Gly Leu Glu Trp Ile
        35                  40                  45

Gly Tyr Met Ser His Ser Gly Gly Arg Asp Tyr Asn Pro Ser Phe Asn
    50                  55                  60

Arg Arg Val Thr Ile Ser Val Asp Thr Ser Lys Asn Gln Val Phe Leu
65                  70                  75                  80

Arg Leu Thr Ser Val Thr Ser Ala Asp Thr Ala Val Tyr Phe Cys Val
                85                  90                  95

Arg Glu Val Gly Ser Tyr Tyr Asp Tyr Trp Gly Gln Gly Ile Leu Val
            100                 105                 110

Thr Val Ser Ser
        115

<210> SEQ ID NO 424
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Asp Ile Glu Met Thr Gln Ser Pro Ser Ser Leu Ser Ala Ser Val Gly
1               5                   10                  15

Asp Arg Ile Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Ser Leu Ile
        35                  40                  45

Phe Ser Thr Ser Ser Leu His Ser Gly Val Pro Ser Lys Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Lys Trp Glu Thr Pro Tyr
                85                  90                  95

Ser Phe Gly Gln Gly Thr Lys Leu Asp Met Ile Arg
            100                 105

<210> SEQ ID NO 425
<211> LENGTH: 116
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 425

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
            20                  25                  30

Gly Val Ser Trp Val Arg Gln Ser Pro Gly Gln Gly Leu Glu Trp Met
        35                  40                  45

Gly Trp Ile Ser Val Tyr Asn Gly Lys Thr Asn Tyr Ser Gln Asn Phe
    50                  55                  60

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

Ala Thr Asp Lys Asn Trp Phe Asp Pro Trp Gly Pro Gly Thr Leu Val
            100                 105                 110

Thr Val Ser Ser
        115

<210> SEQ ID NO 426
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Asp Ile Val Met Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
            20                  25                  30

Ser Trp Tyr Gln His His Pro Gly Lys Ala Pro Lys Val Ile Ile Tyr
        35                  40                  45

Asp Val Lys Lys Arg Pro Ser Gly Val Pro Ser Arg Phe Ser Gly Ser
    50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
                85                  90                  95

Val Phe Gly Ser Gly Thr Lys Val Thr Val Leu
            100                 105

<210> SEQ ID NO 427
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Gln Val Gln Leu Val Glu Ser Gly Gly Gly Val Val Gln Pro Gly Gly
1               5                   10                  15

Ser Leu Arg Val Ser Cys Ala Ala Ser Ala Phe Ser Phe Arg Asp Tyr
            20                  25                  30
```

```
Gly Ile His Trp Val Arg Gln Ala Pro Gly Lys Gly Leu Gln Trp Val
            35                  40                  45

Ala Val Ile Ser His Asp Gly Lys Lys Phe Tyr Ala Asp Ser Val
 50                  55                  60

Arg Gly Arg Phe Thr Ile Ser Arg Asp Asn Ser Glu Asn Thr Leu Tyr
 65                  70                  75                  80

Leu Gln Met Asn Ser Leu Arg Ser Asp Thr Ala Val Tyr Tyr Cys
                 85                  90                  95

Ala Arg Leu Val Ala Ser Cys Ser Gly Ser Thr Cys Thr Thr Gln Pro
            100                 105                 110

Ala Ala Phe Asp Ile Trp Gly Pro Gly Thr Leu Val Thr Val Ser Ser
            115                 120                 125
```

<210> SEQ ID NO 428
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 428

```
Asp Ile Met Leu Thr Gln Pro Pro Ser Val Ser Val Ser Pro Gly Gln
 1               5                  10                  15

Thr Ala Arg Ile Thr Cys Ser Gly Asp Ala Leu Pro Lys Lys Tyr Thr
            20                  25                  30

Tyr Trp Tyr Gln Gln Lys Ser Gly Gln Ala Pro Val Leu Leu Ile Tyr
             35                  40                  45

Glu Asp Arg Lys Arg Pro Ser Glu Ile Pro Glu Arg Phe Ser Ala Phe
 50                  55                  60

Thr Ser Trp Thr Thr Ala Thr Leu Thr Ile Thr Gly Ala Gln Val Arg
 65                  70                  75                  80

Asp Glu Ala Asp Tyr Tyr Cys Tyr Ser Thr Asp Ile Ser Gly Asp Ile
                 85                  90                  95

Gly Val Phe Gly Gly Gly Thr Lys Leu Thr Val Leu
            100                 105
```

<210> SEQ ID NO 429
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 429

```
Gln Val Gln Leu Leu Glu Ser Gly Ala Asp Met Val Gln Pro Gly Arg
 1               5                  10                  15

Ser Leu Arg Leu Ser Cys Ala Ala Ser Gly Phe Asn Phe Arg Thr Tyr
            20                  25                  30

Ala Met His Trp Val Arg Gln Ala Pro Gly Lys Gly Leu Glu Trp Val
            35                  40                  45

Ala Val Met Ser His Asp Gly Tyr Thr Lys Tyr Tyr Ser Asp Ser Val
 50                  55                  60

Arg Gly Gln Phe Thr Ile Ser Arg Asp Asn Ser Lys Asn Thr Leu Tyr
 65                  70                  75                  80

Leu Gln Met Asn Asn Leu Arg Pro Asp Asp Thr Ala Ile Tyr Tyr Cys
                 85                  90                  95
```

Ala Arg Gly Leu Thr Gly Leu Ser Val Gly Phe Asp Tyr Trp Gly Gln
            100                 105                 110

Gly Thr Leu Val Thr Val Ser Ser
        115                 120

<210> SEQ ID NO 430
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Asp Ile Val Leu Thr Gln Ser Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Thr Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Gly
                85                  90                  95

Ser Thr Pro Ala Leu Phe Gly Gly Gly Thr Gln Leu Thr Val Leu
            100                 105                 110

<210> SEQ ID NO 431
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Gln Val Gln Leu Val Gln Ser Gly Gly Gly Leu Val Lys Pro Gly Gly
1               5                   10                  15

Ser Leu Arg Leu Ser Cys Gly Ala Ser Gly Phe Asn Leu Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Val Ser Pro Ser Thr Tyr Tyr Tyr Tyr Gly Met Asp Val Trp
            100                 105                 110

Gly Gln Gly Thr Thr Val Thr Val Ser Ser
        115                 120

<210> SEQ ID NO 432
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 432

Asp Ile Val Leu Thr Gln Pro Ser Ser Val Ser Val Ser Pro Gly Gln
1               5                   10                  15

Thr Ala Arg Ile Thr Cys Ser Gly Asp Glu Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
            100                 105

<210> SEQ ID NO 433
<211> LENGTH: 136
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 433

Gln Val Gln Leu Val Glu Ser Gly Ala Glu Val Lys Lys Pro Gly Ala
1               5                   10                  15

Leu Val Lys Val Ser Cys Lys Ala Ser Gly Tyr Thr Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Lys Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly Gly Pro Ser Asn Leu Glu Arg Phe Leu Glu Arg Leu Gln
            100                 105                 110

Pro Arg Tyr Ser Tyr Asp Asp Lys Tyr Ala Met Asp Val Trp Gly Gln
        115                 120                 125

Gly Thr Thr Val Thr Val Ser Ser
    130                 135

<210> SEQ ID NO 434
<211> LENGTH: 109
<212> TYPE: PRT
<213> ORGANISM: Artificial Sequence
<220> FEATURE:
<223> OTHER INFORMATION: Description of Artificial Sequence: Synthetic
    polypeptide -continued

<400> SEQUENCE: 434

Asp Ile Val Met Thr Gln Ser Pro Gly Thr Leu Ser Leu Ser Pro Gly
1               5                   10                  15

Ala Arg Ala Thr Leu Ser Cys Arg Ala Ser Gln Ser Val Ser Ser Ile
            20                  25                  30

Tyr Leu Ala Trp Tyr Gln Lys Pro Gly Gln Ala Pro Arg Leu Leu
        35                  40                  45

Ile Phe Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg
            100                 105

<210> SEQ ID NO 435
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Gln Val Gln Leu Val Gln Ser Gly Thr Glu Val Lys Lys Pro Gly Glu
1               5                   10                  15

Ser Leu Lys Ile Ser Cys Glu Gly Ser Arg Tyr Asn Phe Ala Arg Tyr
            20                  25                  30

Trp Ile Gly Trp Val Arg Gln Met Pro Gly Lys Gly Leu Asp Trp Met
        35                  40                  45

Gly Ile Ile Tyr Pro Gly Asp Ser Asp Thr Arg Tyr Ser Pro Ser Phe
50                  55                  60

Gln Gly Gln Val Ser Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Leu Gly Ser Glu Leu Gly Val Val Ser Asp Tyr Tyr Phe Asp
            100                 105                 110

Ser Trp Gly Gln Gly Thr Leu Val Thr Val Ser Ser
        115                 120

<210> SEQ ID NO 436
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Arg
            20                  25                  30

Ser Asn Asn Lys Asn Cys Val Ala Trp Tyr Gln Gln Lys Pro Gly Gln
        35                  40                  45

```
Pro Pro Lys Leu Leu Ile Tyr Arg Ala Ala Thr Arg Glu Ser Gly Val
        50                  55                  60

Pro Asp Arg Phe Ser Gly Ser Gly Ser Gly Thr Asp Phe Ser Leu Thr
 65                  70                  75                  80

Ile Ser Ser Leu Gln Ala Glu Asp Val Ala Val Tyr Phe Cys Gln Gln
                 85                  90                  95

Tyr Tyr Ser Ile Pro Asn Thr Phe Gly Gln Gly Thr Lys Leu Glu Ile
            100                 105                 110

Lys Arg

<210> SEQ ID NO 437
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Gln Val Gln Leu Val Glu Ser Gly Gly Gly Leu Val Lys Ala Gly Gly
 1               5                  10                  15

Ser Leu Arg Leu Ser Cys Val Ala Ser Gly Phe Thr Phe Ser Asp Tyr
                20                  25                  30

Tyr Met Ser Trp Ile Arg Gln Ala Pro Gly Lys Gly Leu Glu Trp Ile
            35                  40                  45

Ser Phe Ile Ser Ser Ser Gly Asp Thr Ile Tyr Ala Asp Ser Val
        50                  55                  60

Lys Gly Arg Phe Thr Val Ser Arg Asp Ser Ala Lys Asn Ser Leu Tyr
 65                  70                  75                  80

Leu Gln Met Asn Ser Leu Lys Val Glu Asp Thr Ala Val Tyr Tyr Cys
                 85                  90                  95

Ala Arg Lys Gly Val Ser Asp Glu Leu Leu Arg Phe Trp Gly Gln
            100                 105                 110

Gly Thr Leu Val Thr Val Ser Ser
            115                 120

<210> SEQ ID NO 438
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Asp Ile Val Leu Thr Gln Asp Pro Ser Val Ser Val Ser Pro Gly Gln
 1               5                  10                  15

Thr Ala Arg Ile Thr Cys Ser Gly Asp Ala Leu Pro Lys Tyr Ala
                20                  25                  30

Tyr Trp Tyr Gln Gln Lys Ser Gly Gln Ala Pro Val Leu Val Ile Tyr
            35                  40                  45

Glu Asp Thr Lys Arg Pro Ser Gly Ile Pro Glu Arg Phe Ser Gly Ser
        50                  55                  60

Ser Ser Gly Thr Val Ala Thr Leu Thr Ile Ser Gly Ala Gln Val Glu
 65                  70                  75                  80
```

Asp Glu Ala Asp Tyr Tyr Cys Tyr Ser Thr Asp Ser Ser Gly Asn Gln
                85                  90                  95

Arg Val Phe Gly Gly Gly Thr Lys Leu Thr Val Leu
            100                 105

<210> SEQ ID NO 439
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
                20                  25                  30

Gly Val Ser Trp Val Arg Gln Ser Pro Gly Gln Gly Leu Glu Trp Met
            35                  40                  45

Gly Trp Ile Ser Val Tyr Asn Gly Lys Thr Asn Tyr Ser Gln Asn Phe
        50                  55                  60

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

Ala Thr Asp Lys Asn Trp Phe Asp Pro Trp Gly Pro Gly Thr Leu Val
                100                 105                 110

Thr Val Ser Ser
        115

<210> SEQ ID NO 440
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Asp Ile Val Leu Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
                20                  25                  30

Ser Trp Tyr Gln His His Pro Gly Lys Ala Pro Lys Val Ile Ile Tyr
            35                  40                  45

Asp Val Lys Lys Arg Pro Ser Gly Val Pro Ser Arg Phe Ser Gly Ser
        50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
                85                  90                  95

Val Phe Gly Ser Gly Thr Lys Val Thr Val Leu
                100                 105

<210> SEQ ID NO 441
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Gln Val Gln Leu Val Glu Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
                20                  25                  30

Trp Ile Gly Trp Val Arg Gln Met Pro Gly Lys Gly Leu Glu Trp Met
            35                  40                  45

Gly Val Ile Tyr Pro Asp Asp Ser Asp Thr Arg Tyr Ser Pro Ser Phe
    50                  55                  60

Lys Gly Gln Val Thr Ile Ser Ala Asp Lys Ser Ile Ser Thr Ala Phe
65                  70                  75                  80

Leu Gln Trp Ser Ser Leu Lys Ala Ser Asp Thr Ala Val Tyr His Cys
                85                  90                  95

Ala Arg Pro Pro Asp Ser Trp Gly Gln Gly Thr Leu Val Thr Val Ser
            100                 105                 110

Ser

<210> SEQ ID NO 442
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Asp Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Leu Ala Pro Arg Leu Leu Ile
            35                  40                  45

Val Gly Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Phe Tyr Tyr Cys Gln Gln Tyr Asn Asn Trp Pro Phe
                85                  90                  95

Thr Phe Gly Pro Gly Thr Lys Val Asp Val Lys Arg
            100                 105

<210> SEQ ID NO 443
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Gln Val Gln Leu Leu Glu Ser Gly Pro Gly Leu Val Lys Pro Ser Glu
1               5                   10                  15

Thr Pro Ser Leu Thr Cys Thr Val Ser Gly Gly Ser Ile Arg Ser Tyr
                20                  25                  30

```
Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Met Ser Lys Asn Gln Phe Ser Leu
 65                  70                  75                  80

Lys Leu Ser Ser Val Thr Ala Ala Asp Thr Ala Met Tyr Tyr Cys Ala
                 85                  90                  95

Arg Val Tyr Gly Gly Ser Gly Ser Tyr Asp Phe Asp Tyr Trp Gly Gln
            100                 105                 110

Gly Thr Leu Val Thr Val Ser Ser
            115                 120
```

<210> SEQ ID NO 444
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

```
Asp Ile Val Leu Thr Gln Ser Pro Ser Ala Ser Gly Ser Pro Gly Gln
 1               5                  10                  15

Ser Val Thr Ile Ser Cys Thr Gly Thr Ser Ser Asp Val Gly Gly Tyr
            20                  25                  30

Asn Tyr Val Ser Trp Tyr Gln Gln Leu Pro Gly Lys Ala Pro Lys Leu
            35                  40                  45

Met Ile Tyr Glu Val Thr Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Phe Ala Gly Ser
                 85                  90                  95

Asn Asn His Val Val Phe Gly Gly Gly Thr Lys Leu Thr Val Leu
            100                 105                 110
```

<210> SEQ ID NO 445
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

```
Gln Val Gln Leu Thr Leu Arg Glu Ser Gly Pro Thr Leu Val Lys Pro
 1               5                  10                  15

Thr Gln Thr Leu Thr Leu Thr Cys Thr Phe Ser Gly Phe Ser Leu Ser
            20                  25                  30

Thr Asn Gly Val Gly Val Gly Trp Ile Arg Gln Pro Pro Gly Lys Ala
            35                  40                  45

Leu Glu Trp Leu Ala Ile Ile Tyr Trp Asp Asp Lys Arg Tyr Ser
 50                  55                  60

Pro Ser Leu Lys Ser Arg Leu Thr Ile Thr Lys Asp Thr Ser Lys Asn
 65                  70                  75                  80

Gln Val Val Leu Thr Leu Thr Asn Met Asp Pro Val Asp Thr Gly Thr
                 85                  90                  95
```

```
Tyr Tyr Cys Ala His Ile Leu Gly Ala Ser Asn Tyr Trp Thr Gly Tyr
            100                 105                 110

Leu Arg Tyr Tyr Phe Asp Tyr Trp Gly Gln Gly Thr Leu Val Thr Val
        115                 120                 125

Ser Thr
    130

<210> SEQ ID NO 446
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Asp Ile Glu Met Thr Gln Ser Pro Ser Val Ser Val Ser Pro Gly Gln
1               5                   10                  15

Thr Ala Arg Ile Thr Cys Ser Gly Glu Pro Leu Ala Lys Gln Tyr Ala
            20                  25                  30

Tyr Trp Tyr Gln Gln Lys Ser Gly Gln Ala Pro Val Val Val Ile Tyr
        35                  40                  45

Lys Asp Thr Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr His Cys Glu Ser Gly Asp Ser Ser Gly Thr Tyr
                85                  90                  95

Pro Val Phe Gly Gly Gly Thr Lys Leu Thr Val Leu
            100                 105

<210> SEQ ID NO 447
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Ile Phe Ser Gly Ser
            20                  25                  30

Thr Met His Trp Val Arg Gln Ala Ser Gly Lys Gly Leu Glu Trp Val
        35                  40                  45

Gly Arg Ile Arg Ser Lys Thr Asn Asn Tyr Ala Thr Tyr Ala Ala
50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ile Ser Leu Pro Gly Gly Tyr Ser Ser Gly Gln Gly Thr Leu
            100                 105                 110

Val Thr Val Ser Ser
        115
```

```
<210> SEQ ID NO 448
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Asp Ile Met Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Thr
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Glu Ile Pro Glu Arg Phe Ser Ala Phe
    50                  55                  60

Thr Ser Trp Thr Thr Ala Thr Leu Thr Ile Thr Gly Ala Gln Val Gly
65                  70                  75                  80

Asp Glu Ala Asp Tyr Tyr Cys Tyr Ser Thr Ile Thr Gly Asp Ile
                85                  90                  95

Gly Val Phe Gly Gly Gly Thr Lys Leu Thr Val Leu
            100                 105

<210> SEQ ID NO 449
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Gln Val Gln Leu Val Gln Ser Gly Gly Gly Leu Val Gln Pro Gly Gly
1               5                   10                  15

Ser Leu Lys Val Ser Cys Val Gly Ser Gly Phe Thr Phe Ser Ala Ser
            20                  25                  30

Thr Ile His Trp Val Arg Gln Ala Ser Gly Lys Gly Leu Glu Trp Val
        35                  40                  45

Gly Arg Ile Arg Ser Lys Ala Asn Asn Tyr Ala Thr Val Ser Ala Ala
    50                  55                  60

Ser Leu Lys Gly Arg Phe Thr Ile Ser Arg Asp Asp Ser Lys Asn Thr
65                  70                  75                  80

Ala Tyr Leu Gln Val Asn Ser Leu Lys Ile Glu Asp Thr Ala Ile Tyr
                85                  90                  95

Tyr Cys Thr Arg Pro Thr Ala Cys Gly Asp Arg Val Cys Trp His Gly
            100                 105                 110

Ala Trp Gly Gln Gly Thr Gln Val Thr Val Ser Pro
        115                 120

<210> SEQ ID NO 450
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 450

Asp Ile Val Leu Thr Gln Ser Pro Ser Ala Ser Gly Thr Pro Gly Gln
1               5                   10                  15

Arg Val Thr Ile Ser Cys Ser Gly Ser Arg Ser Asn Leu Gly Asn Asn
            20                  25                  30

Asn Val Asn Trp Tyr Gln Gln Leu Pro Gly Thr Ala Pro Lys Leu Leu
        35                  40                  45

Ile Phe Asp Asn Asn Glu Arg Pro Ser Gly Val Pro Gly Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Asn Gly Trp Val Phe Gly Gly Gly Thr Lys Val Thr Val Leu
            100                 105                 110

<210> SEQ ID NO 451
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Gln Val Gln Leu Val Glu Ser Gly Gly Gly Leu Ala Gln Pro Gly Gly
1               5                   10                  15

Ser Leu Arg Leu Ser Cys Ala Ala Ser Gly Phe Ile Phe Asn Thr Tyr
            20                  25                  30

Ala Met Gly Trp Val Arg Gln Ala Pro Gly Lys Gly Leu Glu Trp Val
        35                  40                  45

Ser Thr Val Ser Ala Pro Gly Ala Gly Thr Tyr Tyr Thr Asp Ser Val
    50                  55                  60

Lys Gly Arg Phe Ile Ile Ser Arg Asp Asn Ser Lys Asn Ile Leu Tyr
65                  70                  75                  80

Leu Gln Met Asn Arg Leu Arg Val Glu Asp Thr Ala Val Tyr Tyr Cys
                85                  90                  95

Ala Arg Asp Gln Gly Gly Pro Ala Val Ala Gly Ala Arg Ile Phe Asp
            100                 105                 110

Tyr Trp Gly Gln Gly Ala Leu Val Thr Val Ser Ser
        115                 120

<210> SEQ ID NO 452
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Asp Ile Val Leu Thr Gln Ser Pro Leu Ser Leu Ser Val Thr Pro Gly
1               5                   10                  15

Gln Pro Ala Ser Ile Ser Cys Lys Ser Ser Gln Ser Leu Leu Arg Ser
            20                  25                  30

Asp Gly Lys Thr Tyr Leu Cys Trp Tyr Leu Gln Lys Pro Gly Gln Pro
        35                  40                  45

Pro Gln Leu Leu Ile Tyr Glu Val Ser Asn Arg Val Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                85                  90                  95

Ile Gln Leu Arg Thr Phe Gly Gln Gly Thr Lys Val Glu Ile Lys Arg
            100                 105                 110

<210> SEQ ID NO 453
<211> LENGTH: 15
<212> TYPE: PRT
<213> ORGANISM: Staphylococcus aureus

<400> SEQUENCE: 453

Ala Ala Arg Lys Gly Arg Asn Pro Gln Thr Gly Lys Glu Ile Asp
 1               5                  10                  15

<210> SEQ ID NO 454
<211> LENGTH: 15
<212> TYPE: PRT
<213> ORGANISM: Staphylococcus aureus

<400> SEQUENCE: 454

Lys Gly Arg Asn Pro Gln Thr Gly Lys Glu Ile Asp Ile Pro Ala
 1               5                  10                  15

<210> SEQ ID NO 455
<211> LENGTH: 13
<212> TYPE: PRT
<213> ORGANISM: Staphylococcus aureus

<400> SEQUENCE: 455

Lys Gly Arg Asn Pro Gln Thr Gly Lys Glu Ile Asp Ile
 1               5                  10

<210> SEQ ID NO 456
<211> LENGTH: 15
<212> TYPE: PRT
<213> ORGANISM: Staphylococcus aureus

<400> SEQUENCE: 456

Val Pro Ala Phe Lys Ala Gly Lys Ala Leu Lys Asp Ala Val Lys
 1               5                  10                  15

<210> SEQ ID NO 457
<211> LENGTH: 15
<212> TYPE: PRT
<213> ORGANISM: Staphylococcus aureus

<400> SEQUENCE: 457

Ser Leu Ala Lys Gly Glu Lys Val Gln Leu Ile Gly Phe Gly Asn
 1               5                  10                  15

<210> SEQ ID NO 458
<211> LENGTH: 15
<212> TYPE: PRT
<213> ORGANISM: Staphylococcus aureus

<400> SEQUENCE: 458

Lys Gly Glu Lys Val Gln Leu Ile Gly Phe Gly Asn Phe Glu Val
 1               5                  10                  15

COMPOSITIONS AND METHODS FOR THE REMOVAL OF BIOFILMS

CROSS-REFERENCE TO RELATED APPLICATIONS

This application is a divisional under 35 U.S.C. § 120 of U.S. application Ser. No. 15/078,987, filed Mar. 23, 2016, now abandoned, which claims priority under 35 U.S.C. § 119(e) to U.S. Application No. 62/199,952, filed Jul. 31, 2015, and U.S. application Ser. No. 15/078,987 which is a continuation-in-part under 35 U.S.C. § 120 of U.S. application Ser. No. 14/967,228, now abandoned, filed Dec. 11, 2015, which in turn is a continuation under 35 U.S.C. § 120 of International Application No. PCT/US2014/042201, filed Jun. 12, 2014, which claims priority under 35 U.S.C. § 119(e) to U.S. Application No. 61/834,846, filed Jun. 13, 2013 the content of each of which is hereby incorporated by reference in its entirety.

STATEMENT OF GOVERNMENT SUPPORT

This invention was made with government support under Contract No. R01DC011818 awarded by the National Institute of Deafness and Communication Disorders (NIDCD) at the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 5, 2019, is named 106887-3885_SL.txt and is 179,389 bytes in size.

FIELD

The present disclosure generally relates to the methods and compositions to lessen and/or cure bacterial biofilms.

BACKGROUND

The DNABII family of proteins are naturally found outside of the bacterial cell and contribute to biofilm formation. At least one protein from the DNSBII family is found in all known eubacteria. While these proteins elicit a strong innate immune response, host subjects fail to naturally produce immunoprotective antibodies to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility, to the point where fouling and corrosive biofilm organisms have even been found on the surfaces of final product storage tanks.

Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water. In the home, biofilms are found in or on any surface that supports microbial growth, e.g., in drains, on food preparation surfaces, in toilets, and in swimming pools and spas.

Thus, a need exists to break through the protective barrier of biofilms to treat or kill the associated bacterial infections and clear them from surfaces and in water systems.

DESCRIPTION OF TABLES

Tables 1-5 are the results of an in vitro bioassay of the reversal of the biofilm in the indicated organism.

Table 6 is the scoring scheme of the relative amount of biomass within the middle ear in the Chinchilla model of otitis media (OM).

Table 7 is the results of an in vitro bioassay of the reversal of the biofilm upon treatment with DNase.

Table 8 is a non-limited summary of DNA binding proteins produced by gram (+) and gram (−) bacteria that can be used in the methods provided herein.

Table 9A is a sequence alignment of relevant portions of the DNA binding proteins of various embodiments disclosed herein. Bold letters indicate an exact match to consensus, light gray lettering indicates a conservative amino acid change, and lightly or darkly shaded sequences are highly conserved across species. Gray shaded undefined sequences at the amino and/or carboxy-terminal are undefined amino acids that do not share consensus sequences. Table 9A is based on information previously published Oberto et al. (1994) Biochimie 76:901-908. Table 9B is a comparison of the 16 amino acid peptide motif to Liu et al. (2008) Cell Microbiol. 10(1):262-276.

Table 10 is a listing of α, β, and C-terminal portions of DNABII proteins from the indicated organism.

Table 11 is a listing of non-limiting exemplary hybridoma cell lines that produce non-limiting exemplary monoclonal antibodies.

SUMMARY

Within bacterial cells, the DNABII proteins are DNA binding proteins that necessarily bend DNA substrates upon binding. Similarly, DNA that is already in a bent conformation is an exemplary substrate as the energy required for bending is rendered unnecessary.

The DNABII family is a member of a class of proteins referred to as nucleoid associated proteins (NAPs), bacterial proteins that, in part, shape the intracellular bacterial nucleoid (Browning et al. (2010) Curr. Opin. Microbiol. 13:773-780). In addition, this family is ubiquitous, expressed by virtually all eubacteria. All characterized family members to date function as either a homodimer or heterodimer of subunits. The family is divided into two types, HU (histone-like protein) and IHF (integration host factor) with *B. cenocepacia* capable of expressing both (strain J2315 genes: BCAL3530, hupA, BCAL1585, hupB; BCAL1487, ihfA and BCAL2949, ihfb). The primary distinction between these family members is that HU binds DNA in a sequence independent manner, while IHF binds a consensus sequence (WATCAANNNNTTR (SEQ ID NO: 36) where W is A or T and R is a purine) conserved across genera (Swinger et al. (2004) Curr. Opin. Struct. Biol. 14:28-35)]. All DNABII proteins bind to and bend DNA considerably e.g. *E. coli* IHF can bend DNA into a virtual U-turn (Rice et al. (1996) Cell 87: 1295-1306). In addition, all family members have a preference for pre-bent or curved DNA structures e.g. Holliday junctions, a cruciform-like structure central to DNA recombination. In fact, DNABII proteins function as accessory factors facilitating all intracellular DNA functions, including gene expression, recombination, repair and replication (Swinger et al. (2004) Curr. Opin. Struct. Biol. 14:28-35).

The DNABII family of proteins is found outside of bacterial cells in the biofilm state. Applicants have shown that these proteins are in fact bound to the extracellular DNA at critical branched junctions. In one aspect, Applicants have shown that by immunizing the host with polypeptides and proteins that produce specific antibodies as well as administrating antibodies and other interfering agents, the DNA-based lattice is sufficiently altered to now permit the host immune system to clear the biofilm.

Applicants also have demonstrated the removal of preformed non-typeable *Haemophilus influenzae* biofilms in the middle ear of the chinchilla host by various modes of immunization with a DNABII family member (*E. coli* integration host factor, IHF). This chinchilla middle ear biofilm animal system has been well documented as an excellent model for human otitis media (or middle ear infections).

The method for using this technology is straightforward. In one embodiment, the polypeptides disclosed herein are used to vaccinate individuals as a prophylactic to chronic/recurrent biofilm disease or as a therapeutic for those with an existing infection. The individual's immune system will then clear the organism by use of the host's innate or acquired immune response, e.g., by binding of antibody and complement, phagocytosis, destruction by binding of effectors of innate immunity etc. Alternatively, antibodies as well as fragments, derivatives, variants and interfering polynucleotides that bind to the polypeptides or microbial DNA can be administered to treat or prevent infection. Bacteria that cannot form functional biofilms are more readily cleared by the remainder of the host's immune system. In this way, antibiotic and drug resistance of the bacteria can be reversed by allowing the therapeutic agents to reach the bacteria.

Thus, in one aspect a method for inhibiting, competing or titrating the binding of a DNABII polypeptide or protein to a microbial DNA is provided, the method comprising, or alternatively consisting essentially of, or yet further consisting of contacting the DNABII polypeptide or protein or the microbial DNA with an interfering agent, thereby inhibiting, competing or titrating the binding of the DNABII protein or polypeptide to the microbial DNA. The contacting can be performed in vitro or in vivo.

In another aspect, provided is a method for inhibiting, preventing or breaking down a microbial biofilm, comprising, or alternatively consisting essentially of, or yet further consisting of contacting the biofilm with an interfering agent, thereby inhibiting, preventing or breaking down the microbial biofilm. The contacting can be performed in vitro or in vivo and therefore can break down, prevent, or inhibit a biofilm on surface or in an industrial or therapeutic setting.

In a further aspect, provided is a method of inhibiting, preventing or breaking down a biofilm in a subject, comprising, or alternatively consisting essentially of, or yet further consisting of administering to the subject an effective amount of an interfering agent, thereby inhibiting, preventing or breaking down the microbial biofilm.

In a yet further aspect, a method for inhibiting, preventing or treating a microbial infection that produces a biofilm in a subject is provided. The method comprises, or alternatively consists essentially of or yet further consists of administering to the subject an effective amount of an interfering agent, thereby inhibiting, preventing or treating the microbial infection that produces the biofilm in the subject.

In one aspect, provided herein is an isolated antibody, an antigen binding fragment, or an interfering agent that specifically recognizes or binds an isolated or recombinant DNABII polypeptide or a fragment or an equivalent each thereof. In one aspect, the isolated antibody, antigen binding fragment, or an interfering agent has affinity for at least one DNABII protein that exceeds the affinity of the DNABII protein for components of a biofilm that includes the DNABII protein. In another aspect, the isolated antibody, antigen binding fragment, or an interfering agent is selected from the group of: a monoclonal antibody, a bispecific antibody, a chimeric antibody, an antigen binding fragment, e.g., an Fv antibody, or a complete antibody that comprises constant regions heterologous to variable regions. In a further aspect, the antigen binding fragment comprises an isolated polypeptide or a polynucleotide. In one aspect, the biofilm component comprises branched DNA. In another aspect the DNABII protein of the biofilm is selected from the group of an IHF or a subunit thereof, HU protein, DPS, Hfq, CbpA or CbpB or a fragment or subunit thereof, e.g., a tip fragment of the protein. In a further aspect, the antibody, interfering agent or antigen binding fragment binds an epitope on the DNABII protein that is conserved across bacterial species. In another aspect, the antibody, antigen binding fragment or interfering agent dissolves a biofilm derived from at least two bacterial species, including both Gram positive and Gram negative species. In one aspect, the DNABII protein is *Staphylococcus aureus* HU or a fragment thereof; and optionally wherein the fragment of *Staphylococcus aureus* HU comprises a tip fragment or a beta hairpin fragment or a biological equivalent thereof. In another aspect the antibody, antigen binding fragment or interfering agent dissolves a biofilm that is produced by *S. aureus*, *P. aeruginosa* and *K. pneumonia*. In another aspect, the affinity of the isolated antibody, an antigen binding fragment, or an interfering agent for the DNABII protein is at least as strong as 100 pM or optionally 40 pM. In a further aspect, the antibody, the antigen binding fragment, or an interfering agent, produces an immune response that is immunodominant and immunoprotective. In a further aspect, the antibody, the antigen binding fragment, or the interfering agent specifically binds the tip fragment of a DNABII polypeptide, e.g., the tip fragment of IHF or HU polypeptide. In another aspect, the antibody, the antigen binding fragment, or the interfering agent is a protein or a nucleic acid, these are prepared for use in a method to a dissolve, interfere, prevent, treat or titrate a biofilm in a subject or to confer passively on a subject a capability to dissolve biofilms.

In a further aspect, a method is provided to prevent formation of or to disperse a biofilm associated with an industrial process by treating a surface or industrial environment (e.g., within a pipe) susceptible to or containing a biofilm with the antibody, antigen binding fragment, or an interfering agent as disclosed herein.

In another aspect, also provided is a polynucleotide encoding the antibody, antigen binding fragment, or the interfering agent as described herein, wherein in one aspect, the polynucleotide is operably linked to a regulatory element, that optionally is contained within an expression vector or a host cell. When the polynucleotide encodes the antibody, antigen binding fragment, or the interfering agent, the polynucleotide can be used to recombinantly produce the antibody, antigen binding fragment or interfering agent by culturing the cells under conditions to produce the antibody, antigen binding fragment or interfering agent and isolating or purifying the product from the cell or cell culture. In one aspect the host cell is a mammalian cell.

Also provided herein is a method to identify a binding moiety, e.g., an antibody, antigen binding fragment or an interfering agent, that has affinity with at least one DNABII protein greater than the affinity of a biofilm component for the DNABII protein, by contacting a candidate binding moiety with a biofilm component and with the at least one DNABII protein, and determining the ratio of the DNABII protein bound to said binding moiety as compared to DNABII bound with the biofilm component, whereby a ratio greater than one identifies a binding moiety that has affinity with respect to at least one DNABII protein greater than the affinity of a biofilm component for the DNABII protein.

In another aspect, also provided is a method to identify an agent, e.g., an antibody, an antigen binding agent or an interfering agent, that reverses drug resistance in multiple species of bacteria by evaluating an agent for activity in disrupting biofilms produced by multiple species, wherein an agent which disrupts said biofilms is identified as an agent that reverses drug resistance, and optionally wherein evaluating an agent for binding to DNABII proteins characteristic of a multiplicity of microbial species and wherein an agent that binds a multiplicity of said proteins is identified as an agent that reverses drug resistance. In one aspect, the agent is effective against biofilms derived from at least two bacterial species, including gram positive and gram negative species, non-limiting examples of such include *S. aureus, P. aeruginosa,* and *K. pneumoniae*.

Also provided herein is an isolated polypeptide comprising the amino acid sequence of the *Haemophilus influenzae* IHFa or a fragment or equivalent thereof; and optionally wherein the polypeptide comprises: the tip portion of the DNABII polypeptide; the A5 fragment of IHFa chain; or a polypeptide consisting of an amino acid sequence selected from the group consisting of an amino acid sequence corresponding to positions 10-25 of the *Haemophilus influenzae* IHFa chain; an amino acid sequence corresponding to positions 56-78 of the *Haemophilus influenzae* IHFa; or an amino acid sequence corresponding to positions 86-96 of the *Haemophilus influenzae* IHFa; or a polypeptide comprises the amino acid sequence selected from the group consisting of TFRPGQKLKSRVENASPKDE (SEQ ID NO: 252), MATITKLDIIEYLSDKYHLS (SEQ ID NO: 348), KYHLSKQDTKNVVENFLEEI (SEQ ID NO: 349), FLEEIRLSLESGQDVKLSGF (SEQ ID NO: 350), KLSGFGNFELRDKSSRPGRN (SEQ ID NO: 351), RPGRNPKTGDVVPVSARRVV (SEQ ID NO: 352), ARRVVTFKPGQKLRARVEKTK (SEQ ID NO: 353), or a biological equivalent each thereof; and optionally wherein the isolated polypeptide further comprises a heterologous amino acid sequence or is coupled to a heterologous non-peptide domain.

In a further aspect, also provided is a non-physiological surface coated with the antibody, an antigen binding fragment, or an interfering agent as described herein. In one aspect the surface is in an industrial setting. In a further aspect, the antibody, antigen binding fragment, further comprises, consists essentially of, or yet further consists of a carrier, such as a pharmaceutically acceptable carrier. In a further aspect, the composition further comprises, consisting essentially of, or yet further consists of an additional agent such as an antibiotic.

In a further aspect, also provided is a method to obtain antibodies immunoreactive with a DNABII protein, e.g., an IHF protein or to generate B cells that secrete antibodies immunoreactive with the DNABII protein, e.g., an IHF protein, by administering the polypeptides identified herein to a subject and then recovering antibodies from the subject; or recovering B cells that produce the antibodies from the subject. In a further aspect, the method further comprises screening the B cells for secretion of an antibody with high affinity for a DNABII, e.g., IHF protein, thus identifying B cells that secrete antibodies immunoreactive with DNABII, e.g., IHF protein; and optionally isolating DNA or mRNA encoding the antibodies from the cells.

Also provided is a method to treat or prevent a condition in a subject or detect the formation of a biofilm in the subject characterized by the formation of a biofilm, by treating the subject with the antibody, the antigen binding fragment or interfering agent as described herein. In one aspect, when the biofilm is to be detected, the method further comprises observing complexation of the antibody, the antigen binding fragment, or the interfering agent with any biofilm present. In one aspect, the antibody, the antigen binding fragment, or the interfering agent dissolves biofilm derived from at least three bacterial species, wherein the three bacteria species comprises a gram negative or a gram positive bacteria. Non-limiting examples of such include *S. aureus, P. aeruginosa,* and *K. pneumoniae*. Non-limiting examples of conditions include chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, and periodontal disease.

In a yet further aspect, a method is provided to identify an immunogen useful to elicit the formation of antibodies for treating, preventing, inhibiting or titrating a biofilm, by screening a library of candidate immunogens for high affinity binding to an antibody, antigen binding fragment or interfering agent as described herein, where a candidate member of the library that binds with high affinity to the antibody, antigen binding fragment or interfering agent, is identified as an immunogen. In a further aspect, an antibody, antigen binding fragment and interfering agent can be prepared by administering to a subject the immunogen.

Yet further provided is a pharmaceutical composition for treating a biofilm in a subject or a condition characterized by formation of biofilms which comprises as active ingredient the antibody, an antigen binding fragment, or an interfering agent as disclosed herein, in an amount effective to prevent or inhibit, disperse or dissolve a biofilm characteristic of the condition. In one aspect, the composition further includes a pharmaceutically acceptable excipient, and optionally at least one antibiotic.

Yet further provided is a method to prepare an interfering nucleic acid by preparing a nucleic acid consisting of 10-20 nucleotides that specifically binds a specific binding partner to antibody, an antigen binding fragment, or an interfering agent as described herein. In a further aspect, the specific binding partner is an epitope of a DNABII protein; and optionally wherein the epitope is conserved across at least three bacterial species. In a further aspect, this disclosure further provides the interfering nucleic acid prepared by this method.

In a further aspect, also provided is a method to identify an antibody, antigen binding fragment or an interfering agent, e.g., a binding moiety that has affinity with respect to at least one DNABII protein greater than the affinity of a biofilm component for the DNABII protein, by contacting a candidate antibody, antigen binding fragment, an interfering agent, or binding moiety with a biofilm component and with the at least one DNABII protein, and determining the ratio of said DNABII protein bound to the antibody, antigen binding fragment, an interfering agent or binding moiety as compared to DNABII bound with the biofilm component, whereby a ratio greater than one identifies the antibody, antigen binding fragment, the interfering agent or the binding moiety that has affinity with respect to at least one DNABII protein greater than the affinity of a biofilm component for the DNABII protein. In one aspect, the antibody, the antigen binding fragment, the interfering agent or the binding moiety binds the DNABII protein in low acid environments or over a range of pH.

Yet further provided is a small molecule that an antibody, an antigen binding fragment, or an interfering agent that mimics the epitope to which the antibody, antigen binding fragment or interfering agent as described herein binds. In one aspect the epitope is a *Staphylococcus aureus* DNABII or a fragment thereof or a biological equivalent thereof; and optionally, wherein the fragment of *Staphylococcus aureus* DNABII comprises a beta hairpin fragment or a biological equivalent thereof. Yet further provided is a method to obtain antisera effective to dissolve biofilm, by immunizing a subject with the small molecule that mimics the epitope to which an antibody, an antigen binding fragment, or an interfering agent as described herein binds, and recovering antiserum from the subject, and optionally isolating polyclonal antiserum or monoclonal antibodies derived therefrom. In a further aspect, the antisera is used to treat biofilm-related conditions in a subject, by administering to the subject this antiserum or monoclonal antibodies.

Also provided is a method to image a biofilm by treating a biofilm with an antibody, an antigen binding fragment, or an interfering agent, e.g., a monoclonal antibody or antigen binding fragment thereof. In one aspect, the antibody or fragment is conjugated to an observable label, and an image is obtained using the label.

For the methods as described herein, any agent that interferes or impedes the binding of the microbial DNA to the DNABII protein or polypeptide is intended within the scope of this disclosure. Non-limiting examples of interfering agents include:

(a) an isolated or recombinant DNABII or an integration host factor (IHF) polypeptide or a fragment or an equivalent of each thereof;
(b) an isolated or recombinant histone-like protein from *E. coli*, e.g., *E. coli* strain U93 (HU) polypeptide or a fragment or an equivalent of each thereof;
(c) an isolated or recombinant protein or polypeptide identified in Table 8, Table 9A, Table 9B, Table 10 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of, the "tip" portion of the DNABII protein or polypeptide, non-limiting examples of such include polypeptides comprising, or alternatively consisting essentially of, or yet further consisting of

KLSGFGNFELRDKSSRPGRN (also referred to herein as hIFA4; (SEQ ID NO. 351));

RGFGSFSLHHRQPRLGRNPK (also referred to B4 (SEQ ID NO. 345));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353)), or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example, IEYLSDKYHL-SKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;
(e) an isolated or recombinant C-terminal polypeptide of SEQ ID NO: 6 through 11, 28, 29, 42 through 100, Table 8 or those C-terminal polypeptides identified in Table 10 or a fragment or an equivalent of each thereof;
(f) a polypeptide or polynucleotide that competes with a DNABII protein on binding to a microbial DNA, e.g., DNABII or an integration host factor IHF and/or HU polypeptide or protein;
(g) a four-way junction polynucleotide resembling a Holliday junction, a 3 way junction polynucleotide resembling a replication fork, a polynucleotide that has inherent flexibility or bent polynucleotide;
(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;
(i) an antibody or antigen binding fragment that specifically recognizes or binds any one of (a) through (g), or an equivalent or fragment of each antibody or antigen binding fragment thereof;

(j) an isolated or recombinant polynucleotide encoding the antibody or antigen binding fragment of (i) or its complement;

(k) a small molecule that competes with the binding of a DNABII protein or polypeptide to a microbial DNA;

(l) an antibody or antigen binding fragment that specifically recognizes or binds any one of an isolated or recombinant polypeptide of SEQ ID NO: 342 through 353 or a fragment or an equivalent of each thereof; and/or (m) polypeptide that comprises, or alternatively consists essentially of, or yet further consists of polypeptides A1 through A6 or B1 through B6 as disclosed in FIG. 18; or

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353)), or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

Also provided herein is a method for inducing an immune response in or conferring passive immunity in a subject in need thereof, comprising, or alternatively consisting essentially of or yet further consisting of, administering to the subject an effective amount of one or more agents of the group:

(a) an isolated or recombinant DNABII or an integration host factor (IHF) polypeptide, or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein polypeptide identified in Table 8, Table 9A, Table 9B, Table 10 or an DNA binding peptide identified in FIGS. 6A-6B, or a fragment or an equivalent of each thereof, a polypeptide A1 to A6, or B1 to B6 as shown in FIG. 18, or a fragment that comprises, or consists essentially of, or yet consists of, the "tip" portion of the DNABII protein or polypeptide, non-limiting examples of such include without limitation a polypeptide that comprises, or alternatively consists essentially of, or yet further consists of

KLSGFGNFELRDKSSRPGRN (also referred to herein as hIFA4; (SEQ ID NO. 351));

RGFGSFSLHHRQPRLGRNPK (also referred to B4 (SEQ ID NO. 345));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353)), or an equivalent of each thereof. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both);

(d) an isolated or recombinant polypeptide of SEQ ID NO: 1 through 353 or a fragment or an equivalent thereof;

(e) an isolated or recombinant C-terminal polypeptide of SEQ ID NO: 6 through 11, 28, 29, 42 through 100, Table 8 or those C-terminal polypeptides identified in Table 10 or a fragment or an equivalent of each thereof;

(f) an isolated or recombinant polynucleotide encoding any one of (a) through (e) or an isolated or recombinant polynucleotide SEQ ID NO: 36 or an equivalent of each thereof, or a polynucleotide that hybridizes under stringent conditions to the polynucleotide, its equivalent or its complement;

(g) an antibody or antigen binding fragment that specifically recognizes or binds any one of (a) through (e), or an equivalent or fragment of each thereof;

(h) an isolated or recombinant polynucleotide encoding the antibody or antigen binding fragment of (g);

(i) an antigen presenting cell pulsed with any one of (a) through (e);

(j) an antigen presenting cell transfected with one or more polynucleotides encoding any one of (a) through (e); and/or (k) an antibody or antigen binding fragment that specifically recognizes or binds any one of an isolated or recombinant polypeptide noted herein as A1, A2, A3, A4, A5, A6, B1, B2, B3, B4, B5, B6 or an isolated or recombinant polypeptide of SEQ ID NO: 342 through 353 or a fragment or an equivalent of each thereof.

Subjects in need of such immune response include those at risk of or suffering from an infection that produces a microbial biofilm.

Also provided herein are compositions for use in the above methods, non-limiting examples of which are discussed below.

In one aspect, provided is an isolated or recombinant polypeptide comprising, or alternatively consisting essentially of an amino acid sequence selected from A1, A2, A3, A4, A5, A6, B1, B2, B3, B4, B5, B6 (see FIG. 18) or SEQ ID NO: 1 to 5 or 12 to 27, 30 to 35, 101-340, or 341-353, or a DNA binding peptide identified in FIGS. 6A-6B, or a DNABII fragment that comprises, or consists essentially of, or yet consists of, the "tip" portion of the DNABII protein or polypeptide, non-limiting examples of such include without limitation a polypeptide that comprises, or alternatively consist essentially of, or yet further consists of

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353));

RGFGSFSLHHRQPRLGRNPK (also referred to B4 (SEQ ID NO. 345));

or an equivalent of each thereof. An example of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), antibody sequences as provided herein, a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both), or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

In another aspect, provided is an isolated or recombinant polypeptide comprising, or alternatively consisting essentially of, or yet further consisting of SEQ ID NO: 1 or 2, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 3, 4 or 5, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, SEQ ID NO: 12, 14, 16, 18, 20, 22, 24, 26, 30 or 32, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 13, 15, 17, 19, 21, 23, 25, 27, 31 or 33, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of SEQ ID NO: 337, 338, 339, or 340, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, SEQ ID NO: 12 and 13 or 14 and 15 or 16 and 17 or 18 and 19 or 20 and 21 or 22 and 23 or 24 and 25, or 26 and 27 or 30 and 31 or 32 and 33, with the proviso that the polypeptide is none of SEQ ID NO: 6 to 11, 28, 29, or 42 through 100.

In one aspect, provided is an isolated or recombinant polypeptide comprising, or alternatively consisting essentially of, or yet further consisting of, one or more of the polypeptides noted above, none limiting examples of such include polypeptides containing the "tip" portion, the "tail portion" or the C-terminal region containing at least 10, or alternatively at least 15, or alternatively at least 20, or alternatively at least 25, or alternatively at least 30, C-terminal amino acids of a polypeptide of the group of a DNABII polypeptide, an IHF polypeptide, a DPS polypeptide, an Hfq polypeptide, a CbpA polypeptide, a CbpB polypeptide, an HU polypeptide, SEQ ID NO: 6 through 11, 28, 29 or those identified in Table 8, Table 10 or a fragment or an equivalent of each thereof.

Also provided are the polynucleotides encoding the polypeptides, recombinant expression systems and host cells comprising the polynucleotides and use of same for the recombinant expression of the polypeptides as well as the recombinant polypeptides encoding by the system and host cells. In one aspect, the host cell is a mammalian cell. The isolated polynucleotides can be operatively linked to regulatory elements necessary for the expression and/or replication of the polynucleotide. The polynucleotide can be contained within a vector. In one aspect, the polynucleotides further comprise an artificial or non-naturally occurring label (e.g., excluding naturally fluorescent polynucleotides) bound to the polynucleotide for use as probes for use in detection of biofilms and monitoring of biofilm treatment.

In one aspect, provided is an isolated or recombinant polypeptide of the group of:
a polypeptide comprising SEQ ID NO: 12 and 13;
a polypeptide comprising SEQ ID NO: 14 and 15;
a polypeptide comprising SEQ ID NO: 16 and 17;
a polypeptide comprising SEQ ID NO: 18 and 19;
a polypeptide comprising SEQ ID NO: 20 and 21;
a polypeptide comprising SEQ ID NO: 23 and 24;
a polypeptide comprising SEQ ID NO: 25 and 26;
a polypeptide comprising SEQ ID NO: 30 and 31;
a polypeptide comprising SEQ ID NO: 32 and 33;
a polypeptide comprising SEQ ID NO: 34 and 35;
a polypeptide comprising SEQ ID NO: 337 and 338; or
a polypeptide comprising SEQ ID NO: 339 and 340;
a polypeptide consisting essentially of any one or more of SEQ ID NO: 342 to 453;
with the proviso that the polypeptide is none of wild-type of any one of IHF alpha, IHF beta or SEQ ID NO: 6 to 11, 28, 29, or 42 through 100.

In one aspect, provided is an isolated or recombinant polypeptide of the group of:
a polypeptide consisting essentially of SEQ ID NO: 12 and 13;

a polypeptide consisting essentially of SEQ ID NO: 14 and 15;
a polypeptide consisting essentially of SEQ ID NO: 16 and 17;
a polypeptide consisting essentially of SEQ ID NO: 18 and 19;
a polypeptide consisting essentially of SEQ ID NO: 20 and 21;
a polypeptide consisting essentially of SEQ ID NO: 23 and 24;
a polypeptide consisting essentially of SEQ ID NO: 25 and 26;
a polypeptide consisting essentially of SEQ ID NO: 30 and 31;
a polypeptide consisting essentially of SEQ ID NO: 32 and 33;
a polypeptide consisting essentially of SEQ ID NO: 34 and 35;
a polypeptide consisting essentially of SEQ ID NO: 337 and 338; or
a polypeptide consisting essentially of SEQ ID NO: 339 and 340;
a polypeptide consisting essentially of any one or more of SEQ ID NO: 342 to 453;
with the proviso that the polypeptide is none of wild-type of any one of IHF alpha, IHF beta or SEQ ID NO: 6 to 11, 28, 29, or 42 through 100.

Also provided are isolated or recombinant polypeptides comprising, or alternatively consisting essentially of or yet further consisting of, two or more, or three or more or four or more, or multiples of the above-identified isolated polypeptides, including fragments and equivalents thereof. Examples of such include isolated polypeptides comprising SEQ ID NO: 1 through 4 and/or 12 through 29, and/or 30 through 33, and/or 30 through 35 e.g., SEQ ID NO: 1 and 2, or alternatively 1 and 3 or alternatively 1 and 4, or alternatively 2 and 3, or alternatively SEQ ID NO: 1, 2 and 3 or alternatively, 2, 3 and 4, or alternatively 1, 3 and 4 or equivalent polypeptides, examples of which are shown in Table 9. The polypeptides can be in any orientation, e.g., SEQ ID NO: 1, 2, and 3 or SEQ ID NO: 3, 2 and 1 or alternatively SEQ ID NO: 2, 1 and 3, or alternatively, 3, 1 and 2, or alternatively 11 and 12, or alternatively 1 and 12, or alternatively 2 and 12, or alternatively, 1 and 12, or alternatively 2 and 13, or alternatively 12, 16 and 1, or alternatively 1, 16 and 12.

In another aspect, this disclosure provides an isolated or recombinant polypeptide comprising SEQ ID NO: 1 or 2 and 3 or 4 or a polypeptide or recombinant polypeptide comprising, or alternatively consisting essentially of, or yet further consisting of an amino acid corresponding to fragments of a DNABII protein such as the tail fragment or the tip fragment, non-limiting examples of such include without limitation a polypeptide that comprises one or more of the sequences identified as A1 through A6; or identified as B1 through B6 (see FIG. 18);

MATITKLDIIEYLSDKYHLS (also referred to herein as hIFA1; (SEQ ID NO. 348));

KYHLSKQDTKNVVENFLEEI (also referred to herein as hIFA2; (SEQ ID NO. 349));

FLEEIRLSLESGQDVKLSGF (also referred to herein as hIFA3; (SEQ ID NO. 350));

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353));

RGFGSFSLHHRQPRLGRNPK (also referred to B4 (SEQ ID NO. 345));

Applicants have determined that the bolded and underlined amino acids are heavily conserved and therefore in one aspect, are not modified or altered in designing an equivalent polypeptide, or an equivalent thereof, (examples of equivalent polypeptides include, for example IEYLSDKYHL-SKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both), the tail fragment, the β-3 and/or α-3 fragments of a DPS polypeptide, an Hfq polypeptide, a CbpA polypeptide, a CbpB polypeptide, an HU polypeptide, a *Haemophilus influenzae* IHFα or IHFβ, non-limiting examples of which include SEQ ID NO: 12 through 27, or a fragment or an equivalent of each of the polypeptides, examples of which are shown in Table 9. In one aspect, isolated wildtype polypeptides are specifically excluded, e.g., that the polypeptide is none of SEQ ID NO: 6 through 11 or a wildtype sequence identified in Table 8. In this embodiment, SEQ ID NO: 1 or 2 or a polypeptide comprising, or alternatively consisting essentially of, or yet further consisting of an amino acid corresponding to the β-3 and/or α-3 fragments of an IHFα or IHFβ microorganism, non-limiting examples of which include SEQ ID NO: 12 through 27 and 30 through 33 or an equivalent of each thereof is located upstream or amino terminus from SEQ ID NO: 3 or 4 or a fragment or an equivalent thereof. In another aspect, the isolated polypeptide comprises SEQ ID NO: 3 or 4 or a polypeptide comprising, or alternatively consisting essentially of, or yet further consisting of an amino acid corresponding to the β-3 and/or α-3 fragments of an IHFα or IHFβ microorganism, non-limiting examples of which include SEQ ID NO: 12 through 27, or an equivalent thereof located upstream or amino terminus to SEQ ID NO: 1 or 2 or an equivalent thereof.

In any of the above embodiments, a peptide linker can be added to the tip fragment (non-limiting examples of such include without limitation a polynucleotide that comprises one or more of the sequences:

RPGRNPKTGDVVPVSARRVV (also referred to herein as hIFA5; (SEQ ID NO. 352));
and RGFGSFSLHHRQPRLGRNPK (also referred to B4 (SEQ ID NO. 345));

or an equivalent of each thereof, the tail fragment, the N-terminus or the C-terminus of the polypeptide, fragment or equivalent thereof. In one aspect, the linker joins the polypeptides disclosed herein, e.g., SEQ ID NO: 1 to 4, 28, 29, 34, or 35 or 30 to 33, 34, or 35 or a polypeptide comprising, or alternatively consisting essentially of, or yet further consisting of an amino acid corresponding to the β-3 and/or α-3 fragments of a *Haemophilus influenzae* IHFα or IHFβ protein (non-limiting examples of full length *Haemophilus influenzae* IHFα and IHFβ are disclosed as SEQ ID NO: 6 and SEQ ID NO: 341, respectively); non-limiting examples of the polypeptides disclosed herein above include SEQ ID NO: 12 through 27 or an equivalent of each thereof. The α polypeptides can further consists of or comprise the above noted polypeptides with the addition of up to 25, or alternatively 20, or alternatively 15, or alternatively up to 10, or alternatively up to 5 random or naturally occurring amino acids on either the amine or carboxy termini (or on both).

A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 37).

Further provided is a fragment or an equivalent of the isolated or recombinant polypeptide of any one of polypeptides identified above as well as an isolated or recombinant polypeptide comprising, or alternatively consisting essentially of, or yet further consisting of, two or more of the isolated or recombinant polypeptides identified above.

Yet further provided is a polynucleotide that interferes with the binding between the microbial DNA and a polypeptide or fragment or equivalent thereof, e.g., SEQ ID 36, or a four-way junction polynucleotide resembling a Holliday junction, a 3 way junction polynucleotide resembling a replication fork, a polynucleotide that has inherent flexibility or bent polynucleotide; an isolated or recombinant polynucleotide encoding a polypeptide described above or an antibody or fragment thereof, which can be operatively linked to regulatory elements necessary for the expression and/or replication of the polynucleotide. The polynucleotide can be contained within a vector.

Also provided is an isolated host cell comprising, or alternatively consisting essentially of, or yet further consisting of an isolated or recombinant polypeptide described above, a four-way junction polynucleotide resembling a Holliday junction, a 3 way junction polynucleotide resembling a replication fork, a polynucleotide that has inherent flexibility or bent polynucleotide; an isolated or recombinant polynucleotide as described above, or a vector as described above.

In one aspect the cell is an isolated antigen presenting cell comprising the isolated or recombinant polypeptide. In a further aspect, the polypeptide is present on the surface of the cell, such as a dendritic cell. In a further aspect, the antigen presenting cell is transfected with one or more polynucleotides encoding the polypeptide.

Yet further provided is an antibody or antigen binding fragment that specifically recognizes and binds the isolated or recombinant polypeptide as describe above, including a fragment or an equivalent of the polypeptide. Non-limiting examples of antibodies include a polyclonal antibody, a monoclonal antibody, a humanized antibody, a human antibody, an antibody derivative, a veneered antibody, a diabody, a chimeric antibody, an antibody derivative, a recombinant human antibody, or an antibody fragment. In a particular aspect, the antibody is a monoclonal antibody. Yet further provided is a hybridoma cell line that produces the monoclonal antibody.

In certain aspects, the disclosure relates to an antibody or antigen binding fragment that specifically recognizes or binds an isolated or recombinant polypeptide comprising, consisting essentially of, or consisting of one or more amino acid sequence selected from A1 to A6 or B1 to B6 (See FIG. 18);

```
SEQ ID NO: 342-353, MATITKLDIIEYLSDKYHLS (also
referred to herein as hIFA1; (SEQ ID NO. 348));

KYHLSKQDTKNVVENFLEEI (also referred to herein as
hIFA2; (SEQ ID NO. 349));

FLEEIRLSLESGQDVKLSGF (also referred to herein as
hIFA3; (SEQ ID NO. 350));

KLSGFGNFELRDKSSRPGRN (also referred to herein as
hIFA4; (SEQ ID NO. 351));

RPGRNPKTGDVVPVSARRVV (also referred to herein as
hIFA5; (SEQ ID NO. 352));

ARRVVTFKPGQKLRARVEKTK (also referred to herein as
hIFA6; (SEQ ID NO. 353));

RGFGSFSLHHRQPRLGRNPK (also referred to herein as
B4 (SEQ ID NO. 345));
``` or the tip or the tail portion of the DNABII protein or polypeptide, a polypeptide that comprises one or more of the sequences MATITKLDIIEYLSDKYHLS (also referred to herein as hIFA1; (SEQ ID NO. 348)); KYHLSKQDTKNVVENFLEEI (also referred to herein as hIFA2; (SEQ ID NO. 349)); or FLEEIRLSLESGQDVKLSGF (also referred to herein as hIFA3; (SEQ ID NO. 350)). The polypeptides may consist of or comprise the above noted polypeptides with the addition of up to 25, or alternatively 20, or alternatively 15, or alternatively up to 10, or alternatively up to 5 random or naturally occurring amino acids on either the amine or carboxy termini (or on both). In some embodiments, such antibodies or antigen binding fragments are administered alone or in combination with each other, or an agent other than the antibody, or yet a further pharmaceutically effective agent, alone or in combination with a pharmaceutically acceptable carrier.

This disclosure also provides isolated or recombinant polynucleotides encoding one or more of the above-identified isolated or recombinant polypeptides or antibodies or a fragment thereof. Vectors comprising the isolated polynucleotides are further provided. In one aspect where more than one isolated polypeptide disclosed herein, the isolated polynucleotides can be contained within a polycistronic vector.

Isolated host cells comprising one or more of isolated or recombinant polypeptides or isolated or recombinant polynucleotides or the vectors, described herein are further provided. In one aspect the isolated host cell is a prokaryotic cell or eukaryotic cell such as antigen presenting cell, e.g., a dendritic cell.

The polynucleotides, polypeptides, antibodies, antigen binding fragment, vectors or host cells can father comprise a detectable label.

Compositions comprising a carrier and one or more of an isolated or recombinant polypeptide disclosed herein, an isolated or recombinant polynucleotide disclosed herein, a vector disclosed herein, an isolated host cell disclosed herein, or an antibody of the embodiments are also provided. The carriers can be one or more of a solid support, a medical device like a stent or dental implant, or a liquid such as a pharmaceutically acceptable carrier. The compositions can further comprise an adjuvant, an antimicrobial or an antigenic peptide.

The compositions can further comprise additional biologically active agents. A non-limiting example of such is a antimicrobial agent such as other vaccine components (i.e., antigenic proteins or peptides) such as surface antigens, e.g., an OMP P5, rsPilA, OMP 26, OMP P2, or Type IV Pilin protein (see Jurcisek and Bakaletz (2007) J. Bacteriology 189(10):3868-3875 and Murphy, T. F. et al. (2009) The Pediatric Infectious Disease Journal 28:S121-S126) and antimicrobial agents.

This disclosure also provides a method for producing an antigenic peptide by growing or culturing a host cell comprising an isolated polynucleotide encoding an antigenic peptide as described above under conditions that favor the expression of the polynucleotide. The polypeptide produced by this method can be isolating for further in vitro or in vivo use.

Also provided are hybridoma cell lines that produce exemplary monoclonal antibodies for use in the methods disclosed herein. The hybridoma cell lines that produce monoclonal antibodies that specifically recognize and bind *Haemophilus influenzae* IhfA fragment A5 (SEQ ID NO. 352)), IhfB4 (RGFGSFSLHHRQPRLGRNPK (also referred to B4 (SEQ ID NO. 345)); were deposited with American Type Culture Collection (ATCC) under Accession Numbers (IhfA5 (Accession No. PTA-122334)) and (IhfB4 (Accession No. PTA-122336)), pursuant to the provisions of the Budapest Treaty on Jul. 30, 2015. Further non-limiting exemplary antibodies include those that specifically recognize and bind *Haemophilus influenzae* IhfA fragment A3 (SEQ ID NO. 350), IhfB fragment B2 (SEQ ID NO. 343) produced by hybridoma cell lines IhfA3 NTHI 9B10.F2.H3 and IhfB2 NTHI 7A4.E4.G4.

A kit is also provided for diagnostic or therapeutic use comprising a composition as described above and instructions for use. A kit is also provided to perform screens for new drugs and/or combination therapies as provided herein.

BRIEF DESCRIPTION OF THE DRAWINGS

FIG. 3A shows a biofilm treated with nonspecific antibody. FIG. 3B shows a biofilm treated with naïve rabbit serum. Note the robust NTHI biofilm with abundant towers (appear as white to light gray clustered areas) and water channels (black spaces). FIG. 3C is a biofilm treated with anti-IHF. Note the eradication of biofilm structure after treatment with an anti-IHF. Individual NTHI (appear as small punctuate white to light gray spots) and sparse, short towers (appear as denser white to light gray clustered areas) remain. FIGS. 3D and 3E further depict that antibodies directed against IHF reverse an established NTHI biofilm. As shown in FIG. 3E, the biofilm showed a dramatic loss of 3-dimensional structure when compared to a biofilm incubated with naive serum (FIG. 3D), Via COMSTAT analysis of multiple replicate assays, the measured parameters of biofilm height, biomass and biofilm thickness were all diminished by a mean of greater than 80% upon incubation with anti-IHF.

FIGS. 8A & 8B—parental strain MG1655; FIGS. 8C & 8D—HU-deficient hupA, hupB double mutant; FIGS. 8E & 8F—IHF-deficient himD, himA double mutant. Note the ability of anti-IHF serum to reduce biomass induced by either the parental isolate or the HU-deficient mutant, but not the IHF-deficient strain, as expected.

FIG. 9A demonstrates that immunization with IHF via a trancutaneous delivery route induced the formation of antibodies that significantly reduced the biomass of an NTHI-induced biofilm resident within the middle ears of chinchillas ($p<0.001$). FIG. 9B depicts representative images of biomasses that remained in the ears of animals immunized with adjuvant alone versus those immunized with IHF+adjuvant. Last column in FIG. 9B shows images of biomasses at the extremes of the scoring system used here. Top image is that of a middle ear that contains a biomass that would receive a score of 4+, whereas lower image is a healthy middle ear that would receive a score of 0, indicating no biomass.

FIGS. 14A-14C show a demonstration of synergism between a sub-optimal concentration of anti-IHF serum (1:200) and DNAseI individually, then mixed (FIG. 14A); a sub-optimal concentration of anti-IHF (1:100) and anti-outer membrane protein P5 serum (OMP P5) individually, then mixed (FIG. 14B); or that of an effective dilution of anti-IHF (in terms of debulking a biofilm but not inducing bacterial cell death) and amoxicillin individually, then mixed (FIG. 14C). In each of these situations, when any agent was combined with anti-IHF, the biofilm debulking and/or killing effect observed was greater than that noted when any single agent was used alone. Note: biofilm height (in microns) is indicated under each image.

Figure 18:
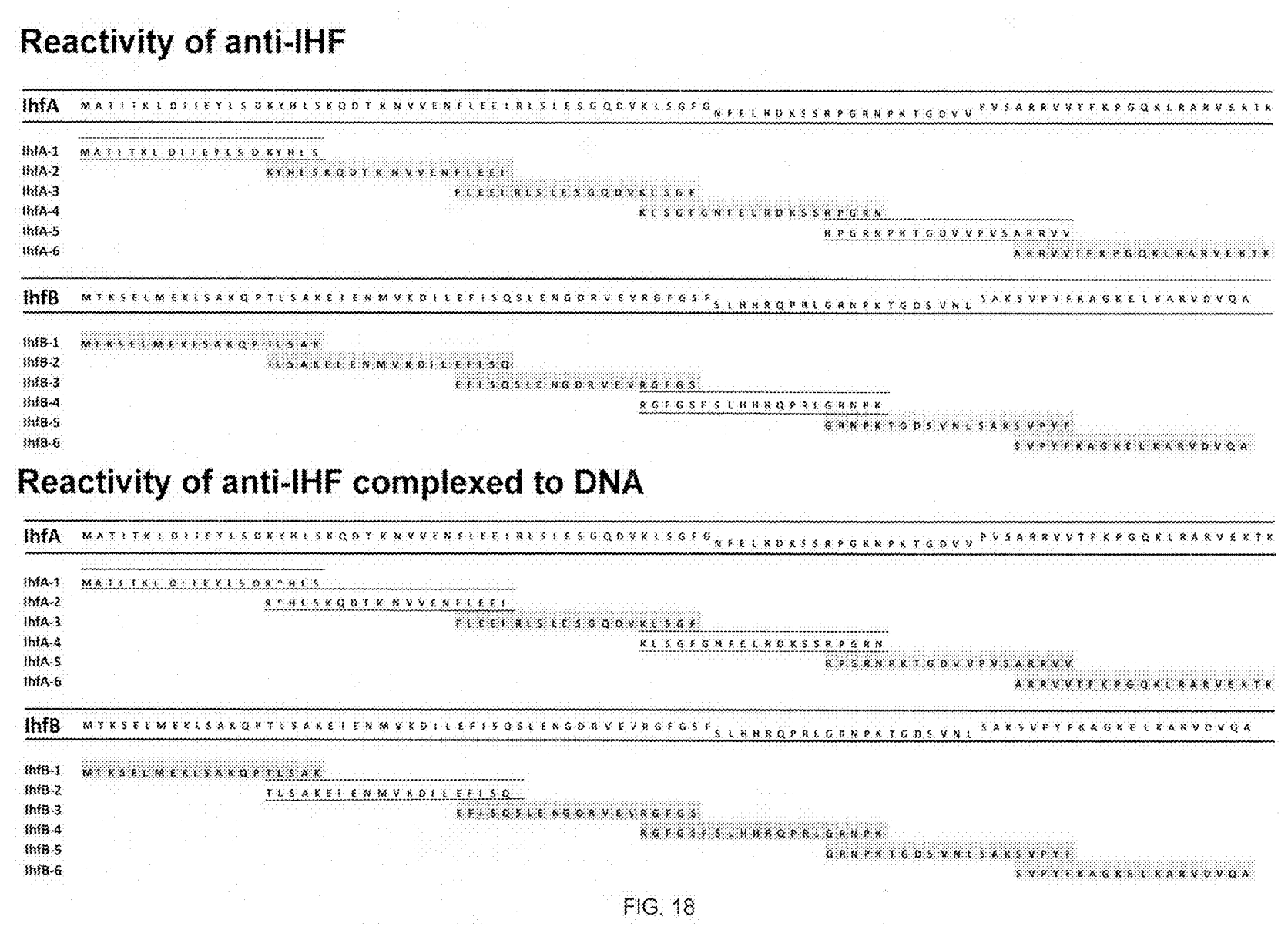

FIG. 18 depicts the peptide sequences generated in the fine mapping process and highlights the peptides of interest based on epitope mapping using chinchilla polyclonal antisera against either IHF from E. coli plus an adjuvant or IHF that has been complexed to an excess of DNA plus the same adjuvant. Figure discloses SEQ ID NOS 6, 348-353, 341-347, 6, 348-353 and 341-347, respectively, in order of appearance.

DETAILED DESCRIPTION

Figure 1A:
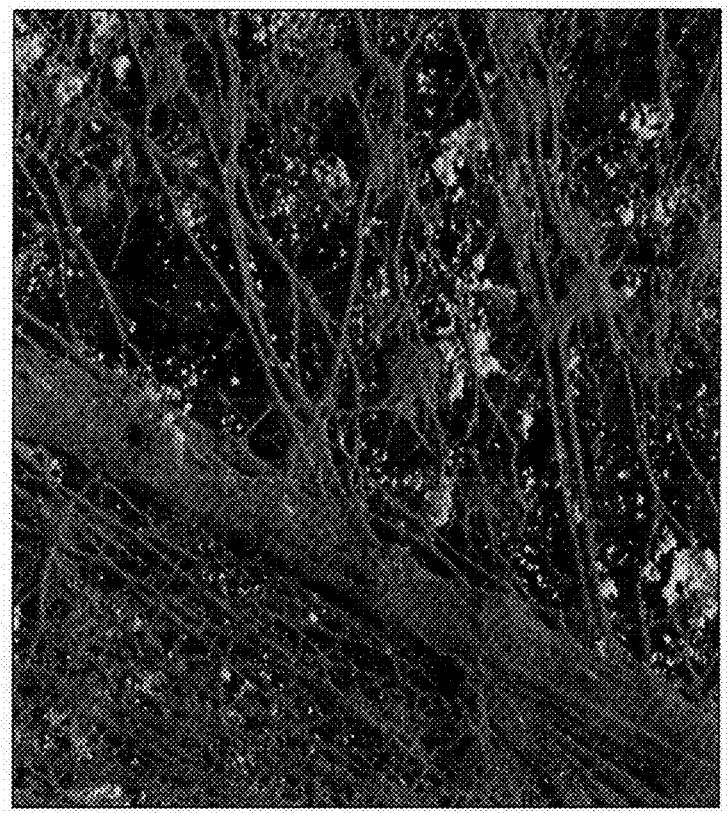
FIG. 1A is a biofilm formed in the chinchilla middle ear by NTHI strain 86-028NP and labeled for NTHI Tfp pilin protein (appears as white or light gray speckles and small clusters in the background of this image), as well as with DAPI for labeling of the double stranded DNA (dsDNA) (appears as dark gray overlapping strands and bundles of material with intermittent clumps in the foreground of this image). This figure has been reproduced from Jurcisek and Bakaletz (2007) J. Bacteriology 189(10):3868-3875.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds, (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure, that may be organic or inorganic, together with the polymers such as DNA that they secrete and/or release. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

Figure 1B:
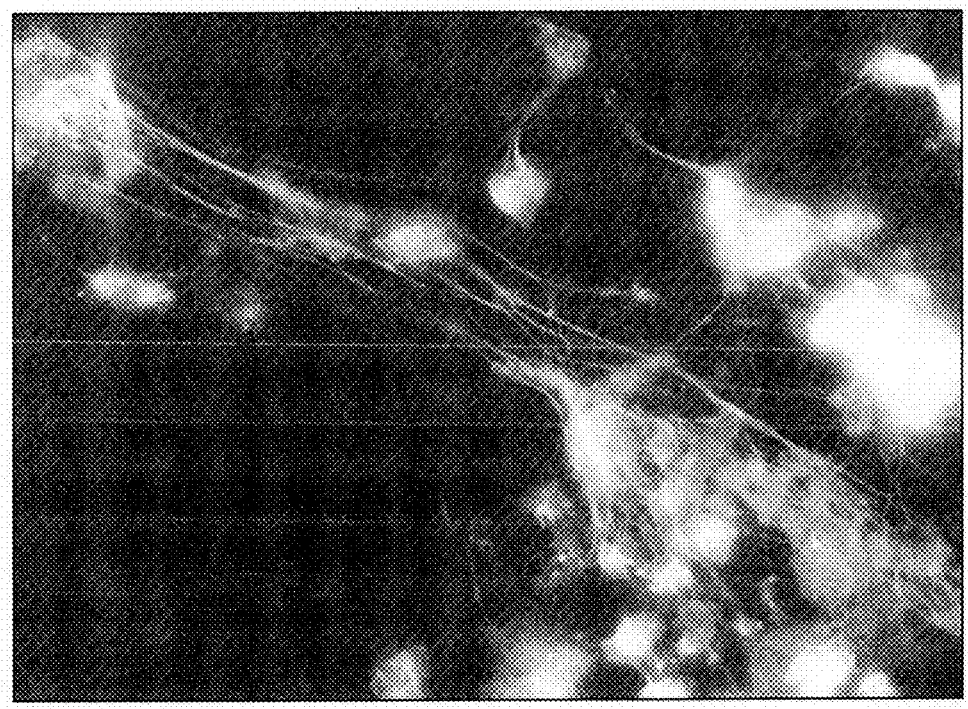
FIG. 1B shows immunolabeling bronchoalveolar lavage (BAL) from the lung of a child with cystic fibrosis. The lung of a child with cystic fibrosis was washed out via BAL and the particulate matter from the wash was frozen and affixed to slides for immunolabeling. The frozen particulate matter was immunolabeled with the anti-IHF antibody. The presence of DNABII positive foci in the biofilm of human cystic fibrosis patients exemplifies that the etiology of human cystic fibrosis includes a biofilm with IHF at the vertices of the dsDNA.
Figure 1C:
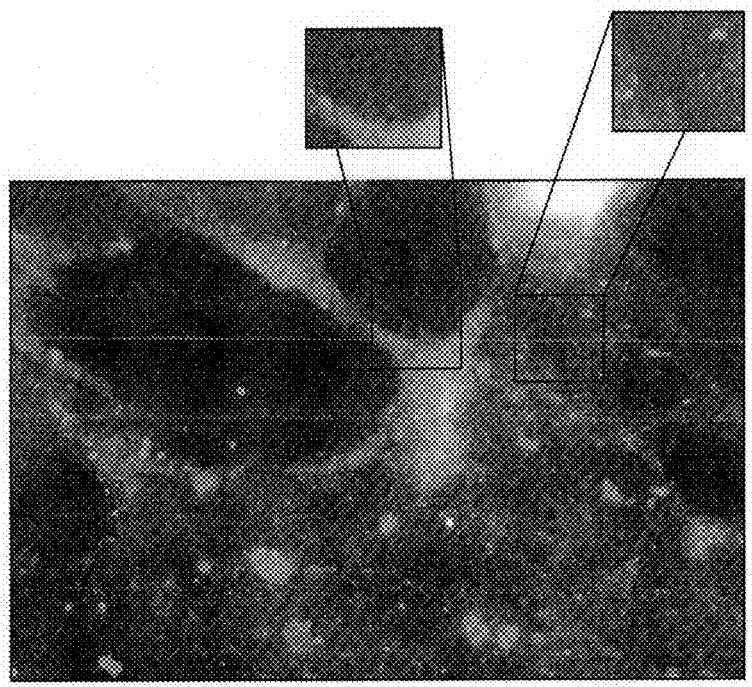
FIG. 1C shows secretions from human sinus collected at the time of sinus surgery and embedded in OCT freezing medium (Optimal Cutting Temperature medium, available commercially from Fisher Scientific Cat. No. 14-373-65). 10 µm frozen sections were cut and labeled with anti-IHF (appearing as gray clusters). dsDNA within the sample was stained with a fluorescent stain, DAPI (4',6-diamidino-2-phenylindole, available commercially from Invitrogen). The presence of IHF positive foci in the biofilm of sinusitis patients exemplifies that the etiology of human sinusitis includes a biofilm with IHF at the vertices of the dsDNA.
Figure 2:
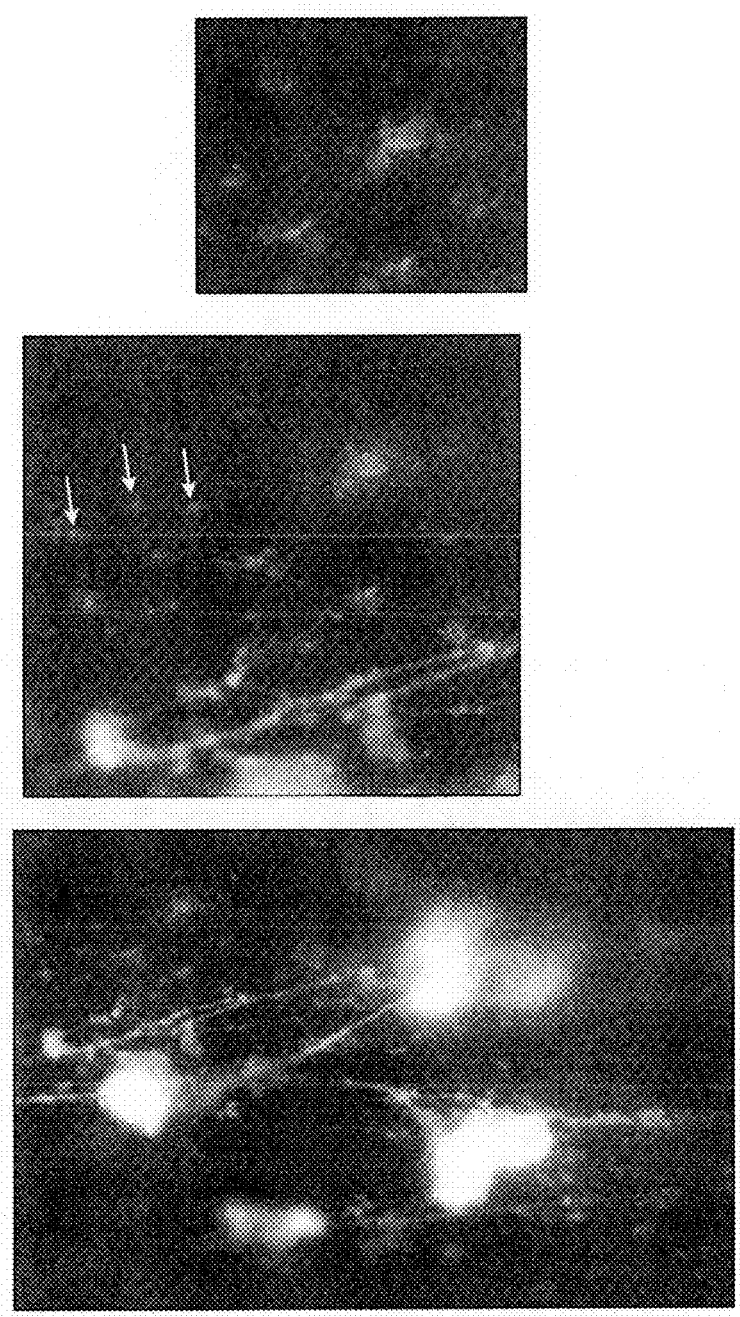
FIG. 2 is an immunohistochemical labeling of double stranded DNA (appears as white strands in this image) within an NTHI biofilm formed in the middle ear of chinchilla. Positive labeling for IHF (as indicated by arrows pointing to punctuate foci in the middle panel of this 3-panel image) was observed at nearly 100% of vertices formed by dsDNA. Mean distance between vertices was approximately 6 µm, or approximately 18 kb between each vertex if one assumes 0.34 nm per base of DNA for B-form DNA. To the best of our knowledge, the only proteins that possess epitopes that cross-react with anti-IHF are HU and IHF. Therefore, based on these observations, it appeared that not only were there extracellular DNABII proteins within the NTHI biofilm matrix, but more importantly that these proteins appeared to be exclusively positioned on eDNA strands that resembled cruciform structures in conformation (see FIG. 6B, bottom section), thus strongly suggesting their role in mediating the resulting bent conformation of the eDNA.
Figure 3A:
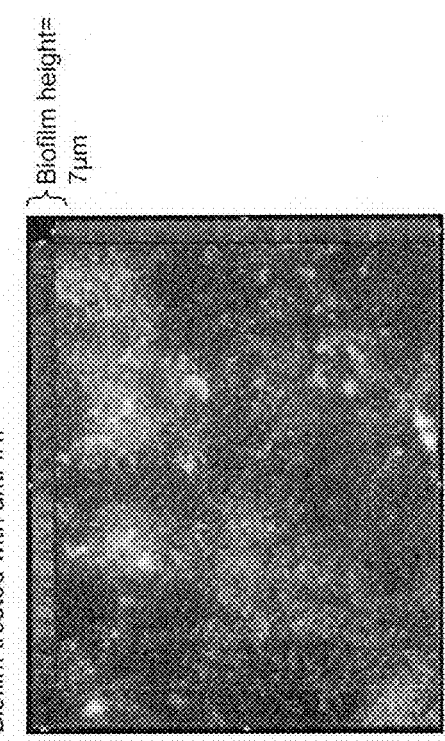
FIGS. 3A-3E shows that antibodies directed against IHF reversed an established NTHI formed in a chamber slide.
Figure 3B:
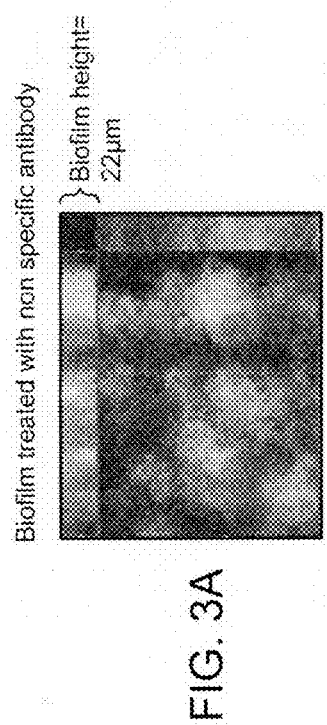
Figure 3C:
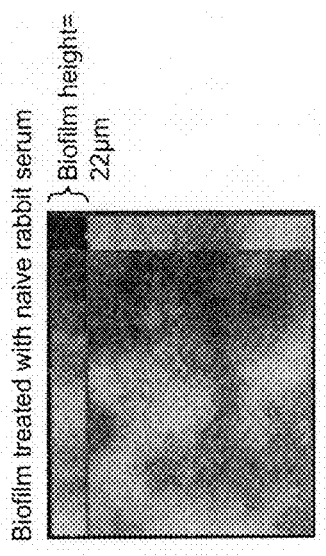
Figures 3D, 3E:
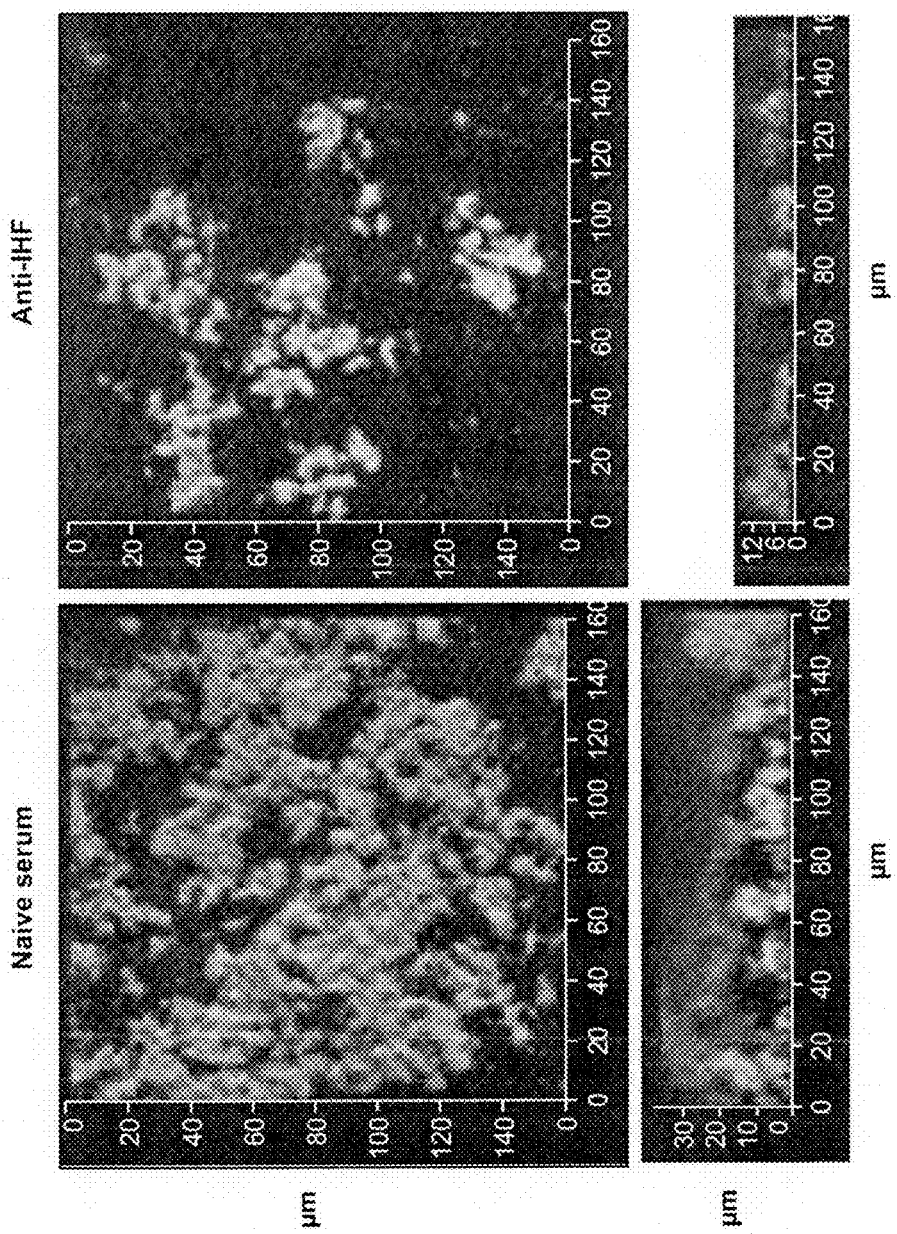

The term "inhibiting, competing or titrating" intends a reduction in the formation of the DNA/protein matrix (for example as shown in FIGS. 1A-1C) that is a component of a microbial biofilm.

A "DNABII polypeptide or protein" intends a DNA binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein from *E. coli* strain U93 (HU). Other DNA binding proteins that may be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" of "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms, and peptides corresponding to these genes from other organisms can be found in Table 10.

"HMGB1" is an high mobility group box (HMGB) 1 protein that is reported to bind to and distort the minor groove of DNA and is an example of an interfering agent. Recombinant or isolated protein and polypeptide are commercially available from Atgenglobal, ProSpecBio, Protein1 and Abnova.

"HU" or "histone-like protein from *E. coli* strain U93" refers to a class of heterodimeric proteins typically associate with *E. coli*. HU proteins are known to bind DNA junctions. Related proteins have been isolated from other microorganisms. The complete amino acid sequence of *E. coli* HU was reported by Laine et al. (1980) Eur. J. Biochem 103(3)447-481. Antibodies to the HU protein are commercially available from Abeam. The genes that encode the HU protein subunits in *E. coli* are hupA and hupB corresponding to SEQ ID Nos: 28 and 29, respectively. Homologs for these genes are found in other organisms, and peptides corresponding to these genes from other organisms can be found in Table 10.

The term "surface antigens" or "surface proteins" refers to proteins or peptides on the surface of cells such as bacterial cells. Examples of surface antigens are Outer membrane proteins such as OMP P5 (Genbank Accession No.: YP_004139079.1), OMP P2 (Genbank Accession No.: ZZX87199.1), OMP P26 (Genbank Accession No.: YP_665091.1), rsPilA or recombinant soluble PilA (Genbank Accession No.: EFU96734.1) and Type IV Pilin (Genbank Accession No.: Yp_003864351.1).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA gene or protein. Some non-limiting examples of different strains of *Haemophilus influenzae* include Rd KW20, 86-028NP, R2866, PittGG, PittEE, R2846, and 2019.

"Microbial DNA" intends single or double stranded DNA from a microorganism that produces a biofilm.

Figure 5:
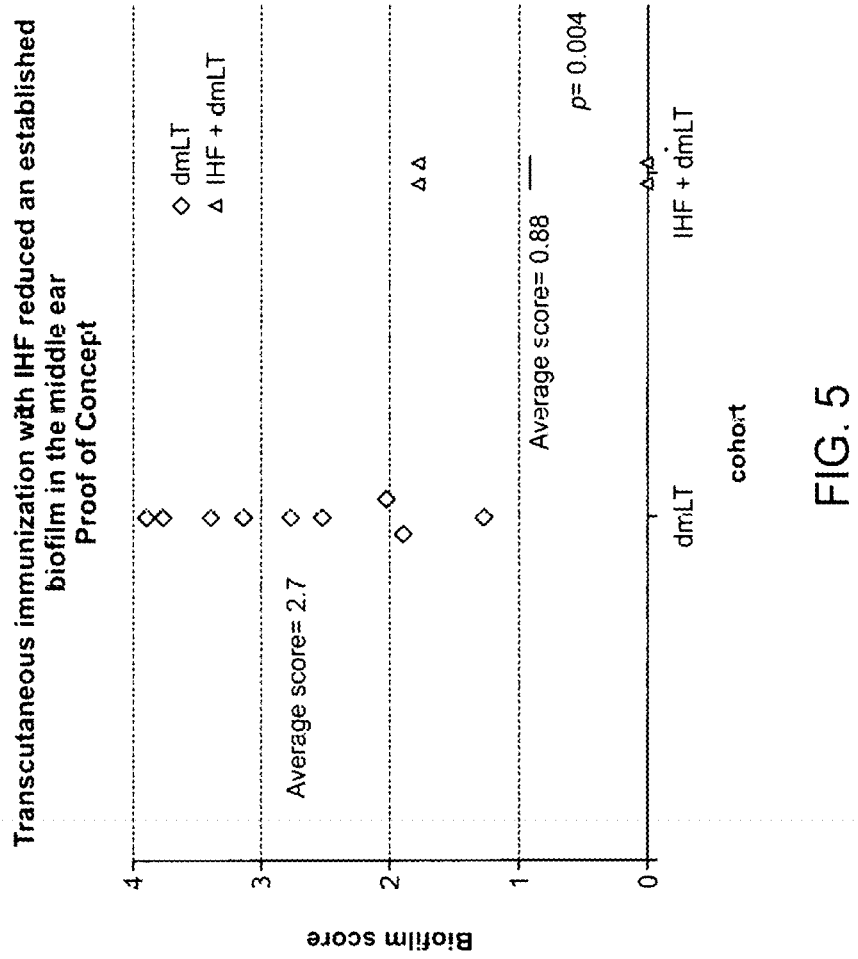
FIG. 5 shows the results of a transcutaneous immunization with IHF reduced an established biofilm in the middle ear. Note that bullae were blindly ranked onto a 0 to 4+ scale of relative remaining biofilm mass.

"Inhibiting, preventing or breaking down" a biofilm intends the prophylactic or therapeutic reduction in the structure of a biofilm. An example of breaking down or reducing a biofilm is shown in FIG. 5.

An "interfering agent" intends an agent that any one or more of competes, inhibits, prevents, titrates a DNABII polypeptide such as IHF to a microbial DNA or also breaks down a microbial biofilm. It can be any one or more of a chemical or biological molecule. For example, DNABII such as IHF can specifically bind, bend or distorted DNA structures such as DNA containing four-way junctions, cis-platinum adducts, DNA loop or base bulges. Examples of such agents, without limitation, include (1) small molecules that inhibit the DNA-binding activity of IHF, (2) small molecules such as polyamines and spermine that compete with IHF in DNA binding, (3) polypeptides such as peptide fragments of IHF that compete with IHF in DNA binding, (4) antibodies or fragments thereof directed to IHF, (5) a short polynucleotide that binds the polypeptide or biofilm forming DNA, or (6) a four-way or bent polynucleotides or other types of polynucleotides containing bent or distorted DNA structures that compete in IHF-binding. A "small molecule that inhibits the binding of an IHF to a nucleic acid" refers to (1) or (2) above and includes those that bind DNA in the minor grove, i.e., minor groove binding molecules. A "four-way polynucleotide" intends a polynucleotide that contains a four-way junction, also known as the Holliday junction, between four strands of DNA.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

Figure 6A:
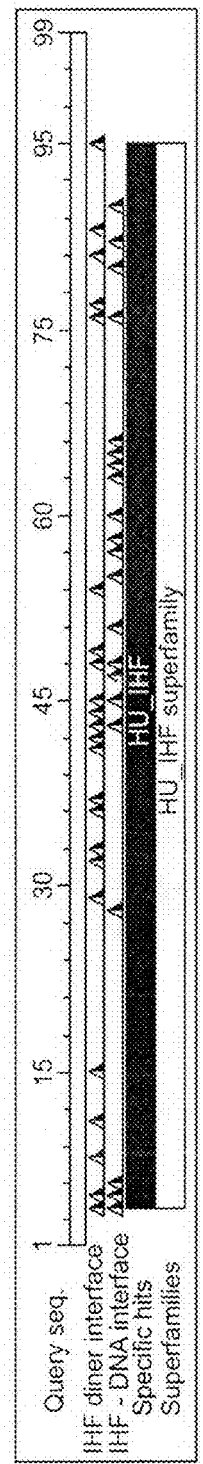
FIG. 6A is a map indicating the amino acid residues of IHF that interact with or bind to another IHF in an IHF-IHF dimer (indicated by triangles at the upper level) or interact with or bind DNA (indicated by triangles at the lower level). The peptide is divided by the short vertical bars into regions containing 3 amino acids.
Figure 6B:
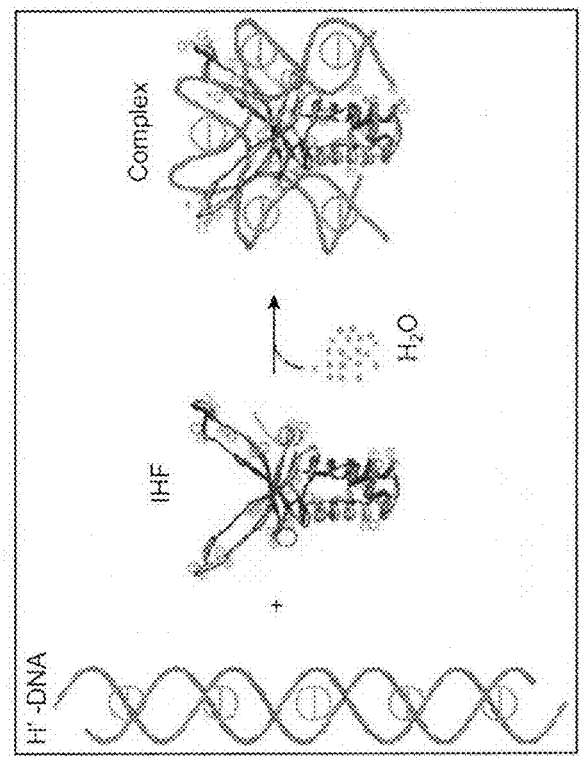
FIG. 6B graphically depicts the interaction of microbial DNA with an IHF.

"Polypeptides that compete with DNABII binding, such as IHF in DNA binding" intend proteins or peptides that compete with DNABII (e.g., IHF) in binding bent or distorted DNA structures but do not form a biofilm with the DNA. Examples, without limitation, include fragments of IHF that include one or more DNA binding domains of the IHF, or the biological equivalents thereof. DNA binding domains are shown in FIGS. 6A-6B.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "C-terminal polypeptide" intends at least the 10, or alternatively at least the 15, or alternatively at least 20, or at least the 25 C-terminal amino acids or alternatively half of a polypeptide. In another aspect, for polypeptides containing 90 amino acids, the C-terminal polypeptide would comprise amino acids 46 through 90. In one aspect, the term intends the C-terminal 20 amino acids from the carboxy terminus.

A "tip fragment" of a DNABII polypeptide intends a DNA polypeptide that, using IHFalpha as an example, forms the two arms of the proteins (see FIG. 6B). Non-limiting examples of such include IhfA, A tip fragment: NFELRDKSSRPGRNPKTGDVV (SEQ ID NO: 356) and IhfB, B tip fragment: SLHHRQPRLGRNPKTGDSVNL (SEQ ID NO: 357).

A "tail fragment" of a DNABII polypeptide intends a region of the protein that is both exposed to the bulk medium and not occluded by DNA or other polypeptides.

An immunodominant antigen intends a region of the protein that is recognized and binds with high affinity to an antibody.

An immunoprotective antigen intends a region of the protein that is recognized and binds with high affinity to an antibody to interfere with protein function; the antibodies generated against an immunoprotective antigen are characterized by enhanced or optimal effect against a target indication as a result to the interference with protein function—in this case, an improve capability to clear biofilms.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen tinder a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Examples of biologically equivalent polypeptides are provided in Table 9 which identifies conservative amino acid substitutions to the disclosed amino acid sequences.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address:align.genome.jp, last accessed on Mar. 7, 2011.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present disclosure can be administered for therapy by any suitable route of administration. It will also be appreciated that the optimal route will vary with the condition and age of the recipient, and the disease being treated.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double $C=C$ bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, Yips (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Application Publication No. WO 95/27071. Ads do not require integration into the host cell genome. Recombinant Ad derived vectors, particularly those that reduce the potential for recombination and generation of wild-type virus, have also been constructed. See, PCT International Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-DNABII, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6$^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6$^{th}$ ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into class I and class II MHC molecules. Class I MHC includes membrane heterodimeric proteins made up of an α chain encoded in the MHC noncovalently linked with the β 2-microglobulin. Class I MHC molecules are expressed by nearly all nucleated cells and have been shown to function in antigen presentation to $CD8^+$ T cells. Class I molecules include HLA-A, B, and C in humans. Class II MHC molecules also include membrane heterodimeric proteins consisting of noncovalently associated α and β chains. Class II MHC molecules are known to function in $CD4^-$ T cells and, in humans, include HLA-DP, -DQ, and DR. In a particular embodiment, compositions and ligands can complex with MHC molecules of any HLA type. Those of skill in the art are familiar with the serotypes and genotypes of the HLA. See: bimas.dcrt.nih.gov/cgi-bin/molbio/hla coefficient viewing page. Rammensee H. G., Bachmann J., and Stevanovic S. MHC Ligands and Peptide Motifs (1997) Chapman & Hall Publishers; Schreuder G. M. Th. et al. The HLA dictionary (1999) Tissue Antigens 54:409-437.

The term "antigen-presenting matrix", as used herein, intends a molecule or molecules which can present antigen in such a way that the antigen can be bound by a T-cell antigen receptor on the surface of a T cell. An antigen-presenting matrix can be on the surface of an antigen-presenting cell (APC), on a vesicle preparation of an APC, or can be in the form of a synthetic matrix on a solid support such as a bead or a plate. An example of a synthetic antigen-presenting matrix is purified MHC class I molecules complexed to β2-microglobulin, multimers of such purified MHC class I molecules, purified MHC Class II molecules, or functional portions thereof, attached to a solid support.

The term "antigen presenting cells (APC)" refers to a class of cells capable of presenting one or more antigens in the form of antigen-MHC complex recognizable by specific effector cells of the immune system, and thereby inducing an effective cellular immune response against the antigen or antigens being presented. While many types of cells may be capable of presenting antigens on their cell surface for T-cell recognition, only professional APCs have the capacity to present antigens in an efficient amount and further to activate T-cells for cytotoxic T-lymphocyte (CTL) responses. APCs can be intact whole cells such as macrophages, B-cells and dendritic cells; or other molecules, naturally occurring or synthetic, such as purified MHC class molecules complexed to β2-microglobulin.

The term "dendritic cells (DCs)" refers to a diverse population of morphologically similar cell types found in a variety of lymphoid and non-lymphoid tissues (Steinman (1991) Ann. Rev. Immunol. 9:271-296). Dendritic cells constitute the most potent mammalian APCs. A subset, if not all, of DCs are derived from bone marrow progenitor cells, circulate in small numbers in the peripheral blood and appear either as immature Langerhans' cells or terminally differentiated mature cells. While DCs can be derived from monocytes, they possess distinct phenotypes. For example, a particular differentiating marker, CD 14 antigen, is not found in dendritic cells but is expressed at very high levels in monocytes by monocytes. See for example Jersmann et al. (2005) Immunol. Cell Biol. 83:462.

Also, mature dendritic cells are not phagocytic, whereas the monocytes are strongly phagocytosing cells. Mature monocytes and DCs endocytose material through different mechanisms. Monocytes engulf by means of phagocytosis, whereas DCs utilize macropinocytosis. Thus, DCs generally engulf cargo of a smaller size than monocytes (See for example Conner and Schmid (2003) Nature 433:37-44. It has been shown that DCs are as endocytically active as other antigen presenting cells, and provide all the signals necessary for T cell activation and proliferation (See, e.g., Levine and Chain (1992) PNAS 89(17):8342.

The term "antigen presenting cell recruitment factors" or "APC recruitment factors" include both intact, whole cells as well as other molecules that are capable of recruiting antigen presenting cells. Examples of suitable APC recruitment factors include molecules such as interleukin 4 (IL4), granulocyte macrophage colony stimulating factor (GM-CSF), Sepragel and macrophage inflammatory protein 3 alpha (MIP3α). These are available from Immunex, Schering-Plough and R&D Systems (Minneapolis, Minn.). They also can be recombinantly produced using the methods disclosed in Current Protocols In Molecular Biology (F. M. Ausubel et al., eds. (1987)). Peptides, proteins and compounds having the same biological activity as the above-noted factors are included within the scope of this disclosure.

The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. Certain diseased tissue expresses specific antigens and CTLs specific for these antigens have been identified.

The term "immune effector molecule" as used herein, refers to molecules capable of antigen-specific binding, and includes antibodies, T cell antigen receptors, B cell antigen receptors, and MHC Class I and Class II molecules.

A "naive" immune effector cell is an immune effector cell that has never been exposed to an antigen capable of activating that cell. Activation of naive immune effector T cells requires both recognition of the antigen:MHC complex and the simultaneous delivery of a costimulatory signal by a professional APC in order to proliferate and differentiate into antigen-specific armed effector T cells. Activated T cells can then activate specific B cells through immunological synapses by providing a co-stimulation signal. Activated B cells subsequently produce antibodies directed to a specific antigen. Naïve B cells can also be activated by T cell-independent mechanisms. This occurs when antigens are capable of binding to the B cell receptor and producing a co-stimulation signal.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

In the context of this disclosure, a "ligand" is a polypeptide. In one aspect, the term "ligand" as used herein refers to any molecule that binds to a specific site on another molecule. In other words, the ligand confers the specificity of the protein in a reaction with an immune effector cell or an antibody to a protein or DNA to a protein. In one aspect it is the ligand site within the protein that combines directly with the complementary binding site on the immune effector cell.

In one aspect, a peptide or ligand disclosed herein binds to an antigenic determinant or epitope on an immune effector cell, such as an antibody or a T cell receptor (TCR). A ligand may be an antigen, peptide, protein or epitope disclosed herein.

In another aspect, ligands may bind to a receptor on an antibody. In one embodiment, the ligand disclosed herein is about 4 to about 8 amino acids in length.

In a further aspect, ligands may bind to a receptor on an MHC class I molecule. In one embodiment, the ligand disclosed herein is about 7 to about 11 amino acids in length.

In a yet further aspect, ligands may bind to a receptor on an MHC class II molecule. In one embodiment, the ligand disclosed herein is about 10 to about 20 amino acids long.

As used herein, the term "educated, antigen-specific immune effector cell", is an immune effector cell as defined above, which has previously encountered an antigen. In contrast with its naive counterpart, activation of an educated, antigen-specific immune effector cell does not require a costimulatory signal. Recognition of the peptide:MHC complex is sufficient.

"Activated", when used in reference to a T cell, implies that the cell is no longer in Go phase, and begins to produce one or more of cytotoxins, cytokines, and other related membrane-associated proteins characteristic of the cell type (e.g., $CD8^+$ or $CD4^+$), is capable of recognizing and binding any target cell that displays the particular antigen on its surface, and releasing its effector molecules.

The term "cross-reactive" is used to describe compounds disclosed herein which are functionally overlapping. More particularly, the immunogenic properties of a native ligand and/or immune effector cells activated thereby are shared to a certain extent by the altered ligand such that the altered ligand is "cross-reactive" with the native ligand and/or the immune effector cells activated thereby. For purposes of this disclosure, cross-reactivity is manifested at multiple levels: (i) at the ligand level, e.g., the altered ligands can bind the TCR of and activate native ligand CTLs; (ii) at the T cell level, i.e., altered ligands disclosed herein bind the TCR of and activate a population of T cells (distinct from the population of native ligand CTLs) which can effectively target and lyse cells displaying the native ligand; and (iii) at the antibody level, e.g., "anti"-altered ligand antibodies can detect, recognize and bind the native ligand and initiate effector mechanisms in an immune response which ultimately result in elimination of the native ligand from the host.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

"Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz (1990) Science 248:1349-1356 and Jenkins (1992) Immunol. Today 13:69-73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu et al. (1992) J. Exp. Med. 175: 437-445), chondroitin sulfate-modified MHC invariant chain (Ii-CS) (Naujokas et al. (1993) Cell 74:257-268), intracellular adhesion molecule 1 (ICAM-1) (Van (1992) Cell 71:1065-1068). These molecules each appear to assist co-stimulation by interacting with their cognate ligands on the T cells. Co-stimulatory molecules mediate co-stimulatory signal(s), which are necessary, under normal physiological conditions, to achieve full activation of naive T cells. One exemplary receptor-ligand pair is the B7 co-stimulatory molecule on the surface of APCs and its counter-receptor CD28 or CTLA-4 cells (Freeman et al. (1993) Science 262:909-911; Young et al. (1992) J. Clin. Invest. 90:229 and Nabavi et al. (1992) Nature 360:266-268). Other important co-stimulatory molecules are CD40, CD54, CD80, and CD86. The term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an antigen-presenting matrix such as an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter, Inc. (Fullerton, Calif.). It is intended, although not always explicitly stated, that molecules having similar biological activity as wild-type or purified co-stimulatory molecules (e.g., recombinantly produced or muteins thereof) are intended to be used within the spirit and scope of the disclosure.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

The term "immunomodulatory agent", as used herein, is a molecule, a macromolecular complex, or a cell that modulates an immune response and encompasses a synthetic antigenic peptide disclosed herein alone or in any of a variety of formulations described herein; a polypeptide comprising a synthetic antigenic peptide disclosed herein; a polynucleotide encoding a peptide or polypeptide disclosed herein; a synthetic antigenic peptide disclosed herein bound to a Class I or a Class II MHC molecule on an antigen-presenting matrix, including an APC and a synthetic antigen-presenting matrix (in the presence or absence of co-stimulatory molecule(s)); a synthetic antigenic peptide disclosed herein covalently or non-covalently complexed to another molecule(s) or macromolecular structure; and an educated, antigen-specific immune effector cell which is specific for a peptide disclosed herein.

The term "modulate an immune response" includes inducing (increasing, eliciting) an immune response; and reducing (suppressing) an immune response. An immunomodulatory method (or protocol) is one that modulates an immune response in a subject.

As used herein, the term "cytokine" refers to any one of the numerous factors that exert a variety of effects on cells, for example, inducing growth or proliferation. Non-limiting examples of cytokines which may be used alone or in combination in the practice of the present disclosure include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1α), interleukin-11 (IL-11), MIP-11, leukemia inhibitory factor (LIF), c-kit ligand, thrombopoietin (TPO) and flt3 ligand. The present disclosure also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the disclosure.

Diagnostic and Therapeutic Methods

A method is provided for inhibiting, competing or titrating the binding of a DNABII polypeptide or protein to a microbial DNA, by contacting the DNABII polypeptide or protein or the microbial DNA with an interfering agent, thereby inhibiting, competing or titrating the binding of the DNABII protein or polypeptide to the microbial DNA. In a further aspect, the DNABII polypeptide and the microbial DNA are detectably labeled, for example with luminescent molecules that will emit a signal when brought into close contact with each other. The contacting can be performed in vitro or in vivo.

In another aspect, a method for inhibiting, preventing or breaking down a microbial biofilm is provided by contacting the biofilm with an interfering agent, thereby inhibiting, preventing or breaking down the microbial biofilm. In a further aspect, the DNABII polypeptide and the microbial DNA are detectably labeled, for example with luminescent molecules that will emit a signal when brought into close contact with each other. The contacting can be performed in vitro or in vivo.

When practiced in vitro, the methods are useful to screen for or confirm interfering agents having the same, similar or opposite ability as the polypeptides, polynucleotides, antibodies, host cells, small molecules and compositions disclosed herein. Alternatively, they can be used to identify which interfering agent is best suited to treat a microbial infection or if the treatment has been effective. For example, one can screen for new agents or combination therapies by having two samples containing for example, the DNABII polypeptide and microbial DNA and the agent to be tested. The second sample contains the DNABII polypeptide and microbial DNA and an agent known to active, e.g., an anti-IHF antibody or a small molecule to serve as a positive control. In a further aspect, several samples are provided and the interfering agents are added to the system in increasing dilutions to determine the optimal dose that would likely be effective in treating a subject in the clinical setting. As is apparent to those of skill in the art, a negative control containing the DNABII polypeptide and the microbial DNA can be provided. In a further aspect, the DNABII polypeptide and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro, see for example Experiment No. 1 below. The interfering agent (such as anti-DNABII or IHF antibody) or potential interfering agent biofilm is added alone or in combination with another agent to the culture with or without increasing dilutions of the potential interfering agent or interfering agent such as an anti-DNABII or IHF (or other antibody, small molecule, agent, etc.) to find the optimal dose that would likely be effective at treating that patient when delivered to the subject where the infection existed. As apparent to those of skill in the art, a positive and negative control can be performed simultaneously.

In a further aspect, the method is practiced in a high throughput platform with the interfering agent (such as anti-DNABII or IHF antibody) and/or potential interfering agent (alone or in combination with another agent) in a flow cell. The interfering agent (such as anti-DNABII or IHF antibody) or potential interfering agent biofilm is added alone or in combination with another agent to the culture with or without increasing dilutions of the potential interfering agent or interfering agent such as an anti-DNABII or IHF (or other antibody, small molecule, agent, etc.) to find the optimal dose that would likely be effective at treating that patient when delivered to the subject where the infection existed. Biofilm isolates are sonicated to separate biofilm bacteria from DNABII polypeptide such as IHF bound to microbial DNA. The DNABII polypeptide—DNA complexes are isolated by virtue of the anti-DNABII or IHF antibody on the platform. The microbial DNA is then be released with e.g., a salt wash, and used to identify the biofilm bacteria added. The freed DNA is then identified, e.g., by PCR sequenced. If DNA is not freed, then the interfering agent(s) successfully performed or bound the microbial DNA. If DNA is found in the sample, then the agent did not interfere with DNABII polypeptide-microbial DNA binding. As is apparent to those of skill in the art, a positive and/or negative control can be simultaneously performed.

The above methods also can be used as a diagnostic test since it is possible that a given bacterial species will respond better to reversal of its biofilm by one agent more than another, this rapid high throughput assay system could allow one skilled the art to assay a panel of possible anti-DNABII or IHF-like agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in the art, bacteria generally do not grow planktonic ally when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective interfering agents in an industrial setting. Thus, the interfering agents can be used to treat, inhibit or titrate a biofilm in an industrial setting.

In a further aspect of the above methods, an antibiotic or antimicrobial known to inhibit growth of the underlying infection is added sequentially or concurrently, to determine if the infection can be inhibited. It is also possible to add the interfering agent to the microbial DNA or DNABII polypeptide before adding the missing complex to assay for biofilm inhibition.

When practiced in vivo in non-human animal such as a chinchilla, the method provides a pre-clinical screen to identify interfering agents that can be used alone or in combination with other agents to break down biofilms. Examples of this method are shown in Experiment Nos. 2 through 7, below.

In another aspect, provided herein is a method of inhibiting, preventing or breaking down a biofilm in a subject by administering to the subject an effective amount of an interfering agent, thereby inhibiting, preventing or breaking down the microbial biofilm. Examples of this method are shown in Experiment Nos. 2 through 7, below. Non-limiting examples of such subjects include mammals, e.g., pets, and human patients.

For the purpose of the above noted in vitro and in vivo methods, the interfering agent is of the group of:

(a) an isolated or recombinant DNABII or an integration host factor (IHF) polypeptide or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein or polypeptide identified in Table 8, Table 9A, Table 9B, Table 10 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of the "tip" portion of the DNABII protein or polypeptide, comprising, or alternatively consisting essentially of, or yet further consisting of

KLSGFGNFELRDKSSRPGRN (also referred to herein as hIFA4; (SEQ ID NO. 351);

RPGRNPKTGDVVPVSARRVV (also referred to herein as hIFA5; (SEQ ID NO. 352);

ARRVVTFKPGQKLRARVEKTK (also referred to herein as hIFA6; (SEQ ID NO. 353), or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;

(e) an isolated or recombinant C-terminal polypeptide of SEQ ID NO: 6 through 11, 28, 29, 42 through 100, Table 8 or those C-terminal polypeptides identified in Table 10 or a fragment or an equivalent of each thereof;

(f) a polypeptide or polynucleotide that competes with a DNABII protein on binding to a microbial DNA, e.g., DNABII or an integration host factor IHF and/or HU polypeptide or protein;

(g) a four-way junction polynucleotide resembling a Holliday junction, a 3 way junction polynucleotide resembling a replication fork, a polynucleotide that has inherent flexibility or bent polynucleotide;

(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;

(i) an antibody or antigen binding fragment that specifically recognizes or binds any one of (a) through (g), or an equivalent or fragment of each antibody or antigen binding fragment thereof;

(j) an isolated or recombinant polynucleotide encoding the antibody or antigen binding fragment of (i) or its complement;

(k) a small molecule that competes with the binding of a DNABII protein or polypeptide to a microbial DNA;

(l) an antibody or antigen binding fragment that specifically recognizes or binds any one of an isolated or recombinant polypeptide of SEQ ID NO: 342 through 353 or a fragment or an equivalent of each thereof; and/or (m) polypeptide that comprises, or alternatively consists essentially of, or yet further consists of polypeptides A1 through A6 or B1 through B6 as disclosed in FIG. 18; or

KLSGFGNFELRDKSSRPGRN (also referred to herein as hIFA4; (SEQ ID NO. 351);

RPGRNPKTGDVVPVSARRVV (also referred to herein as hIFA5; (SEQ ID NO. 352);

ARRVVTFKPGQKLRARVEKTK (also referred to herein as hIFA6; (SEQ ID NO. 353), or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

Also provided herein is a method for inducing an immune response in or conferring passive immunity in a subject in need thereof, comprising, or alternatively consisting essentially of or yet further consisting of, administering to the subject an effective amount of one or more agents of the group:

(a) an isolated or recombinant DNABII or an integration host factor (IHF) polypeptide, or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein polypeptide identified in Table 8, Table 9A, Table 9B, Table 10 or an DNA binding peptide identified in FIGS. 6A-6B, or a fragment or an equivalent of each thereof, a polypeptide A1 to A5, or B1 to B5 as shown in FIG. 18, or a fragment that comprises, or consists essentially of, or yet consists of, the "tip" portion of the DNABII protein or polypeptide, non-limiting examples of such include without limitation a polypeptide that comprises, or alternatively consists essentially of, or yet further consists of

KLSGFGNFELRDKSSRPGRN (also referred to herein as hIFA4; (SEQ ID NO. 351);

RPGRNPKTGDVVPVSARRVV (also referred to herein as hIFA5; (SEQ ID NO. 352);

ARRVVTFKPGQKLRARVEKTK (also referred to herein as hIFA6; (SEQ ID NO. 353), or an equivalent of each thereof. Additional examples of equivalent polypeptides include, for example IEYLSDKYHLSKQDTK (SEQ ID NO. 354), DKSSRPGRNPKTGDVVAASARR (SEQ ID NO.: 355), AND KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random or naturally occurring amino acids on either the amine or carboxy termini (or on both);

(d) an isolated or recombinant polypeptide of SEQ ID NO: 1 through 353 or a fragment or an equivalent thereof;

(e) an isolated or recombinant C-terminal polypeptide of SEQ ID NO: 6 through 11, 28, 29, 42 through 100, Table 8 or those C-terminal polypeptides identified in Table 10 or a fragment or an equivalent of each thereof;

(f) an isolated or recombinant polynucleotide encoding any one of (a) through (e) or an isolated or recombinant polynucleotide SEQ ID NO: 36 or an equivalent of each thereof, or a polynucleotide that hybridizes under stringent conditions to the polynucleotide, its equivalent or its complement;

(g) an antibody or antigen binding fragment that specifically recognizes or binds any one of (a) through (e), or an equivalent or fragment of each thereof;

(h) an isolated or recombinant polynucleotide encoding the antibody or antigen binding fragment of (g);

(i) an antigen presenting cell pulsed with any one of (a) through (e);

(j) an antigen presenting cell transfected with one or more polynucleotides encoding any one of (a) through (e); and/or (k) an antibody or antigen binding fragment that specifically recognizes or binds any one of an isolated or recombinant polypeptide noted herein as A1, A2, A3, A4, A5, A6, B1, B2, B3, B4, B5, B6 (se FIG. 18) or an isolated or recombinant polypeptide of SEQ ID NO: 342 through 353 or a fragment or an equivalent of each thereof.

In one particular aspect, the interfering agent is an isolated or recombinant DNABII protein, e.g., an integration host factor (IHF) polypeptide or a fragment thereof, a C-terminal fragment of an IHF polypeptide, a tip fragment, of an equivalent of each thereof. In another particular aspect, the interfering agent is an isolated or recombinant HU polypeptide or a fragment thereof, a tip fragment, a C-terminal fragment of HU polypeptide, or an equivalent of each thereof. Non-limiting examples of such are an IHF or HU alpha or beta polypeptide; an IHF polypeptide; *Moraxella catarrhalis* HU; *E. coli* HupA, HupB, himA, himD; *E. faecalis* HU (such as V583), HMGB1 (High Mobility Group Box 1, a protein with similar DNA binding and DNA substrate specificities but not in primary amino acid sequence to the DNABII family of proteins; a functional orthologue) and those identified in Table 8 or Table 10.

In a further aspect, the methods further comprise, or alternatively consist essentially of, or yet further consist of administering to the subject an effective amount of one or more of an antimicrobial, an antigenic peptide or an adjuvant.

A non-limiting example of an antimicrobial agent is another vaccine component such as a surface antigen, e.g., an OMP P5, rsPilA, OMP 26, OMP P2, or Type IV Pilin protein (see Jurcisek and Bakaletz (2007) J. Bacteriology 189(10):3868-3875; Murphy, T. F. et al. (2009) The Pediatric Infectious Disease Journal 28:S121-S126).

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneously, intramuscularly, intraperitoneally, intranasally, by inhalation or orally.

Microbial infections and disease that can be treated by the methods disclosed herein include infection by the organisms identified in Experiment No. 1 and Table 8, e.g., *Streptococcus agalactiae, Neisseria meningitidis, Treponemes, denticola, pallidum, Burkholderia cepacia,* or *Burkholderia pseudomallei*. In one aspect, the microbial infection is one or more of *Haemophilus influenzae* (nontypeable), *Moraxella catarrhalis, Streptococcus pneumoniae, Streptococcus pyogenes, Pseudomonas aeruginosa, Mycobacterium tuberculosis*. These microbial infections may be present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans, Porphyromonas gingivalis, Aggregatibacter actinomvctemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Infections caused by *Streptococcus agalactiae* can also be treated by the methods disclosed herein and it is the major cause of bacterial septicemia in newborns. Infections caused by *Neisseria meningitidis* which can cause meningitis can also be treated.

Thus, routes of administration applicable to the methods disclosed herein include intranasal, intramuscular, urethrally, intratracheal, subcutaneous, intradermal, transdermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The interfering agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200 to about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Polypeptides

Also provided herein are interfering agents and compositions for use in the methods described herein, wherein the interfering agent is of the group:

(a) an isolated or recombinant DNABII or an integration host factor (IHF) polypeptide or a fragment or an equivalent of each thereof;

(b) an isolated or recombinant histone-like protein from *E. coli*, e.g., *E. coli* strain U93 (HU) polypeptide or a fragment or an equivalent of each thereof;

(c) an isolated or recombinant protein or polypeptide identified in Table 8, Table 9A, Table 9B, Table 10 or a DNA binding peptide identified in FIGS. 6A-6B, or a fragment or an equivalent of each thereof, wherein in one aspect the fragment comprises, or consists essentially of, or yet consists of, the polypeptides identified as A1 through A6 or B1 through B6 as disclosed in FIG. 18; or comprising, or alternatively consisting essentially of, or yet further consisting of the "tip" portion of the DNABII protein or polypeptide, comprising, or alternatively consisting essentially of, or yet further consisting of

KLSGFGNFELRDKSSRPGRN (also referred to herein as hIFA4; (SEQ ID NO. 351);

RPGRNPKTGDVVPVSARRVV (also referred to herein as hIFA5; (SEQ ID NO. 352);

ARRVVTFKPGQKLRARVEKTK (also referred to herein as hIFA6; (SEQ ID NO. 353);

or an equivalent of each thereof, or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17), described in U.S. Ser. Nos. 14/497,147 and 14/668,767 now abandoned). Equivalent polypeptides also include a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both);

(d) an isolated or recombinant polypeptide of SEQ ID NO: 1 through 353, or a fragment or an equivalent of each thereof;

(e) an isolated or recombinant C-terminal polypeptide of SEQ ID NO: 6 through 11, 28, 29, 42 through 100, Table 8 or those C-terminal polypeptides identified in Table 10 or a fragment or an equivalent of each thereof;
(f) a polypeptide or polynucleotide that competes with a DNABII protein on binding to a microbial DNA, e.g., DNABII or an integration host factor IHF and/or HU polypeptide or protein;
(g) a four-way junction polynucleotide resembling a Holliday junction, a 3 way junction polynucleotide resembling a replication fork, a polynucleotide that has inherent flexibility or bent polynucleotide;
(h) an isolated or recombinant polynucleotide encoding any one of (a) through (f) or an isolated or recombinant polynucleotide of SEQ ID NO: 36 or an equivalent of each thereof, or a polynucleotide that hybridizes under stringent conditions to the polynucleotide its equivalent or its complement;
(i) an antibody or antigen binding fragment that specifically recognizes or binds any one of (a) through (g), or an equivalent or fragment of each antibody or antigen binding fragment thereof;
(j) an isolated or recombinant polynucleotide encoding the antibody or antigen binding fragment of (i) or its complement;
(k) a small molecule that competes with the binding of a DNABII protein or polypeptide to a microbial DNA;
(l) an antibody or antigen binding fragment that specifically recognizes or binds any one of an isolated or recombinant polypeptide of SEQ ID NO: 342 through 353 or a fragment or an equivalent of each thereof; and/or
(m) polypeptide that comprises, or alternatively consists essentially of, or yet further consists of polypeptides A1 through A6 or B1 through B6, as disclosed in FIG. 18; or

KLSGFGNFELRDKSSRPGRN (also referred to herein as hIFA4; (SEQ ID NO. 351);

RPGRNPKTGDVVPVSARRVV (also referred to herein as hIFA5; (SEQ ID NO. 352);

ARRVVTFKPGQKLRARVEKTK (also referred to herein as hIFA6; (SEQ ID NO. 353), or an equivalent of each thereof or a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example IEYLSDKYHLSKQDTK (SEQ ID NO. 354), DKSSRPGRNPKTGDVVAASARR (SEQ ID NO.: 355), and KLRARVEKTK (SEQ ID NO. 17) described in U.S. Ser. Nos. 14/497,147 and 14/668,767 now abandoned), a polypeptide consisting of or comprising the above noted polypeptides with the addition of up to 25, or alternatively 20, or alternatively 15, or alternatively up to 10, or alternatively up to 5 random amino acids on either the amine or carboxy termini (or on both).

In one particular aspect, the interfering agent is an isolated or recombinant DNABII polypeptide or a fragment or an equivalent of each thereof. Non-limiting examples of such are an IHF or HU alpha or beta polypeptide; an IHF a polypeptide; *Moraxella catarrhalis* HU; *E. coli* HupA, HupB, himA, himD; *E. faecalis* HU (such as V583), HMGB1 and those identified in Table 8.

In another aspect, the interfering agent is an isolated or recombinant polypeptide consisting essentially of an amino acid sequence selected from SEQ ID NO: 1 to 5 or 12 to 27, 30 to 35, 101-353 or a DNA binding peptide identified in FIGS. 6A-6B.

In another aspect, the isolated or recombinant polypeptide comprises, or alternatively consists essentially of or yet further consists of SEQ ID NO: 1 or 2, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 3, 4 or 5, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 12, 14, 16, 18, 20, 22, 24, 26, 30 or 32, with the proviso that the polypeptide is none of SEQ ID NO: 6 to 11, 28, 29, or 42 through 100.

In another aspect, the isolated or recombinant polypeptide comprises, or alternatively consists essentially of, or yet further consists of SEQ ID NO: 13, 15, 17, 19, 21, 23, 25, 27, 31 33, 34, or 35 with the proviso that the polypeptide is none of SEQ ID NO: 6 to 11, 28, 29, or 42 through 100.

In another aspect, the isolated or recombinant polypeptide comprises, or alternatively consists essentially of, or yet further consists of an isolated or recombinant polypeptide of the group of:
a polypeptide comprising SEQ ID NO: 12 and 13;
a polypeptide comprising SEQ ID NO: 14 and 15;
a polypeptide comprising SEQ ID NO: 16 and 17;
a polypeptide comprising SEQ ID NO: 18 and 19;
a polypeptide comprising SEQ ID NO: 20 and 21;
a polypeptide comprising SEQ ID NO: 23 and 24;
a polypeptide comprising SEQ ID NO: 25 and 26;
a polypeptide comprising SEQ ID NO: 30 and 31;
a polypeptide comprising SEQ ID NO: 32 and 33;
a polypeptide comprising SEQ ID NO: 34 and 35;
a polypeptide comprising SEQ ID NO: 337 and 338; or
a polypeptide comprising SEQ ID NO: 339 and 340;
a polypeptide consisting essentially of any one or more of SEQ ID NO: 342 to 353;
with the proviso that the polypeptide is none of wild-type of any one of IHF alpha, IHF beta or SEQ ID NO: 6 to 11, 28, 29, or 42 through 100.

In another aspect, the isolated or recombinant polypeptide is of the group:
a polypeptide consisting essentially of SEQ ID NO: 12 and 13;
a polypeptide consisting essentially of SEQ ID NO: 14 and 15;
a polypeptide consisting essentially of SEQ ID NO: 16 and 17;
a polypeptide consisting essentially of SEQ ID NO: 18 and 19;
a polypeptide consisting essentially of SEQ ID NO: 20 and 21;
a polypeptide consisting essentially of SEQ ID NO: 23 and 24;

a polypeptide consisting essentially of SEQ ID NO: 25 and 26;
a polypeptide consisting essentially of SEQ ID NO: 30 and 31;
a polypeptide consisting essentially of SEQ ID NO: 32 and 33;
a polypeptide consisting essentially of SEQ ID NO: 34 and 35;
a polypeptide consisting essentially of SEQ ID NO: 337 and 338; or
a polypeptide consisting essentially of SEQ ID NO: 339 and 340;
a polypeptide consisting essentially of any one or more of SEQ ID NO: 342 to 353;
with the proviso that the polypeptide is none of wild-type of any one of IHF alpha, IHF beta or SEQ ID NO: 6 to 11, 28, 29, or 42 through 100.

Further provided as agents for use in the methods disclosed herein are fragments or an equivalent of the isolated or recombinant polypeptides described above. Examples of fragments are A1 through A6; B1 through B6 (see FIG. 18); or a C-terminal polypeptide. In another aspect, the fragment is a tip portion of the DNABII, non-limiting examples of such includes without limitation a polypeptide that comprises

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353));

or an equivalent of each thereof. In a further aspect, the isolated or recombinant polypeptide comprises, or alternatively consists essentially of, or yet further consists of two or more of the isolated or recombinant polypeptides described above.

Additionally, the isolated or recombinant polypeptide comprises, or alternatively consists essentially of, or yet further consists of any one of SEQ ID NO: 1 to 6, 12 to 27 or 30 to 33, or a fragment or an equivalent polypeptide, examples of which are identified in Table 8 or shown in Table 9A, Table 9B or Table 10. In one aspect, isolated wild-type polypeptides are excluded, i.e., that the polypeptide is none of SEQ ID NO: 6 through 11, 28, 29, or a wildtype sequence identified in Table 8 or shown in Table 9A.

In one aspect, this disclosure provides an isolated or recombinant polypeptide consisting essentially of an amino acid sequence of the group SEQ ID NO: 1 to 6, 12 to 27 or 30 to 35, 1 to 6 and 13 to 35, or a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27, or a fragment or equivalent thereof of each thereof. In another aspect, the disclosure provides an isolated or recombinant polypeptide comprising, or alternatively consisting essentially of, or yet further consisting of an amino acid sequence of the group SEQ ID NO: 1 to 4, or a fragment or an equivalent of each thereof, or a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27 or a fragment or a biological equivalent thereof which further comprises independently at least 2, or alternatively at least 3, or alternatively at least 4, or alternatively at least 5, or at least 6, or alternatively at least 7, or alternatively at least 8, or alternatively at least 9 or alternatively at least 10 amino acids at the amino and/or carboxyl terminus of the polypeptide. In one aspect, isolated wildtype DNA binding polypeptides are excluded, i.e., that the polypeptide is none of SEQ ID NO: 6 through 11, 28, 29, or 42 through 100 or an isolated wildtype polypeptide sequence listed in Table 8 or shown in Table 9A.

In another aspect, this disclosure provides an isolated or recombinant polypeptide comprising, or alternatively consisting essentially of, or yet further consisting of, SEQ ID. NO 1 or 2 alone or in combination with a polypeptide comprising, or alternatively consisting essentially of, or yet further consisting of an amino acid corresponding to the β-3 and/or α-3 fragments of a *Haemophilus influenzae* IHFα or IHFβ, on-limiting examples of which include SEQ ID NO: 12 through 27 or a fragment or a biological equivalent of each thereof. In one aspect, isolated wildtype DNA binding polypeptides are excluded, i.e., that the polypeptide is none of SEQ ID NO: 6 through 11, 28, 29, or 42 through 100 or an isolated polypeptide sequence listed in Table 8 or shown in Table 9A.

In a yet further aspect, this disclosure provides an isolated or recombinant polypeptide comprising or alternatively consisting essentially of, or yet further consisting of, SEQ ID NO: 3 or 4 or a fragment or an equivalent of each thereof alone or in combination with a polypeptide comprising, or alternatively consisting essentially of, or yet further consisting of an amino acid corresponding to the β-3 and/or α-3 fragments of a *Haemophilus influenzae* IHFα or IHFβ, non-limiting examples of which include SEQ ID NO: 12 through 27, and 34-35 or a biological equivalent of each thereof. In one aspect, isolated wildtype DNA binding polypeptides are excluded, i.e., that the polypeptide is none of SEQ ID NO: 6 through 11, 28, 29, or 42 through 100 or an isolated wildtype polypeptide sequence listed in Table 8 or shown in Table 9A, or a polypeptide that comprises

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353)), or an equivalent of each thereof.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof. Non-limiting examples of such include isolated or recombinant polypeptides comprising SEQ ID NO: 1 through 4, e.g., SEQ ID NO: 1 and 2, or alternatively 1 and 3 or alternatively 1 and 4, or alternatively 2 and 3, or alternatively SEQ ID NO: 1, 2 and 3 or alternatively, 2, 3 and 4, or alternatively 1, 3 and 4. The polypeptides can be in any orientation, e.g., SEQ ID NO: 1, 2, and 3 or SEQ ID NO: 3, 2 and 1 or alternatively 2, 1 and 3, or alternatively, 3, 1 and 2. Biological equivalents of these polypeptides are further included in this disclosure with the proviso that the sequences do not include isolated wildtype sequences such as those identified in Tables 8 and 9.

In another aspect, this disclosure provides an isolated or recombinant polypeptide comprising or alternatively consisting essentially of, or yet further consisting of, SEQ ID NO: 1 or 2 and 3 or 4, or a fragment or an equivalent of each thereof, with the proviso that the polypeptide is none of SEQ ID NO: 5 through 10, and they may further comprise any one or more of SEQ ID NO: 11 through 26, e.g., 11 and 12, or alternatively 1 and 11, or alternatively 2 and 11, or alternatively, 1 and 12, or alternatively 2 and 12, or alternatively 11, 12 and 1, or alternatively 2, 11 and 12. In this embodiment, SEQ ID NO: 1 or 2 is located upstream or amino terminus from SEQ ID NO: 3 or 4, with the proviso that the amino acid sequence is not an isolated wildtype polypeptide, e.g., none of SEQ ID NO: 6 through 11, 28 and 29. In another aspect, the isolated polypeptide comprises SEQ ID NO: 3 or 4 located upstream or amino terminus to SEQ ID NO: 1 or 2. Biological equivalents of these polypeptides are further included in this disclosure with the proviso that the sequence do not include isolated wildtype polypeptides.

In one embodiment, any polypeptide or protein having sequence identity to the wildtype polypeptides or those disclosed in Pedulla et al. (1996) PNAS 93:15411-15416 is excluded from this disclosure.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 37). Other examples include Gly-Gly-Gly; Gly-Pro-Ser-Leu (SEQ ID NO: 38); Gly-Pro-Ser; Pro-Ser-Leu-Lys (SEQ ID NO: 39); Gly-Pro-Ser-Leu-Lys (SEQ ID NO: 40) and Ser-Leu-Lys-Leu (SEQ ID NO: 41).

The isolated polypeptides disclosed herein are intended to include isolated wildtype and recombinantly produced polypeptides and proteins from prokaryotic and eukaryotic host cells, as well as muteins, analogs and fragments thereof, examples of such cells are described above. In some embodiments, the term also includes antibodies and anti-idiotypic antibodies as described herein. Such polypeptides can be isolated or produced using the methods known in the art and briefly described herein.

It is understood that functional equivalents or variants of the wild type polypeptide or protein also are within the scope of this disclosure, for example, those having conservative amino acid substitutions of the amino acids, see for example, Table 9. Other analogs include fusion proteins comprising a protein or polypeptide disclosed herein which can include a polypeptide joined to an antigen presenting matrix.

In a further aspect, the polypeptides are conjugated or linked to a detectable label. Suitable labels are known in the art and described herein.

In a yet further aspect, the polypeptides with or without a detectable label can be contained or expressed on the surface of a host prokaryotic or eukaryotic host cell, such as a dendritic cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., .beta.-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta, turns, beta, sheets, gamma-turns, and cyclic peptides can be generated. Generally, it is believed that .alpha.-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support. These compositions are useful for various diagnostic and therapeutic methods as described herein.

Polynucleotides

This disclosure also provides isolated or recombinant polynucleotides encoding one or more of the above-identified isolated or recombinant polypeptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

In another aspect, this disclosure provides an interfering agent that is a polynucleotide that interferes with the binding of the DNA to a polypeptide or protein in a microbial biofilm, or a four-way junction polynucleotide resembling a Holliday junction, a 3 way junction polynucleotide resembling a replication fork, a polynucleotide that has inherent flexibility or bent polynucleotide which can treat or inhibit DNABII polynucleotide from binding to microbial DNA as well treat, prevent or inhibit biofilm formation and associated infections and disorders. One of skill in the art can make such polynucleotides using the information provided herein and knowledge of those of skill in the art. See Goodman and Kay (1999) J. Biological Chem. 274(52):37004-37011 and Kamashev and Rouviere-Yaniv (2000) EMBO J. 19(23): 6527-6535.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see, Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See, Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Examples of CDR sequences include without limitation comprise, consist essentially of, or yet further consist of, the following: the heavy chain variable region of the antibody or a fragment thereof comprises, or alternatively consists essentially of, or yet further consists of, the polypeptide encoded by the below polynucleotide sequence:

SEQ ID NO. (358): Non-limiting exemplary heavy chain variable region nucleotide sequence, IhfA5 fragment
GAGGTGCAGCTGCAGGAGTCTGGACCTGGCCTGGTGACGCCCTCACAGAG

CCTGTCCATGACTTGCACTGTCTCTGGGTTTTCATTAACCAGCTATAGTG

TACACTGGGTTCGCCAGCCTCCAGGAAAGAGTCTGGAGTGGCTGGGAGTA

ATATGGGCTGGTGGAAGCACAAATTATAATTCGGCTCTCATGTCCAGACT

GAGCATCAGCAAAGACAACTCCAAGAGCCAAGTTTTCTTAAAAATGGACA

GTCTGCAAACTGATGACACAGCCATATACTACTGTGCCAGAGAGGACTCC

TGGGGTCAAGGAACCTCAGTCACCGTCTCCTCA

In some embodiments, the heavy chain variable region of the antibody or a fragment thereof comprises, or alternatively consists essentially of, or yet further consists of, the amino acid sequence:

SEQ ID NO. (359): Non-limiting exemplary heavy chain variable region amino acid sequence, IhfA5 fragment
EVQLQESGPGLVTPSQSLSMTCTVSGFSLTSYSVHWVRQPPGKSLEWLGV

IWAGGSTNYNSALMSRLSISKDNSKSQVFLKMDSLQTDDTAIYYCAREDS

WGQGTSVTVSS

In some embodiments, the light chain variable region of the antibody or a fragment thereof comprises, or alternatively consists essentially of, or yet further consists of, the polypeptide encoded by the below polynucleotide sequence:

SEQ ID NO. (360): Non-limiting exemplary light chain variable region nucleotide sequence, IhfA5 fragment
GACATTGTGATGACCCAGTCTCAAAAATTCATGTCCACATCAGTAGGAGA

CAGGGTCAGCGTCACCTGCAAGGCCAGTCAGAATGTGGGTACTAATGTAG

CCTGGTATCAACAGAAACCAGGGCAATCTCCTAAAGCACTGATTTACTCG

GCATCCTACCGGTACAGTGGAGTCCCTGATCGCTTCACAGGCAGTGGATC

TGGGACAGATTTCACTCTCACCATCAGCAATGTGCAGTCTGAAGACTTGG

CAGAGTATTTCTGTCAGCAATATAACAGCTATCCCACGTTCGGAGGGGGG

ACCAAGTTGGAAATAAAA

In some embodiments, the light chain variable region of the antibody or a fragment thereof comprises, or alternatively consists essentially of, or yet further consists of, the amino acid sequence:

SEQ ID NO. (361): Non-limiting exemplary light chain variable region amino acid sequence, IhfA5 fragment
DIVMTQSQKFMSTSVGDRVSVTCKASQNVGTNVAWYQQKPGQSPKALIYS

ASYRYSGVPDRFTGSGSGTDFTLTISNVQSEDLAEYFCQQYNSYPTFGGG

TKLEIK

In some embodiments the antibodies disclosed herein comprise, or alternatively consists essentially of, or yet further consists of, the polypeptide encoded by the polynucleotide sequence comprising one or more of the CDR sequences listed herein below:

SEQ ID NO. (362) Partial non-limiting exemplary CDRH1 sequence, IhfA5 fragment FSLTSYS SEQ ID NO. (363) Partial non-limiting exemplary CDRH1 sequence, IhfA5 fragment FSLTSYSV SEQ ID NO. (364): Partial non-limiting exemplary CDRH1 sequence, IhfA5 fragment
FSLTSYSVH SEQ ID NO. (365): Partial non-limiting exemplary CDRH1 sequence, IhfA5 fragment
GFSLTSYS SEQ ID NO. (366): Partial non-limiting exemplary CDRH2 sequence, IhfA5 fragment IWAGGST SEQ ID NO. (367): Partial non-limiting exemplary CDRH2 sequence, IhfA5 fragment VIWAGGST SEQ ID NO. (368): Partial non-limiting exemplary CDRH2 sequence, IhfA5 fragment GVIWAGGST SEQ ID NO. (369): Partial non-limiting exemplary CDRH2 sequence, IhfA5 fragment LGVIWAGGST SEQ ID NO. (370): Partial non-limiting exemplary CDRH2 sequence, IhfA5 fragment WLGVIWAGGST SEQ ID NO. (371): Partial non-limiting exemplary CDRH2 sequence, IhfA5 fragment IWAGGSTN SEQ ID NO. (372): Partial non-limiting exemplary CDRH2 sequence, IhfA5 fragment VIWAGGSTN SEQ ID NO. (373): Partial non-limiting exemplary CDRH2 sequence, IhfA5 fragment GVIWAGGSTN SEQ ID NO. (374): Partial non-limiting exemplary CDRH2 sequence, IhfA5 fragment LGVIWAGGSTN SEQ ID NO. (375): Partial non-limiting exemplary CDRH2 sequence, IhfA5 fragment WLGVIWAGGSTN SEQ ID NO. (376): Partial non-limiting exemplary CDRH2 sequence, IhfA5 fragment IWAGGSTNY SEQ ID NO. (377): Partial non-limiting exemplary CDRH2 sequence, IhfA5 fragment VIWAGGSTNY SEQ ID NO. (378): Partial non-limiting exemplary CDRH2 sequence, IhfA5 fragment GVIWAGGSTNY SEQ ID NO. (379): Partial non-limiting exemplary CDRH2 sequence, IhfA5 fragment LGVIWAGGSTNY SEQ ID NO. (380): Partial non-limiting exemplary CDRH2 sequence, IhfA5 fragment WLGVIWAGGSTNY SEQ ID NO. (381): Partial non-limiting exemplary CDRH3 sequence, IhfA5 fragment REDS SEQ ID NO. (382): Partial non-limiting exemplary CDRH3 sequence, IhfA5 fragment AREDS SEQ ID NO. (383): Partial non-limiting exemplary CDRL1 sequence, IhfA5 fragment QNVGTN SEQ ID NO. (384): Partial non-limiting exemplary CDRL1 sequence, IhfA5 fragment QNVGTNV SEQ ID NO. (385): Partial non-limiting exemplary CDRL1 sequence, IhfA5 fragment QNVGTNVA SEQ ID NO. (386): Partial non-limiting exemplary CDRL2 sequence, IhfA5 fragment SAS SEQ ID NO. (387): Partial non-limiting exemplary CDRL2 sequence, IhfA5 fragment YSAS SEQ ID NO. (388): Partial non-limiting exemplary CDRL2 sequence, IhfA5 fragment IYSAS SEQ ID NO. (389) Partial non-limiting exemplary CDRL2 sequence, IhfA5 fragment LIYSAS SEQ ID NO. (390): Partial non-limiting exemplary CDRL2 sequence, IhfA5 fragment ALIYSAS SEQ ID NO. (391) Partial non-limiting exemplary CDRL2 sequence, IhfA5 fragment SASY SEQ ID NO. (392): Partial non-limiting exemplary CDRL2 sequence, IhfA5 fragment YSASY SEQ ID NO. (393): Partial non-limiting exemplary CDRL2 sequence, IhfA5 fragment IYSASY SEQ ID NO. (394): Partial non-limiting exemplary CDRL2 sequence, IhfA5 fragment LIYSASY SEQ ID NO. (395): Partial non-limiting exemplary CDRL2 sequence, IhfA5 fragment ALIYSASY SEQ ID NO (396): Partial non-limiting exemplary CDRL2 sequence, IhfA5 fragment SASYR SEQ ID NO. (397): Partial non-limiting exemplary CDRL2 sequence, IhfA5 fragment YSASYR SEQ ID NO. (398) Partial non-limiting exemplary CDRL2 sequence, IhfA5 fragment IYSASYR SEQ ID NO. (399): Partial non-limiting exemplary CDRL2 sequence, IhfA5 fragment LIYSASYR SEQ ID NO. (400): Partial non-limiting exemplary CDRL2 sequence, IhfA5 fragment ALIYSASYR SEQ ID NO. (401): Partial non-limiting exemplary CDRL2 sequence, IhfA5 fragment SASYRY SEQ ID NO. (402): Partial non-limiting exemplary CDRL2 sequence, IhfA5 fragment YSASYRY SEQ ID NO. (403): Partial non-limiting exemplary CDRL2 sequence, IhfA5 fragment IYSASYRY SEQ ID NO. (404): Partial non-limiting exemplary CDRL2 sequence, IhfA5 fragment LIYSASYRY SEQ ID NO. (405): Partial non-limiting exemplary CDRL2 sequence, IhfA5 fragment ALIYSASYRY SEQ ID NO. (406): Partial non-limiting exemplary CDRL2 sequence, IhfA5 fragment SASYRYS SEQ ID NO. (407): Partial non-limiting exemplary CDRL2 sequence, IhfA5 fragment YSASYRYS SEQ ID NO. (408): Partial non-limiting exemplary CDRL2 sequence, IhfA5 fragment IYSASYRYS SEQ ID NO. (409): Partial non-limiting exemplary CDRL2 sequence, IhfA5 fragment LIYSASYRYS SEQ ID NO. (410): Partial non-limiting exemplary CDRL2 sequence, IhfA5 fragment ALIYSASYRYS SEQ ID NO. (411): Partial non-limiting exemplary CDRL3 sequence, IhfA5 fragment QQYNSYP SEQ ID NO. (412): Partial non-limiting exemplary CDRL3 sequence, IhfA5 fragment QQYNSYPT Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Antibodies specific to DNABII polypeptides, e.g., IHFα and IHFβ can be generated by injection of polypeptides corresponding to different epitopes of IHFα and IHFβ. For example, antibodies can be generated using the 20 amino acids of each subunit such as TFRPGQKLKSRVENASPKDE (SEQ ID NO:34) for IHFα and KYVPHFKPGKELRDRANIYG (SEQ ID NO:35) for IHFβ or A1 to A6 or B1 to B6 (See FIG. 18). Antibodies specific to the "tip" or "tail" portion of the DNABII protein or polypeptide can be generated. Additional non-limiting examples include without limitation a polypeptide fragment that comprises one or more of MATITKLDIIEYLSDKYHLS (also referred to herein as hIFA1; (SEQ ID NO. 348));

KYHLSKQDTKNVVENFLEEI (also referred to herein as hIFA2; (SEQ ID NO. 349));

FLEEIRLSLESGQDVKLSGF (also referred to herein as hIFA3; (SEQ ID NO. 350));

KLSGFGNFELRDKSSRPGRN (also referred to herein as hIFA4; (SEQ ID NO. 351));

RPGRNPKTGDVVPVSARRVV (also referred to herein as hIFA5; (SEQ ID NO. 352));

ARRVVTFKPGQKLRARVEKTK (also referred to herein as hIFA6; (SEQ ID NO. 353));

or an equivalent thereof. Other exemplary antibodies include monoclonal antibodies that specifically recognize and bind *Haemophilus influenzae* IhfA fragment A5 (SEQ ID NO. 352)). The hybridoma cell lines that produce monoclonal antibodies that specifically recognize and bind *Haemophilus influenzae* IhfA fragment A5 (SEQ ID NO. 352)) and IhfB4 (RGFGSFSLHHRQPRLGRNPK (also referred to B4 (SEQ ID NO. 345)); were deposited with American Type Culture Collection (ATCC) under Accession Numbers (IhfA5 (Accession No. PTA-122334)) and (IhfB4 (Accession No. PTA-122336)), pursuant to the provisions of the Budapest Treaty on Jul. 30, 2015; the respective hybridoma cell lines designated: IhfA5-NTHI 14GB.F5.G6; and IhfB4-NTHI 4EII.E5.G2. Further non-limiting exemplary antibodies include those that specifically recognize and bind *Haemophilus influenzae* IhfA fragment A3 (SEQ ID NO. 350), IhfB fragment B2 (SEQ ID NO. 343) produced by hybridoma cell lines IhfA3 NTHI 9B10.F2.H3 and IhfB2 NTHI 7A4.E4.G4, respectively.

Further, non-limiting exemplary antibodies that fall within the scope of this disclosure include but are not limited to those disclosed in now abandoned U.S. Ser. No. 14/497,147, filed Sep. 25, 2014; U.S. Ser. No. 14/668,767, filed Mar. 25, 2015; and U.S. Ser. No. 14/789,842, filed Jul. 1, 2015, and provided under the following designations: TRL295, TRL299, TRL1012, TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347, and TRL1361, the heavy chain and light chain sequences of which are provided herein below.

TRL295 HC,
SEQ ID NO: 413
QVQLVESGGGLVQPGGSLRLSCAASGFPFSSYAMSWVRQAPGKGLEWVSA

ISGNGADSYYADSVKGRFTTSRDKSKNTVYLQMNRLRAEDTAVYYCAKDM

RRYHYDSSGLHFWGQGTLVTVSS

TRL295 LC,
SEQ ID NO: 414
DIELTQAPSVSVYPGQTARITCSGDALPKQYAYWYQQKPGQAPVVVIYKD

SERPSGISERFSGSSSGTTVTLTISGVQAGDEADYYCQSVDTSVSYYVVF

GGGTKLTVL

TRL299 HC,
SEQ ID NO: 415
QVQLVQSGGGLVQPGGSLRLSCAASGFTFSHYNMNWVRQAPGKGPEWVSY

ISSGSDIIYYADSVKGRFTISRDNAKNSLYLQMNSLRDEDTAVYYCARAL

DRDGFDIWGQGTMVTVSS

TRL299 LC,
SEQ ID NO: 416
DIVLTQSPSSLSASVGDKVTITCRASQSISTFLNWYQHKPGKAPKLLIYG

ASSLQSGVPSRFSGSGSGTDFTLTISSLQPEDFATYYCQQSYSTPTFGQG

TKVEIK

TRL1012 HC,
SEQ ID NO: 417
QVQLVESGGGLVQPGGSLRLSCAASGFPFSSYAMSWVRQAPGKGLEWVSA

ISGNGADSYYADSVKGRFTTSRDKSKNTVYLQMNRLRAEDTAVYYCAKDM

RRYHYDSSGLHFWGQGTLVTVSS

TRL1012 LC,
SEQ ID NO: 418
DIMLTQPPSVSAAPGQKVTISCSGSSSNIGTNYVSWFQQVPGTAPKFLIY

DNYKRPSETPDRFSGSKSGTSATLDITGLQTGDEANYYCATWDSSLSAWV

FGGGTKVTVL

TRL1068 HC,
SEQ ID NO: 419
QVQLVESGPGLVKPSETLSLTCRVSGDSNRPSYWSWIRQAPGKAMEWIGY

VYDSGVTIYNPSLKGRVTISLDTSKTRFSLKLTSVIAADTAVYYCARERF

DRTSYKSWWGQGTQVTVSS

TRL1068 LC,
SEQ ID NO: 420
DIVLTQAPGTLSLSPGDRATLSCRASQRLGGTSLAWYQHRSGQAPRLILY

GTSNRATDTPDRFSGSGSGTDFVLTISSLEPEDFAVYYCQQYGSPPYTFG

QGTTLDIK

TRL1070 HC,
SEQ ID NO: 421
QVQLVQSGGTLVQPGGSLRLSCAASGFTFSYYSMSWVRQAPGKGLEWVAN

IKHDGTERNYVDSVKGRFTISRDNSEKSLYLQMNSLRAEDTAVYYCAKYY

YGAGTNYPLKYWGQGTRVTVSS

TRL1070 LC,
SEQ ID NO: 422
DILMTQSPSSLSASVGDRVTITCRASQGIRNDLGWYQQKPGKAPKLLIYA

ASSLQSGVPSRFSGSGSGTDFTLTISSLQPEDFATYYCLQDYNYPLTFGG

GTKVEIKR

TRL1087 HC,
SEQ ID NO: 423
QVQLLESGPGLVRPSDTLSLTCTFSADLSTNAYWTWIRQPPGKGLEWIGY

MSHSGGRDYNPSFNRRVTISVDTSKNQVFLRLTSVTSADTAVYFCVREVG

SYYDYWGQGILVTVSS

TRL1087 LC,
SEQ ID NO: 424
DIEMTQSPSSLSASVGDRITITCRASQGISTWLAWYQQKPGKAPKSLIFS

TSSLHSGVPSKFSGSGSGTDFTLTITNLQPEDFATYYCQQKWETPYSFGQ

GTKLDMIR

TRL1215 HC,
SEQ ID NO: 425
QVQLVESGTEVKNPGASVKVSCTASGYKFDEYGVSWVRQSPGQGLEWMGW

ISVYNGKTNYSQNFQGRLTLTTETSTDTAYMELTSLRPDDTAVYYCATDK

NWFDPWGPGTLVTVSS

TRL1215 LC,

```
                                        SEQ ID NO: 426
DIVMTQSPSASGSPGQSITISCTGTNTDYNYVSWYQHHPGKAPKVIIYDV

KKRPSGVPSRFSGSRSGNTATLTVSGLQTEDEADYYCVSYADNNHYVFGS

GTKVTVL

TRL1216 HC,
                                        SEQ ID NO: 427
QVQLVESGGGVVQPGGSLRVSCAASAFSFRDYGIHWVRQAPGKGLQWVAV

ISHDGGKKFYADSVRGRFTISRDNSENTLYLQMNSLRSDDTAVYYCARLV

ASCSGSTCTTQPAAFDIWGPGTLVTVSS

TRL1216 LC,
                                        SEQ ID NO: 428
DIMLTQPPSVSVSPGQTARITCSGDALPKKYTYWYQQKSGQAPVLLIYED

RKRPSEIPERFSAFTSWTTATLTITGAQVRDEADYYCYSTDISGDIGVFG

GGTKLTVL

TRL1218 HC,
                                        SEQ ID NO: 429
QVQLLESGADMVQPGRSLRLSCAASGFNFRTYAMHWVRQAPGKGLEWVAV

MSHDGYTKYYSDSVRGQFTISRDNSKNTLYLQMNNLRPDDTAIYYCARGL

TGLSVGFDYWGQGTLVTVSS

TRL1218 LC,
                                        SEQ ID NO: 430
DIVLTQSASVSGSPGQSITISCTGTSSDVGGYNYVSWYQQHPGKAPKLMI

YDVTTRPSGVSDRFSGSKSGNTASLTISGLQAEDEADYYCSSYSSGSTPA

LFGGGTQLTVL

TRL1230 HC,
                                        SEQ ID NO: 431
QVQLVQSGGGLVKPGGSLRLSCGASGFNLSSYSMNWVRQAPGKGLEWVSS

ISSRSSYIYYADSVQGRFTISRDNAKNSLYLQMNSLRAEDTAIYYCARVS

PSTYYYYGMDVWGQGTTVTVSS

TRL1230 LC,
                                        SEQ ID NO: 432
DIVLTQPSSVSVSPGQTARITCSGDELPKQYAYWYQQKPGQAPVLVIYKD

NERPSGIPERFSGSSSGTTVTLTISGVQAEDEADYYCQSADSSGTYVVFG

GGTKLTVL

TRL1232 HC,
                                        SEQ ID NO: 433
QVQLVESGAEVKKPGALVKVSCKASGYTFSGYYMHWVRQAPGQGLEWMGW

INPKSGGTKYAQKFQGRVTMTRDTSISTAYMELSRLRSDDTAVYFCARGG

PSNLERFLERLQPRYSYDDKYAMDVWGQGTTVTVSS

TRL1232 LC,
                                        SEQ ID NO: 434
DIVMTQSPGTLSLSPGARATLSCRASQSVSSIYLAWYQQKPGQAPRLLIF

GASSRATGIPDRFSGSGSGTDFTLTISRLEPEDFAVYYCQQYGSSPYTFG

QGTKLEIKR

TRL1242 HC,
                                        SEQ ID NO: 435
QVQLVQSGTEVKKPGESLKISCEGSRYNFARYWIGWVRQMPGKGLDWMGI

IYPGDSDTRYSPSFQGQVSISADKSISTAYLQWNSLKASDTAMYYCARLG

SELGVVSDYYFDSWGQGTLVTVSS

TRL1242 LC,
                                        SEQ ID NO: 436
DIVLTQSPDSLAVSLGERATINCKSSQSVLDRSNNKNCVAWYQQKPGQPP

KLLIYRAATRESGVPDRFSGSGSGTDFSLTISSLQAEDVAVYFCQQYYSI

PNTFGQGTKLEIKR

TRL1245 HC,
                                        SEQ ID NO: 437
QVQLVESGGGLVKAGGSLRLSCVASGFTFSDYYMSWIRQAPGKGLEWISF

ISSSGDTIFYADSVKGRFTVSRDSAKNSLYLQMNSLKVEDTAVYYCARKG

VSDEELLRFWGQGTLVTVSS

TRL1245 LC,
                                        SEQ ID NO: 438
DIVLTQDPSVSVSPGQTARITCSGDALPKKYAYWYQQKSGQAPVLVIYED

TKRPSGIPERFSGSSSGTVATLTISGAQVEDEADYYCYSTDSSGNQRVFG

GGTKLTVL

TRL1330 HC,
                                        SEQ ID NO: 439
QVQLVESGTEVKNPGASVKVSCTASGYKFDEYGVSWVRQSPGQGLEWMGW

ISVYNGKTNYSQNFQGRLTLTTETSTDTAYMELTSLRPDDTAVYYCATDK

NWFDPWGPGTLVTVSS

TRL1330 LC,
                                        SEQ ID NO: 440
DIVLTQSPSASGSPGQSITISCTGTNTDYNYVSWYQHHPGKAPKVIIYDV

KKRPSGVPSRFSGSRSGNTATLTVSGLQTEDEADYYCVSYADNNHYVFGS

GTKVTVL

TRL1335 HC,
                                        SEQ ID NO: 441
QVQLVESGAEVKKPGESLKISCKGSGYNFTSYWIGWVRQMPGKGLEWMGV

IYPDDSDTRYSPSFKGQVTISADKSISTAFLQWSSLKASDTAVYHCARPP

DSWGQGTLVTVSS

TRL1335 LC,
                                        SEQ ID NO: 442
DIVMTQSPATLSVSPGERATLSCRASQSVSSNLAWYQQKPGLAPRLLIVG

ASNRATGIPARFSGSGSGTEFTLTISSLQSEDFAFYYCQQYNNWPFTFGP

GTKVDVKR

TRL1337 HC,
                                        SEQ ID NO: 443
QVQLLESGPGLVKPSETPSLTCTVSGGSIRSYYWSWIRQPPGKGLEWIGY

IYYSGSTNYNPSLKSRVTISVDMSKNQFSLKLSSVTAADTAMYYCARVYG

GSGSYDFDYWGQGTLVTV

SS

TRL1337 LC,
                                        SEQ ID NO: 444
DIVLTQSPSASGSPGQSVTISCTGTSSDVGGYNYVSWYQQLPGKAPKLMI

YEVTKRPSGVPDRFSGSKSGNTASLTVSGLQAEDEADYYCSSFAGSNNHV

VFGGGTKLTVL

TRL1338 HC,
```

SEQ ID NO: 445
QVQLTLRESGPTLVKPTQTLTLTCTFSGFSLSTNGVGVGWIRQPPGKALE

WLAIIYWDDDKRYSPSLKSRLTITKDTSKNQVVLTLTNMDPVDTGTYYCA

HILGASNYWTGYLRYYFDYWGQGTLVTVST

TRL1338 LC,
SEQ ID NO: 446
DIEMTQSPSVSVSPGQTARITCSGEPLAKQYAYWYQQKSGQAPVVVIYKD

TERPSGIPERFSGSSSGTTVTLTISGVQAEDEADYHCESGDSSGTYPVFG

GGTKLTVL

TRL1341 HC,
SEQ ID NO: 447
QVQLQESGGGLVQPGGSLKLSCAASGFIFSGSTMHWVRQASGKGLEWVGR

IRSKTNNYATAYAASVKGRFTISRDDSKNTAYLQMNSLKTEDTAVYYCIS

LPGGYSSGQGTLVTVSS

TRL1341 LC,
SEQ ID NO: 448
DIMLTQPPSVSVSPGQTARITCSGDALPKKYTYWYQQKSGQAPVLVIYED

SKRPSEIPERFSAFTSWTTATLTITGAQVGDEADYYCYSTDITGDIGVFG

GGTKLTVL

TRL1347 HC,
SEQ ID NO: 449
QVQLVQSGGGLVQPGGSLKVSCVGSGFTFSASTIHWVRQASGKGLEWVGR

IRSKANNYATVSAASLKGRFTISRDDSKNTAYLQVNSLKIEDTAIYYCTR

PTACGDRVCWHGAWGQGTQVTVSP

TRL1347 LC,
SEQ ID NO: 450
DIVLTQSPSASGTPGQRVTISCSGSRSNLGNNNVNWYQQLPGTAPKLLIF

DNNERPSGVPGRFSGSKSGTSASLAISGLRSEDEADYYCASWDDSLNGWV

FGGGTKVTVL

TRL1361 HC,
SEQ ID NO: 451
QVQLVESGGGLAQPGGSLRLSCAASGFIFNTYAMGWVRQAPGKGLEWVST

VSAPGAGTYYTDSVKGRFIISRDNSKNILYLQMNRLRVEDTAVYYCARDQ

GGPAVAGARIFDYWGQGALVTVSS

TRL1361 LC,
SEQ ID NO: 452
DIVLTQSPLSLSVTPGQPASISCKSSQSLLRSDGKTYLCWYLQKPGQPPQ

LLIYEVSNRVSGVPDRFSGSGSGTDFTLKISRVEAEDVGVYYCMQSIQLR

TFGQGTKVEIKR

Further non-limiting exemplary antibodies contemplated are antibodies having the CDR regions of the above-noted TRL295, TRL299, TRL1012, TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347, and TRL1361. Methods of identifying CDR regions are known in the art. For example, CDR predictions may be made based on the heavy and/or light chain sequences—e.g. based on the Kabat, Clothia, AbM, or contact definitions of CDR specificity; details of these CDR prediction methods are known in the art (see, e.g., bioinf.org.uk/abs/#cdrid), utilizing the CDR prediction algorithms provided by the Ofran Lab (Paratome available at ofranservices.biu.ac.il/site/services/paratome/index.html) and Green Mountain Antibodies' CDR prediction program, and/or other commercially available resources.

The disclosed antibodies are known to bind to DNABII proteins. For example. TRL295 is reported to bind to residues 61-80 of *Haemophilus influenzae* IHF—also known as IhfA5. TRL1068 and TRL1337 are reported to exhibit high affinity binding for the amino acid fragments AARKGRNPQTGKEID (SEQ ID NO: 453) and KGRNPQTGKEIDIPA (SEQ ID NO: 454) of *Staphylococcus aureus* HU (SEQ ID NO: 59). TRL1330 is reported to exhibit high affinity binding for the amino acid fragment KGRNPQTGKEIDI (SEQ ID NO: 455) of *Staphylococcus aureus* HU (SEQ ID NO: 59). TRL1338 is reported to exhibit high affinity binding for the amino acid fragment VPAFKAGKALKDAVK (SEQ ID NO: 456) of *Staphylococcus aureus* HU (SEQ ID NO: 59). TRL1361 is reported to exhibit high affinity binding for the amino acid fragments SLAKGEKVQLIGFGN (SEQ ID NO: 457) and KGEKVQLIGFGNFEV (SEQ ID NO: 458) of *Staphylococcus aureus* HU (SEQ ID NO: 59).

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/0) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), Bioinvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Flood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6): 1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Rabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9): 1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10): 1057-1062. Briefly, these antibodies comprise a pair of tandem Ed segments ($V_H$-$C_H$1-VH-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, *Aleurites fordii* proteins, dianthin proteins, *Phytolacca americana* proteins (PAPI, PAPII, and PAP-S), *Momordica charantia* inhibitor, curcin, crotin, sapaonaria *officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In certain aspects, the disclosure relates to an antibody or antigen binding fragment that specifically recognizes or binds an isolated or recombinant polypeptide consisting essentially of an amino acid sequence of a DNABII protein or fragment thereof, the tail fragment or tip fragment. Non-limiting examples of such fragments include without limitation a polypeptide that comprises one or more of the sequences: polypeptides designated as B1 through B6 (see FIG. 18);

```
MATITKLDIIEYLSDKYHLS (also referred to herein as
hIFA1; (SEQ ID NO. 348));

KYHLSKQDTKNVVENFLEEI (also referred to herein as
hIFA2; (SEQ ID NO. 349));

FLEEIRLSLESGQDVKLSGF (also referred to herein as
hIFA3; (SEQ ID NO. 350));

KLSGFGNFELRDKSSRPGRN (also referred to herein as
hIFA4; (SEQ ID NO. 351));

RPGRNPKTGDVVPVSARRVV (also referred to herein as
hIFA5; (SEQ ID NO. 352));

ARRVVTFKPGQKLRARVEKTK (also referred to herein as
hIFA6; (SEQ ID NO. 353));
``` or an equivalent of each thereof, that may include additional amino acids as described above;

Non-limiting exemplary antibodies produced by the disclosed hybridomas disclosed in Table 11. The hybridoma cell lines that produce monoclonal antibodies that specifically recognize and bind *Haemophilus influenzae* IHfA fragment A5 (SEQ ID NO: 352) and Ihf fragment B4 (SEQ ID NO: 345), were deposited with American Type Culture Collection (ATCC) pursuant to the provisions of the Budapest Treaty on Jul. 30, 2015 and the CDRs of the antibodies can be identified by sequence using conventional techniques. Further non-limiting exemplary antibodies include those that specifically recognize and bind *Haemophilus influenzae* IHfA fragment A3 (SEQ ID NO: 350), IhfB fragment B2 (SEQ ID NO: 343) produced by hybridoma cell lines IhfA3 NTHI 9B10.F2.H3 and IhfB2 NTHI 7A4.E4.G4. 42 T1

TABLE 11

| Specificity | SEQ ID NO: | ATCC Accession No. | Hybridoma Cell Line |
| --- | --- | --- | --- |
| IhfA frag. A5 | SEQ ID NO: 352 | PTA-122334 | IhfA5 NTHI 14G8.F5.G6 |
| IhfB frag. B4 | SEQ ID NO: 345 | PTA-122335 | IhfB4 NTHI 4E11.E5.G2 |

In one aspect, the present disclosure provides an isolated antibody, derivative or fragment thereof that is at least 85% identical to an antibody selected from the group consisting of (i) the antibody produced by hybridoma cell line IhfA5 NTHI 14G8.F5.G6 or (ii) the antibody produced by hybridoma cell line IhfB4 NTHI 4E11.E5.G2.

In one aspect, the present disclosure provides an isolated antibody, derivative or fragment thereof comprising the CDRs of (i) the antibody produced by hybridoma cell line IhfA5 NTHI 14G8.F5.G6; or (ii) the antibody produced by hybridoma cell line IhfB4 NTHI 4E11.E5.G2. In one aspect, the present disclosure provides an isolated antibody, derivative or fragment thereof that has CDR that is at least 85% identical to (i) the antibody produced by hybridoma cell line IhfA5 NTHI 14G8.F5.G6 or (ii) the antibody produced by hybridoma cell line IhfB4 NTHI 4E11.E5.G2.

In some aspects of the antibodies provided herein, the HC variable domain sequence comprises the HC variable domain sequence of (i) the antibody produced by hybridoma cell line IhfA5 NTHI 14G8.F5.G6 or (ii) the antibody produced by hybridoma cell line IhfB4 NTHI 4E11.E5.G2, and/or the LC variable domain sequence comprises the LC variable domain sequence of (i) the antibody produced by hybridoma cell line IhfA5 NTHI 14G8.F5.G6 or (ii) the antibody produced by hybridoma cell line IhfB4 NTHI 4E11.E5.G2.

In some aspects of the antibodies provided herein, the HC variable domain sequence comprises a HC variable domain sequence at least 85% identical to a HC variable domain sequence of (i) the antibody produced by hybridoma cell line IhfA5 NTHI 14G8.F5.G6; or (ii) the antibody produced by hybridoma cell line IhfB4 NTHI 4E11.E5.G2; and/or the LC variable domain sequence comprises a LC variable domain sequence at least 85% identical to the of LC variable domain sequence of (i) the antibody produced by hybridoma cell line IhfA5 NTHI 14G8.F5.G6; or (ii) the antibody produced by hybridoma cell line IhfB4 NTHI 4E11.E5.G2.

In one aspect, the present disclosure provides an isolated antibody comprising a heavy chain (HC) variable domain sequence and a light chain (LC) variable domain sequence, wherein the heavy chain and light chain immunoglobulin variable domain sequences form an antigen binding site that binds to an epitope of a DNABII protein.

In some embodiments, the heavy chain variable region comprises a CDRH1 sequence comprising, or alternatively consisting essentially of, or yet further consisting of, an amino acid sequence comprising the CDRH1 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises a CDRH2 sequence comprising, or alternatively consisting essentially of, or yet further consisting of, an amino acid sequence comprising the CDRH2 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises a CDRH3 sequence comprising, or alternatively consisting essentially of, or yet further consisting of, an amino acid sequence comprising the CDRH3 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the heavy chain variable region comprises, or alternatively consists essentially of, or yet further consists of, the amino acid sequence comprising the heavy chain variable region sequence of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL1 sequence comprising, or alternatively consisting essentially of, or yet further consisting of, an amino acid sequence comprising the CDRL1 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL2 sequence comprising, or alternatively consisting essentially of, or yet further consisting of, an amino acid sequence comprising the CDRL2 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises a CDRL3 sequence comprising, or alternatively consisting essentially of, or yet further consisting of, an amino acid sequence comprising the CDRL3 of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In some embodiments, the light chain variable region comprises, or alternatively consists essentially of, or yet further consists of, the polypeptide encoded by the polynucleotide sequence comprising the light chain variable region sequence of any one of the following antibodies: (i) the antibody produced by hybridoma cell line IhfA5 NTHI 14G8.F5.G6; or (ii) the antibody produced by hybridoma cell line IhfB4 NTHI 4E11.E5.G2.

In another aspect of the present technology, the isolated antibody includes one or more of the following characteristics:

(a) the light chain immunoglobulin variable domain sequence comprises one or more CDRs that are at least 85% identical to a CDR of a light chain variable domain of any of the disclosed light chain sequences;

(b) the heavy chain immunoglobulin variable domain sequence comprises one or more CDRs that are at least 85% identical to a CDR of a heavy chain variable domain of any of the disclosed heavy chain sequences;

(c) the light chain immunoglobulin variable domain sequence is at least 85% identical to a light chain variable domain of any of the disclosed light chain sequences;

(d) the HC immunoglobulin variable domain sequence is at least 85% identical to a heavy chain variable domain of any of the disclosed light chain sequences; and/or (e) the antibody binds an epitope that overlaps with an epitope bound by any of the disclosed sequences.

In some of the aspects of the antibodies provided herein, the antibody binds a DNABII protein with a dissociation constant ($K_D$) of less than $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some of the aspects of the antibodies provided herein, the antigen binding site specifically binds to a DNABII protein.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind a DNABII protein with similar specificity and sensitivity profiles as the disclosed antibodies. This may be tested by way of the binding assays.

In a further aspect, th antibodies are characterized by being both immunodominant and immunoprotective, as determined using appropriate assays and screens.

Isolation, Culturing and Expansion of APCs, Including Dendritic Cells

This disclosure also provides isolated host cells comprising one or more of an isolated polypeptides or isolated polynucleotides or the vectors disclosed herein. In one aspect the isolated host cell is a eukaryotic cell such as antigen presenting cell (APC), e.g., a dendritic cell. In another aspect, the isolated host cell is a prokaryotic cell. In one aspect, the disclosure is an isolated host cell that is cultured under conditions that promote expression of the polynucleotide. This disclosure also provides the host cell, expression system and polypeptide produced by the expression system.

The following is a brief description of two fundamental approaches for the isolation of APC. These approaches involve (1) isolating bone marrow precursor cells (CD34$^+$) from blood and stimulating them to differentiate into APC; or (2) collecting the precommitted APCs from peripheral blood. In the first approach, the patient must be treated with cytokines such as GM-CSF to boost the number of circulating CD34$^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. (1990) PNAS 87:7698-7702); Percoll gradient separations (Mehta-Damani et al. (1994) J. Immunol. 153:996-1003); and fluorescence activated cell sorting techniques (Thomas et al. (1993) J. Immunol. 151:6840-6852).

One technique for separating large numbers of cells from one another is known as countercurrent centrifugal elutriation (CCE). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

In one aspect disclosed herein, the APC are precommitted or mature dendritic cells which can be isolated from the white blood cell fraction of a mammal, such as a murine, simian or a human (See, e.g., WO 96/23060). The white blood cell fraction can be from the peripheral blood of the mammal. This method includes the following steps: (a) providing a white blood cell fraction obtained from a mammalian source by methods known in the art such as leukapheresis; (b) separating the white blood cell fraction of step (a) into four or more subfractions by countercurrent centrifugal elutriation, (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c), and (e) collecting the enriched fraction of step (d), optionally at about 4° C. One way to identify the dendritic cell-enriched fraction is by fluorescence-activated cell sorting. The white blood cell fraction can be treated with calcium ionophore in the presence of other cytokines, such as recombinant (rh) rhIL-12, rhGM-CSF, or rhIL-4. The cells of the white blood cell fraction can be washed in buffer and suspended in $Ca^{++}/Mg^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD16, CD56, CD57, and CD19, CD20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen et al. (1991) J. Clin. Apheresis. 6:48-53). In this technique, cells are subject to simultaneous centrifugation and a washout stream of buffer which is constantly increasing flow rate. The constantly increasing countercurrent flow of buffer leads to fractional cell separations that are largely based on cell size.

Quality control of APC and more specifically DC collection and confirmation of their successful activation in culture is dependent upon a simultaneous multi-color FACS analysis technique which monitors both monocytes and the dendritic cell subpopulation as well as possible contaminant T lymphocytes. Cell sorting is based on differential expression of cell surface markers including CD3 (T cells), CD16/CD56/CD57 (NK/LAK cells), and CD19/CD20 (B cells). DCs are distinguishable from monocytes based in part on levels of CD 14, which is expressed at very high levels in monocytes compared to DCs. DCs show high levels of expression of HLA-DR, significant HLA-DQ and B7.2 (but little or no B7.1) at the time they are circulating in the blood (in addition they express Leu M7 and M9, myeloid markers which are also expressed by monocytes and neutrophils).

When combined with a third color reagent for analysis of dead cells, propidium iodide (PI), it is possible to make positive identification of all cell subpopulations The goal of FACS analysis at the time of collection is to confirm that the DCs are enriched in the expected fractions, to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. It may not be necessary to routinely separate DCs from monocytes because, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture.

Alternatively, others have reported that a method for upregulating (activating) dendritic cells and converting monocytes to an activated dendritic phenotype. This method involves the addition of calcium ionophore to the culture media convert monocytes into activated dendritic cells. Adding the calcium ionophore A23187, for example, at the beginning of a 24-48 hour culture period resulted in uniform activation and dendritic cell phenotypic conversion of the pooled "monocyte plus DC" fractions: characteristically, the activated population becomes uniformly CD 14 (Leu M3) negative, and upregulates HLA-DR, HLA-DQ, ICAM-1, B7.1, and B7.2. Furthermore this activated bulk population functions as well on a small numbers basis as a further purified.

Specific combination(s) of cytokines have been used successfully to amplify (or partially substitute) for the activation/conversion achieved with calcium ionophore: these cytokines include but are not limited to purified or recombinant ("rh") rhGM-CSF, rhIL-2, and rhIL-4. Each cytokine when given alone is inadequate for optimal upregulation.

Presentation of Antigen to the APC

For purposes of immunization, the polypeptides (e.g., SEQ ID NO: 1 through 33) can be delivered to antigen-presenting cells as protein/peptide or in the form of cDNA encoding the protein/peptide. Antigen-presenting cells (APCs) can consist of dendritic cells (DCs), monocytes/macrophages, B lymphocytes or other cell type(s) expressing the necessary MHC/co-stimulatory molecules. The methods described below focus primarily on DCs which are the most potent APCs.

Pulsing is accomplished in vitro/ex vivo by exposing APCs to the antigenic protein or polypeptide(s) disclosed herein. The protein or peptide(s) are added to APCs at a concentration of 1-10 μm for approximately 3 hours. Transfection of APCs with polynucleotides encoding antigens or antigenic polypeptides is accomplished by exposing APCs to the nucleic acids in the presence of transfection agents known in the art, including but not limited to cationic lipids.

Transfected or pulsed APCs can subsequently be administered to the host via an intravenous, subcutaneous, intranasal, intramuscular or intraperitoneal route of delivery.

Protein/peptide antigen can also be delivered in vivo with adjuvant via the intravenous, subcutaneous, intranasal, intramuscular or intraperitoneal route of delivery.

Foster Antigen Presenting Cells

Foster antigen presenting cells are particularly useful as a target cell. Foster APCs are derived from the human cell line 174X CEM.T2, referred to as T2, which contains a mutation in its antigen processing pathway that restricts the association of endogenous peptides with cell surface MHC class I molecules (Zweerink et al. (1993) J. Immunol. 150:1763-1771). This is due to a large homozygous deletion in the MHC class II region encompassing the genes TAP 1, TAP2, LMP 1, and LMP2, which are required for antigen presentation to MHC class 1-restricted CD8$^+$ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to herein as "foster" APCs. They can be used in conjunction with this disclosure to present antigen(s).

Transduction of T2 cells with specific recombinant MHC allows for redirection of the MHC restriction profile. Libraries tailored to the recombinant allele will be preferentially presented by them because the anchor residues will prevent efficient binding to the endogenous allele.

High level expression of MHC molecules makes the APC more visible to the CTLs. Expressing the MHC allele of interest in T2 cells using a powerful transcriptional promoter (e.g., the CMV promoter) results in a more reactive APC (most likely due to a higher concentration of reactive MHC-peptide complexes on the cell surface).

Expansion of Immune Effector Cells

The present disclosure makes use of these APCs to stimulate production of an enriched population of antigen-specific immune effector cells. The antigen-specific immune effector cells are expanded at the expense of the APCs, which die in the culture. The process by which naive immune effector cells become educated by other cells is described essentially in Coulie (1997) Molec. Med. Today 3:261-268.

The APCs prepared as described above are mixed with naive immune effector cells. In specific embodiments, the cells may be cultured in the presence of a cytokine, for example IL2. Because dendritic cells secrete potent immunostimulatory cytokines, such as IL12, it may not be necessary to add supplemental cytokines during the first and successive rounds of expansion. In any event, the culture conditions are such that the antigen-specific immune effector cells expand (i.e., proliferate) at a much higher rate than the APCs. Multiple infusions of APCs and optional cytokines can be performed to further expand the population of antigen-specific cells.

In one embodiment, the immune effector cells are T cells. In a separate embodiment, the immune effector cells can be genetically modified by transduction with a transgene coding for example, IL-2, IL-11 or IL-13. Methods for introducing transgenes in vitro, ex vivo and in vivo are known in the art.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

The antibodies disclosed herein may be used for vaccination or to boost vaccination, alone or in combination with peptides or protein-based vaccines or dendritic-cell based vaccines.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g., an OMP P5, OMP 26, OMP P2, or Type IV Pilin protein (see Jurcisek and Bakaletz (2007) J. of Bacteriology 189(10):3868-3875 and Murphy, T F, Bakaletz, L O and Smeesters, P R (2009) The Pediatric Infectious Disease Journal, 28:S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself, e.g., by an elastic bladder).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852; and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the interfering agent (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection. In various embodiments, these methods disclosed herein span almost any available method and route suitable for drug delivery, including in vivo and ex vivo methods, as well as systemic and localized routes of administration.

Screening Assays

The present disclosure provides methods for screening for equivalent agents, such as equivalent monoclonal antibodies to a polyclonal antibody as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule, a peptide, a protein (e.g., antibody), a polynucleotide anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

One embodiment is a method for screening agents capable of interacting with, binding to, or inhibiting the DNA-DNABII (e.g., IHF) interaction. The present disclosure provides in FIG. 6B the three-dimensional structure of the microbial DNA and IHF. Accordingly, the disclosure permits the use of virtual design techniques, also known as computer-aided, in silico design or modeling, to design, select, and synthesize agents capable of interacting with, binding to, or inhibiting the DNA-DNABII (e.g., IHF) interaction. In turn, the candidate agents may be effective in the treatment of biofilms and associated diseases or conditions (medical, industrial or veterinary) as described herein. Thus, the present disclosure also provides agents identified or designed by the in silico methods.

Three-dimensional structure of a IHF-DNA complex is illustrated in FIG. 6B and a representative structure, with X, Y and Z coordinates, are provided in Protein Data Bank Accession Number: 1IHF, with relevant details provided in Rice et al. (1996) Cell 87:1295-1306. The three-dimensional structure of the IHF protein in the IHF-DNA complex can be used for the screening method. A suitable agent is one that can be positioned relative to the IHF protein structure in the IHF-DNA complex with interactions at least one, or alternatively two, or three, or four, or five, or six, or seven, or eight, or nine, or at least ten of the amino acid residues that are identified to be involved in interacting with DNA.

FIG. 6A illustrates the amino acid residues involved in IHF-DNA interaction, using the E. coli IHF sequence (SEQ ID NO: 42) as an example. Such amino acid residues, indicated by the lower level of arrows in FIG. 6A, are further described below, indicated with bold and underlined letters. Namely, with the E. coli IHF, the amino acids involved in DNA binding are T4, K5, A6, E28, Q43, K45, S47, G48, N51, R55, K57, R60, R63, N64, P65, K66, R76, T80, R82 or Q85.

(SEQ ID NO: 42)
MAL TKA EMSE YLFDKLGLSK RDAKELV E LF FEEIRRALEN

GE Q V K L SG FG N FDL R D K NQ R PG RNPK TGED

IPITA R RVV T F R PG Q KLKSR VENASPKDE

Thus, one embodiment of the present disclosure provides a computer-implemented method for identifying an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, comprising positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

In one aspect, a candidate agent interacts with the IHF protein at least one, or two, or three of amino acids 63, 64, 65, or 66. In one aspect, a candidate agent interacts with the IHF protein at least one, or two, or three of R63, N64, P65, K66. In another aspect, a candidate agent interacts with the IHF protein at least at one of 63 or 66. In another aspect, a candidate agent interacts with the IHF protein at least at one of R63 or K66.

It would be appreciated in the art that the exact locations and amino acid residues vary depending on the IHF sequence. One of the skill in the art, however, can readily identify such locations and amino acid residues based on the sequences. For instance, an IHF sequence can be aligned with the IHF sequence of E. coli (SEQ ID NO: 42), as illustrated in Table 9, to reveal those that correspond to the amino acids in E. coli IHF that interact with DNA. Likewise, the three-dimensional structure of such an IHF sequence in an IHF-DNA complex can be used for the screening.

In addition to the computer-implemented methods as provided herein, the present disclosure also provides custom computer system that includes, e.g., processor, memory and/or program, for performing the methods, as well as a computer readable medium, such as a non-transitory computer readable medium that stores suitable computer program or code for carrying out the methods.

Accordingly, another embodiment provides a custom computing apparatus comprising:

at least one processor;

a memory coupled to the at least one processor;

a storage medium in communication with the memory and the at least one processor, the storage medium containing a set of processor executable instructions that, when executed by the processor configure the custom computing apparatus to identify an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, wherein the configuration comprises:

positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

Yet another embodiment provides a non-transitory computer medium comprising a set of processor executable instructions that, when executed by a processor, identifying an agent that inhibits, competes or titrates the binding of a DNABII polypeptide or protein to a microbial DNA, that inhibits, prevents or breaks down a microbial biofilm, that inhibits, prevents or breaks down a biofilm in a subject, or that inhibits, prevents or treats a microbial infection that produces a biofilm in a subject, comprising positioning a three-dimensional structure of a candidate agent against a three-dimensional structure of an integration host factor (IHF) protein, wherein the three-dimensional structure of the IHF protein is based on X, Y and Z atomic structure coordinates determined from a crystalline form of an IHF and DNA complex, wherein interaction of the agent with the IHF at two or more IHF amino acids selected from T4, K5, A6, E28, Q43, K45, S47, G48, N51, R55, K57, R60, R63, N64, P65, K66, R76, T80, R82 or Q85 as represented in SEQ ID NO: 42, or the equivalent of each, identifies that the agent inhibits, competes or titrates the binding of a DNABII polypeptide or protein to a microbial DNA, inhibits, prevents or breaks down a microbial biofilm, inhibits, prevents or breaks down a biofilm, or inhibits, prevents or treats a microbial infection that produces a biofilm.

Methods of in silico molecule or drug designs are well known in the art, see generally Kapetanovic (2008) Chem Biol. Interact., 171 (2): 165-76. Briefly, the atomic coordinates of the three-dimensional structure are input into a computer so that images of the structure and various parameters are shown on the display. The design typically involves positioning a three-dimensional structure to the three-dimensional structure of the target molecule. The positioning can be controlled by the user with assistance from a computer's graphic interface, and can be further guided by a computer algorithm looking for potential good matches. Positioning also involves moving either or both of the three-dimensional structures around at any dimension.

Then, the resultant data are input into a virtual compound and/or agent library. Since a virtual library is contained in a virtual screening software such as DOCK-4 (Kuntz, UCSF), the above-described data may be input into such a software. Candidate agents may be searched for, using a three-dimensional structure database of virtual or non-virtual drug candidate compounds, such as MDDR (Prous Science, Spain).

A candidate agent is found to be able to bind to DNA and/or DNABII protein if a desired interaction between the candidate agent and either or both is found. The interaction can be quantitative, e.g., strength of interaction and/or number of interaction sites, or qualitative, e.g., interaction or lack of interaction. The output of the method, accordingly, can be quantitative or qualitative. In one aspect, therefore, the present disclosure also provides a method for identifying an agent that does not inhibit the interaction or alternatively, strengthens the interaction between the DNA and protein.

The potential inhibitory or binding effect (i.e., interaction or association) of an agent such as a small molecule compound may be analyzed prior to its actual synthesis and testing by the use of computer modeling techniques. If the theoretical structure of the given compound suggests insufficient interaction and association between it and microbial DNA in the biofilm and/or DNABII protein, synthesis and testing of the agent can be obviated. However, if computer modeling indicates a strong interaction, the agent can then be synthesized and tested for its ability to bind to or inhibit the interaction using various methods such as in vitro or in vivo experiments. Methods of testing an agent's ability to inhibit or titrate a biofilm, alone or in connection with another agent, are disclosed herein. In this manner, synthesis of inoperative agents and compounds can be avoided.

One skilled in the art may use any of several methods to screen chemical or biological entities or fragments for their ability to associate with DNABII or microbial DNA and more particularly with the specific binding sites. Selected fragments or chemical entities may then be positioned in a variety of orientations, or docked, within an individual binding site of DNA or DNABII polypeptide. Docking may be accomplished using software such as QUANTA, SYBYL, followed by energy minimization and molecular dynamics with standard molecular mechanics force fields, such as CHARMM and AMBER.

Commercial computer programs are also available for in silico design. Examples include, without limitation, GRID (Oxford University, Oxford, UK), MCSS (Molecular Simulations, Burlington, Mass.), AUTODOCK (Scripps Research Institute, La Jolla, Calif.), DOCK (University of California, San Francisco, Calif.), GLIDE (Schrodinger Inc.), FlexX (Tripos Inc.) and GOLD (Cambridge Crystallographic Data Centre).

Once an agent or compound has been designed or selected by the above methods, the efficiency with which that agent or compound may bind to each other can be tested and optimized by computational evaluation. For example, an effective DNABII fragment or may demonstrate a relatively small difference in energy between its bound and free states (i.e., a small deformation energy of binding).

A compound designed or selected can be further computationally optimized so that in its bound state it may optionally lack repulsive electrostatic interaction with the target protein. Such non-complementary (e.g., electrostatic) interactions include repulsive charge-charge, dipole-dipole, and charge-dipole interactions. Specifically, the sum of all electrostatic interactions between the agent and DNABII and/or microbial DNA in the biofilm when the agent or compound is bound to either agent, optionally making a neutral or favorable contribution to the enthalpy of binding.

Computer softwares are also available in the art to evaluate compound deformation energy and electrostatic interaction. Examples include, without limitation, Gaussian 92 [Gaussian, Inc., Pittsburgh, Pa.]; AMBER [University of California at San Francisco]; QUANTA/CHARMM [Molecular Simulations, Inc., Burlington, Mass.]; and Insight II/Discover [Biosysm Technologies Inc., San Diego, Calif.].

Once an binding agent has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to the DNABII protein and/or microbial DNA in the biofilm by the same computer methods described in detail, above.

Certain embodiments relate to a method for screening small molecules capable of interacting with the protein or polynucleotide disclosed herein. For the purpose of this disclosure, "small molecules" are molecules having low molecular weights (MW) that are, in one embodiment, capable of binding to a protein of interest thereby altering the function of the protein. In some embodiments, the MW of a small molecule is no more than 1,000. Methods for screening small molecules capable of altering protein function are known in the art. For example, a miniaturized arrayed assay for detecting small molecule-protein interactions in cells is discussed by You et al. (1997) Chem. Biol. 4:961-968.

To practice the screening method in vitro, suitable cell culture or tissue infected with the microbial to be treated are first provided. The cells are cultured under conditions (temperature, growth or culture medium and gas ($CO_2$)) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" a mount must be added which can be empirically determined, When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

The agents and compositions can be used in the manufacture of medicaments and for the treatment of humans and other animals by administration in accordance with conventional procedures, such as an active ingredient in pharmaceutical compositions.

Combination Therapy

The compositions and related methods of the present disclosure may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (i.e., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation or as a separate formulation.

Kits

Kits containing the agents and instructions necessary to perform the in vitro and in vivo methods as described herein also are claimed. Accordingly, the disclosure provides kits for performing these methods which may include an interfering disclosed herein as well as instructions for carrying out the methods disclosed herein such as collecting tissue and/or performing the screen, and/or analyzing the results, and/or administration of an effective amount of an interfering agent as defined herein. These can be used alone or in combination with other suitable antimicrobial agents.

For example, a kit can comprise, or alternatively consist essentially of, or yet further consist of any one or more agent identified above, e.g., an agent of the group of an isolated or recombinant DNABII polypeptide, an integration host factor (IHF) polypeptide or a fragment or an equivalent of each thereof; an isolated or recombinant protein polypeptide identified in Table 8, Table 9, Table 10 a DNA binding peptide identified in FIGS. 6A-6B, or a fragment or an equivalent of each thereof; an isolated or recombinant polypeptide of SEQ ID NO: 1 through 33, or a fragment or an equivalent of each thereof; an isolated or recombinant polypeptide of SEQ ID NO: 342 through 353, or a fragment or an equivalent of each thereof; an isolated or recombinant C-terminal polypeptide of SEQ ID NO: 5 through 11, 28, 29, 340 or those identified in Table 8, Table 10 or a fragment or an equivalent of each thereof; a polypeptide that competes with an integration host factor on binding to a microbial DNA; a four-way junction polynucleotide resembling a Holliday junction, a 3 way junction polynucleotide resembling a replication fork, a polynucleotide that has inherent flexibility or bent polynucleotide; an isolated or recombinant polynucleotide encoding any one of the above noted polypeptides; an antibody that specifically recognizes or binds any one of the above noted polypeptides, or an equivalent or fragment thereof; or a small molecule that competes with the binding of a DNABII protein or polypeptide to a microbial DNA, and instructions for use. The kit can further comprising one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

TABLE 8

Gram (+) - only HU, Gram (−) - all have HU some also IHF

| Bacteria strain | Abbreviation | Protein name(s) | |
|---|---|---|---|
| *S. sobrinus* 6715 | Ss | 1310 | (HU) (not fully sequenced) |
| *S. pyogenes* MGAS10270 | Spyog | Spy1239 | (HU) |
| *S. gordonii* Challis NCTC7868 | Sg | SGO_0701 | (HlpA) |
| *S. agalactiae* (Group B Strep) 2603V/R | GBS | SAG_0505 | (Hup) |
| *S. mutans* UA159 | Sm | Smu_589 | (HU) |
| *S. pneumoniae* R6 | Spneu | spr1020 | (HU) |
| *S. gallolyticus* UCN34 (S. bovis) | Sgall | YP_003430069 | (HlpA) |
| *S. aureus* MW2 | Sa | MW1362 | (HU) |
| *S. epidermidis* RP62A | Se | SERP1041 | (Hup) |
| *E. coli* K12-MG1655 | Ec | b1712 | (HimA) |
|  |  | b0912 | (HimD) |
|  |  |  | (HupA) |
|  |  |  | (HupB) |
| *H. influenza* KW20 Rd | Hi | HI1221 | (HimA) |
|  |  | HI1313 | (HimD) |
|  |  | HI0430 | (HupA) |
| *Salmonella enteric serovar typhi* CT18 | Salm | Sty1771 | (HimA) |
|  |  | Sty0982 | (HimD) |
| *Aggregatibacter actinomycetemcomitans* D11S-1 | Aa | YP_003255965 | (IHFalpha) |
|  |  | YP_003256209 | (IhfB) |
|  |  | YP_003255304 | (HU) |
| *P. gingivalis* W83 | Pg | PG 0121 | (Hup-1) |
|  |  | PG_1258 | (Hup-2) |
| *N. gonorrhoeae* FA1090 (Oklahoma) | Ng | NGO603 | (IHFβ) |
|  |  | NGO030 | (IHFα) |
| *N. meningitides* MC58 | Nm | NMB_0729 | (HimA) |
|  |  | NMB_1302 | (HimA) |
| *P. aeruginosa* | Pa | PA3161 | (HimD) |
|  |  | PA1804 | (HupB) |
|  |  | PA2758 | (HimA) |
| *H. pylori* 26695 | Hp | Hp0835 | (Hup) |
| *B. burgdorferi* B31 | Bb | BB_0232 | (Hbb) |
| *Moraxella catarrhalis* RH4 | Mc | YP_003626307 | (HimA) |
|  |  | YP_003627027 | (HimD) |
|  |  | YP_003626775 | (HupB) |
| *V. cholera* El Tor N16961 | Vc | VC_0273 | (HupA) |
|  |  | VC_1914 | (HipB) |
|  |  | VC_1919 | (HupB) |
|  |  | VC_1222 | (HimA) |
| *Burkholderia cenocepacia* HI2424 | Bc | Bcen2424_1048 | (IHFB) |
|  |  | Bcen2424_1481 | (IHFA) |
| *Burkholderia pseudomallei* 668 | Bp | BURPS668_2881 | (IHFB) |
|  |  | BURPS668_1718 | (IHFA) |
| *Mycobacterium tuberculosis* CDC1551 | Mtb | MT_3064 | (HU) |
| *Mycobacterium smegmatis* MC2 | Ms | MSMEG_2389 | (Hup) |
| *Treponema denticola* ATCC 35405 | Td | TDE_1709 | (HU) |
| *Treponema palladum* Nichols | Tp | TP_0251 | (DNA binding protein II) |
| *Prevotella melaninogenica* ATCC 25845 | Pm | PREME0022_2103 | (HupB) |
|  |  | PREME0022_0268 | (HupA) |
|  |  | PREME0022_0341 | (Hup) |
|  |  | PREME0022_0340 | (HimA) |
| *Prevotella intermedia* 17 | Pi | PIN_A0704 | (Hup) |
|  |  | PIN_A1504 | (Hup-2) |
|  |  | PIN_0345 | (HimA) |
|  |  | PIN_0343 | (Hypothetical protein) |
| *Bordetella pertusis* Tohama 1 | Bpert | BP2572 | (IhfA) |
|  |  | BP3530 | (HupB) |
|  |  | BP0951 | (IhfB) |
| *Enterococcus faecalis* V583 | Ef | Ef1550 | (hup) |

TABLE 9A1

9A 9A (cont.) SEQ ID NOS 42-72, respectively, in order of appearance

|  |  | α-1 | Turn | α-2 | T |
|---|---|---|---|---|---|
| Ec_HimA | ------MALT | KAEMSEYLFDK | LG-LS-----KR | DAKELVELFFEEIRRAL | EN |
| Salm_HimA | ------MALT | KAEMSEYLFDK | LG-LS-----KR | DAKELVELFFEEIRRAL | EN |
| Vc_HimA | ------MALT | KAELAEALFEQ | LG-MS-----KR | DAKDRVEVFFEEIRKAL | ES |
| Pa_HimA | -----MGALT | KAEIAERLYEE | LG-LN-----KR | EAKELVELFFEEIRQAL | EH |
| Hi_HimA | -----MATIT | KLDIIEYLSDK | YH-LS-----KQ | DTKNVVENFLEEIRLSL | ES |
| Aa_IHFalpha | ------MTLT | KVELAENLIEK | FH-LS-----KR | EAKDLVESFFEEIRVAL | ET |
| Mc_HimA | -----MGALT | KADMVDELTIR | LR-LT-----RQ | QARKLVDGFFEEISQSL | AQ |
| Ng_IHFalpha | ------MTLT | KAELADILVDK | VSNVT-----KN | DAKEIVELFFEEIRSTL | AS |
| Nm_HimA | ------MTLT | KAELADILVDK | VSNVT-----KN | DAKEIVELFFEEIRSTL | AS |
| Bc_IHFA | +30aa ASTE-TPLT | KAELAELLFDS | VG-LN-----KR | EAKDMVEAFFEVIRDAL | EN |
| Bp_IHFA | +27aa TSAGDTPTLT | KAELAELLFDS | VG-LN-----KR | EAKDMVEAFFEVIRDAL | EN |
| Bpert_IhfA | MGTTMLAEPRTLT | KAELAELLFER | VG-LN-----KR | EAKDIVDTFFEEIRDAL | AR |
| Pm_HimA | --------MN | NKEFIAALAAR | TGYT------QD | ESQKMVKTVVDMMGKSF | ET |
| Pi_HimA | --------MN | NKEFITALANR | VGRS------QD | ETQKLVKTALQAMGDNF | ES |
| Tp_Dbp II | ----MKRVRR | TRSFVVDALCD | EVDLS-----RR | HVARVVDSFVSVVTAAL | ER |
| Pm_Hup | ------MAKS | AIQLITSALAK | QHNLS----ADD | AAAFVDAFFDIISSELK | N- |
| Pi_hypo | ------MAKT | ALQLIADAVAK | KHKIT-----VK | EAEKFVSAIFDVVNEGL | KT |
| Sa_HU | --------MN | KTDLINAVAEQ | ADLT------KK | EAGSAVDAVFESIQNSL | AK |
| Ec_hupA | --------MN | KTQLIDVIAEK | AELS------KT | QAKAALESTLAAITESL | KE |
| Se_Hup | --------MN | KTDLINAVAEQ | ADLT------KK | EAGSAVDAVFESIQNSL | AK |
| Ss_Hu | -------MAN | KQDLIAKVAEA | TELT------KK | DSAAAVDTVFSSIEGFL | SK |
| Spyog_HU | -------MAN | KQDLIAKVAEA | TELT------KK | DSAAAVDAVFSTIEAFL | AE |
| Sgall_HlpA | -------MAN | KQDLIAKVAEA | TELT------KK | DSAAAVDAVFSAIESFL | SE |
| GBS_Hup | -------MAN | KQDLIAKVAEA | TELT------KK | DSAAAVDAVFAAVADYL | AE |
| Spneu_HU | -------MAN | KQDLIAKVAEA | TELT------KK | DSAAAVEAVFAAVADYL | AA |
| Sg_HlpA | -------MAN | KQDLIAKVAAA | TELT------KK | DSAAAVDAVFAAVTEYL | SK |
| Sm_HU | -------MAN | KQDLIAKVAEA | TELT------KK | DSAAAVDAVFSAVSSYL | AK |
| Ef_Hup | -------MAN | KAELIENVASS | TGLT------KK | DATAAVDAVFSTIQETL | AK |
| Hi_HupA | --------MN | KTDLIDAIANA | AELN------KK | QAKAALEATLDAITASL | KE |
| Vc_HupA | --------MN | KTQLIDFIAEK | ADLT------KV | QAKAALEATLGAVEGAL | KD |
| Pa_HupB | --------MN | KSELIDAIAAS | ADIP------KA | VAGRALDAVIESVTGAL | KA |

| β-1 | T | β-2 | Binding domain | Turn | Returning strand | β-3 | α-3 |
|---|---|---|---|---|---|---|---|
| GEQVK | LSG | FGNFD | LRDKNQRP-GR | NPKT | GEDIPITARRVV | TFRPGQ | KLKSRV ENASPKDE- |
| GEQVK | LSG | FGNFD | LRDKNQRP-GR | NPKT | GEDIPITARRVV | TFRPGQ | KLKSRV ENASPKEE- |
| GEQVK | LSG | FGNFD | LRDKNQRP-GR | NPKT | GEDIPITARRVV | TFRPGQ | KLKARV ENIKVEK-- |
| NEQVK | LSG | FGNFD | LRDKRQRP-GR | NPKT | GEEIPITARRVV | TFRPGQ | KLKARV EAYAGTKS- |
| GQDVK | LSG | FGNFE | LRDKSSRP-GR | NPKT | GDVVPVSARRVV | TFKPGQ | KLRARV EKTK----- |

TABLE 9A1-continued

| | | | | | | | | |
|---|---|---|---|---|---|---|---|---|
| GNDVK | LSG | FGNFE | LRDKASRP-GR | NPKT | GESVPVSARRVV | VFKPGQ | KLRNRV | EKVKPKA- |
| GHEVK | LSG | FGNFE | LKDKKPRP-GR | NPKT | GESVPIQARRVV | TFKAGQ | KLRGWI | DSQNEG |
| GEEIK | ISG | FGNFQ | LRDKPQRP-GR | NPKT | GEEVPITARRVV | TFHASQ | KLKGMV | EHYYDKQR- |
| GEEIK | ISG | FGNFQ | LRDKPQRP-GR | NPKT | GEEVPITARRVV | TFHASQ | KLKSMV | EHYYDKQR |
| GESVK | LSG | FGNFQ | LRDKPQRP-GR | NPKT | GEAIPIAARRVV | TFHASQ | KLKALV | ENGAE |
| GESVK | LSG | FGNFQ | LRDKPQRP-GR | NPNT | GEAIPIAARRVV | TFHASQ | KLKALV | ENGAEPDLAR |
| GDSVK | LSG | FGNFQ | VRDKPPRP-GR | NPKT | GETIPIAARRVV | TFHASQ | KLKSVV | EQPNSPPDPASAE |
| GDPVP | VIG | FGTFE | VKKRLERV-MV | NPST | GLRMLVPPKLVL | NFKPAA | TIKGHV | RKGGQDNG |
| GEPVL | VSG | FGSFE | VKKRLERI-MT | NPAT | GLRMLVPPKLVL | NFRATA | SVKEKL | KKGGAE |
| GETVE | LRD | FGVFE | SRVRKASV-GK | SINT | GEVVSIPSHCVV | VFRPSK | RLKSAV | RGYRSGEVGAD |
| GNQVK | IKG | LGTFK | VQAVKPR-ESV | NVNT | GERVLIEGHDKI | SFTPDT | MVKELV | NKPFSQFET+354aa |
| GEKVQ | LIG | FGNFE | VRERAARK-GR | NPQT | GKEIDIPASKVP | AFKAGK | ALKDAV | K-------- |
| GDAVQ | LVG | FGTFK | VNHRAERT-GR | NPQT | GKEIKIAAANVP | AFVSGK | ALKDAV | K |
| GEKVQ | LIG | FGNFE | VRERAARK-GR | NPQT | GKEIDIPASKVP | AFKAGK | ALKDAV | K-------- |
| GEKVQ | LIG | FGNFE | VRERAARK-GR | NPQT | GAEIKIAASKVP | AFKAGK | ALKDAV | K-------- |
| GEKVQ | LIG | FGNFE | VRERAARK-GR | NPQT | GAEIEIAASKVP | AFKAGK | ALKDAV | K-------- |
| GEKVQ | LIG | FGNFE | VRERAARK-GR | NPQT | GEEIEIAASKVP | AFKAGK | ALKDAV | K-------- |
| GEKVQ | LIG | FGNFE | VRERAARK-GR | NPQT | GAEIEIAASKVP | AFKAGK | ALKDAV | K-------- |
| GEKVQ | LIG | FGNFE | VRERAERK-GR | NPQT | GKEMTIAASKVP | AFKAGK | ALKDAV | K-------- |
| GEKVQ | LIG | FGNFE | VRERAARK-GR | NPQT | GKEIKIAASKVP | AFKAGK | ALKDAV | K-------- |
| GEKVQ | LIG | FGNFE | VRERAARK-GR | NPQT | GEEIKIKASKVP | AFKAGK | ALKDAV | K-------- |
| GEKVQ | LIG | FGNFE | VRERAARK-GR | NPQT | GQEIQIAASKVP | AFKPGK | ALKDAV | K |
| GEKVQ | LIG | FGNFE | VNERAART-GR | NPQT | GAEIQIAASKVP | AFVSGK | ALKDAI | K-------- |
| GDQVQ | LIG | FGTFK | VNHRSART-GR | NPQT | GEEIKIAAANVP | AFVAGK | ALKDAI | K-------- |
| GDSVV | LVG | FGTFA | VKERAART-GR | NPQT | GKPIKIAAAKIP | GFKAGK | ALKDAV | N-------- |
| | | | ------------ARM------------ | | | | | |

TABLE 9A2

9A2 9A2 (cont.) SEQ ID NOS 73-76, respectively, in order of appearance

| | | α-1 | | Turn | | α-2 | | T |
|---|---|---|---|---|---|---|---|---|
| Aa HU | --------MN | KTDLIDAIASS | | AELN------KK | | QAKAALEATLDAITGSL | | KK |
| Vc_HupB | --------MN | KTQLVEQIAAN | | ADIS------KA | | SAGRALDAFIEAVSGTL | | QS |
| Ec hupB | --------MN | KSQLIDKIAAG | | ADIS------KA | | AAGRALDAIIASVTESL | | KE |
| Mc HupB | --------MN | KSELVDSIAQS | | AGLT------KE | | QAAKAVNAFTESVQGAL | | QR |

| β-1 | T | β-2 | Binding domain | Turn | Returning strand | β-3 | α-3 | |
|---|---|---|---|---|---|---|---|---|
| GEAVQ | LIG | FGTFK | VNARKART-GR | NPQT | GAEIKIAASKVP | AFVSGK | ALKDAV | K - |
| GDQVA | LVG | FGTFS | VRTRAART-GR | NPKT | GEEIKIAEAKVP | SFKAGK | ALKDAC | N------- |
| GDDVA | LVG | FGTFA | VKERAART-GR | NPQT | GKEITIAAAKVP | SFRAGK | ALKDAV | N |
| GDDVV | LVG | FGTFS | VKERAARM-GR | NPKT | GEAIQIAASKVP | SFKAGK | VLKESV | N |
| | | | ------------ARM------------ | | | | | |

TABLE 9A3

9A3 9A3(cont.) SEQ ID NOS 77-100, respectively, in order of appearance

| | | α-1 | Turn | α-2 | T |
|---|---|---|---|---|---|
| Bpert HupB | --------MN | KTELIDHIASK | ADIS-----------KA | AAGRSLDALIGAVKTTL | KK |
| Mc HimD | ----MQAVIN | KSNLIANLASV | CEEL-----------EED | VVDEAVRLMIAMMVNEL | VY |
| Pm HupB | --------MN | KTELIEKIAAN | AEVS-----------KA | AAKKALDATTEAIKEAL | AA |
| Pi Hup | --------MN | KTELIEKIAAG | AGLS-----------KA | DSKKALDAMTAAIKEAL | VA |
| Td HU | --------MK | QKRSKIDIIDS | VYRNNPQYQLKQ | INAIANLFLDELSVLLQ | QG |
| Pg_Hup-1 | --------MN | KTDFIAAVAEK | ANLT-----------KA | DAQRAVNAFAEVVTEQM | NA |
| Hp_Hup | --------MN | KAEFIDLVKEA | GKYNS----------KR | EAEEAISAFTLAVETAL | SK |
| Pm HupA | --------MT | KADIINEIATS | TGIA-----------KK | DVSAVVESFMETIKDSL | LE |
| Pi 1-14-2 | --------MT | KADIINEIASS | TGIS-----------KK | DVSAVVESFMDAIKDSL | LE |
| Pg_Hup-2 | --------MT | KADVVNAIAKS | TGID-----------KE | TTLKVVESFMDTIKDSL | SE |
| Mt HU | --------MN | KAELIDVLTQK | LGSG-----------RR | QATAAVENVVDTIVRAV | HK |
| Ms Hup | --------MN | KAELIDVLTTK | MGTD-----------RR | QATTAVENVVDTIVRAV | HK |
| Ec_HimD | --------MT | KSELIERLATQ | QS-----------H/PAK | TVEDAVKEMLEHMASTL | AQ |
| Salm_HimD | --------MT | KSELIERLATQ | QS-----------H/PAK | AVEDAVKEMLEHMASTL | AQ |
| Vc_HipB | --------MT | KSELIERLCAE | QT----------HLSAK | EIEDAVKNILEHMASTL | EA |
| Pa_HimD | --------MT | KSELIERIVTH | QG----------QLSAK | DVELAIKTMLEQMSQAL | AT |
| Hi_HimD | --------MT | KSELMEKLSAK | QP-----------TLPAK | EIENMVKGILEFISQSL | EN |
| Aa-IHFB | --------MT | KSELIELLVQK | NS-----------NIPVK | HVEEAVKAILEQMSYVL | EH |
| Ng_IHFI3 | ------------- | -----MVRLAEV | FAAKNGTHLLAK | DVEYSVKVLVDTMTRSL | AR |
| Nm HimD | --------MT | KSELMVRLAEV | FAAKNGTHLLAK | DVEYSVKVLVDTMTRSL | AR |
| Bc IHFB | --------MT | KSELVAQLASR | FP-----------QLVLK | DADFAVKTMLDAMSDAL | AK |
| Bp IHFB | --------MT | KSELVAQLASR | FP-----------QLVLK | DADFAVKTMLDAMSDAL | SK |
| Bpert IhfB | --------MT | KSELIAALAAR | YP-----------QLAAR | DTDYAVKTMLDAMTQAL | AS |
| Bb_Hbb | MSFSRRPKVT | KSDIVDQISLN | IKNNNL---KLEKK | YIRLVIDAFFEELKSNL | CS |

| β-1 | T | β-2 | Binding domain | Turn | Returning strand | β-3 | α-3 | |
|---|---|---|---|---|---|---|---|---|
| GGTVT | LVG | FGTFA | VSARAART-GR | NPRT | GEITIKIKKAKVP | KFRPGK | ALKDAV | N |
| DGRIE | VRG | FGSFC | LHHRSARI-AR | NPRT | GESVSVKAKATP | YFKPGK | ALRESV | NLVND |
| GDKVQ | LVG | FGTFA | TTERPAHE-GI | NPRS | KEKIKIAAKKVA | KFKAGA | ELADAV | NK |
| GDKVQ | LVG | FGTYS | VTERPAHE-GI | NPAT | KQKIQIAAKKVA | KFKPGA | ELADAV | NA |
| IPVEI | RGL | GSFDF | AVLHGR-KNAR | NPKT | GEAVLTADRCKV | RFKPGK | ELKEAL | HKIDTQELIES |
| GEKIA | LIG | FGTFS | VSERAARK-GI | NPKT | KKSISIPARKVV | RFKPGS | TLELK- | --------- |
| GESVE | LIG | FGKFE | TAEQKGKE-GK | VPGS | DKTYKTEDKRVP | KFKFGK | TLKQKV | EEGK----- |
| KKENV | YLR | GFGSF | IVKHRAEKTAR | NISK | NTTITIPAHDFP | SFKPAK | TFIEDM | KK |
| NKENV | YLR | GFGSF | IVKHRAEKTAR | NISK | NTTITIPAHDFP | SFKPAK | TFIEDM | KK |
| GDNVY | LRG | FGSFI | VKERAEKT-AR | NISK | QTTIIIPKRNIP | AFKPSK | IFMSQV | KQD------ |
| GDSVT | ITG | FGVFE | QRRRAAR-VAR | NPRT | GETVKVKPTSVP | AFRFGA | QFKAVV | SGAQRLPAEGF+114aa |
| GDSVT | ITG | FGVFE | QRRRAAR-VAR | NPRT | GETVKVKPTSVP | AFRFGA | QFKAVI | SGAQKLPAEGF+108aa |

TABLE 9A3-continued

| | | | | | | | | |
|---|---|---|---|---|---|---|---|---|
| GERIE | IRG | FGSFS | LHYRAPRT-GR | NPKT | GDKVELEGKYVP | HFKPGK | ELRDRA | NIYG----- |
| GERIE | IRG | FGSFS | LHYRAPRT-GR | NPKT | GDKVELEGKYVP | HFKPGK | ELRDRA | NIYG----- |
| GERIE | IRG | FGSFS | LHYREPRV-GR | NPKT | GDKVELEGKYVP | HFKPGK | ELRERV | NL------- |
| GDRIE | IRG | FGSFS | LHYRAPRV-GR | NPKT | GESVRLDGKFVP | HFKPGK | ELRDRV | NEPE----- |
| GDRVE | VRG | FGSFS | LHHRQPRL-GR | NPKT | GDSVNLSAKSVP | YFKAGK | ELKARV | DVQA----- |
| GERIE | VRG | FGSFS | LHCRQPRI-GR | NPKT | GEQVKLDAKCVP | YFKAGK | ELRERV | DVYAA---- |
| GQRIE | IRG | FGSFD | LNHRPARI-GR | NPKT | GERVEVPEKHVP | HFKPGK | ELRERV | DLALKENAN |
| GQRIE | IRG | FGSFD | LNHRPARI-GR | NPKT | GERVEVPEKHVP | HFKPGK | ELRERV | DLALKENAN |
| GHRIE | IRG | FGSFG | LNRRPARV-GR | NPK | GEKVQVPEKFVP | HFKPGK | ELRERV | DGRAGEPLKADDPDDDR |
| GHRIE | IRG | FGSFG | LNRRPARV-GR | NPK | GEKVQVPEKFVP | HFKPGK | ELRERV | DGRAGEPLKNDEPEDAQ |
| GQRIE | IRG | FGSFS | LSQRSPRI-GR | NPK | GEKQVLVPGKQVP | HFKPGK | ELREWV | DLVGNDQGDDS +18aa |
| NNVIE | FRS | FGTFE | VRKRKGRLNAR | NPQT | GEYVKVLDHHVA | YFRPGK | DLKERV | WGIKG---- |
| | | | ------------ARM------------ | | | | | |

TABLE 9B

Comparison to Liu et al 16 as peptide motif

SEQ ID NOS 101-128, respectively, in order of appearance

| | |
|---|---|
| Strep inter HU | EVRERAARK-GRNPQTG |
| Ec_HimA | DLRDKNQRP-GR NPKT G |
| SalmHimA | DLRDKNQRP-GR NPKT G |
| Vc_HimA | DLRDKNERP-GR NPKT G |
| Pa_HimA | DLRDKRQRP-GR NPKT G |
| Hi_HimA | ELRDKSSRP-GR NPKT G |
| Aa_IHFalpha | ELRDKASRP-GR NPKT G |
| Mc HimA | ELKDKKPRP-GR NPKT G |
| Ng_IHFalpha | QLRDKPQRP- GR NPKT G |
| Nm HimA | QLRDKPQRP-GR NPKT G |
| Bc IHFA | QLRDKPQRP-GR NPKT G |
| Bp IHFA | QLRDKPQRP-GR NPNT G |
| Bpert IhfA | QLRDKPQRP-GR NPKT G |
| Pm HimA | EVKKRLERV-MV NP ST G |
| Pi HimA | EVKKRLERI-MT NP A T G |
| Tp Dbp II | ESRVRKASV-GKS NT G |
| Pm Hup | KVQAVKPR-ESV N VN T G |
| Pi hypo | KVQAVKPR-ESV N VN T G |
| Sa_HU | EVRERAARK-GR NPQT G |
| Ec hupA | KVNHRAERT-GR NPQT G |
| Se_Hup | EVRERAARK-GR NPQT G |
| Ss Hu | EVRERAARK-GR NPQT G |
| Spyog_HU | EVRERAARK-GR NPQT G |
| Sgall_HipA | EVRERAARK-GR NPQT G |
| GBS_Hup | EVRERAARK-GR NPQT G |
| Spneu_HU | EVRERAARK-GR NPQT G |
| Sg_HlpA | EVRERAERK-GR NPQT G |
| Sm_HU | EVRERAARK-GR NPQT G |
| Ef Hup | EVRERAARK-GR NPQT G |
| Hi_HupA | KVNERAART-GR NPQT G |

TABLE 9B-continued

Comparison to Liu et al 16 as peptide motif

| | |
|---|---|
| Vc_HupA | KVNHRSART-GR NPQT G |
| Bpert HupB | AVSARAART-GR NPRT G |
| Pa_HupB | AVKERAART-GR NPQT G |
| Aa HU | SVRTRAART-GR NPKT G |
| Pm HupB | ATTERPAHE-GI NP RSK |
| Pi Hup | SVTERPAHE-GI NP A T K |
| Td HU | FAVLHGR-KNAR NPKT G |
| Pg_Hup-1 | SVSERAARK-GI NPKT K |
| Hp_Hup | ETAEQKGKE-GKV P GSD |

SEQ ID NOS 140-159, respectively, in order of appearance

| | |
|---|---|
| Pm HupA | FIVKHRAEKTAR N ISKN |
| Pi Hup-2 | FIVKHRAEKTAR N ISKN |
| Pg_Hup-2 | IVKERAEKT-AR N ISKQ |
| Mt HU | EQRRRAAR-VAR NP R T G |
| Ms Hup | EQRRRAAR-VAR NP R T G |
| Ec_HimD | SLHYRAPRT-GR NPKT G |
| Salm_HimD | SLHYRAPRT-GR NPKT G |
| Vc_HipB | SLHYREPRV-GR NPQT G |
| Ec hupB | AVKERAART-GR NPKT G |
| Mc HupB | SVKERAARM-GR NPKT G |
| Pa_HimD | SLHYRAPRV-GR NPKT G |
| Hi_HimD | SLHHRQPRL-GR NPKT G |
| Aa_IHFB | SLHCRQPRI-GR NPKT G |
| Ng_IHFβ | DLNHRPARI-GR NPKT G |
| Nm HimD | DLNHRPARI-GR NPKT G |
| Bc IHFB | GLNRRPARV- GR NPK SG |
| Bp IHFB | GLNRRPARV-GR NPK SG |
| Bpert IhfB | SLSQRSPRI- GR NPK SG |
| Mc HimD | CLHHRSARI-AR NP R T G |
| Bb_Hbb | EVRKRKGRLNAR NPQT G |

TABLE 10

(SEQ ID NOS 160-336, respectively, in order of appearance)

| Bacteria strain, protein name | β3 sequence | α3 sequence | C-terminal 20 aa |
|---|---|---|---|
| S. pyogenes MGAS10270, HU | AFKAGKALKDAVK | | IAASKVPAFKAGKALKDAVK |
| S. gallolyticus UCN34 (S. bovis), HlpA | AFKAGKALKDAVK | | IAASKVPAFKAGKALKDAVK |
| S. sobrinus 6715 HU | AFKAGKALKDAVK | | IAASKVPAFKAGKALKDAVK |
| S. agalactiae (Group B Strep)2603V/R Hup | AFKAGKALKDAVK | | IAASKVPAFKAGKALKDAVK |
| S. pneumoniae R6 HU | AFKAGKALKDAVK | | IAASKVPAFKAGKALKDAVK |
| S. gordonii Challis NCTC7868, HlpA | AFKAGKALKDAVK | | IAASKVPAFKAGKALKDAVK |
| S. mutans UA159, HU | AFKAGKALKDAVK | | IKASKVPAFKAGKALKDAVK |
| Enterococcus faecalis V583, Hup | AFKPGK ALKDAVK | | IAASKVPAFKPGKALKDAVK |
| S. aureus MW2, HU | AFKAGKALKDAVK | | IPASKVPAFKAGKALKDAVK |
| S. epidermidis RP62A Hup | AFKAGKALKDAVK | | IPASKVPAFKAGKALKDAVK |
| H. influenza KW20 Rd HupA | AFVSGK ALKDAIK | | IAASKVPAFVSGKALKDAIK |
| Aggregatibacter actinomycetemcomitans D11S-1 HU | AFVSGK ALKDAVK | | IAASKVPAFVSGKALKDAVK |
| V. cholera El Tor N16961, HupA | AFVAGKALKDAIK | | IAAANVPAFVAGKALKDAIK |
| E. coli K12-MG1655 hupA | AFVSGK ALKDAVK | | IAAANVPAFVSGKALKDAVK |
| P. aeruginosa HupB | GFKAGKALKDAVN | | IAAAKIPGFKAGKALKDAVN |
| E. coli K12-MG1655 hupB | SFRAGK ALKDAVN | | IAAAKVPSFRAGKALKDAVN |
| V. cholera El Tor N16961 HupB | SFKAGK ALKDACN | | IAEAKVPSFKAGKALKDACN |
| Bordetella pertusis Tohama 1 HupB | KFRPGK ALKDAVN | | IKKAKVPKFRPGKALKDAVN |
| Prevotella melaninogenica ATCC 25845 HupB | KFKAGAELADAVNK | | AAKKVAKFKAGAELADAVNK |
| Prevotella intermedia 17 Hup | KFKPGA ELADAVNA | | AAKKVAKFKPGAELADAVNA |
| Moraxella catarrhalis RH4 HupB | SFKAGK VLKESVN | | IAASKVPSFKAGKVLKESVN |
| P. gingivalis W83 Hup-1 | RFKPGS TLELK | | ISIPARKVVRFKPGSTLELK |
| H. pylori 2669 Hup | KFKPGK TLKQKVEEGK | | KRVPKFKPGKTLKQKVEEGK |
| Prevotella melaninogenica ATCC 25845 HupA | SFKPAK TFIEDMKK | | PAHDFPSFKPAKTFIEDMKK |
| Prevotella intermedia 17 Hup-2 | SFKPAK TFIEDMKK | | PAHDFPSFKPAKTFIEDMKK |
| P. gingivalis W83 Hup-2 | AFKPSK IFMSQMKQD | | KRNIPAFKPSKIFMSQMKQD |
| Mycobacterium tuberculosis MC2 Hup | AFRPGA | QFKAVISGAQKLPADGPAVKRG | AKAPAKKAAAKKAPAKKGRR |
| Prevotella melaninogenica ATCC 25845 HimA | NFKPAA TIKGHVRKGGQDNG | | NFKPAATIKGHVRKGGQDNG |
| Prevotella intermedia 17 HimA | NFRATA SVKEKLKKGGAE | | VLNFRATASVKEKLKKGGAE |
| E. coli K12-MG1655 HimA | TFRPGQ KLKSRVENASPKDE | | TFRPGQKLKSRVENASPKDE |
| Salmonella enteric serovar typhi CT18 HimA | TFRPGQ KLKSRVENASPKEE | | TFRPGQKLKSRVENASPKEE |
| V. cholera El Tor N1696 HimA | TFRPGQ KLKARVENIKVEK | | VTFRPGQKLKARVENIKVEK |
| P. aeruginosa HimA | TFRPGQ KLKARVEAYAGTKS | | TFRPGQKLKARVEAYAGTKS |
| Burkholderia cenocepacia HI2424 IHFA | TFHASQ KLKALVENGAE | | RVVTFHASQKLKALVENGAE |
| Burkholderia pseudomallei 668 IHFA | TFHASQ KLKALVENGAEPDLAR | | HASQKLKALVENGAEPDLAR |
| Bordetella pertusis Tohama 1 IhfA | TFHASQ KLKSVVEQPNSPPDPASAE | | QKLKSVVEQPNSPPDPASAE |
| N. gonorrhoeae FA1090 (Oklahoma) IHFa | TFHASQ KLKGMVEHYYDKQR | | TFHASQKLKGMVEHYYDKQR |
| N. meningitides MC58 HimA | TFHASQ KLKSMVEHYYDKQR | | TFHASQKLKSMVEHYYDKQR |
| H. influenza KW20 Rd HimA | TFKPGQ KLRARVEKTK | | RRVVTFKPGQKLRARVEKTK |
| Aggregatibacter actinomycetemcomitans D11 S-1 HimA | VFKPGQ KLRNRVEKVKPKA | | VVFKPGQKLRNRVEKVKPKA |
| Moraxella catarrhalis RH4 HimA | TFKAGQ KLRGWIDSQNEG | | VVTFKAGQKLRGWIDSQNEG |
| Treponema palladium Nichols DNA_binding_protein_II | VFRPSK RLKSAVRGYRSGEVGAD | | PSKRLKSAVRGYRSGEVGAD |
| Prevotella melaninogenica ATCC 25845 Hup | SFTPDT VMKELVNKPFSQFETVVINDGV | | MQAGDTMKVPKVELRPEYRK |
| Prevotella intermedia 17 hypothetical | SFTPDA TMKELVNKPFAQFETVVLNDGV | | SAGDTMKVPKVELRPQYRTK |
| E. coli K12-MG1655 HimD | HFKPGK ELRDRANIYG | | KYVPHFKPGKELRDRANIYG |
| Salmonella enteric serovar typhi CT18 bHimD | HFKPGK ELRDRANIYG | | KYVPHFKPGKELRDRANIYG |
| V. cholera El Tor N1696 HipB | HFKPGK ELRERVNL | | EGKYVPHFKPGKELRERVNL |
| P. aeruginosa HimD | HFKPGK ELRDRVNEPE | | KFVPHFKPGKELRDRVNEPE |
| H. influenza KW20 Rd HimD | YFKAGKELKARVDVQA | | KSVPYFKAGKELKARVDVQA |

TABLE 10-continued (SEQ ID NOS 160-336, respectively, in order of appearance)

| Bacteria strain, protein name | β3 sequence | α3 sequence | C-terminal 20 aa |
|---|---|---|---|
| *Aggregatibacter actinomycetemcomitans* D11S-1 IHFB | YFKAGKELRERVDVYAA | | CVPYFKAGKELRERVDVYAA |
| *N. gonorrhoeae* FA1090 (Oklahoma) IHFβ | HFKPGK ELRERVDLALKENAN | | FKPGKELRERVDLALKENAN |
| *N. meningitides* MC58 HimD | HFKPGK ELRERVDLALKENAN | | FKPGKELRERVDLALKENAN |
| *Burkholderia cenocepacia* HI2424 IHFB | HFKPGK ELRERVDGRAGEPLKADDPDDDR | | ERVDGRAGEPLKADDPDDDR |
| *Burkholderia pseudomallei* 668 IHFB | HFKPGK ELRERVDGRAGEPLKNDEPEDAQ | | ERVDGRAGEPLKNDEPEDAQ |
| *Bordetella pertusis* Tohama 1 IhfB | HFKAGKELREWVDLVGNDQGDDSSNGSS | | DSSNGSSDPLQSVMDMHAMH |
| *Moraxella catarrhalis* RH4 HimD | YFKPGK ALRESVNLVND | | ATPYFKPGKALRESVNLVND |
| *B. burgdorferi* B31 Hbb | YFRPGK DLKERVWGIKG | | HVAYFRPGKDLKERVWGIKG |
| *Treponema denticola* ATCC 35405 HU | RFKPGK ELKEALHKIDTQELIES | | PGKELKEALHKIDTQELIES |

The following examples are intended to illustrate, and not limit the embodiments disclosed herein.

EXPERIMENTAL

Experiment No. 1

Some of the IHF antibodies, proteins and polypeptides were a generous gift from Nash. The methods to produce them are well known to the skilled artisan, e.g., as described in Granston and Nash (1993) J. Mol. Biol. 234:45-59; Nash et al. (1987) Journal of Bacteriology 169(9):4124-4127; and Rice et al. (1996) Cell 87:1295-1306. Briefly, to overproduce IHF-α, the himA gene was inserted downstream from the $P_L$ promoter in the bacterial plasmid pAD284. Transformants of strain K5607, a lambda lysogen of strain C600himA42 that had received the desired plasmid, were identified by screening ampicillin-resistant transformants for the ability to grow bacteriophage Mu (13). DNA was prepared from himA$^+$ transformants according to standard DNA isolation techniques, and the orientation of the himA gene was determined by restriction enzyme cleavage. Plasmid p$P_L$himA-1, which has the himA gene in the proper orientation for expression by the $P^L$ promoter, was transformed into strain N5271, which contains a cryptic lambda prophage expressing the cI857 thermoinducible repressor, to yield strain K5770.

To overproduce IHF-β, plasmid pKT23-hip323, which contains a fusion of the IHF-β coding sequence to the bacteriophage lambda $P_L$ promoter was used. pKT23-hip323 was introduced into N5271 to give strain E443. To facilitate the selection of pKT23-hip323 in the presence of another plasmid, changed its selectable marker was changed from ampicillin resistance (bla$^+$) to chloramphenicol resistance (cat$^-$). A cat-containing fragment was isolated from plasmid pBR325 as described by Flamm and Weisberg and was inserted into the unique SeaI site in bla. The ligated DNA was introduced into strain E403, which carries a hip mutation and which synthesizes temperature-sensitive λ repressor, and chloramphenicol-resistant transformants were selected at low temperature. One such transformant (E735) was hip$^+$ and ampicillin sensitive; it therefore appears to carry a bla cat$^+$ derivative of pKT23-hip323 (pE735).

To generate a strain that overproduces both subunits of IHF, E735 was transformed with plasmid p$P_L$himA-1, selecting transformant (E738) that had become ampicillin resistant and had retained chloramphenicol resistance. The generation of a second strain that overproduces both subunits of depended on the construction of plasmid p$P_L$hip himA-5, which was made by ligating blunted (SstII restriction enzyme site) containing the pheT and himA genes into the pKT23-hip323 plasmid. This is described in further detail in (Nash et al. (1987) J. Bacteriology 169(9):4124-4127. himA$^+$ transformants of strain K5607 were identified by screening for HimA$^+$, and the plasmid DNA was analyzed by restriction digestion. In all cases where the plasmid structure was obvious, two copies of himA had been ligated as a tandem direct repeat into the vector. It is not known if the presence of two copies of the himA gene on this plasmid is demanded by the selection, but it should be recalled that a single copy of the himA gene in plasmid p$P_L$himA-1 is sufficient to complement a himA mutant. Plasmid p$P_L$hiphimA-5 was used to transform strain N5271 to yield strain K5746.

Cells were grown in shaking water bath at 31° C. in TBY medium (10 g of tryptone, 5 g of yeast extract, and 5 g of sodium chloride per liter). At mid-log phase (optical density at 650 nm, ca. 0.6), the cells were shifted to a 42° C. water bath and shaking was continued. Typically, 300 ml of culture was centrifuged and suspended in 0.6 to 0.9 ml of TEG (20 mM Tris hydrochloride (pH 7.4), 1 mM sodium EDTA, 10% glycerol) containing 20 mM NaCl. The cells were disrupted with six 20-s bursts of sonication, with 40 s between each burst. A portion of the sonic extract was centrifuged in a Sorvall SS34 rotor for 20 min at 15,000 rpm. Samples of the sonic extract were analyzed by sodium dodecyl sulfate (SDS) gel electrophoresis according to standard molecular biology techniques.

Purification of was done according to the following: A 3.6-liter batch of cells was induced for 3 h. All subsequent steps were carried out at 0 to 4° C. The cell pellet from 3.3-liters was suspended in 10 ml of TEG containing 20 mM NaCl to give a total volume of 29 ml; this suspension was disrupted in two batches, each receiving six bursts of 3 min of sonication separated by 90-s intervals. The sonic extract was centrifuged for 20 min at 15,000 rpm, yielding 16.9 ml of clarified extract. A 10% (vol/vol) solution (1.1 ml) of polymin P (BDH Chemicals Ltd.) was added slowly to the clarified extract; after being stirred for 20 mm, the mixture was centrifuged for 30 mm at 10,000 rpm. The resulting pellet was suspended in 10 ml of TEG containing 500 mM NaCl; after being stirred for 15 min, the mixture was centrifuged for 20 min at 12,000 rpm. The supernatant (10.3 ml) was adjusted to 50% saturation by the addition of 3.2 g of ammonium sulfate, stirred for 20 min, and centrifuged for 15 min at 15,000 rpm. The resulting supernatant was adjusted to 70% saturation by the addition of 1.64 g of ammonium sulfate, stirred for 20 min, and centrifuged for 15 min at 15,000 rpm. The resulting pellet was suspended in 1 ml of TG (50 mM Tris hydrochloride (pH 7.4) containing 10% glycerol) and dialyzed against two changes of TG. The dialyzed material (2.0 ml) was loaded onto a 1-ml column (0.5 by 5.8 cm) of phosphocellulose (P11; Whatman, Inc.) that had been equilibrated with TG. The column was washed with 3 ml of TG and developed with 20 ml of a linear gradient (0 to 1.2 M) of KCl in TG. Fractions of 0.5 ml were collected, stored at −20° C., and assayed for IHF activity.

Polyclonal anti-IHF was prepared as follows. Rabbits were injected with 250 μg of purified IHF with Freund's complete adjuvant. Booster immunizations of 250 μg of IHF with Freund's incomplete adjuvant were given 1, 7, and 12 weeks later. As determined by immunoblotting of IHF, sera collected 13 weeks after the initial injection had a high titer of IHF-reactive material. The animals were maintained for several years and, when necessary, given further booster immunization in order to maintain a high titer of anti-IHF in their sera. The antibody was not purified further. Crude sera was stored at −70° C.

Antibodies specific to each subunit were generated by using synthetic polypeptides corresponding to the most C-terminal 20 amino acid residues of each subunit (SEQ ID NO: 34 and 35), to immunize rabbits according to Ditto et al. (1994) J. Bacteriology 176(12):3738-3748.

Experiment 2

This experiment describes an in vitro model for reversal of an established biofilm in 8-well chamber slide. The materials used in this experiment were: Chocolate Agar; sBHI (BHI with 2 mg heme/mL and 2 mg b-NAD/mL); 8-well Chamber slides (Nunc* Lab-Tek* Fisher catalog #12-565-18); Sterile 0.9% saline; LIVE/DEAD BacLight Bacterial Viability Kit (Fisher catalog #NC9439023) and Formalin.

On day 1, NTHI was struck for isolation on chocolate agar. It was then incubated for 20 hrs at 37° C. and 5% $CO_2$. The next day, bacteria were suspended in 5 mL equilibrated (37° C., 5% $CO_2$) and optical density was adjusted to $OD_{490}$=0.65 in sBHI. Bacteria were diluted 1:6 in equilibrated sBHI (1 mL bacterial suspension+5 mL sBHI). Bacteria was then incubated for 3 hours at 37° C. in 5% $CO_2$, static ($OD_{490}$ should be approx 0.65). Next, the bacteria were again diluted 1:2500 in equilibrated sBHI and 200 mL of the bacterial suspension was added to each well of the chamber slide. For dilution, 10 μL bacteria was added to 990 μL sBHI in an eppendorf tube and 8 μL dilution was added to 192 μL sBHI in each chamber and incubated at 37° C., 5% $CO_2$, static.

On the third day after 16 hours of incubation medium was aspirated from chamber by aspirating medium from the corner of the well so as not to disturb biofilm. Then 200 mL of equilibrated sBHI was added to each chamber and incubated for 37° C., 5% $CO_2$, static for 8 hours. After 8 hours, the medium was aspirated and 200 mL equilibrated sBHI was added to each untreated chamber; and 200 mL of interfering agent such as Rabbit anti-rsPilA; diluted 1:50 in sBHI and 200 mL Naive rabbit serum (or other appropriate serum control) diluted 1:50 in sBHI was added. They were then incubate at 37° C. and 5% $CO_2$, static.

On day 4, after approximately 16 hours of incubation, aspirate sBHI was aspirated and the biofilm was washed twice with 200 mL sterile saline. The saline was aspirated and 200 mL Live/Dead stain was added. Next, 3 mL component A plus 3 mL component B in 1 mL sterile 10 mM phosphate buffered saline was added. It was then incubated for 15 minutes at room temperature, static, protected from light. Stain was aspirated and biofilm was washed twice with 200 mL sterile saline. Saline was aspirated and 200 mL formalin was added to fix biofilm. It was then incubated 15 minutes at room temperature, static, protected from light. Formalin was aspirated and biofilm was washed twice with 200 mL sterile saline. Gasket was removed and coverslip were placed on slide; coverslip were sealed with nail polish and dried prior to viewing by confocal microscopy.

Using this method and anti-IHF antibody described in Experiment No. 1, Applicants reduced a biofilm produced by *Haemophilus influenzae* which is prevalent in sinusitis, bronchitis, otitis media and exacerbations of chronic obstructive pulmonary disease (COPD). Untreated biofilm mass was measured to be 4.24 $\mu m^3/\mu m^2$ with a mean thickness of 11.68 μm. After treatment, the biofilm mass was reduced to 0.53 $\mu m^3/\mu m^2$ with a mean thickness of 1.31 μm. Thus, this shows a 88.8% reduction in mean thickness and an 87.5% reduction in biomass.

Polyclonal antisera directed against the *E. coli* IHF raised against an IHF promoter purified from *E. coli* K12 was prepared in rabbits according to standard techniques using purified Integration Host Factor (IHF). Experiment 1 describes the expression and purification of IHF from *E. coli*. This antibody is the anti-IHF antibody used to generate the data in the experiments disclosed below.

Using this method and anti-IHF antibody, Applicants reduced a biofilm produced by *Streptococcus mutans* which is prevalent in initiation and progression of dental caries. Untreated biofilm mass was measured to be 1.17 $\mu m^3/\mu m^2$ with a mean thickness of 5.43 μm. After treatment, the biofilm mass was reduced to 0.1 $\mu m^3/\mu m^2$ with a mean thickness of 0.47 μm. Thus, this shows a 91.3% reduction in mean thickness and an 91.6% % reduction in biomass. In vitro biofilm assays were repeated 3 times, on separate days. The percent reduction in the max height, average thickness, and biomass is depicted in Table 1 below.

TABLE 1

| | | Assay 1 | Assay 2 | Assay 3 |
|---|---|---|---|---|
| S. mutans | Max height (μm) | 56 | 24 | 41 |
| | Ave thickness (μm) | 65 | 65 | 67 |
| | biomass ($\mu m^3/\mu m^2$) | 37 | 58 | 66 |

Figure 7:
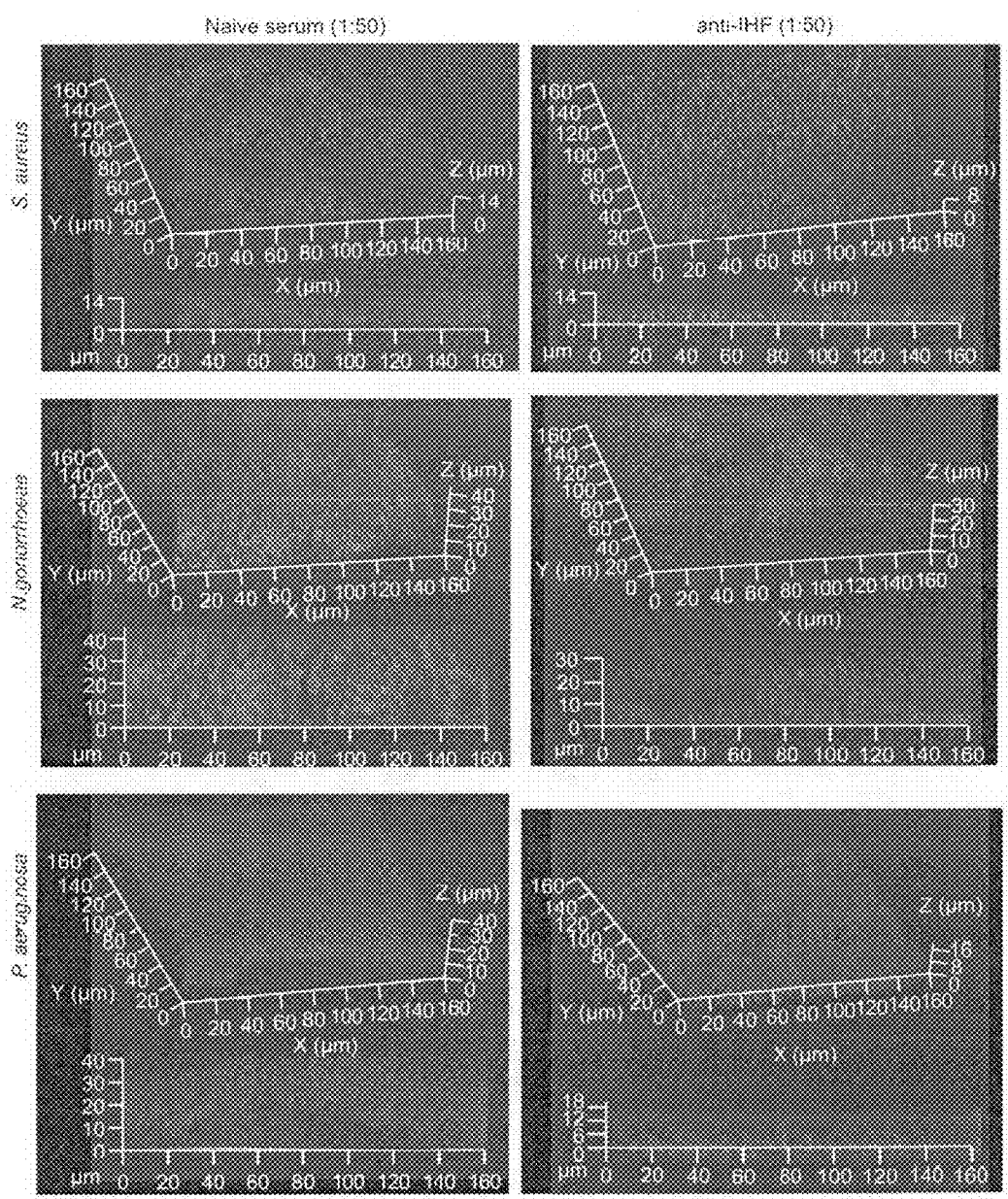
FIG. 7 depicts the reduction of biofilms formed by *S. aureus*, *N. gonorrhoeae* and *P. aeruginosa* upon incubation with rabbit anti-IHF compared to incubation with naïve rabbit serum.
Figure 8A:
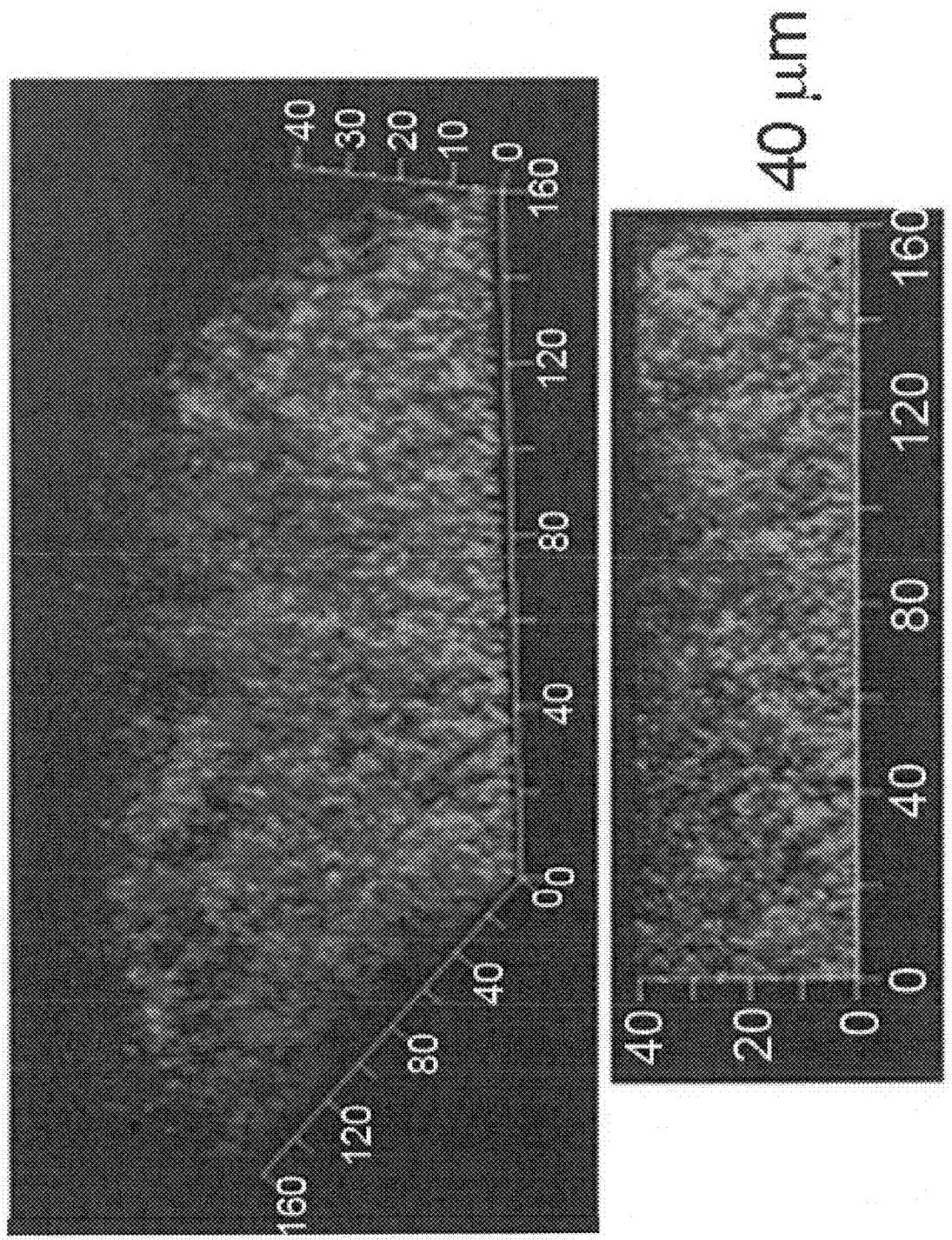
FIGS. 8A-8F show the effect of incubation of biofilms formed in vitro by E. coli with either naïve serum or with anti-IHF serum. Representative images of biofilms are shown in FIGS. 8A-8F with height of individual biofilms shown to the right of each image, whereas mean values in terms of percent reduction in biofilm height, biomass and mean thickness as mediated by incubation with anti-IHF are shown in the tables at the end of each row.
Figure 8B:
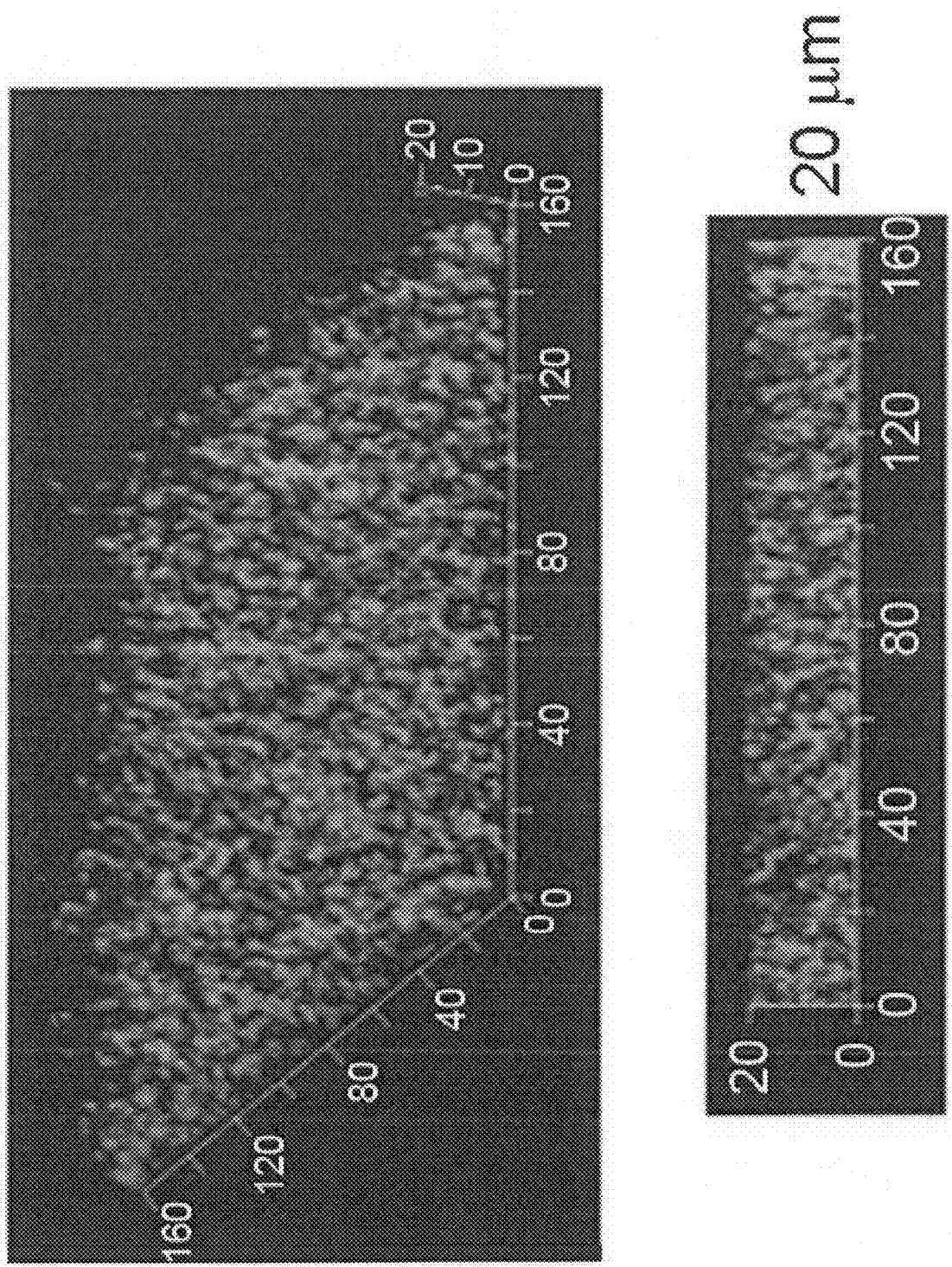
Figure 8C:
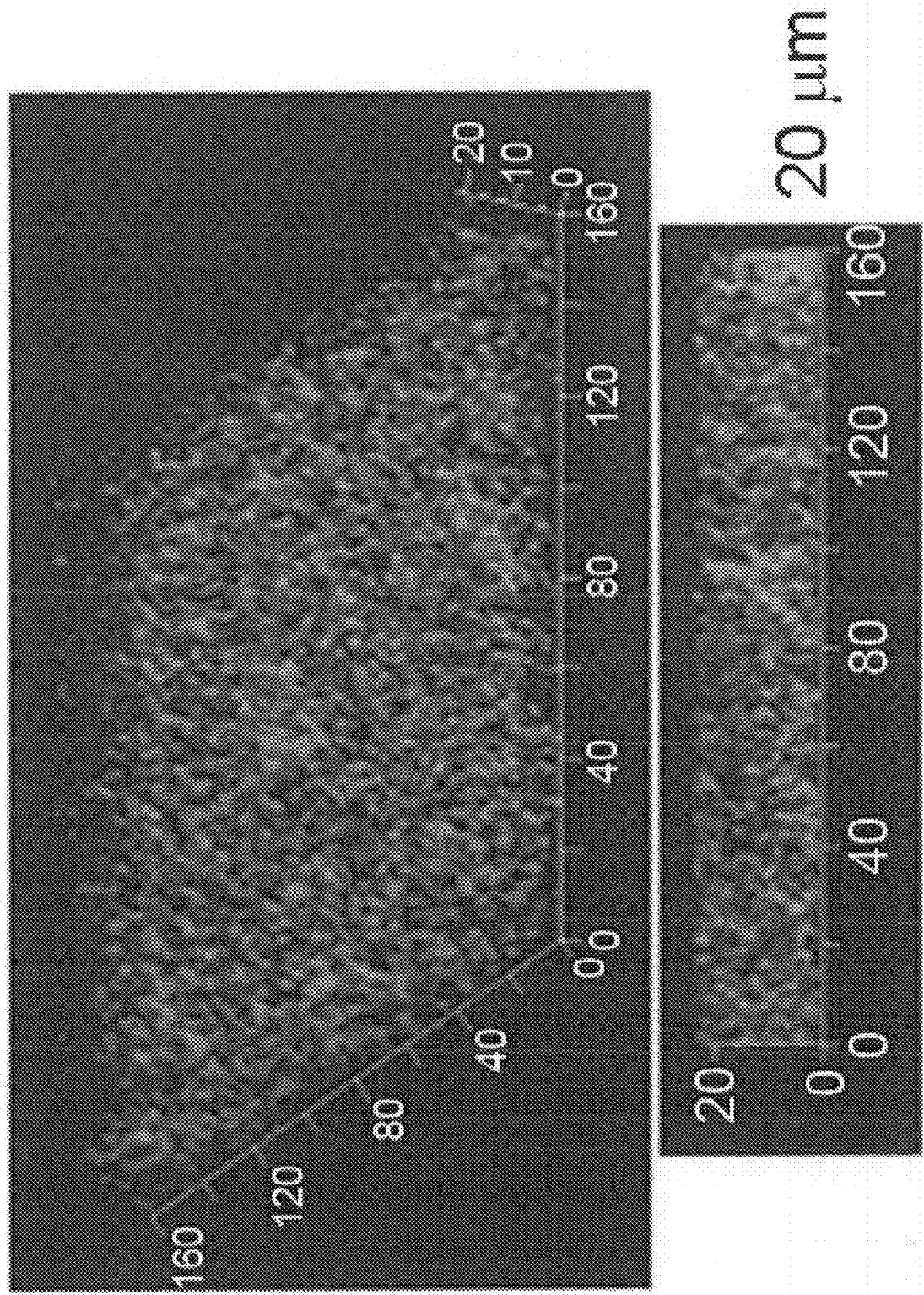
Figure 8D:
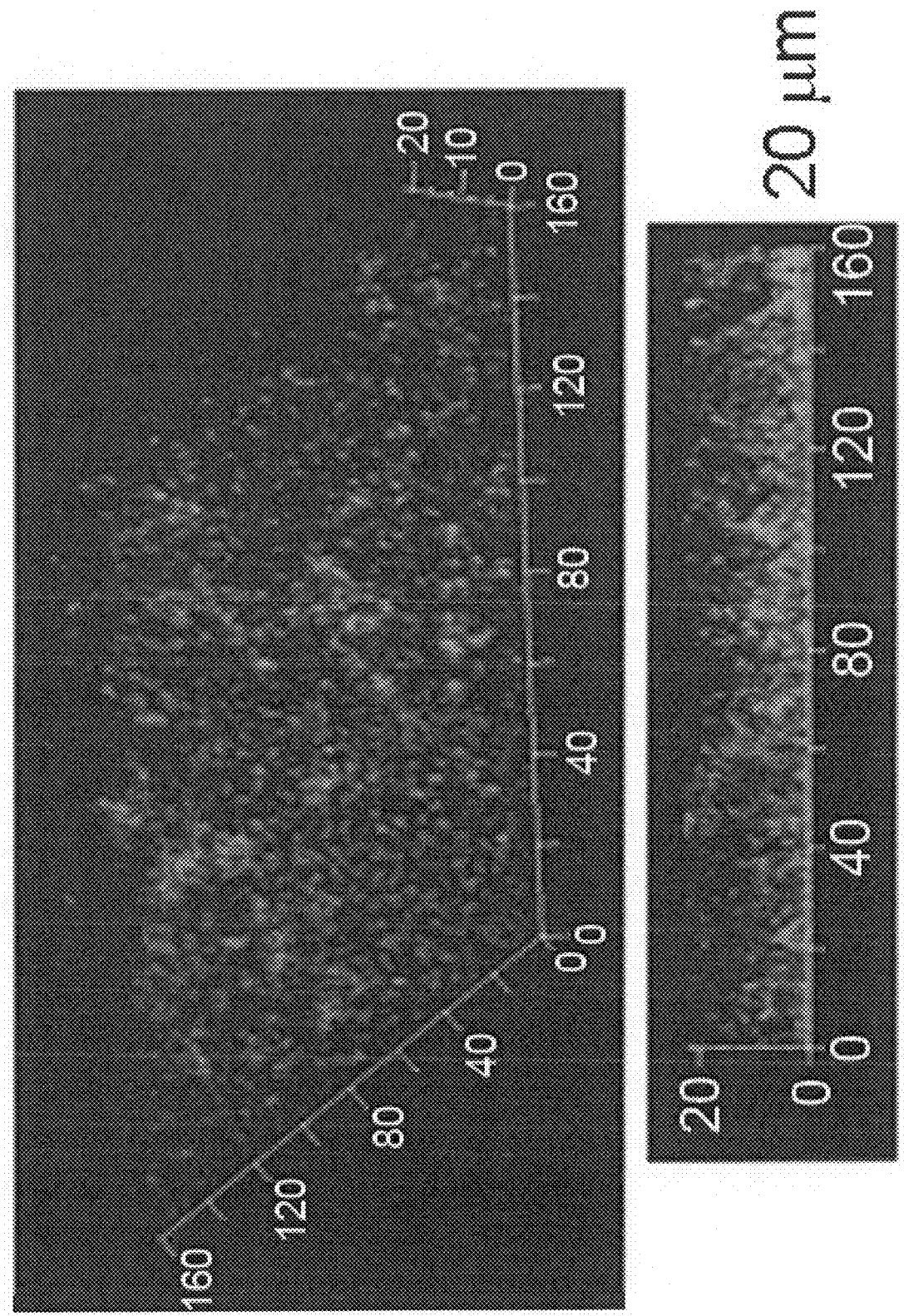
Figure 8E:
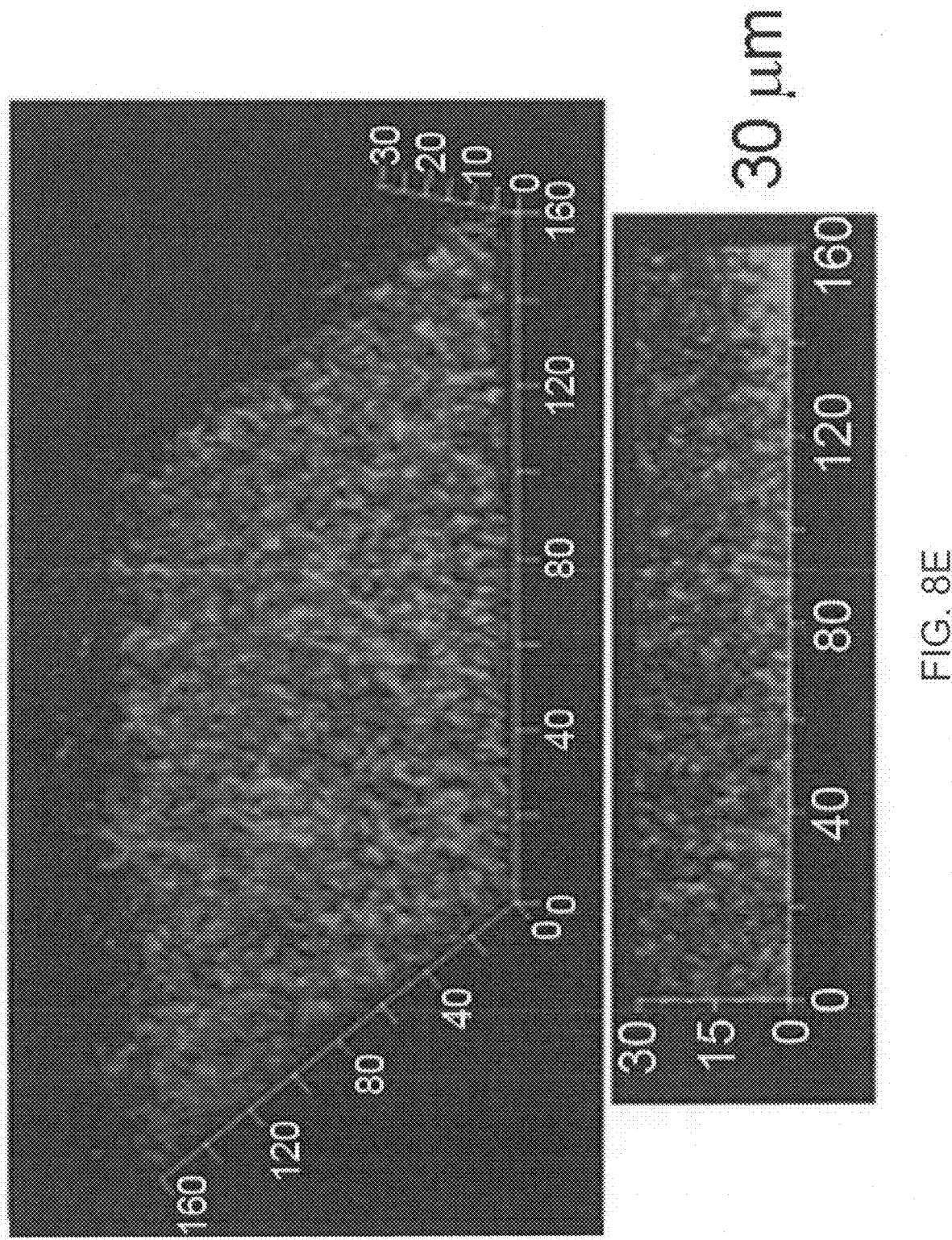
Figure 8F:
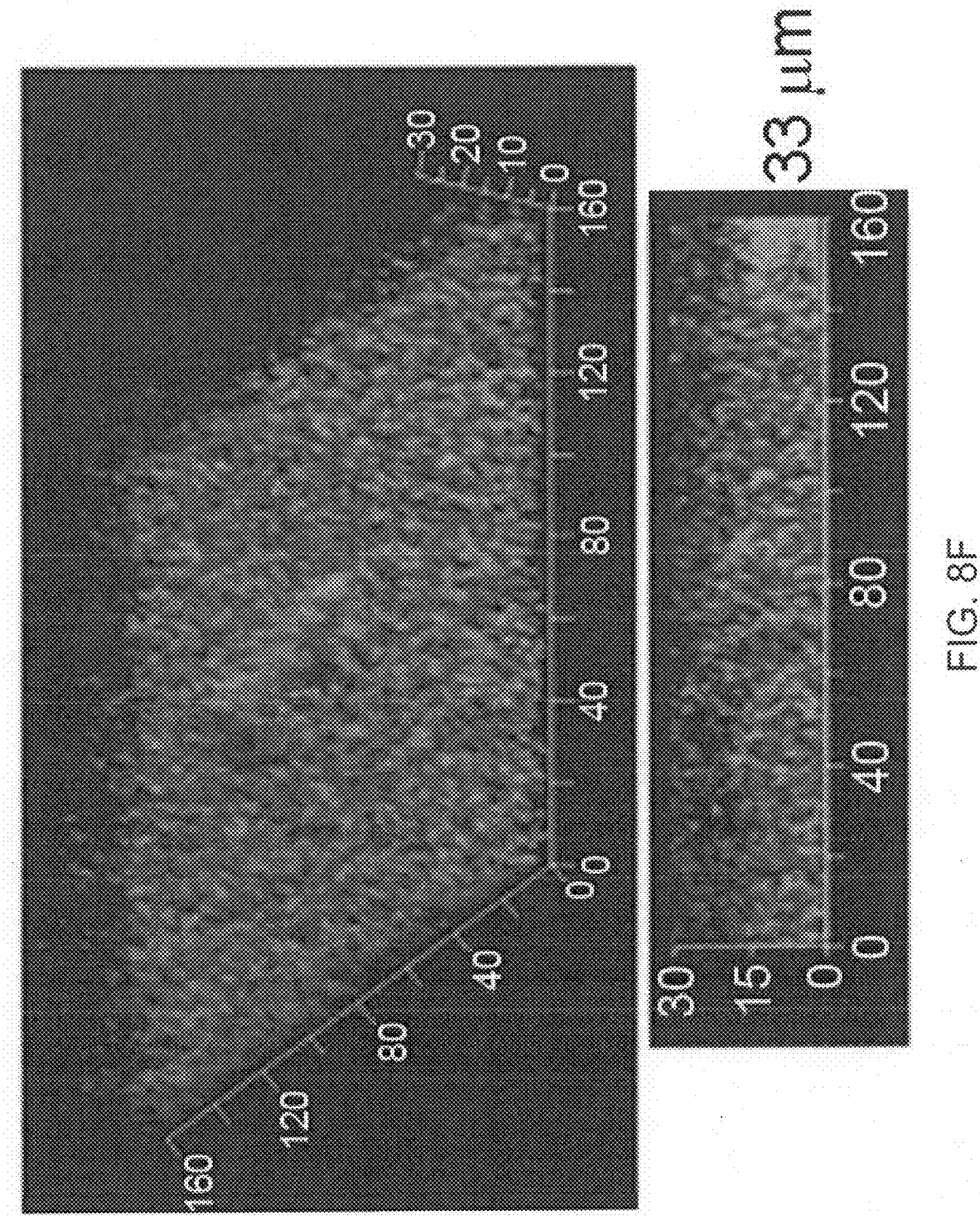

Using this method and anti-IHF antibody, Applicants reduced a biofilm produced by *Staphylococcus aureus* which is prevalent in localized and diffuse skin infections, chronic rhinosinusitis and nosocomial infections. Untreated biofilm mass was measured to be 0.3 $\mu m^3/\mu m^2$ with a mean thickness of 2.2 μm and a biofilm height of 17.5 μm. After treatment, the biofilm mass was reduced to 0.3 $\mu m^3/\mu m^2$ with a mean thickness of 1.1 μm and a biofilm height of 8 μm. Thus, this shows a 48.8% reduction in mean thickness and an 2.7% reduction in biomass (FIG. 7).

Using this method and anti-IHF antibody, Applicants reduced a biofilm produced by *Moraxella catarrhalis* which is prevalent in exacerbation of COPD and otitis media.

Untreated biofilm mass was measured to be 0.72 $\mu m^3/\mu m^2$ with a mean thickness of 1.48 μm. After treatment, the biofilm mass was reduced to 0.13 $\mu m^3/\mu m^2$ with a mean thickness of 0.65 μm. Thus, this shows a 55.8% reduction in mean thickness and an 82.1% reduction in biomass. In vitro biofilm assays were repeated 3 times, on separate days. The percent reduction in the max height, average thickness, and biomass is depicted in Table 2 below.

TABLE 2

| | | Assay 1 | Assay 2 | Assay 3 |
|---|---|---|---|---|
| M. catarrhalis | Max height (μm) | 61 | 33 | 36 |
| | Ave thickness (μm) | 92 | 34 | 84 |
| | biomass ($\mu m^3/\mu m^2$) | 92 | 35 | 92 |

Using this method and anti-IHF antibody, Applicants reduced a biofilm produced by Streptococcus pneumoniae which is prevalent in sinusitis, pneumonia and otitis media. Untreated biofilm mass was measured to be 0.64 $\mu m^3/\mu m^2$ with a mean thickness of 3.99 μm. After treatment, the biofilm mass was reduced to 0.14 $\mu m^3/\mu m^2$ with a mean thickness of 0.82 μm. Thus, this shows a 79.5% reduction in mean thickness and a 78.6% reduction in biomass. In vitro biofilm assays were repeated 3 times, on separate days. The percent reduction in the max height, average thickness, and biomass is depicted in Table 3 below.

TABLE 3

| | | Assay 1 | Assay 2 | Assay 3 |
|---|---|---|---|---|
| S. pneumoniae | Max height (μm) | 49 | 51 | 44 |
| | Ave thickness (μm) | 25 | 64 | 79 |
| | biomass ($\mu m^3/\mu m^2$) | 51 | 61 | 79 |

Using this method and anti-IHF antibody, Applicants reduced a biofilm produced by Pseudomonas aeruginosa which is prevalent in cystic fibrosis, pneumonia, skin and soft tissue infections and on medical devices. Untreated biofilm mass was measured to be 7.0 $\mu m^3/\mu m^2$ with a mean thickness of 25.70 μm and a biofilm height of 40 μm. After treatment, the biofilm mass was reduced to 3.4 $\mu m^3/\mu m^2$ with a mean thickness of 10.3 μm and a biofilm height of 27.5 μm. Thus, this shows a 60.1% reduction in mean thickness and an 50.8% reduction in biomass (FIG. 7).

Using this method and anti-IHF antibody, Applicants reduced a biofilm produced by Neisseria gonorrhoeae which is in gonorrhea. Untreated biofilm mass was measured to be 9.5 $\mu m^3/\mu m^2$ with a mean thickness of 22.02 μm and a biofilm height of 40 μm. After treatment, the biofilm mass was reduced to 0.8 $\mu m^3/\mu m^2$ with a mean thickness of 3.4 μm and a biofilm height of 27.5 μm. Thus, this shows a 84.5% reduction in mean thickness and an 92.1% reduction in biomass (FIG. 7).

Using this method and anti-IHF antibody, Applicants reduced a biofilm produced by Uropathogenic E. coli which is prevalent in urinary tract infections. Untreated biofilm mass was measured to be 1.75 $\mu m^3/\mu m^2$ with a mean thickness of 31.73 μm. After treatment, the biofilm mass was reduced to 0.75 $\mu m^3/\mu m^2$ with a mean thickness of 1.62 μm. Thus, this shows a 94.9% reduction in mean thickness and an 56.9% reduction in biomass. In vitro biofilm assays were repeated 3 times, on separate days. The percent reduction in the max height, average thickness, and biomass is depicted in Table 4 below.

TABLE 4

| | | Assay 1 | Assay 2 | Assay 3 |
|---|---|---|---|---|
| UPEC | Max height (μm) | 69 | 65 | 76 |
| | Ave thickness (μm) | 97 | 33 | 95 |
| | biomass ($\mu m^3/\mu m^2$) | 98 | 96 | 57 |

Using this method and anti-IHF antibody, Applicants reduced a biofilm produced by Staphylococcus epidermidis which is prevalent in infections of the skin. In vitro biofilm assays were repeated 3 times, on separate days. The percent reduction in the max height, average thickness, and biomass is depicted in Table 5 below.

TABLE 5

| | | Assay 1 | Assay 2 | Assay 3 |
|---|---|---|---|---|
| S. epidermidis | Max height (μm) | 42 | 38 | 56 |
| | Ave thickness (μm) | 62 | 71 | 92 |
| | biomass ($\mu m^3/\mu m^2$) | 62 | 76 | 88 |

Experiment No. 3

Middle ear infection (or otitis media, OM) is a highly prevalent disease worldwide, afflicting 50-330 million children globally each year. The socioeconomic burden of OM is also great, with cost estimates between $5-6 billion in the United States alone annually. All three of the predominant bacterial pathogens of OM are known to form biofilms both in vitro and in vivo and recently, clinicians have come to appreciate that the chronicity and recurrence of OM is due, at least in part, to the formation of bacterial biofilms within the middle ear cavity. In one chinchilla model of OM, juvenile chinchillas are first given a viral 'cold', followed a week later by their being challenged intranasally with an inoculum viable bacteria. Similar to the human condition wherein "my child has a cold and a week later gets an ear infection" chinchillas will also develop a bacterial OM approximately one week after a challenge, and while experiencing the viral upper respiratory tract infection. Once bacteria gain access to the middle ear (either via ascension of the Eustachian tube or following direct challenge to the middle ear space), they will form a robust biofilm. Applicants thus contemplated and indeed have already used chinchilla models as reported herein to demonstrate the protective efficacy of IHF immunization which results in rapid resolution of existing biofilms. This model is also useful for therapeutic approaches via either passive delivery of anti-DNABII antibody or via delivery of a small molecule or other agent known to bind to IHF or other DNABII family members.

Because the chinchilla model is used for development and pre-clinical testing of human vaccines, it is important to establish meaningful immunological parallels with the human host, particularly the child. Applicants have shown that effusions recovered from children with AOM due to NTHI, and middle ear fluids from chinchillas with experimental NTHI-induced OM, recognized immunodominant regions of OMP P5 in a similar hierarchical manner (see for e.g., Novotny, L. A. et al. (2000) Infect 68(4):2119-28; Novotny, L. A. et al. (2007) 9th International Symposium on Recent Advances in Otitis Media; St. Pete Beach, Fla.; Novotny, L. A. et al. (2002) Vaccine 20(29-30):3590-97). Applicants have also shown that chinchillas with experimental OM, children with natural OM, and adults with exacerbations of COPD, all recognized peptides representing PilA in a highly analogous manner (see for e.g., Adams, L. D. et al. (2007) 107th General Meeting, American Society for Microbiology; 2007; Toronto, ON; Adams, L. D. et al. (2007) 9th International Symposium on Recent Advances in Otitis Media; St. Pete Beach, Fla.). Thus, chinchillas with experimental OM and children with natural disease respond similarly immunologically to at least two unrelated NTHI protein adhesins. This parallel was put to the ultimate test recently, when the chinchilla AV-NTHI superinfection model was used to conduct pre-clinical efficacy testing of a novel 11-valent Protein D-pneumococcal polysaccharide conjugate vaccine. Data obtained in the chinchilla predicted an efficacy of 34% whereas, when tested in children, the efficacy obtained against *H. influenzae*-induced OM was 35.6% (see for e.g., Novotny, L. A. et al. (2006) Vaccine 24(22):4804-11 and Prymula, R. et al. (2006) Lancet. 367 (9512):740-8), thus lending strong support to the relevancy of this model for the development and testing of OM vaccine candidates.

Applicants have shown a dramatic reduction in the preformed biofilm remaining within the middle ears of chinchillas after receipt of 2 weekly TC immunizations with an IHF promoter purified from *E. coli* K12 (the full length combination of both IHF subunits) delivered with a mucosal/systemic adjuvant.

48 adults were ordered from Rauscher's Chinchilla Ranch (LaRue, Ohio) and were acclimated to the vivarium for 7-10 days prior to the beginning of the study. Prior to TB [transbullar or direct challenge into the middle ear cavity] challenge, baseline otoscopy and tympanometry were performed as well as a limited volume prebleed to collect serum. Chinchillas were anesthetized and 300 µl of NTHI (strain #86-028NP) suspension containing approximately 1000 cfu were introduced into the middle ear space via transbullar challenge. Animals were allowed to recover, then monitored daily for adverse reactions as per IACUC accepted animal use protocols. Routine otoscopy and tympanometry were performed every 2-3 days throughout the study.

Four days after challenge (day +4), chinchillas were anesthetized and a CT scan was performed to visualize biofilms present within the middle ear and to obtain pre-immunization images. The surface of the pinnae were cleaned and hydrated by wiping with a sterile gauze pad moistened with sterile pyrogen free saline. After ~2 minutes (to allow the pinnae to dry), 50 µl of either the dmLT, IHF (purified *E. coli* IHF according to Experiment 1)+dmLT, or IHF+rsPiLA+dmLT solution will be added to the pinna and gently massaged in. Three chinchillas per cohort were sacrificed and tissues/samples collected (on days +4, and +11) to begin to determine mechanism of action.

Eleven days after challenge (day +11), the secondary immunization occurred as described above wherein the pinnae are cleaned/hydrated and immunogens were topically administered. Three chinchillas per cohort were sacrificed and tissues/samples collected to begin to determine mechanism of action.

Eighteen days after challenge (day +18), chinchillas were anesthetized and a CT scan were performed to identify any biofilms present, as well as to compare to the pre-immunization CT scans. The animals were then bled to collect serum and euthanized. The bullae are dissected and any fluids present were aseptically collected, the bullae were then opened to visualize the inferior bulla and any biofilm present. Images were collected and the bulla were washed with 1 ml of sterile saline and re-imaged. The mucosa, along with any biofilm present, were collected from the right bulla and placed in a preweighed tube. These tissues were homogenized, serially diluted, and plated to determine cfu NTHI/mg wet weight tissue. The left bullae were filled with OCT compound and snap frozen for histological analysis.

Images of the left and right middle ear cavities, with resident biofilms, were scrambled and two images per animal were compiled into a single file for ranking by blinded evaluators. The relative amount of biomass remaining within the middle ear of each animal was ranked on a 0 to 4+ scale by blinded reviewers using the scale shown in Table 6 below. Titer ELISAs, cytokine arrays, and Biacore were run on the serum as well as on the collected middle ear effusions. The OCT embedded middle ears were sectioned and stained either for basic morphology and architecture (H&E) or for the presence of IHF using immunohistochemistry and/or immunofluorescence.

TABLE 6

| Score | Criteria |
| --- | --- |
| 0 | No evidence of biomass. |
| 1+ | Biomass fills ≤25% of middle ear space. Junction of the bony septa to inferior bulla is visible. |
| 2+ | Biomass tills >25% to ≤50% of middle ear space. Unable to visualize where the bony septa meet the inferior bulla. |
| 3+ | Biomass fills >50% to ≤75% of middle ear space. Biomass covers >50% of the length of bony septa. |
| 4+ | Biomass tills >75% to ≤100% of middle ear space. Bony septa ot visible; obscured by biomass. |

Immunofluorescence imaging of frozen sections of biofilms formed in vivo was preformed according to the following. After dissection, the middle ear of each chinchilla was filled with OCT embedding compound (Fisher Scientific, Pittsburgh, Pa.) and flash frozen over liquid nitrogen. The bone which forms the inferior bulla was removed to leave the middle ear mucosa and existing biofilm intact. The resulting block was then bisected to reveal a cross section of the biofilm and re-embedded in OCT. Ten micron serial sections were cut using a Microm rotary cryotome, adhered to glass slides (Mercedes Medical, Sarasota, Fla.) and stored at −80° C. Sections were later stained to determine the relative incorporation of IHF within biofilms that had formed in vivo. Briefly, slides were air-dried, fixed in cold acetone, then equilibrated in buffer (0.05M Tris-HCl, 0.15M NaCl and 0.05% Tween 20, pH 7.4). Sections were blocked with image-iT FX signal enhancer (Molecular Probes, Eugene, Oreg.) and with Background Sniper (BioCare Medical, Concord, Calif.) per manufacturer's instructions. Sections were then incubated with a 1:200 dilution of polyclonal rabbit anti-IHF overnight at 4° C., in a humidified chamber. Slides were further rinsed and incubated with goat anti-rabbit IgG conjugated to AlexaFluor 594 (Invitrogen) for 30 minutes at room temp. As a counterstain, sections were incubated with DAPI and cover-slipped using ProLong Gold antifade reagent (Molecular Probes, Eugene, Oreg.). Naive rabbit serum served as the negative control. Sections were viewed with a Zeiss LSM 510 Meta confocal system attached to a Zeiss Axiovert 200 inverted microscope (Carl Zeiss Inc., Thornwood, N.Y.).

Significant differences in mean CFU/mg tissue and mean CFU NTHI/ml supernatant were determined by paired t-test. A p-value≤0.05 was considered significant. Significance in relative biomass among cohorts was assessed by unpaired t-test. A p-value≤0.05 was considered significant.

Figure 10A:
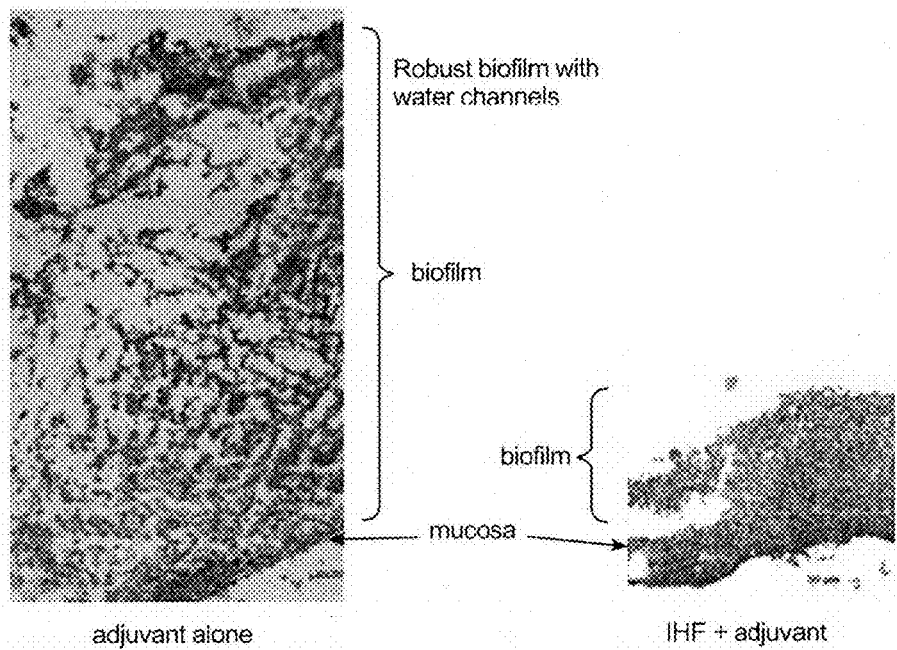
FIG. 10A shows H&E staining of a frozen section of a biofilm recovered from the middle ear of a chinchilla that had been immunized via TCI with adjuvant alone versus immunization with IHF+adjuvant. Note condensed and collapsed appearance of biofilm recovered from the animal immunized with IHF+adjuvant compared to that immunized with adjuvant alone. Images shown in FIG. 10A are shown at identical magnifications to illustrate the differences in height and density between the two representative biomasses.
Figure 10B:
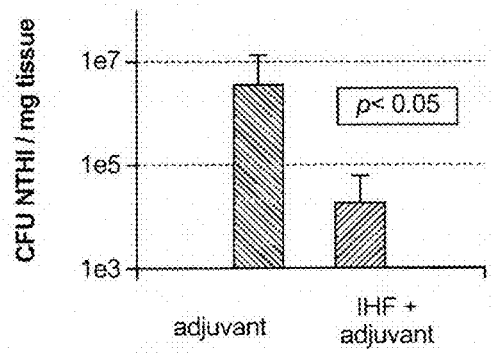
FIG. 10B demonstrates that there is a significant reduction of bacterial load present in the middle ears of animals immunized with adjuvant alone versus those immunized with IHF+adjuvant ($p<0.05$).

As shown in FIG. 9A, the mean score for remaining biomass within the middle ears of chinchillas immunized with adjuvant only was 2.8 which indicated significant remaining disease and a lack of resolution of pre-formed biomass in most animals by day 18 after bacterial challenge of the middle ear. In contrast, the mean score for an *E. coli* IHF+ adjuvant immunized animal was 1.5. Representative images of a residual biomass that received a mean score of +2.8 and one that received a mean score of +1.5 are shown in FIG. 9B. Also, as shown in FIGS. 10A-10B, the disease resolution was additionally measured by both histological evidence of altered biomass architecture within the middle ear (see FIG. 10A) as well as a statistically significant reduction of bacterial load present within remaining biomass as measured by homogenization of the biomass and culture on chocolate agar (see FIG. 10B). Furthermore, all animals immunized with isolated *E. coli* IHF mounted a strong local and systemic immune response and no animal presented with obvious secondary sequelae as the result of immunization as noted upon necropsy (data not shown).

The notable observed efficacy when anti-IHF raised against an IHF promoter purified from *E. coli* K12 (the full length combination of both IHF subunits) used in vitro to debulk biofilms and also of purified *E. coli* IHF, when used as an immunogen in vivo to induce the formation of polyclonal antibodies that could resolve an ongoing biofilm disease, created a conundrum as to why mammalian hosts do not naturally mount an effective immune response to DNABII proteins that are associated with eDNA within the bacterial biofilms of recurrent and/or chronic disease states. In review of the solved structure of IHF when it is bound to DNA (Rice et al. (1996) Cell 87(7): 1295-1306), it is clear that a significant portion of the protein structure is occluded by bound DNA, which suggested the potential for occlusion of protective epitopes or domains of IHF and/or HU when bound to eDNA within a bacterial biofilm. It was hypothesized that use of native IHF, to which no DNA was bound, as the immunogen might provide a mechanism to overcome such occlusion and thereby foster production of protective antibodies.

To determine if eDNA could indeed prevent the development of protective antibodies directed against a DNABII family member upon immunization, whereas use of native protein was effective, a second larger cohort study was performed wherein the chinchilla study as detailed previously was essentially repeated.

For the second animal immunization study, twenty adult chinchillas (body mass between 500-700 g), shown to have no evidence of middle ear disease by tympanometry and video otoscopy, were enrolled and divided into four cohorts of 5 animals each. All animals were again challenged transbullarly with approximately 1000 CFU NTHI strain 86-028NP per bulla. Four days later, after a biofilm formed in the middle ear cavities of these animals, they were immunized by a transcutaneous route (TCI) as described above. Formulations consisted of either: 10 µg IHF admixed with 10 µg dmLT, 10 µg IHF that had been pre-bound to DNA+dmLT, DNA+dmLT, or 10 µg dmLT alone.

To determine if TCI with IHF pre-bound to DNA resulted in a similar immune response to that induced when the same nucleoprotein complex was delivered subcutaneously (SQ), and compared to that induced by IHF alone, two adult chinchillas were immunized to generate antisera. Each animal received a priming dose followed by two identical boosts delivered at 30-day intervals. Immunogens were admixed with the adjuvant monophosphoryl lipid A (MPL) (10 µg/dose) (Sigma-Aldrich, St. Louis, Mo.) due to its demonstrated strong adjuvant properties in the chinchilla host (See for example Bakaletz et al. (1999) Infect Immun. 67(6):2746-2762 and Kennedy et al. (2000) Infect. Immun. 68(5):2756-2765. One chinchilla was immunized with 10 µg of IHF+MPL and the other received 10 µg IHF bound to DNA+MPL. All doses were delivered SQ in a total volume of 200 µl. Fifteen days after receiving the final boost, animals were bled to procure serum and sera were assayed via Western blot and ELISA to determine both reciprocal titer and specificity of antibody reactivity to IHF.

Figure 11:
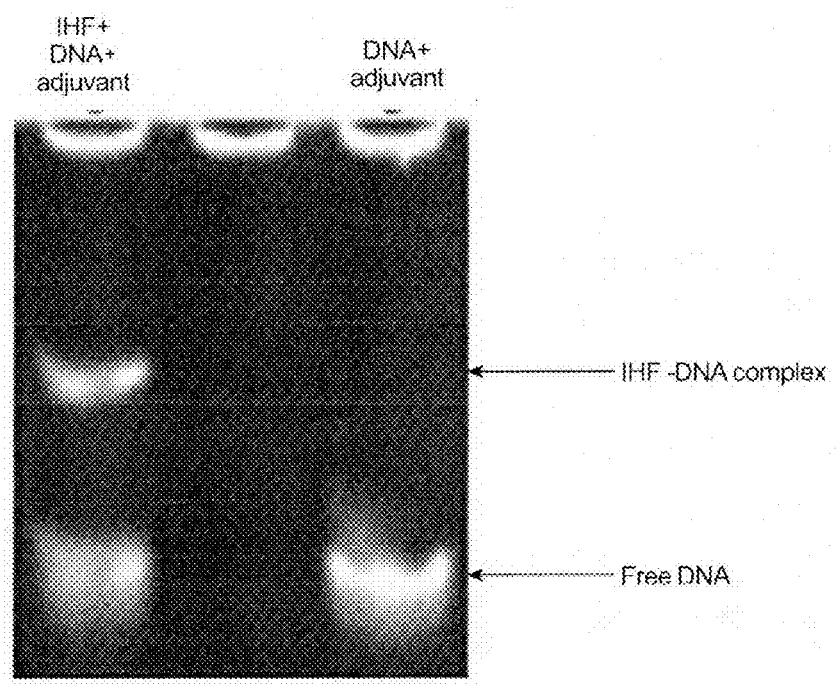
FIG. 11 depicts an electrophoretic mobility shift assay which demonstrated that IHF formed specific complexes with dsDNA under conditions used to immunize chinchillas.

Middle ears were again subsequently scored from 0 to 4+ for disease severity upon completion of the study. To better assure that the IHF and DNA remained in complex for immunization, synthetic oligonucleotides identical to those used in the published co-crystallization study (see for e.g., Rice et al. (1996) Cell 87(7): 1295-1306) of a high affinity IHF binding site from the bacteriophage lambda recombination site attP at a molar ratio of 2:1 [DNA (10 µM) to IHF (5 µM)] was used. This amount was at least 3 orders of magnitude over the $K_d$ of IHF bound to this DNA target. As shown in FIG. 11, IHF indeed bound dsDNA as demonstrated by its reduced mobility in an electrophoretic mobility shift assay.

Figure 12:
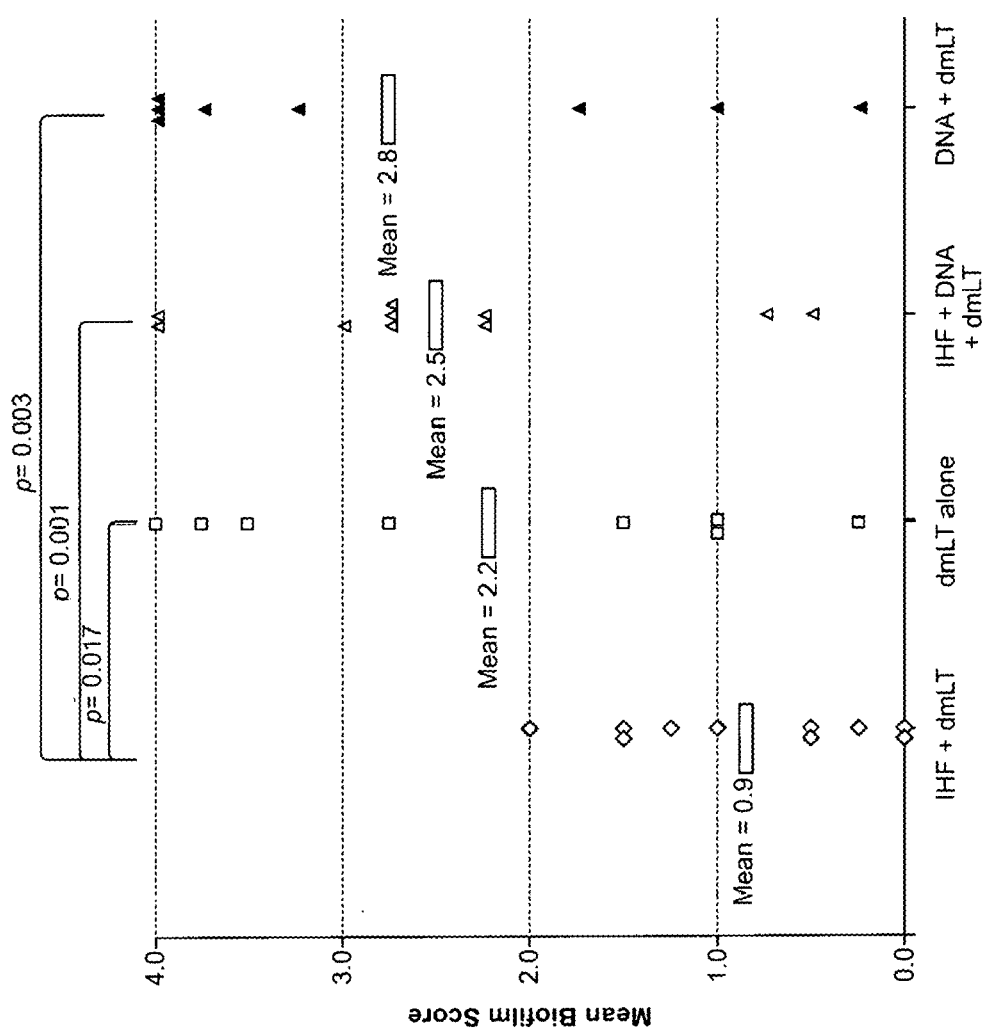
FIG. 12 graphically represents transcutaneous immunization with native IHF+adjuvant induced the formation of antibodies that significantly reduced the biomass resident within the middle ears of chinchillas compared to receipt of either adjuvant alone ($p<0.017$), dsDNA alone ($p<0.003$) or IHF to which dsDNA was already bound+adjuvant ($p<0.001$). This outcome suggested that binding of dsDNA to native IHF masked protective epitopes of this DNABII family member.

As shown in FIG. 12, animals immunized with isolated *E. coli* IHF showed a dramatic reduction in disease state with a mean residual middle ear biomass score of 0.9 as compared to the controls that had been immunized with adjuvant alone (mean biomass score=2.2) or to those that had been immunized with DNA that had been admixed with adjuvant (mean biomass score=2.8). Interestingly, those animals that had been immunized with the IHF-DNA complex also demonstrated middle ears with significant remaining bacterial biomass, yielding a mean biomass score of 2.5 which was not statistically significantly different from cohorts that received either the adjuvant alone or DNA that had been admixed with adjuvant. This outcome strongly suggested that if sufficient eDNA fragments were present, as one could hypothesize would be the case during natural disease, this situation could result in occlusion of critical IHF epitopes necessary for the generation of neutralizing antibodies.

Figure 13:
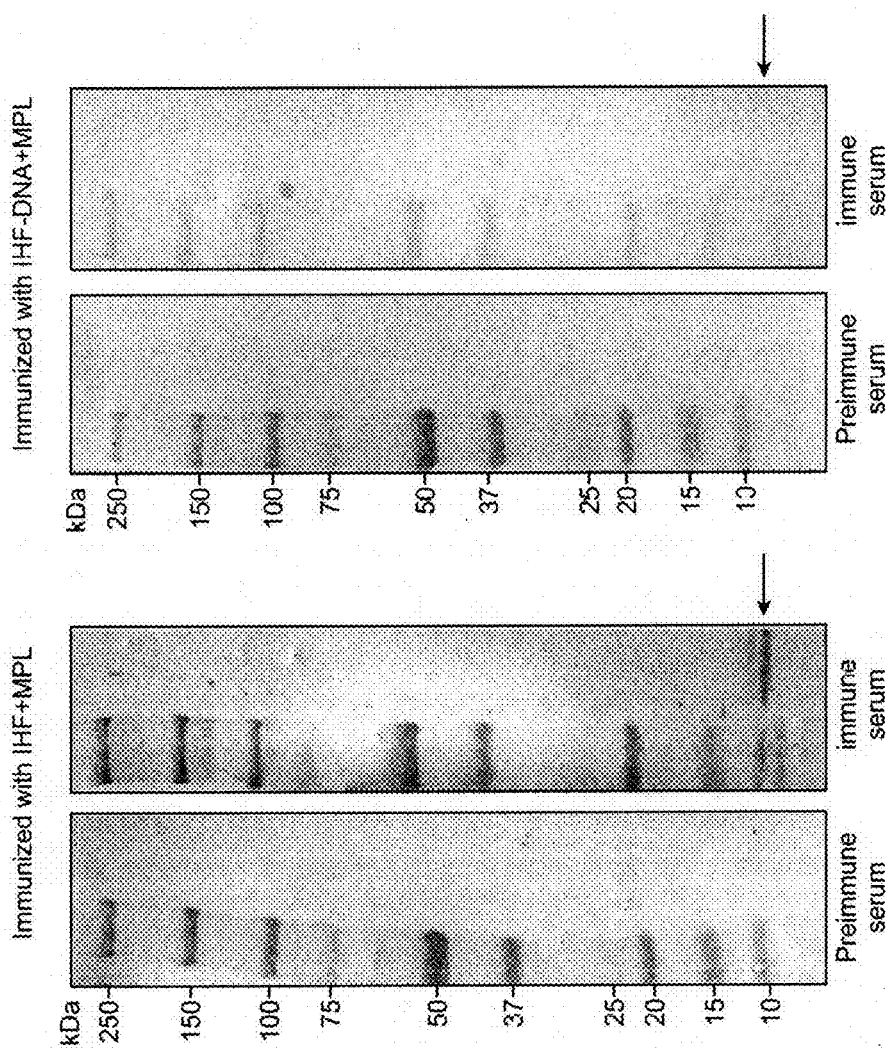
FIG. 13 depicts the recognition of IHF (arrows) by antibody in serum after subcutaneous immunization with IHF or with IHF to which dsDNA was bound.
Figure 15:
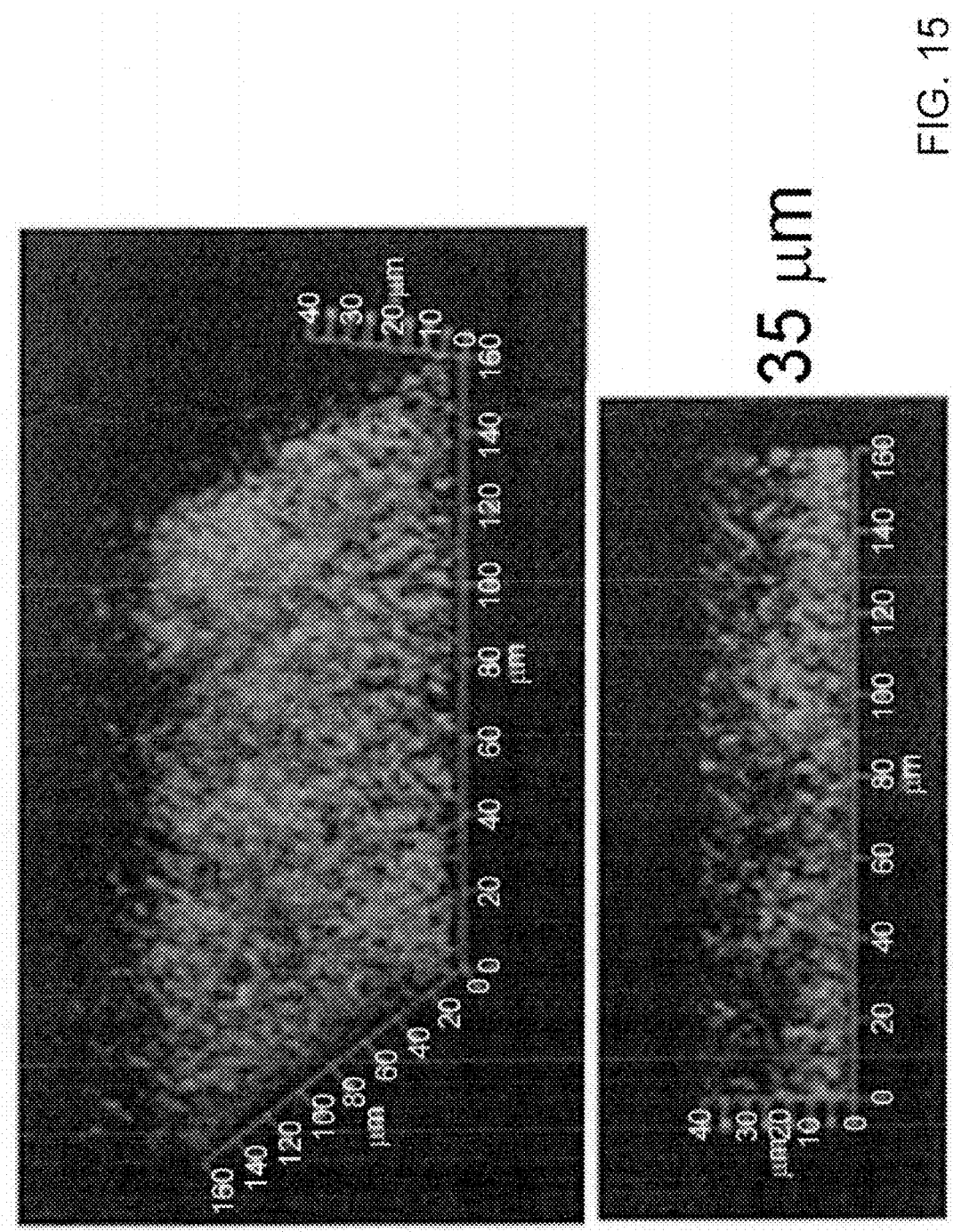
FIG. 15 is a comparison of E. coli treated with either naive rabbit serum or rabbit anti-IHF serum (top row of images); with naive rat serum or rat anti-HNS serum (middle row of images); or with naive mouse serum or with mouse anti-DPS serum (bottom row of images). Note marked reduction in biomass following treatment with anti-IHF serum, however neither anti-HNS nor anti-DPS serum induced a reduction in biomass as used herein. Treatment with anti-IHF resulted in a 48.2% reduction in the biofilm height, an 81% reduction in the biofilm average thickness, and a 64.5% reduction in the biomass. In contrast treatment with the anti-HNS or anti-DPS resulted in a nominal height reduction of 0.7% and 4.2%, respectively, a reduction in the average thickness of 5.8% and 6.4% respectively, and a reduction in the biomass of 0.3% and −17.4% respectively.
Figure 15:
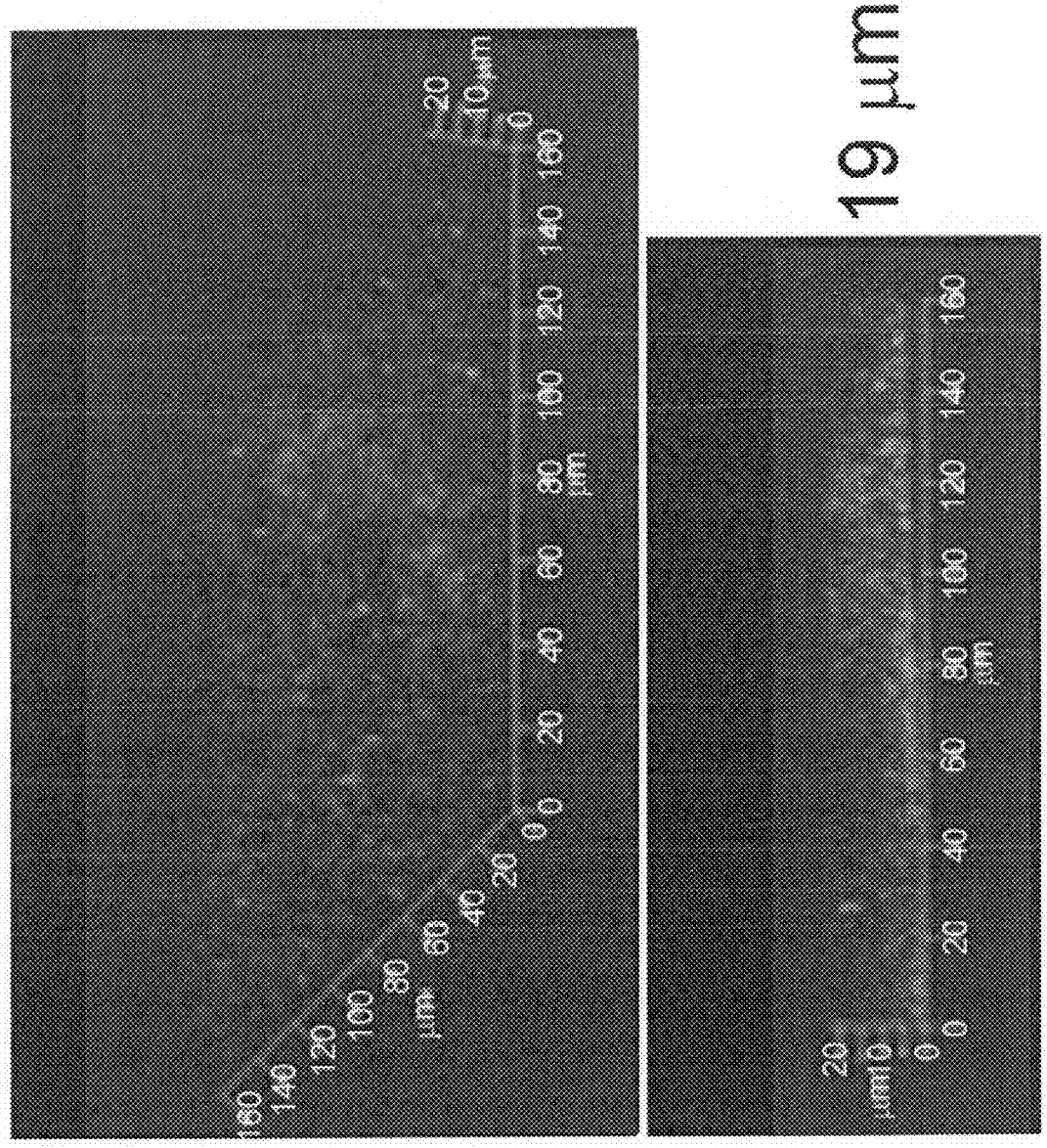
Figure 15:
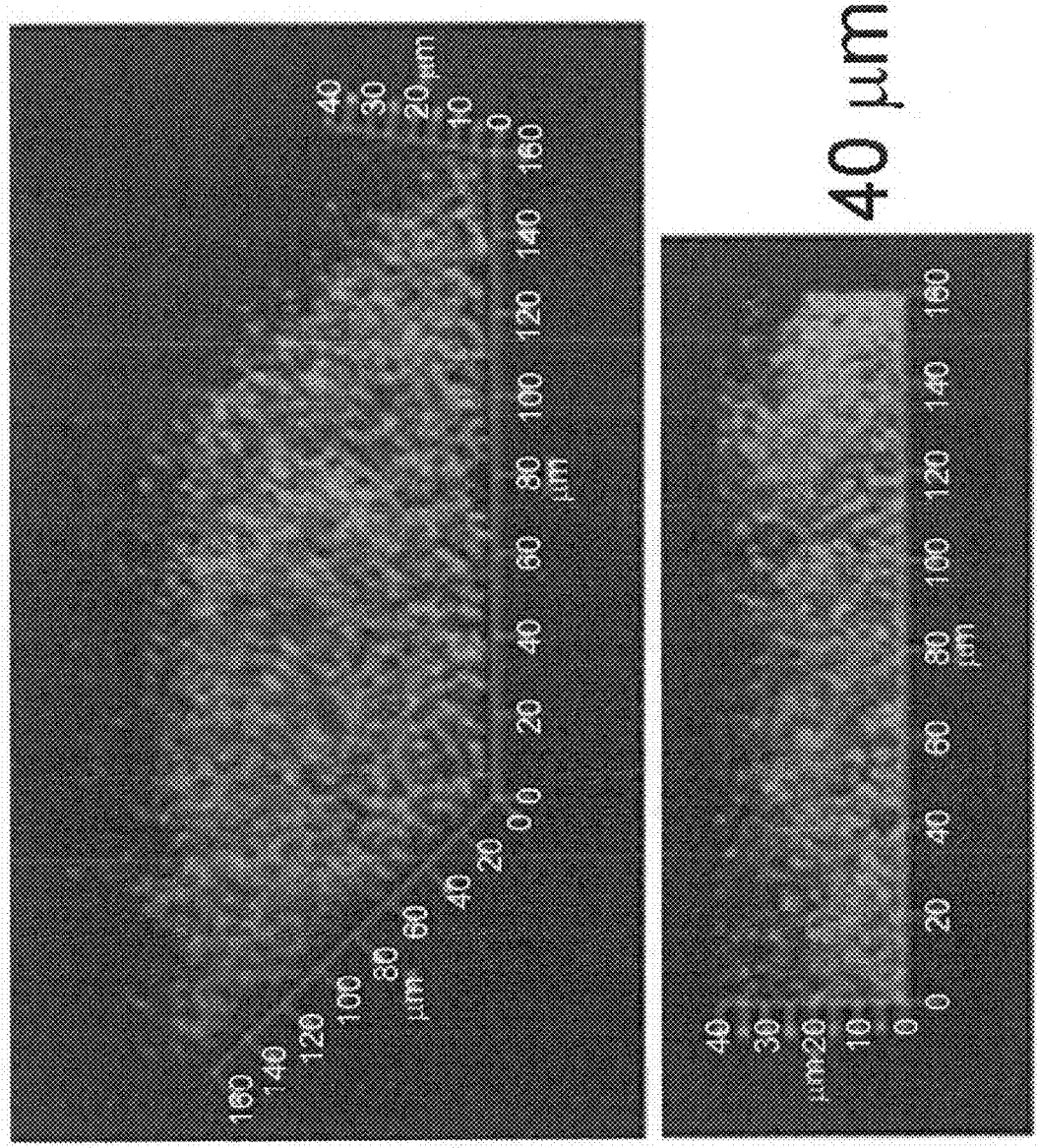
Figure 15:
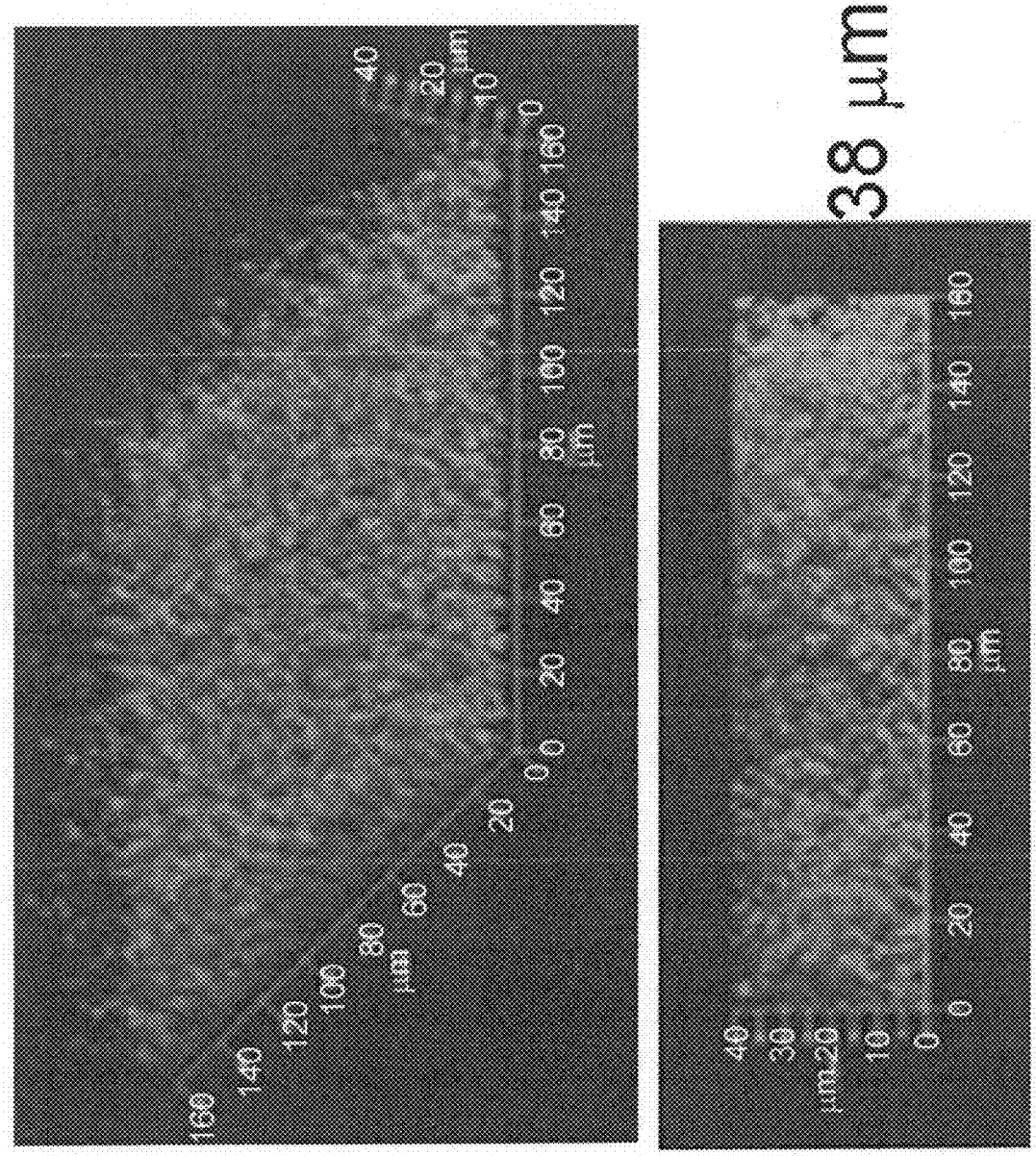
Figure 15:
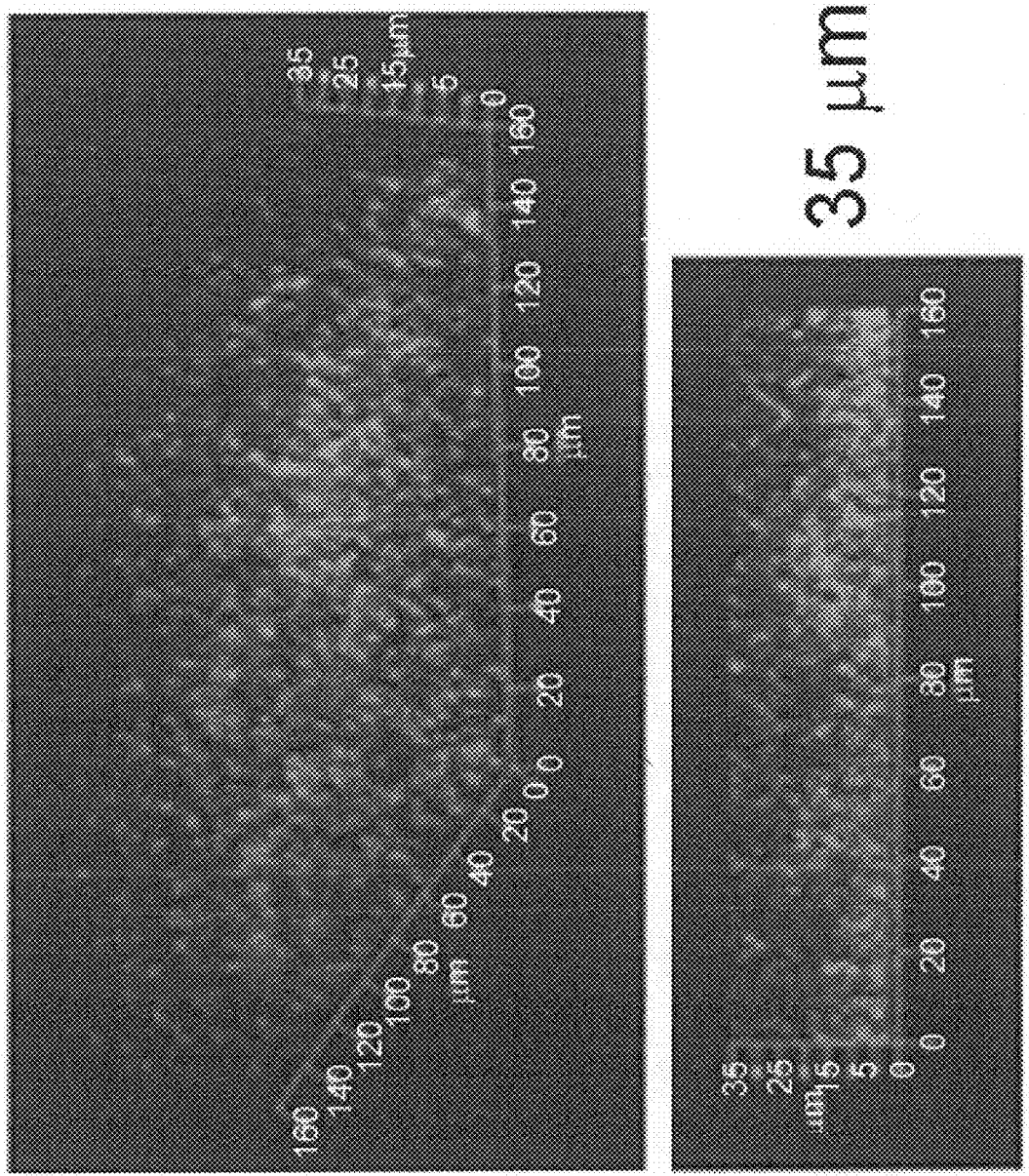
Figure 15:
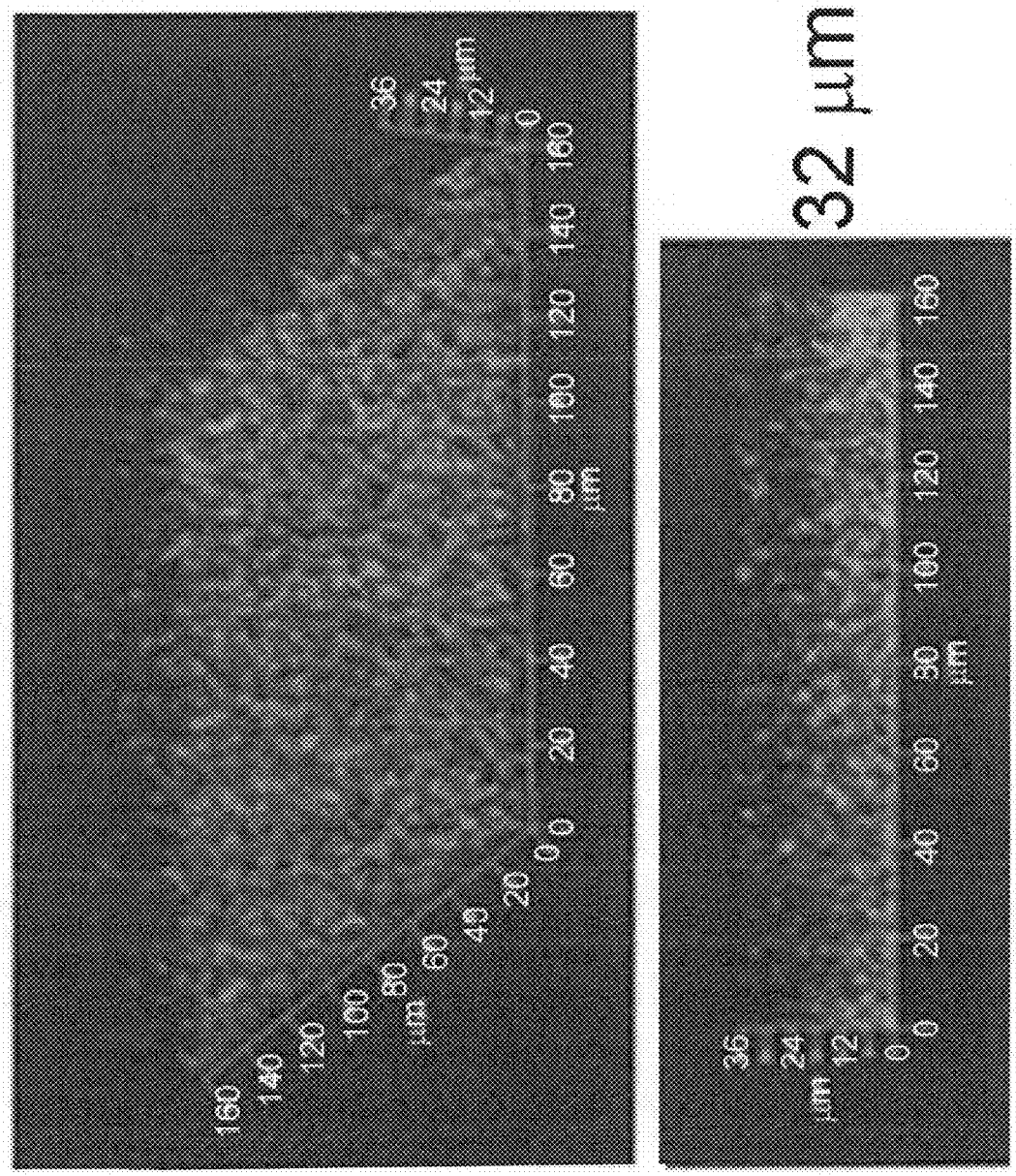
Figure 16:
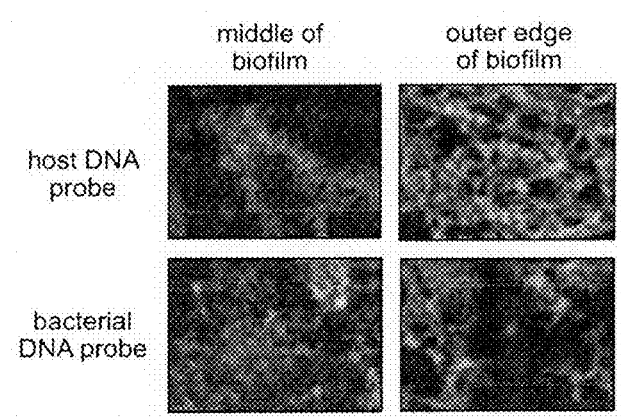
FIG. 16 shows in situ hybridization to demonstrate relative spatial distribution of DNA from either a host organism or from the bacterium when organized within a biofilm. In each circumstance, DNA appears as brighter, whiter areas within the foreground of these black and white images. DNA from the host is more densely labeled within the upper right hand image, demonstrating its more heavy distribution on the outer periphery of the biofilm, whereas DNA from the bacterium is more densely labeled in the lower left hand image of this 4-panel composite, thereby demonstrating its more dense distribution within the inner reaches of the biofilm.

To be assured that the observed DNA occlusion result was not specific to the use of a transcutaneous immunization route, these immunizations using a subcutaneous (SQ) immunization route to ensure delivery of the antigens to antigen presenting cells within the chinchilla host were repeated. As shown in FIG. 13, whereas SQ immunization with isolated *E. coli* IHF yielded the generation of a strong immune response to isolated IHF, immunization with *E. coli* IHF that had been pre-bound to an excess of DNA failed to induce detectable antibodies that recognized IHF when assayed by Western blot. When assayed by ELISA, reciprocal titer versus isolated IHF was 1000 for the animal immunized with IHF that had been pre-bound to oligonucleotides, whereas that for the animal immunized with native IHF was 8000 (both animal's pre-immune reciprocal titers against IHF were 100). Collectively, these results are consistent with our hypothesis that the binding of IHF to eDNA, as would occur during a natural disease state, has the potential to block epitopes or domains of IHF necessary for generation of a protective acquired immune response. Further, immunization with native IHF (to which no DNA is bound) appeared to allow for the effective direction of the immune response toward the generation of protective or neutralizing antibodies, as demonstrated in both pre-clinical chinchilla studies described here.

Experiment No. 4

A number of oral bacteria (e.g., *Aggregatibacter actinomycetemcomitans*, *Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria wilt greatly aid in elucidating their pathogenic mechanisms.

The surface of machined titanium dental implants (1.2× 4.5 mm) was modified by grit blasting with A103 (100 μm) and HCl etching (pH 7.8 for 20 min at 80° C.). Machined and nano-textured implants were incubated in TSB medium inoculated with D7S clinical strain of *Aggregatibacter actinomycetemcomitans* (Aa) for 1 to 3 days at 37° C. The bacterial biofilm on the implants were analyzed by SEM, as well as by confocal laser scanning microscopy following staining with LIVE/DEAD® BacLight™. Implants with and without established Aa biofilm were transmucosally placed into the alveolar bone of female rats between premolar and incisor region of the maxillae. To detect the presence of Aa biofilm on the implants placed in vivo, bacterial samples were collected from saliva and the oral surfaces of implants after 2 days. Aa was detected by culture, as well as by PCR analysis. Micro-CT and histological analysis of peri-implant bone and mucosal tissues was performed six weeks after implantation.

After one day of cultivation, agglomerates of coccoid-shaped Aa cells were found scattered throughout the implant. After two days, the number and size of the agglomerates decreased and more cells of varying lengths were observed ranging between bacteria with coccoid morphology. After three days of incubation, the agglomerates had almost disappeared, while large areas of the implant surface were covered with bacteria with rod-shaped morphology, forming a densely packed biofilm. LIVE/DEAD® staining of such three days Aa biofilm on the implants showed green signal for 75-80% of all biofilm bacteria, indicating living cells with uncompromised membrane integrity. Microbiological and PCR detection of Aa biofilm on implants placed in vivo were positive for samples from die implant surfaces and negative for the saliva samples as well as control implants. Clinical examination demonstrated significant peri-implant mucosal inflammation around implants with Aa biofilm, compared with control untreated implants. Micro-CT and histological analysis of peri-implant bone and mucosal tissues is pending. Nano-textured implant surfaces favor the establishment of Aa biofilm and increase risk of peri-implantitis.

Experiment No. 5

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. Reported cases have more than doubled between 1992 and 2006, with approximately 29,000 new cases confirmed in 2008. Estimates are that the actual number of cases of Lyme disease may exceed that reported by a factor of 6-12 in endemic areas. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions disclosed herein are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Experiment No. 6

This experiment provides a porcine model for pre-clinical testing of interfering agents to treat cystic fibrosis. See Stoltz et al. (2010) Science Translational Medicine 2(29):29-31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the interfering agents to either 1) immunize these CF pigs with a polypeptide or other immunogenic agent thereby inducing the formation of antibodies which will eradicate bacterial biofilms in the lungs (similarly to how antibodies to IHF eradicated biofilms resident within the middle ears of chinchillas following active immunization as shown in Experiment No. 1, to deliver anti-IHF (or other interfering agent) to the lungs of these animals by nebulization to assess the amelioration of the signs of disease and associated pathologies.

Experiment No. 7

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman KOI bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Experiment No. 8

Multiple animal models of catheter/indwelling device biofilm infections are known. See Otto (2009) Nature Reviews Microbiology 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to *S. epidermidis* amount to $2 billion annually in the United States. In addition to *S. epidermidis, E. faecalis* and *S. aureus* are also contaminations found on indwelling medical devices. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with *E. faecalis, S. aureus* and *S. epidermidis* biofilm formation. Biofilm reduction is often measured three ways-(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Experiment No. 9

Methods described herein may be used to elicit immune responses in humans and animals. Immunogenic compositions may be administered to a human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally or alternatively, immunogenic compositions may take the form of APCs pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Experiment No. 10

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Experiment 11

Members of the DNABII family are highly pleiotropic for multiple nucleoprotein systems including gene transcription, and moreover, are thus often essential. In contrast, both HU and IHF mutants have been generated in laboratory strains of *E. coli* and studied extensively. To determine what role IHF and HU have in eDNA formation, biofilms formed by *E. coli* strain MG1655 or its HU and IHF deficient derivatives were incubated with anti-IHF (prepared as described in Granston and Nash (1993) J. Mol. Biol. 234:45-59.) As shown in FIGS. 8A-8F, whereas the parental isolate, strain MG1655 produced a robust biofilm in vitro (FIG. 8A), both HU and IHF mutant strains were less robust (FIGS. 8C and 8E, respectively). An HU deficient mutant yielded a biofilm that was approximately ½ the height of the wild type biofilm, whereas IHF deficient strains produced a biofilm that was approximately ⅔ rds the height of the parental isolate. This result suggested that both proteins were involved in either the production and/or integrity of the *E. coli* biofilm EPS. After treatment with anti-IHF, the biofilm formed by the wild type isolate showed notable debulking and a mean percent reduction of 58.1% in height, 73.1% percent reduction in biomass and 87% reduction in mean thickness (FIG. 8B), whereas that formed by the HU mutant showed no reduction in height and only a 30.9% reduction on biomass and 37.2% reduction on mean thickness (FIG. 8D). In contrast, no effect on the biofilm formed by the IHF mutant was observed in terms of loss of height (−3.4% reduction), biomass (−20.5% reduction) or mean thickness (−19.8% reduction) (FIG. 8F). Collectively, these data indicated that for this strain of *E. coli*, IHF was likely the only structural element that could be targeted by use of the anti-IHF antibody. Since to date only the highly structured interwoven eDNA in biofilms that have been formed in vivo have been seen, confirmation of the expression of remaining DNABII family member by each respective mutant and any change in the resultant DNA structure awaits an in vivo immunofluorescent analysis.

Experiment 12

Whereas it was demonstrated in this application in vitro and in vivo that both anti-IHF and the use of IHF as an immunogen show utility in debulking biofilms and/or resolving biofilm disease respectively, it was unknown if dispersing of NTHI biofilms with anti-IHF might also allow synergism when used in conjunction with other therapeutic modalities. To this end the ability to induce augmented structural destabilization of pre-formed NTHI biofilms was assessed when a sub-optimal concentration of anti-IHF was used along with one of each of three unique reagents. These three reagents include 1) a DNA degrading enzyme (DNaseI) known to be able to degrade an NTHI biofilm in vitro (but used here at a suboptimal concentration), 2) antisera to an outer membrane protein of NTHI that did not destabilize a pre-formed NTHI biofilm when used alone (anti-OMP P5) (data not shown), and 3) an antibiotic typically used as a first line choice in children with chronic and/or recurrent OM (amoxicillin) but which has limited efficacy against bacteria resident within a biofilm community.

FIG. 14A shows that treatment of an NTHI biofilm with a concentration of DNase shown to be sub-optimal has a marginal effect (see FIG. 14A, Panel II). Likewise, a 1:200 dilution of anti-IHF had little effect on the pre-formed NTHI biofilm (see FIG. 14A, Panel III). In contrast however, when these two reagents were used in concert, the biofilm was notably diminished (see FIG. 14A, Panel IV). Upon repeat of this experiment three times, we found that the most marked synergistic effect of debulking of the biofilm was measured as a diminution in height. Table 7 below depicts these results.

TABLE 7

|  | DNase | Anti-IHF | DNase + anti-IHF | |
| --- | --- | --- | --- | --- |
| Max height (μm) | 3.9 | 37.3 | 51.0 | Assay 1 |
| Max height (μm) | −11.5 | 16.4 | 37.7 | Assay 2 |
| Max height (μm) | −1.6 | 19.4 | 38.7 | Assay 3 |

One simple explanation for this outcome was that as the DNABII protein was being titrated away from the periphery of the biofilm, the eDNA became more accessible to the action of the DNase.

FIG. 14B shows the results of treatment with anti-OMP P5 on pre-formed NTHI biofilms. Although this antisera is strongly reactive with isolated NTHI OMP P5 (data not shown) and further, active immunization with isolated OMP P5 is effective in mediating significant protection against experimental OM in chinchilla models (see for e.g., Bakaletz et al. (1997) Vaccine 15(9):955-961; Bakaletz et al. (1999) Infect Immun 67(6):2746-2762; Kennedy et al. (2000) Infect Immun 68(5):2756-2765; Kyd, J. M. et al. (2003) Infect Immun 71(8):4691-4699; Novotny, L. A. et al. (2000) Infect Immun 68(4):2119-2128; Novotny, L. A. et al. (2002) Vaccine 20(29-30):3590-3597; Novotny, L. A. et al. (2003) J Immunol 171 (4): 1978-1983) this antiserum does not induce a change in the structural integrity of an NTHI biofilm that has been formed in vitro when used at a dilution of 1:50 (see FIG. 14B, Panel II). Likewise a marginal effect when these biofilms were incubated with a sub-optimal dilution of anti-IHF (used at a 1:100 dilution here) was observed (see FIG. 14B, Panel I). When combined, however, the use of anti-P5 plus anti-IHF resulted in a reduction in the height of the biofilm that exceeded the sum of the two antisera when used singly (see FIG. 14B, Panel III), thus indicating a synergistic outcome. Hence, it was concluded that use of anti-IHF to destabilize the NTHI EPS matrix resulted in the exposure of the targeted bacterial cell surface protein (e.g., OMP P5) that would otherwise be obscured by eDNA as well as perhaps other components of the EPS, thus allowing immune mediated bacterial clearance by as yet unknown mechanisms.

Figure 4A:
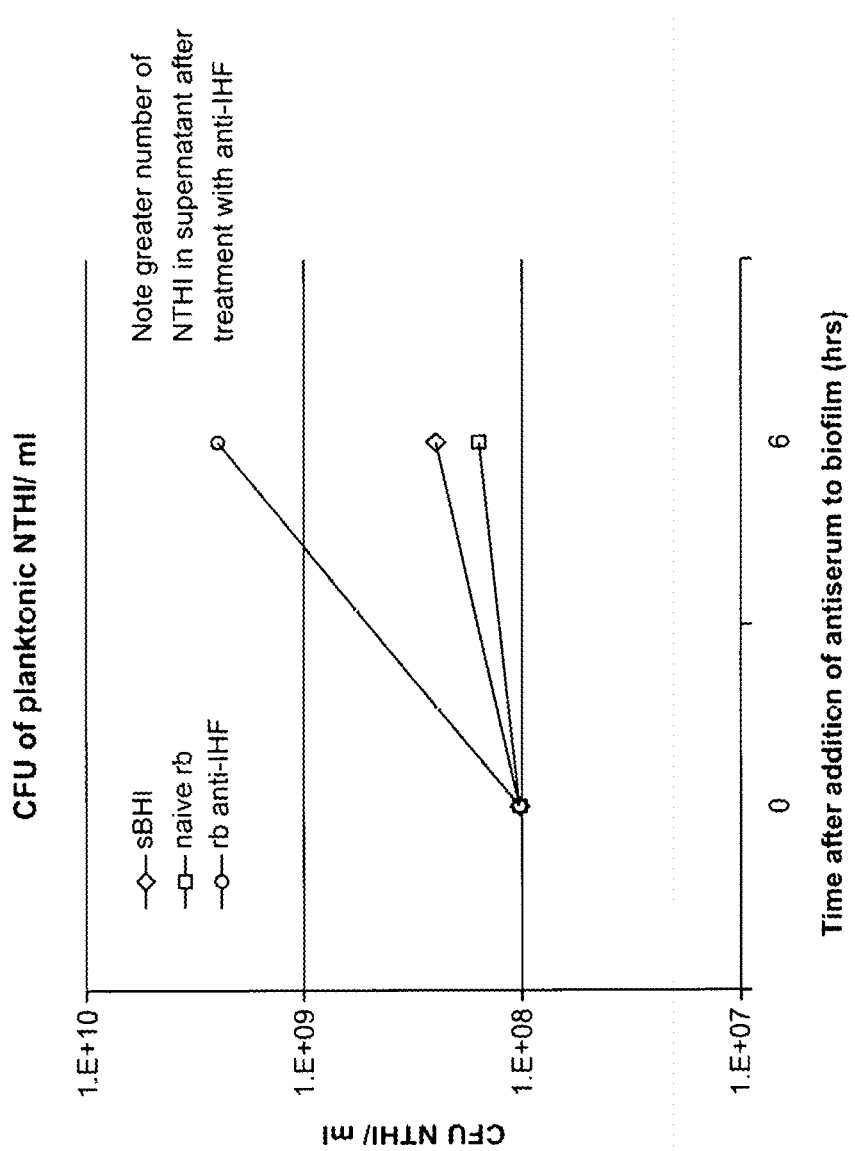
FIGS. 4A and 4B are graphs showing treatment of an established biofilm formed by NTHI with anti-IHF results in more NTHI released into the supernatant. Sixteen (16) hour NTHI biofilms grown in chamber slides were sham treated with sterile medium (sBHI) or treated with naïve rabbit serum or rabbit anti-IHF. Six hours later (FIG. 4A) or 10 hours later (FIG. 4B), supernatants were collected and analyzed. Note the greater number of NTHI in supernatant after treatment with anti-IHF. Incubation with anti-IHF resulted in a marked increase in planktonic bacteria available for culture from the medium within the chamber slide within approximately 6 hrs, and increasing notably at 10 hours of incubation. These results suggested release of bacteria from the biofilm matrix.
Figure 4B:
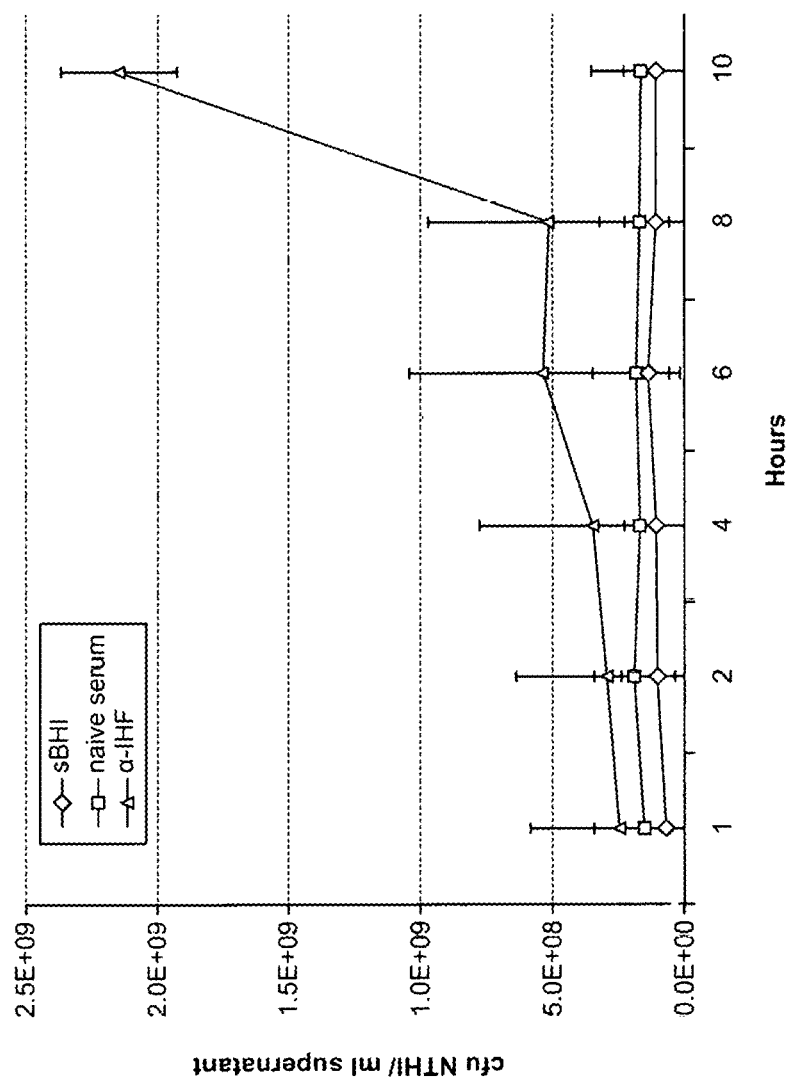

Lastly, FIG. 14C shows the results of treating pre-formed NTHI biofilms with amoxicillin. When used at a concentration of 64 μg/ml, amoxicillin had no measurable effect on the architecture of pre-formed NTHI biofilms (see FIG. 14C, Panel II) despite evidence of limited bacterial cell death. Treatment with IHF antisera at a 1:50 dilution substantially reduced the height of the biofilm as shown previously (see FIG. 14C, Panel III). Interestingly however, when the two reagents were used simultaneously, not only was there a dramatic reduction in the height of the biofilm (see FIG. 14C, Panel IV), but use of a vital dye indicated that the majority of the bacteria remaining in the biofilm were now dead as noted by the predominant fluorescence in the red channel within the imaged biofilm. This result showed that debulking of the biofilm with anti-IHF likely exposed the bacteria sufficiently so as to create conditions more akin to susceptibility to amoxicillin concentrations known to be effective when assayed against planktonic NTHI. This outcome may have been mediated by either increased physical exposure of bacteria within the remaining biofilm matrix to the action of amoxicillin and/or via increased release of bacteria into the planktonic phase as we showed earlier can occur during biofilm debulking by exposure to anti-IHF antibodies (see FIGS. 4A-4B).

Lastly, FIG. 14C shows the results of treating pre-formed NTHI biofilms with amoxicillin. When used at a concentration of 64 μg/ml, amoxicillin had no measurable effect on the architecture of pre-formed NTHI biofilms (see FIG. 14C, Panel II) despite evidence of limited bacterial cell death. Treatment with IHF antisera at a 1:50 dilution substantially reduced the height of the biofilm as shown previously (see FIG. 14C, Panel III). Interestingly however, when the two reagents were used simultaneously, not only was there a dramatic reduction in the height of the biofilm (see FIG. 14C, Panel IV), but use of a vital dye indicated that the majority of the bacteria remaining in the biofilm were now dead as noted by the predominant fluorescence in die red channel within the imaged biofilm. This result showed that debulking of the biofilm with anti-IHF likely exposed the bacteria sufficiently so as to create conditions more akin to susceptibility to amoxicillin concentrations known to be effective when assayed against planktonic NTHI. This outcome may have been mediated by either increased physical exposure of bacteria within the remaining biofilm matrix to the action of amoxicillin and/or via increased release of bacteria into the planktonic phase as we showed earlier can occur during biofilm debulking by exposure to anti-IHF antibodies (see FIGS. 4A-4B).

Experiment 13

Applicants sought to identify the immunodominant and immunoprotective domains of IHF 20-mer peptides with a 5-mer overlap were prepared from the deduced amino acid sequences of the genes that encode for IHF and HU in nontypeable *Haemophilus influenzae* (NTHI) strain 86-028NP (disclosed in FIG. 18). These peptides mimic the deduced amino acid sequence from N- to C-terminus but do not accommodate for either discontinuous or conformational epitopes within the properly folded native protein. Gross epitope mapping was performed using antiserum derived from chinchillas that had been parenterally immunized with native IHF isolated from *E. coli*+(the full length combination of both IHF subunits) and an adjuvant in order to determine if immunization with this protein would induce the formation of antibodies that could resolve pre-existing biofilms that had been formed in their middle ears by NTHI strain 86-028NP. The immunization was efficacious, thus inducing the formation of antibodies that eradicating experimental otitis media significantly earlier than controls which had received adjuvant only. Using BIACORE biosensor, the 20-mer peptides and antiserum from these animals, it was determined that the greatest immune recognition was to peptides that represented peptides A5 and B4 (from the alpha and beta subunit respectively). This was unexpected, as individuals suffering from biofilm diseases do not resolve biofilms thus suggesting that the observed result was a therapeutically induced environment Applicants considered how DNABII proteins would be available for responding to immunologically by the immune system in an individual with active disease wherein the DNABII proteins would most likely be complexed with eDNA within the biofilm matrix. Without being bound by theory, it was hypothesized that since IHF or HU would be complexed with eDNA in the biofilm during disease, this might mask the immunoprotective domains of the protein, thus making them unavailable to the immune system for recognition and generation of antibodies.

To test this hypothesis, additional cohorts of chinchillas were immunized with either native full length IHF from *E. coli* (obtained from Nash) or with native full length IHF from *E. coli* (obtained from Nash) that had been complexed to an excess of double stranded DNA in order to best mimic how it would be presented in nature. Again, using BIACORE biosensor, the 20-mer peptides and antiserum from these two cohorts of animals, it was again determined that for those animals immunized with native IHF, the greatest recognition was to peptides A5 and B4, however, when using serum derived from animals immunized with IHF that had been pre-complexed to an excess of DNA (to best mimic how the immune system "sees" this protein during disease, the greatest recognition was to peptides A3 and B2. Typically, for development of a novel vaccine or therapeutic, one epitope maps a protein based on how it is presented during disease, then one identifies the most immunodominant epitopes of that protein and uses these to attempt to design a vaccine candidate or immune target for treatment.

However, the epitope mapping data indicates that targeting the most immunodominant epitopes of IHF as available for responding to immunologically during disease for either vaccine or therapeutic development would be a flawed approach. Instead, it was necessary to immunize with epitopes that are not available for responding to immunologically during disease in order to redirect the immune system to the appropriate and immunoprotective targets. This would not have been determined had Applicants not immunized chinchillas with both native protein and protein that had been pre-complexed to an excess of DNA and performed both efficacy studies and comparative epitope mapping efforts.

Once these unexpected protective domains were identified, Applicants performed more fine mapping studies to better understand the mechanism(s) that underlied the results. To do so, the sequences of the 20-mer peptides were overlaid upon a theoretical 3D model of IHF or HU from NTHI (the deduced amino acid sequences of these NTHI proteins were substituted for those from *E. coli* for which a 3D crystal structure has already been obtained). It was found that the peptides A3 (amino acids 31 to 50 of IHF; SEQ ID NO: 350) and B2 (amino acids 16 to 35 of IHF; SEQ ID NO: 343) mapped to the "tails" of IHF whereas the peptides A5 (amino acids 61 to 80 of IHF; SEQ ID NO: 352) and B4 (46 to 65 of IHF; SEQ ID NO: 345) mapped to the 'tips' of the IHF protein. These data showed that during disease, the immune system likely only 'sees' the tails of these proteins as the tips are bound to eDNA and thus masked from the immune system. This observation would be counterintuitive to what is typically done to determine the most immunodominant epitope of a protein as presented by a bacterial pathogen during disease.

The generated 20-mer peptide were simply made in a sequence from N- to C-terminus, e.g., amino acids 1 to 20, 16 to 35, etc., and did not necessarily mimic the most optimal peptide sequence in terms of best reproducing either the structure of a discontinuous epitope or the 3-dimensional structure of these proteins (the latter of which is essential for their ability to bind to and bend DNA). Therefore, when needed, the amino acid sequence of a given 20-mer peptide was modified to better fit the new information obtained from the prior study on how these proteins interact with DNA, combined with our new understanding that the immunodominant epitopes of DNABII proteins bound to DNA were not the ones that would likely mediate a protective effect.

Experiment No. 14

Antibodies were raised in chinchillas against the IHFA and IHFB of *Haemophilus influenzae* according to the methods described in Experiment No. 1 specific to the polypeptide epitopes disclosed in SEQ ID NO: 342 to 353.

Figure 17:
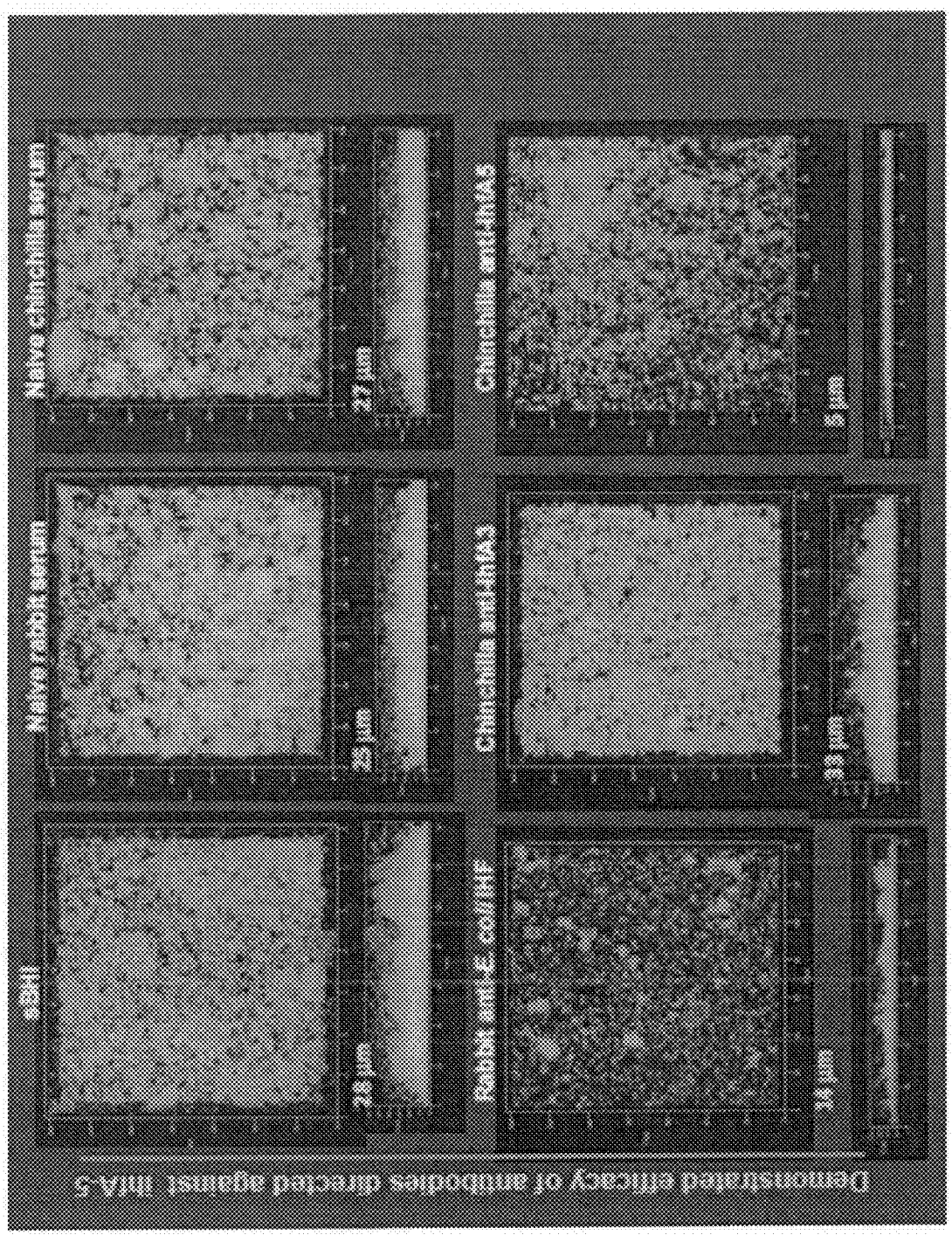
FIG. 17 depicts the reduction of biofilms formed by NTHI upon incubation with rabbit anti-IHF E. coli and chinchilla antibodies raised against IhfA, fragment A5 and A3, compared to incubation with naïve rabbit serum, chinchilla serum, and sBHI.

Using the in vitro model for reversal of an established biofilm described in Experiment 2 and these polyclonal antibodies, Applicants reduced a biofilm produced by NTHI. The disruption of the biofilm using the anti-IHF-A5 (raised against SEQ ID NO: 352) was significant (FIG. 17).

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scoped of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method to prevent formation of or to dissolve a biofilm in a subject in need thereof, comprising administering to the subject an isolated polypeptide consisting of the amino acid sequence of RPGRNPKTGDVVPVSARRVV (SEQ ID NO: 352) or an equivalent thereof, wherein the equivalent consists of the amino acid sequence of SEQ ID NO: 352 and either or both of the following:
   (i) up to 20 random amino acids on the amine terminus of the amino acid sequence of SEQ ID NO: 352; or
   (ii) up to 15 random amino acids on the carboxy terminus of the amino acid sequence of SEQ ID NO: 352.

2. A method to prevent formation of or to dissolve a biofilm in a subject in need thereof, comprising administering to the subject an isolated polypeptide consisting of the amino acid sequence of SEQ ID NO: 352.

3. The method of claim 1, wherein the subject is selected from the group of: human, simians, rats, mice, chinchilla, canine, leporids, livestock, sport animals, or pets.

4. The method of claim 1, wherein the biofilm comprises a DNABII protein.

5. The method of claim 4, wherein the DNABII protein comprises a histone-like protein from *E. coli* strain U93 (HU) or an integration host factor (IHF) protein.

6. The method of claim 1, wherein the biofilm is produced by a microorganism selected from one or more of the group of: *Haemophilus influenzae, Streptococcus mutans, Staphylococcus aureus, Moraxella catarrhalis, Streptococcus pneumonia, Pseudomonas aeruginosa, Neisseria gonorrhoeae,* Uropathogenic *Escherichia coli, Staphylococcus epidermidis, Haemophilus influenzae* (nontypeable)(NTHI), *Streptococcus agalactiae, Neisseria meningitidis, Treponema denticola, Treponema pallidum, Burkholderia cepacia, Burkholderia pseudomallei, Streptococcus pyogenes, Mycobacterium tuberculosis, Porphyromonas gingivalis, Aggregatibacter actinomvctemcomitans, Borrelia burgdorferi, Escherichia coli, Salmonella enterica* serovar, *Vibrio cholerae, Helicobacter pylori,* or *Enterococcus faecalis.*

7. The method of claim 1, further comprising administering an effective amount of one or more of the following concurrently or sequentially: an antibiotic, an antimicrobial, an antigenic peptide, an adjuvant, a DNase enzyme, or an antibody.

8. The method of claim 1, wherein the administration is selected from the group of: locally to the site of the infection, by direct injection, by inhalation, transdermally, urethrally, sublingually, rectally, vaginally, ocularly, subcutaneous, intramuscularly, intraperitoneally, intranasally, or orally.

9. The method of claim 1, wherein the isolated polypeptide is administered in a composition further comprising a pharmaceutically acceptable carrier, or wherein the isolated polypeptide is administered in a composition further comprising a solid phase carrier selected from the group of: an implant, a stent, a paste, a gel, a dental implant, or a medical implant.

10. The method of claim 1, wherein the isolated polypeptide is conjugated to a detectable agent.

11. The method of claim 1, wherein the subject has been selected for the method by assaying a sample isolated from the subject for infection by a microorganism selected from one or more of the group of: *Haemophilus influenzae, Streptococcus mutans, Staphylococcus aureus, Moraxella catarrhalis, Streptococcus pneumonia, Pseudomonas aeruginosa, Neisseria gonorrhoeae,* Uropathogenic *Escherichia coli, Staphylococcus epidermidis, Haemophilus influenzae* (nontypeable)(NTHI), *Streptococcus agalactiae, Neisseria meningitidis, Treponema denticola, Treponema pallidum, Burkholderia cepacia, Burkholderia pseudomallei, Streptococcus pyogenes, Mycobacterium tuberculosis, Porphyromonas gingivalis, Aggregatibacter actinomvctemcomitans, Borrelia burgdorferi, Escherichia coli, Salmonella enterica* serovar, *Vibrio cholerae, Helicobacter pylori,* or *Enterococcus faecalis.*

12. The method of claim 1, further comprising administering to the subject an effective amount of an antibody or antigen binding fragment that specifically recognizes or binds the polypeptide of SEQ ID NO: 352, wherein the antibody or antigen binding fragment comprises:
   (a) the heavy chain variable region comprising SEQ ID NO: 359 and the light chain variable region comprising SEQ ID NO: 361; or
   (b) a heavy chain variable region comprising the complementarity determining regions of SEQ ID NOs: 362, 366, and 381 and a light chain variable region comprising the complementarity determining regions of SEQ ID NOs: 383, 386 and 411.

13. The method of claim 2, wherein the subject is selected from the group of: human, simians, rats, mice, chinchilla, canine, leporids, livestock, sport animals, or pets.

14. The method of claim 2, wherein the biofilm comprises a DNABII protein.

15. The method of claim 14, wherein the DNABII protein comprises a histone-like protein from *E. coli* strain U93 (HU) or an integration host factor (IHF) protein.

16. The method of claim 2, wherein the biofilm is produced by a microorganism selected from one or more of the group of: *Haemophilus influenzae, Streptococcus mutans, Staphylococcus aureus, Moraxella catarrhalis, Streptococcus pneumonia, Pseudomonas aeruginosa, Neisseria gonorrhoeae,* Uropathogenic *Escherichia coli, Staphylococcus epidermidis, Haemophilus influenzae* (nontypeable)(NTHI), *Streptococcus agalactiae, Neisseria meningitidis, Treponema denticola, Treponema pallidum, Burkholderia cepacia, Burkholderia pseudomallei, Streptococcus pyogenes, Mycobacterium tuberculosis, Porphyromonas gingivalis, Aggregatibacter actinomvctemcomitans, Borrelia burgdorferi, Escherichia coli, Salmonella enterica* serovar, *Vibrio cholerae, Helicobacter pylori,* or *Enterococcus faecalis.*

17. The method of claim 2, further comprising administering an effective amount of one or more of the following concurrently or sequentially an antibiotic or an antimicrobial.

18. The method of claim 2, wherein the administration is selected from the group of: locally to the site of the infection, by direct injection, by inhalation, transdermally, urethrally, sublingually, rectally, vaginally, ocularly, subcutaneous, intramuscularly, intraperitoneally, intranasally, or orally.

19. The method of claim 2, wherein the isolated polypeptide is administered in a composition further comprising a pharmaceutically acceptable carrier, or wherein the isolated polypeptide is administered in a composition further comprising a solid phase carrier selected from the group of: an implant, a stent, a paste, a gel, a dental implant, or a medical implant.

20. The method of claim 2, wherein the isolated polypeptide is conjugated to a detectable agent.

21. The method of claim 2, wherein the subject has been selected for the method by assaying a sample isolated from the subject for infection by a microorganism selected from one or more of the group of: *Haemophilus influenzae, Streptococcus mutans, Staphylococcus aureus, Moraxella catarrhalis, Streptococcus pneumonia, Pseudomonas* aeruginosa, Neisseria gonorrhoeae, Uropathogenic Escherichia coli, Staphylococcus epidermidis, Haemophilus influenzae (nontypeable)(NTHI), Streptococcus agalactiae, Neisseria meningitidis, Treponema denticola, Treponema pallidum, Burkholderia cepacia, Burkholderia pseudomallei, Streptococcus pyogenes, Mycobacterium tuberculosis, Porphyromonas gingivalis, Aggregatibacter actinomvctemcomitans, Borrelia burgdorferi, Escherichia coli, Salmonella enterica serovar, Vibrio cholerae, Helicobacter pylori, or Enterococcus faecalis.

* * * * *